(12) United States Patent
Thakker et al.

(10) Patent No.: US 8,207,138 B2
(45) Date of Patent: Jun. 26, 2012

(54) METHODS AND DEVICES FOR IMPROVED EFFICIENCY OF RNA DELIVERY TO CELLS

(75) Inventors: Deepak Ramesh Thakker, Blaine, MN (US); Carl A. Schu, Plymouth, MN (US); Eric Neal Burright, Eagan, MN (US); Paul W. Wacnik, Pittsburgh, PA (US); Jennifer M. Heisel, Princeton, MN (US); Lothar Krinke, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 22 days.

(21) Appl. No.: 12/468,685

(22) Filed: May 19, 2009

(65) Prior Publication Data

US 2010/0298762 A1   Nov. 25, 2010

(51) Int. Cl.
*C12N 15/11* (2006.01)
(52) U.S. Cl. .................................................. 514/44 A
(58) Field of Classification Search ................. 514/44 A
See application file for complete search history.

(56) References Cited

U.S. PATENT DOCUMENTS

| | | | |
|---|---|---|---|
| 5,964,726 A * | 10/1999 | Korenstein et al. | 604/21 |
| 6,009,345 A * | 12/1999 | Hofmann | 604/20 |
| 6,110,161 A | 8/2000 | Mathiesen et al. | |
| 6,261,281 B1 | 7/2001 | Mathiesen et al. | |
| 6,316,243 B1 | 11/2001 | Palese | |
| 6,506,559 B1 | 1/2003 | Driver et al. | |
| 6,544,785 B1 | 4/2003 | Palese et al. | |
| 6,593,130 B1 | 7/2003 | Sen et al. | |
| 6,610,044 B2 | 8/2003 | Mathiesen | |
| 6,743,779 B1 | 6/2004 | Unger et al. | |
| 6,958,060 B2 | 10/2005 | Mathiesen et al. | |
| 7,276,356 B1 | 10/2007 | Palese et al. | |
| 7,384,774 B2 | 6/2008 | Palese et al. | |
| 8,039,445 B2 * | 10/2011 | Behar-Cohen et al. | 514/44 R |
| 2002/0010414 A1 * | 1/2002 | Coston et al. | 604/20 |
| 2003/0045830 A1 * | 3/2003 | de Bizemont et al. | 604/20 |
| 2004/0110711 A1 * | 6/2004 | Krueger et al. | 514/44 |
| 2004/0193097 A1 | 9/2004 | Hofmann et al. | |
| 2004/0253304 A1 | 12/2004 | Gross et al. | |
| 2006/0211637 A1 | 9/2006 | Scaria et al. | |
| 2006/0239990 A1 | 10/2006 | Nabel et al. | |
| 2006/0270623 A1 | 11/2006 | McSwiggen | |
| 2008/0147131 A1 | 6/2008 | Mathiesen et al. | |
| 2009/0053813 A1 * | 2/2009 | Evans | 435/461 |
| 2009/0264809 A1 * | 10/2009 | Sen | 604/20 |

FOREIGN PATENT DOCUMENTS

| | | |
|---|---|---|
| JP | 2005/224198 A | 8/2005 |
| WO | WO 2006/123248 A2 * | 11/2006 |
| WO | WO 2007/120557 A2 | 10/2007 |

OTHER PUBLICATIONS

Yukio Akaneya, et al, RNAi-Induced Gene Silencing by Local Electroporation in Targeting Brain Region, J. Neurophysiol.;93:594-602; 2005.

* cited by examiner

*Primary Examiner* — Brian Whiteman
(74) *Attorney, Agent, or Firm* — Fox Rothschild

(57) ABSTRACT

The instant invention provides a method for improving efficiency of RNA delivery to cells. The method comprises applying a low strength electric field to the cells and then after a certain time period, administering the ribonucleic acid sequence to the cells. Devices, kits, and RNA molecules suitable for delivery and devices suitable for practicing the disclosed methods are also provided.

19 Claims, 16 Drawing Sheets

HEK-293T Kidney Cells: Imaged 48 hour post-stimulation

C2C12 Cardiac Myoblast Cells: Imaged 48 hour post-stimulation

BE(2)-C Neuronal Cells: Imaged 48 hour post-stimulation

Neuro2a Neuronal Cells: Imaged 48 hour post-stimulation

*** p<0.001; significantly different from siRNA or respective delivery agent alone, one-way ANOVA with Tukey's post-hoc test; n indicated within each bar.

Cx  Cerebral Cortex
CC  Corpus Callosum
St  Dorsal Striatum

Cx Cerebral Cortex

CC Corpus Callosum

St Dorsal Striatum

METHODS AND DEVICES FOR IMPROVED EFFICIENCY OF RNA DELIVERY TO CELLS

FIELD OF THE INVENTION

The instant invention is directed to a method of delivering RNA to a cell of a patient, comprising electrically stimulating an area in a patient's body containing said cell, with a low-voltage electric stimulation followed by delivery of the RNA.

BACKGROUND OF THE INVENTION

RNA interference (RNAi) is a natural method of gene silencing in plant and mammalian cells. RNAi provides a mechanism for the sequence specific silencing of genes. RNAi has been adopted by researchers as a tool to investigate gene function and it has potential applications in the clinical arena such as treatment of neurodegenerative diseases, heart diseases, cancer, and other diseases where silencing of a specific gene or genes is desirable.

However, the efficient delivery of RNAi agents has been a major roadblock on the way to establish RNAi as a suitable gene therapy agent in modern medicine, mostly due to inefficient intake of RNAi agents and quick degradation thereof by RNAses present in blood, lymph, CSF, and intercellular space.

Initial work in the electroporation of siRNAs recommends conditions for transfecting cells in vitro have been to recommend pulse length to 100 µs and pulse voltages from 150-900 V (i.e., 150, 300 . . . 900 V) and then directly transferring the transfected cells to a growth medium (siRNA transfection protocol, Ambion, 2008). Bio-Rad, a maker of in vitro electroporation devices, has published recommended conditions between 200 and 300 volts as optimal for transfection followed by transferring to the cell growth medium (BioTechniques Protocol Guide 2009 (p. 19) doi 10.2144/000113012).

In-Vivo methods for electroporation of RNA to patients has also been described in the literature. In vivo two different electroporation procedures are being used in ongoing clinical trials. In the first procedure, DNA is injected (by needle and syringe) followed by insertion of a four-needle electrode array at the site of injection to deliver electrical pulses, and in the second procedure two standard syringes with injection needles are mounted on a movable sled. As the needles are advanced into the muscle tissue, DNA is injected at a predetermined rate. When DNA injection is completed, electrical pulses are delivered via the two injection needles now serving as electrodes. These clinical studies are sponsored separately by Southampton University Hospitals, and Merck.

Three electroporation devices are known to be approved for use in clinical trials; however, none of these devices are presently commercially available (S. Li (ed.), Electroporation Protocols: Preclinical and Clinical Gene Medicine. 497. From Methods in Molecular Biology, Vol. 423. Humana Press 2008). The first system, the Elgen system, consists of a square wave pulse generator, interfacing with a combined injection/electrode device, which injects the DNA during needle insertion and uses of-the-shelf syringes and needles. The output pulses used in human studies so far were set at a constant current of 250 mA, corresponding to about 60-70 V. The second system, the MedPulser DNA Delivery System (DDS) made by Inovio Biomedical Corporation consists of a pulse generator and a reusable applicator with a disposable tip containing a four-needle array electrode. The MedPulser DDS delivers two unipolar pulses of 60 ms at 106 V, with a frequency of 4 Hz. Typically, DNA vaccine is injected intramuscularly, followed by insertion of the electrode array encompassing the injection site and subsequent pulse delivery. The third system, also made by MedPulser, is the DNA Electroporation Therapy System, and also supplied by Inovio Biomedical Corporation, is similar to the MedPulser DDS. However, it uses a six-needle electrode array, with the needles either integrated into the applicator or contained in a disposable tip (needle length up to 3 cm; electrode distance, 8.6 mm). This system delivers six bipolar, rotating pulses of 100 µs each at 1,130 V, with a frequency of 4 Hz.

So far there does not appear to be any current human studies directed to delivery of RNA molecules subsequent to electroporation. Further the RNA protocol methods are directed to use of relative higher voltages to achieve transfection of these molecules. The present invention overcomes several limitations of the art by providing more efficient delivery of RNAs that does not require the high voltages presently used, which may require sedation during the electroporation process. Further, current electroporation procedures do not provide for chronic delivery of RNA agents. As discussed previously, current delivery protocols couple the nucleic acid delivery with providing the siRNA.

Other delivery methods also have their drawbacks. For example, viral delivery is unproven as an effective in vivo delivery mechanism in humans, and is not approved by the FDA. Lipofection entails administration of extraneous compounds to the patient in addition to the therapeutic agent itself. It is also not approved by the FDA.

Accordingly, new methods of efficient delivery of RNA to the patients are needed.

SUMMARY OF THE INVENTION

The instant invention addresses these and other needs of the prior art by providing, in one aspect, a method of delivering RNA to a cell of a patient, comprising electrically stimulating an area in a patient's body containing said cell, with a low-voltage electric stimulation followed by delivery of the RNA. Preferably, the cell is selected from cardiomyocytes, skeletal muscle cells, kidney cells, neurons, and glial cells.

In other words, an aspect of the invention is related to a use of RNA in the manufacture of a medicament for use in a method of delivering said RNA to a cell of a patient, wherein a plurality of pulses of an electric field is or is to be applied to the cell for a time period between about two and about 24 hours, said RNA is or is to be administered after the administration of the plurality of pulses, and wherein the electric field has strength of between about 0.5 V/cm and about 40 V/cm, calculated according to Formula I:

$$E=V/d$$

wherein in said formula E is the strength, V is Voltage and d is distance between electrodes. Preferably, the cell is selected from cardiomyocytes, skeletal muscle cells, kidney cells, neurons, and glial cells.

The parameters of the electric stimulation are tailored to each cell type as to ensure the maximal efficiency of the RNA delivery.

In different embodiments, the RNA comprises a siRNA, an shRNA, an aptamer, a spiegelmer, and antimir, a template for a protein or a protein fragment, or a combination thereof.

In another aspect, the invention also provides a device suitable for the methods of the instant invention, the device generally comprising a plurality of electrodes and a catheter for delivery of the RNA.

In one embodiment, the device comprises a plurality of electrodes, a catheter, the catheter comprising a wall and a cavity, wherein the members of said plurality of electrodes are disposed within or on the surface of said wall, a reservoir containing a composition comprising the nucleic acid sequence, said reservoir fluidly connected with said catheter, a pump or syringe operably connected to said reservoir, a processor operably connected to the members of said plurality of electrodes and adapted to receive electrical signals from said members and to deliver an electric field to said members.

Preferably, the device of the instant invention is treated to ensure the absence of RNAse to prolong the lifespan of the administered RNA.

In another aspect, the invention provides a kit comprising a plurality of electrodes, a composition comprising RNA, a processor adapted to actuate an electric stimulation by the members of said plurality of electrodes receive a signal from the members of said plurality of electrodes and, within a predetermined time period after receiving said signal from the members of said plurality of electrodes to actuate release of at least a portion of said composition comprising RNA.

DETAILED DESCRIPTION OF THE INVENTION

Figure 1:
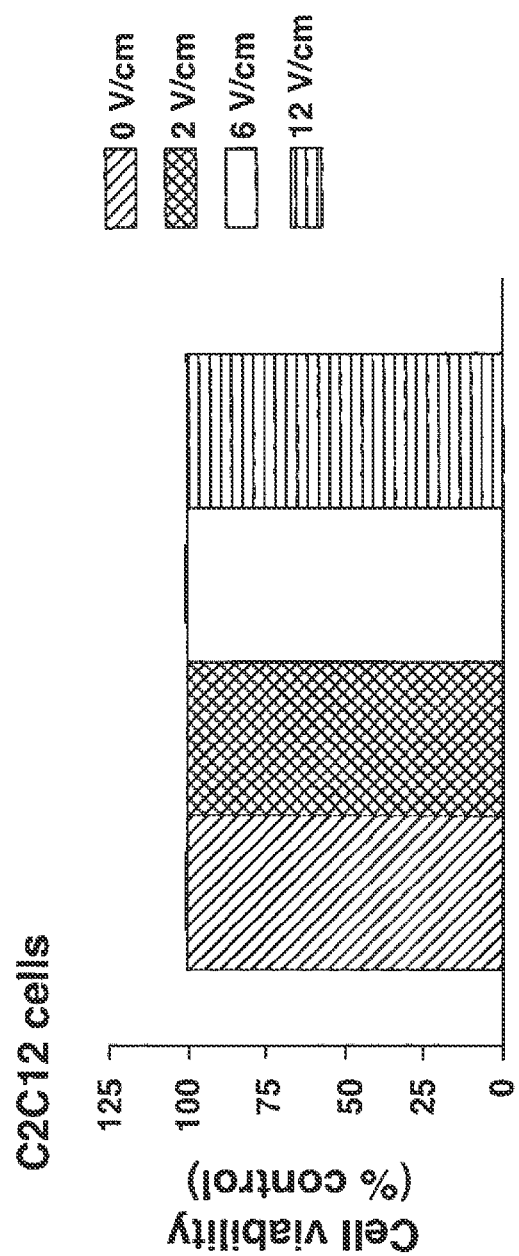
FIG. 1 demonstrates that the electric stimulation according to the instant invention does not affect cell viability.
Figure 2:
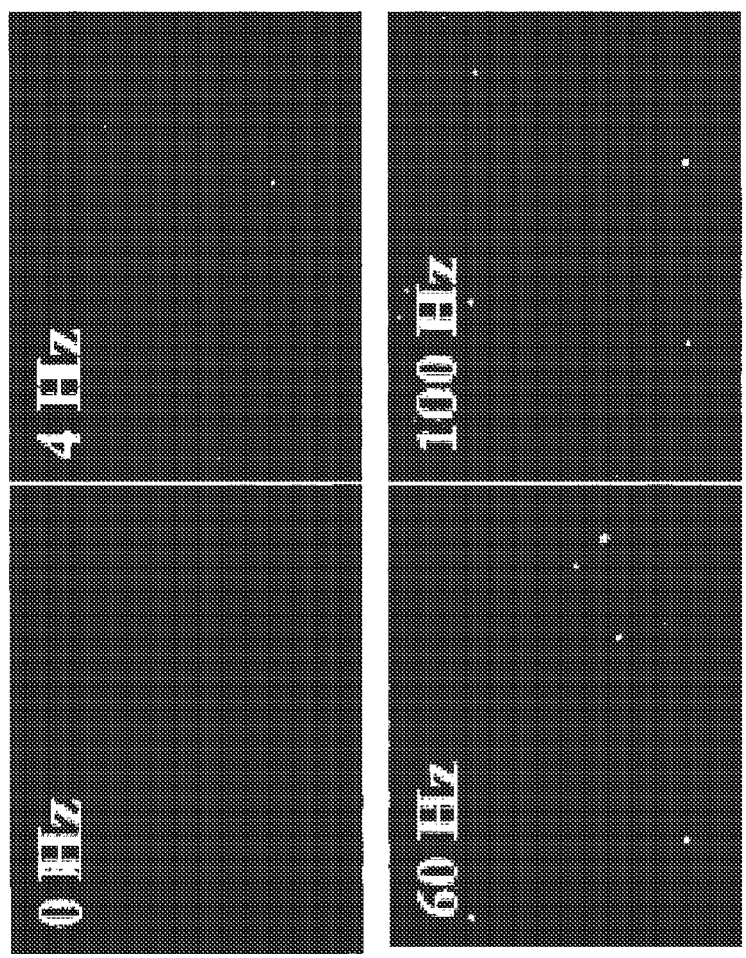
FIG. 2 demonstrates that stimulation-mediated uptake of siRNA is frequency-dependent.
Figure 3:
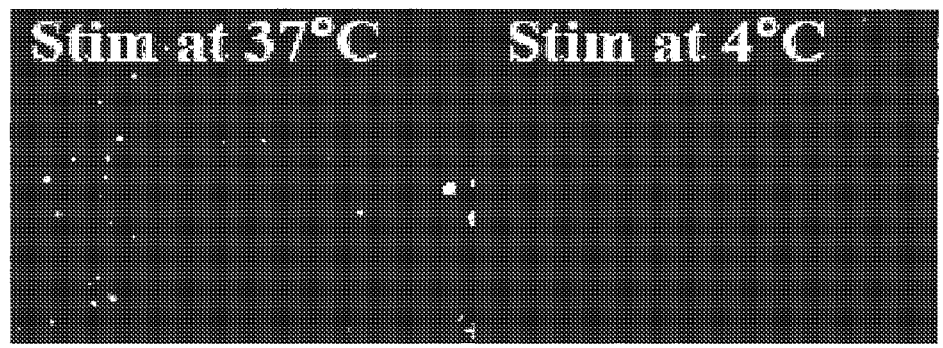
FIG. 3 demonstrates that the RNA uptake caused by electrical stimulation is due to a cell-based process.

For purposes of better understanding the instant disclosure, the following non-limiting definitions have been provided:

The term "chronically implanted" with respect to a device refers to a device that remains in the body of a patient, after being positioned in a bodily tissue of the patient by a practitioner, for any period of time after the patient encounter with the practitioner is completed and the patient has departed from the presence of the practitioner.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The term "patient" refers to a biological system to which a treatment can be administered. A biological system can include, for example, an individual cell, a set of cells (e.g., a cell culture), a pathogen, an organ, a tissue, or a multi-cellular organism. A "patient" can refer to a human patient or a non-human patient.

The term "practitioner" refers to a person who uses methods, kits and compositions of the current invention on the patient. The term includes, without limitations, doctors, nurses, scientists, and other medical or scientific personnel.

The terms "field strength" and "electric field strength" refer to a parameter equal to the ratio of voltage to distance between electrodes, i.e., $E=V/d$, wherein "E" is the field strength, "V" is the voltage and "d" is the distance between electrodes.

The term "uniform" as applied to a parameter of the electric field stimulation does not indicate absolute uniformity and may be 10% of the base parameter (e.g., field strength, duration, frequency, etc).

The term "about" will be understood by persons of ordinary skill in the art and will vary to some extent according to the context in which it is used. If there are uses of the term which are not clear to persons of ordinary skill in the art given the context in which it is used, "about" will mean up to plus or minus 10% of the particular term.

The terms "RNA" or "RNA agent" refer to nucleic acid molecules comprising a plurality of nucleotides. The majority of these nucleotides comprise ribose, rather than other sugars (e.g., deoxyribose). Thus, in one embodiment, the term RNA may refer to DNA-RNA hybrid, with a proviso that greater than 50% of the nucleotides comprise ribose. Preferably, such molecules comprises at least 55%, or at least 60%, or at least 65%, or at least 70%, or at least 75%, or at least 80%, or at least 85%, or at least 90%, or at least 95%, or at least 99% or 100% of nucleotides having ribose as a sugar.

The nucleotides may be modified in other ways, such as, for example, Such modifications include phosphorothioate linkages, fluorine-derivatized nucleotides (e.g., 2'-O-trifluoromethyl nucleotides2'-O-ethyl-trifluoromethoxy nucleotides, or 2'-O-difluoromethoxy-ethoxy nucleotides), deoxynucleotide overhangs, 2'-O-methylation, 2'-O-allylation, and locked nucleic acid (LNA) substitutions (Dorset and Tuschl, *Nat. Rev. Drug Discov.* 3:318 (2004); Gilmore et al., *J. Drug Targeting* 12:315 (2004)). Also see U.S. Patent Publication No. 20060270623 (McSwiggen).

In one embodiment, the 2'-deoxy-2'-fluoronucleotides are present at specifically selected locations in the RNAi agent that are sensitive to cleavage by ribonucleases, such as locations having pyrimidine nucleotides.

In a further set of embodiments, the RNAi agent may be chemically modified on a 3' end, a 5' end, or both the 3' end and the 5' end. These terminal modifications protect the nucleic acid molecule from exonuclease degradation and may help in delivery and/or localization within a cell. Examples of moieties suitable for the modification of the 5' end of the RNAi agent include, without limitations, glyceryl, inverted deoxy abasic residue (moiety); 4',5'-methylene nucleotide; 1-(beta-D-erythrofuranosyl)nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety;

3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the moieties suitable for modification of the 3'-end of the RNAi agent include glyceryl, inverted deoxy abasic residue (moiety), 4',5'-methylene nucleotide; 1-(beta-D-erythrofuranosyl)nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threopentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties. Yet additional suitable modifications of the RNAi agent are described in details in U.S. patent application Ser. No. 11/450,856, filed on Jun. 9, 2006 (McSwiggen), which is incorporated herein by reference to the extent it is not inconsistent with the instant disclosure.

The RNA of the instant invention may be in a single-stranded form (i.e., ssRNA) or a double-stranded form (i.e., dsRNA).

The methods of the present invention utilize routine techniques in the field of molecular biology. Basic texts disclosing general molecular biology methods include Sambrook et al., *Molecular Cloning, A Laboratory Manual* (3d ed. 2001) and Ausubel et al., *Current Protocols in Molecular Biology* (1994).

In a general aspect, the instant invention provides methods for improved efficiency of delivering ribonucleic acids to cells and devices suitable for implementation of these methods.

The methods generally comprise stimulation of cells. In one aspect, the method comprises electrically stimulating an area in a patient's body containing said cell, with a low-voltage electric stimulation followed by delivery of the RNA.

In other words, an aspect of the invention is related to a use of RNA in the manufacture of a medicament for use in a method of delivering said RNA to a cell of a patient, wherein, in said method, a low-voltage electric stimulation is or is to be applied to the cell and said RNA is or is to be administered after the application of the low-voltage stimulation.

In different embodiments, the cells are selected from Adipocytes, Alzheimer type II astrocytes, Ameloblasts, Astrocytes, B cells, Basophil activation cells, Basophil granulocytes, Boettcher cells, Cementoblasts, Chondrocytes, Chromaffin cells, Clara cells, Corticotropes, Cytotoxic T cells, Dendritic cells, Eosinophil granulocytes, Extraglomerular mesangial cells, Gastric chief cells, Goblet cells, Gonadotropes, Hepatocytes, Hypersegmented neutrophils, Intraglomerular mesangial cells, Juxtaglomerular cells, Keratinocytes, Kidney proximal tubule brush border cells, Kupffer cells, Lactotrophs, Leydig cells, Macrophages, Macula densa cells, Magnocellulars, neurosecretory cells, Mast cells, Megakaryocytes, Melanocytes, Microglia, Monocytes, Myocardiocytes, Myocytes, Naive B cells, Natural Killer T cells, Natural killer cells, Neutrophil granulocytes, Nuclear chain cells, Osteoblasts, Osteoclasts, Osteocytes, Ovums, Oxyphil cells (parathyroid), Paneth cells, Parafollicular cells, Parathyroid chief cells, Parietal cells, Pericytes, Perivitelline space cells, Platelets, Pneumocytes, Podocytes, Pre-B cells, Red blood cells, Regulatory T cells, Reticulocytes, S cells, Sertoli cells, Somatotropes, Spermatozoons, Stellate cells, T helper cells, Tendon cells, Thrombocytes, Thyroid epithelial cells, Thyrotropes, Trichocytes (human), Type pneumocytes, Type II pneumocytes, etc. Notably, the inventors were able to show unexpectedly advantageous results in neurons and muscle cells, which are known to be difficult to transfect. Thus, the other cell types disclosed above would also be susceptible to the methods described in the instant invention.

In other embodiments of invention, cells comprising pathogenic organisms (e.g., viruses) are treated.

In yet other embodiments, the treatment is directed against pathogenic organisms, including, without limitation, bacteria, fungi, protozoa, helmints, etc.

In certain embodiments, the cells are selected from the group consisting of brain cells (such as neurons and glial cells), cardiomyocytes, skeletal muscle cells, and kidney cells, with an electric field having specific parameters for a time period up to about 24 hours, prior to administering the RNA. Importantly, the parameters of the electric field strength are generally insufficient to perforate the membrane, and thus, the methods of the instant invention cannot be considered an "electroporation" in an art-accepted definition of that term (i.e., delivery of genetic material to cells via electrically caused perforations of respective cell membranes).

Generally, the electric stimulation of the instant invention comprises an electric field that has a strength of between about 0.5 V/cm and about 40 V/cm, calculated according to formula I:

$$E = V/d$$

wherein in said formula E is the strength, V is Voltage and d is distance between electrodes. The frequency of the stimulation is below about 400 Hz and the duration of each pulse is preferably between about 100 μs and about 500 μs.

In different embodiments, the strength of the electric field is between about 0.5 V/cm and about 2 V/cm, or between about 2 V/cm and about 6 V/cm, or between about V/cm and about 12 V/cm, or between about 12 V/cm and about 28 V/cm, or between about 28 V/cm and about 40 V/cm. Preferably, the strength of the electric field is below 20 V/cm.

The pulse duration is between about 100 μs and about 200 μs, or between about 200 μs and about 300 μs, or between about 300 μs and about 400 μs, or between about 400 μs and about 500 μs.

In different embodiments, the frequency is between about 4 Hz and about 100 Hz, or between about 100 Hz and about 200 Hz or between about 200 Hz and about 250 Hz or between about 250 Hz and about 300 Hz, or between about 300 Hz and about 350 Hz, or between about 350 Hz and about 400 Hz.

Thus, the instant invention discloses 120 different treatment combinations. Ninety six of these combinations are summarized in the following table.

TABLE 1

| No. | Voltage range (≈, V/cm) | Frequency range (≈, Hz) | Pulse duration (≈, ms) |
|---|---|---|---|
| 1 | 0.5-2 | 100-200 | 4-100 |
| 2 | 0.5-2 | 100-200 | 100-200 |
| 3 | 0.5-2 | 100-200 | 200-250 |

TABLE 1-continued

| No. | Voltage range (≈, V/cm) | Frequency range (≈, Hz) | Pulse duration (≈, ms) |
|---|---|---|---|
| 4 | 0.5-2 | 100-200 | 250-300 |
| 5 | 0.5-2 | 100-200 | 300-350 |
| 6 | 0.5-2 | 100-200 | 350-400 |
| 7 | 0.5-2 | 200-300 | 4-100 |
| 8 | 0.5-2 | 200-300 | 100-200 |
| 9 | 0.5-2 | 200-300 | 200-250 |
| 10 | 0.5-2 | 200-300 | 250-300 |
| 11 | 0.5-2 | 200-300 | 300-350 |
| 12 | 0.5-2 | 200-300 | 350-400 |
| 13 | 0.5-2 | 300-400 | 4-100 |
| 14 | 0.5-2 | 300-400 | 100-200 |
| 15 | 0.5-2 | 300-400 | 200-250 |
| 16 | 0.5-2 | 300-400 | 250-300 |
| 17 | 0.5-2 | 300-400 | 300-350 |
| 18 | 0.5-2 | 300-400 | 350-400 |
| 19 | 0.5-2 | 400-500 | 0.5-2 |
| 20 | 0.5-2 | 400-500 | 0.5-2 |
| 21 | 0.5-2 | 400-500 | 0.5-2 |
| 22 | 0.5-2 | 400-500 | 0.5-2 |
| 23 | 0.5-2 | 400-500 | 0.5-2 |
| 24 | 0.5-2 | 400-500 | 0.5-2 |
| 25 | 2-6 | 100-200 | 4-100 |
| 26 | 2-6 | 100-200 | 100-200 |
| 27 | 2-6 | 100-200 | 200-250 |
| 28 | 2-6 | 100-200 | 250-300 |
| 29 | 2-6 | 100-200 | 300-350 |
| 30 | 2-6 | 100-200 | 350-400 |
| 31 | 2-6 | 200-300 | 4-100 |
| 32 | 2-6 | 200-300 | 100-200 |
| 33 | 2-6 | 200-300 | 200-250 |
| 34 | 2-6 | 200-300 | 250-300 |
| 35 | 2-6 | 200-300 | 300-350 |
| 36 | 2-6 | 200-300 | 350-400 |
| 37 | 2-6 | 300-400 | 4-100 |
| 38 | 2-6 | 300-400 | 100-200 |
| 39 | 2-6 | 300-400 | 200-250 |
| 40 | 2-6 | 300-400 | 250-300 |
| 41 | 2-6 | 300-400 | 300-350 |
| 42 | 2-6 | 300-400 | 350-400 |
| 43 | 2-6 | 400-500 | 4-100 |
| 44 | 2-6 | 400-500 | 100-200 |
| 45 | 2-6 | 400-500 | 200-250 |
| 46 | 2-6 | 400-500 | 250-300 |
| 47 | 2-6 | 400-500 | 300-350 |
| 48 | 2-6 | 400-500 | 350-400 |
| 49 | 6-12 | 100-200 | 4-100 |
| 50 | 6-12 | 100-200 | 100-200 |
| 51 | 6-12 | 100-200 | 200-250 |
| 52 | 6-12 | 100-200 | 250-300 |
| 53 | 6-12 | 100-200 | 300-350 |
| 54 | 6-12 | 100-200 | 350-400 |
| 55 | 6-12 | 200-300 | 4-100 |
| 56 | 6-12 | 200-300 | 100-200 |
| 57 | 6-12 | 200-300 | 200-250 |
| 58 | 6-12 | 200-300 | 250-300 |
| 59 | 6-12 | 200-300 | 300-350 |
| 60 | 6-12 | 200-300 | 350-400 |
| 61 | 6-12 | 300-400 | 4-100 |
| 62 | 6-12 | 300-400 | 100-200 |
| 63 | 6-12 | 300-400 | 200-250 |
| 64 | 6-12 | 300-400 | 250-300 |
| 65 | 6-12 | 300-400 | 300-350 |
| 66 | 6-12 | 300-400 | 350-400 |
| 67 | 6-12 | 400-500 | 4-100 |
| 68 | 6-12 | 400-500 | 100-200 |
| 69 | 6-12 | 400-500 | 200-250 |
| 70 | 6-12 | 400-500 | 250-300 |
| 71 | 6-12 | 400-500 | 300-350 |
| 72 | 6-12 | 400-500 | 350-400 |
| 73 | 12-20 | 100-200 | 4-100 |
| 74 | 12-20 | 100-200 | 100-200 |
| 75 | 12-20 | 100-200 | 200-250 |
| 76 | 12-20 | 100-200 | 250-300 |
| 77 | 12-20 | 100-200 | 300-350 |
| 78 | 12-20 | 100-200 | 350-400 |
| 79 | 12-20 | 200-300 | 4-100 |
| 80 | 12-20 | 200-300 | 100-200 |
| 81 | 12-20 | 200-300 | 200-250 |
| 82 | 12-20 | 200-300 | 250-300 |
| 83 | 12-20 | 200-300 | 300-350 |
| 84 | 12-20 | 200-300 | 350-400 |
| 85 | 12-20 | 300-400 | 4-100 |
| 86 | 12-20 | 300-400 | 100-200 |
| 87 | 12-20 | 300-400 | 200-250 |
| 88 | 12-20 | 300-400 | 250-300 |
| 89 | 12-20 | 300-400 | 300-350 |
| 90 | 12-20 | 300-400 | 350-400 |
| 91 | 12-20 | 400-500 | 4-100 |
| 92 | 12-20 | 400-500 | 100-200 |
| 93 | 12-20 | 400-500 | 200-250 |
| 94 | 12-20 | 400-500 | 250-300 |
| 95 | 12-20 | 400-500 | 300-350 |
| 96 | 12-20 | 400-500 | 350-400 |

It should be further understood that the methods and/or uses of the instant invention are sufficiently flexible as to allow embodiments where the parameters of the pulses are not uniform. Thus, for example, the pulses may vary in duration or amplitude, the bursts of pulses may vary in the interburst and intraburst characteristics. Such non-uniform electrical stimulation may be potentially advantageous for the embodiments wherein the electrical stimulation is administered to an organ with natural rhythmic electrical activity, such as, for example, heart.

Optionally, the RNA of the instant invention may be administered to the cells within a composition comprising an imaging agent. This embodiment will allow verification of distribution of the composition comprising the RNA, thus optimizing the targeting of the desired cells within the patient's body.

Using the methods of the instant invention, including, without limitation, the combinations selected from those disclosed in Table 1, it is possible to increase the uptake of the RNA by up to at least about 1000% (e.g., at least by about 25%, about 50%, about 75%, about 100%, about 125%, about 150%, about 175%, about 200%, about 250%, about 300%, about 350%, about 400%, about 450%, about 500%, about 550%, about 600%, about 650%, about 700%, about 750%, about 800%, about 850%, about 900%, about 950%).

Stimulation of Brain Cells

The parameters of the stimulation with the electric field are specifically tailored to the targeted cell types. If the selected cells are brain cells, e.g., neurons, advantageously, the parameters for the electric stimulation may be those used for DBS, or deep brain stimulation. For example, the inventors have surprisingly discovered that the field strength of about 28 V/cm administered for about 2 hours results in increased uptake of the RNA by Neuro2a cells.

Thus, in different embodiments of the method of administration of RNA to neuronal cells, the following parameters may be used:

a) field strength of greater than about 0.5, 1, 2, 3, 4, 5, 6, 7, 8, 9, 10, 11, 12, 13, 14, 15, 16, 17, 18, 19, 20, 21, 22, 23, 24, 25, 26, or 27 and up to about 28 V/cm;

b) duration of treatment of at least about 2, 4, 6, 8, 10, 12, 14, 16, 18, 20, 22 and up to about 24 hours;

c) frequency of greater than about 20 Hz, 40 Hz, 60 Hz, 80 Hz, 100 Hz, 120 Hz, 140 Hz, 160 Hz, 180 Hz, or 200 Hz;

d) pulse width of at least about 0.1 msec, 0.2 msec, 0.3 msec, 0.4 msec, 0.5 msec, 0.6 msec, 0.7 msec, 0.8 msec, 0.9 msec, or 1 msec. In some embodiments, the pulses of the electric stimulation may be administered in bursts, such as, for example bursts of several pulses separated by a time interval. The time interval may be greater than about 100 msec, 200 msec, 300 msec, 400 msec, 500 msec, 600 msec, 700 msec, 800 msec, 900 msec, and 1 sec.

In one selected embodiment, the electric field strength is between about 2 and about 12 V/cm, the duration of electric stimulation is greater than about 1 and less than 24 hours (e.g., about 2, 3, 4, 5, 6, 7, 8, 9, 10, 11, 12, 13, 14, 15, 16, 17, 18, 19, 20, 21, 22, 23 hrs), pulse duration is between about 0.1 msec and about 0.5 msec (e.g., about 0.3 msec), and the frequency of the pulses is between about 50 Hz and about 150 Hz (e.g., about 100 Hz).

In another embodiment, the electric field strength is greater than 24 and less than 40 V/cm (e.g., between 26 and 30 V/cm, preferably, about 28 V/cm), with the duration of the stimulation of less than six hours (e.g., about 5, or about 4, or about 3, or about 2, or about 1, or about 0.5 hr), pulse frequency of between about Hz and about 150 Hz (e.g., about 100 Hz) and pulse duration between about 0.1 msec and about 0.5 msec (e.g., about 0.3 msec).

The inventors have also discovered that even though high field strength (e.g., about 28 V/cm) successfully improves uptake of RNA into neuronal cells, some cytotoxicity may be seen in vitro and in vivo. Accordingly, in yet another embodiment, low field strength (below 20 V/cm, such as, for example 10, 6, or 2 V/cm) may be used, for as little as two hours (but, of course, the duration may be greater than two hours), with pulse frequency of between about 50 Hz and about 150 Hz (e.g., about 100 Hz) and pulse duration between about 0.1 msec and about 0.5 msec (e.g., about 0.3 msec).

Notably, Deep Brain Stimulation (DBS) for patients with certain diseases (e.g., Parkinson's disease or Essential tremor) fall within these ranges. For example, typical stimulus parameters employed for DBS for movement disorders are in the range of 2-4 V (or 2-4 mA for a typical DBS electrode impedance of 1,000), 90-180 μs pulse width, and 100-185 Hz. Testerman R L et al., IEEE Eng Med Biol Mag. 2006 September-October; 25(5):74-8. Review. Thus, in selected embodiments, the methods of the instant invention may be administered in conjunction with the DES to a patient in need thereof, wherein the DBS provides the electrical stimulation according to the instant invention.

Using the parameters outlined in this section, one may improve the uptake of RNA by up to at least about 1000% (e.g., at least by about 25%, about 50%, about 75%, about 100%, about 125%, about 150%, about 175%, about 200%, about 250%, about 300%, about 350%, about 400%, about 450%, about 500%, about 550%, about 600%, about 650%, about 700%, about 750%, about 800%, about 850%, about 900%, about 950%).

Inventors have also discovered that out of the multiple cell types present in the brain, neurons are among the cell types most susceptible to the electric field stimulation. Thus, in another embodiment of the invention, the electric stimulation (and the RNA therapy) may also be used for treatment of any part of the patient's body where neuronal bodies are present and where uptake of dsRNA into neurons is desired. For example, such body parts may include spinal cord, dorsal root ganglia, brain and neurons comprising the peripheral nervous system, and enteric nervous system.

Stimulation of cardiac and skeletal muscle cells.

In this set of embodiments of the instant invention, the electric field is preferably less than 28 V/cm, preferably less than 20 V/cm, more preferably, between about 0.5 V/cm and about 12 V/cm, even more preferably, between about 2 V/cm and about 12 V/cm, e.g., 3, 4, 5, 6, 7, 8, 9, 10, or 11 V/cm.

Due to natural electric activity of the heart muscle, it may be advantageous to tailor the electric stimulation parameters to the natural rhythms of the heart. Thus, especially advantageous embodiments are those where the pulses are administered in bursts. It is necessary to note, nevertheless, that the stimulation in burst is not absolutely necessary to successfully improve RNA uptake by the targeted cells. Thus, in different embodiments, the frequency of stimulation is between about 10 Hz and about 150 Hz. In selected embodiments, the frequency may be between about 80 Hz and about 120 Hz, e.g., about 90 Hz, about 100 Hz, or about 110 Hz. In other embodiments, the stimulation is delivered in bursts, as discussed above. For example, the frequency may be between about 10 Hz and about 50 Hz, e.g., about 15 Hz, about 20 Hz, about 25 Hz, about 30 Hz, about 35 Hz, about 40 Hz, about 45 Hz). In an exemplary embodiment, the frequency is about 20 Hz, and the stimulation comprises bursts of 10 pulses, separated by 500 msec, with the duration of each pulse of about 0.3 msec. However, these numbers (i.e., duration of each pulse, number of bursts, number of pulses in each burst, and interburst interval) may be varied (e.g., the duration of each pulse of about 0.5 msec and correspondingly decreased interburst interval).

The duration of the electric field treatment may be varied between about two and about 24 hours, e.g., 4 hrs, 6, hrs, 8 hrs, 10 hrs, 12 hrs, 14 hrs, 16 hrs, 18 hrs, 20 hrs, 22 hrs.

In selected embodiments, the method comprises determining the heart rate of a patient, and then administering the electrical stimulation according to that heart rate. Further, the bursts of the heart activity may be sensed, and the occurrence of these bursts would provide a signal for administering the respective bursts of the electrical stimulation.

Using these parameters, one can improve RNA intake by up to at least about 1000% (e.g., at least by about 25%, about 50%, about 75%, about 100%, about 125%, about 150%, about 175%, about 200%, about 250%, about 300%, about 350%, about 400%, about 450%, about 500%, about 550%, about 600%, about 650%, about 700%, about 750%, about 800%, about 850%, about 900%, about 950%).

Stimulation of Kidney Cells

In another embodiment of the invention, kidney cells are treated with the combination of electric field stimulation and RNA. The inventors have surprisingly discovered that kidney cells are susceptible to the wide varieties of the electric field stimulation. Thus, if the kidney cells are to be treated according to the methods of the instant invention, the strength of the electric field may be in a range of between about 0.5 V/cm and about 60 v/cm, such as for example, 0.8 V/cm, 1 V/cm, 2 V/cm, 5 V/cm, 10 V/cm, 12 V/cm, 15 V/cm, 20 V/cm, 25 V/cm, 20 V/cm, 25 V/cm, 30 V/cm, and 35 V/cm. The frequency of the stimulation may be as low as e.g., about 4 Hz and as high as at least 100 Hz. The duration of the stimulus may be in the range between about 0.1 msec and about 1 msec, e.g., 0.2 msec, 0.3 msec, 0.4 msec, 0.5 msec, 0.6 msec, 0.7 msec, 0.8 msec, or 0.9 msec. The precise duration of the electric stimulation is also not crucial and may be from about 1 hr to about 24 hours, e.g., 2, 3, 4, 5, 6, 7, 8, 9, 10, 11, 12, 13, 14, 15, 16, 17, 18, 19, 20, 21, 22 or 23 hours.

Using these parameters, one can improve RNA intake by up to at least about 1000% (e.g., at least by about 25%, about 50%, about 75%, about 100%, about 125%, about 150%, about 175%, about 200%, about 250%, about 300%, about 350%, about 400%, about 450%, about 500%, about 550%, about 600%, about 650%, about 700%, about 750%, about 800%, about 850%, about 900%, about 950%).

RNA

It is important to note that for all embodiments, the RNA may, but does not need to, be administered immediately after the electric field stimulation. In various embodiments, the RNA is administered up to about 24 hours after the disclosed cells have been stimulated for the predetermined amount of time, as described above (e.g., 0.5, 1, 2, 3, 4, 5, 5, 6, 7, 8, 9, 10, 11, 12, 13, 14, 15, 16, 17, 18, 19, 20, 21, 22, 23 hours). It is also important to know that the electric field stimulation does not need to stop when RNA is administered. Thus, in some embodiments, the cells may be pre-treated with electric stimulation for the desired amount of time, and then essentially co-treated with the electric stimulation and the RNA. However, as demonstrated in the examples, it is important not to withdraw the RNA treatment within a short time after the electrical stimulation.

Thus, generally, the practitioner of the described method may stimulate the disclosed cells according to the suitable parameters as recited above, then optionally wait for a desired amount of time (up to about hours, as noted in the previous paragraph), and then administer the RNA according to this invention. During the optional waiting time (or any part thereof) or during the RNA delivery, the electric field stimulation may be on or off.

The RNA agents of the instant invention may be used for multiple purposes, such as, for example, as RNA interference agents or to supplement expression of a desired gene. Most generally, the RNA agents may be used either to suppress expression of an undesirable gene (e.g., huntingtin, SCA-1, etc) or to suppress gene expression and/or function implicated in the pathogenesis of a disorder (BACE-1, alpha synuclein, ect). Table 2 describes in part examples of triplet repeat expansion diseases and the mutant gene associated with each disease.

TABLE 2

Triplet Repeat Expansion Disorders

| Disease | Symptoms | Gene | Locus | Protein |
|---|---|---|---|---|
| Non-coding repeats | | | | |
| Dystrophia myotonica 1 | Weakness, Myotonia | DMPK | 19q13 | Dystrophia myotonica Protein kinase |
| Spinocerebellar ataxia 8 | Ataxia | Antisense to KLHL1 | 13q21 | Undetermined |
| Huntington disease-like2 | Chorea, dementia | JPH3 | 16q24.3 | Junctophilin 3 |
| Polyglutamine disorders | | | | |
| Spinal and bulbar muscular atrophy | Weakness | AR | Xq13-q21 | Androgen receptor |
| Huntington disease | Chorea, dementia | IT15 | 4P16.3 | Huntingtin |
| Dentatorubral-pallidoluysian atrophy | Ataxia, myoclonic epilepsy, dementia | DRPLA | 12p13.31 | Atrophin 1 |
| Spinocerebellar ataxia 1 | Ataxia | SCA1 | 6p23 | Ataxin 1 |
| Spinocerebellar ataxia 2 | Ataxia | SCA2 | 12q24.1 | Ataxin 2 |
| Spinocerebellar ataxia 3 (Machado-Joseph disease) | Ataxia | SCA3/MJD | 14q32.1 | Ataxin 3 |
| Spinocerebellar ataxia 6 | Ataxia | CACNA1A | 19p13 | $\alpha_{1A}$-voltage-dependent calcium channel subunit |
| Spinocerebellar ataxia 7 | Ataxia | SCA7 | 3p12-p13 | Ataxin 7 |
| Spinocerebellar ataxia 17 | Ataxia | TBP | 6q27 | TATA box binding protein |
| Polyalanine disorders* | | | | |
| Oculopharyngeal dystrophy | Weakenss | PABPN1 | 14q11.2-q13 | Poly(A)-binding protein 2 |
| Congential central hypoventilation syndrome | Respiratory difficulties | PHOX2B | 4p12 | Paired-like homeobox 2B |
| Infantile spasms | Mental retardation, epilepsy | ARX | Xp22.13 | Aristaless-related homeobox, X-linked |
| Synpolydactyly | Limb malformation | HOXD13 | 2q31-q32 | Homeobox D13 |

*Polyalanine expansions have also been reported among mutations in other genes, including RUNX2 (runt-related transcription factor2) in cleidocranial dysplasia, ZIC2 (Zic family member 2) in holoprosencephaly HOXA13 (homeobox A13) in hand-foot-genital syndrome, and FOXL2 (forkhead box L2) in type II blepharophimosis, ptosis, and epicanthus inversus syndrome. Small aspartic acid repeat expansions have been reported among other mutations in the COMP (cartilage oligomeric matrix protein) gene in patients with multiple epiphyseal dysplasia.

Suitable classes of RNA agents for RNA interference include, without limitations, siRNA, shRNA and miRNA. These agents may target selected regions within their respective target mRNAs, including, without limitations, sequences recited in the following Table 3.

TABLE 3

| SEQ ID NO: | Target Gene | Nucleotide Base Sequence | Target Gene Accession # |
|---|---|---|---|
| 1 | SCA1 | AACCAAGAGCGGAGCAACGAA | NM_000332.3 |
| 2 | IT15 (Htt) | TGACAGCAGTGTTGATAAA | NM_002111.6 |
| 3 | IT15 (Htt) | AAGAACGAGTGCTCAATAA | NM_002111.6 |
| 4 | IT15 (Htt) | TTTATGAACTGACGTTACA | NM_002111.6 |
| 5 | IT15 (Htt) | GGAGTATTGTGGAACTTAT | NM_002111.6 |
| 6 | IT15 (Htt) | GAGTATTGTGGAACTTATA | NM_002111.6 |
| 7 | IT15 (Htt) | AGACCGTGTGAATCATTGT | NM_002111.6 |
| 8 | IT15 (Htt) | GGTTACAGCTCGAGCTCTA | NM_002111.6 |
| 9 | IT15 (Htt) | GGTTTTGTTAAAGGCCTTC | NM_002111.6 |
| 10 | IT15 (Htt) | TGACAGCAGTGTTGATAAATTTGTGTT | NM_002111.6 |
| 11 | IT15 (Htt) | AAGAACGAGTGCTCAATAATGTTGTCA | NM_002111.6 |
| 12 | IT15 (Htt) | TTTATGAACTGACGTTACATCATACAC | NM_002111.6 |
| 13 | IT15 (Htt) | GGAGTATTGTGGAACTTATAGCTGGAG | NM_002111.6 |
| 14 | IT15 (Htt) | GAGTATTGTGGAACTTATAGCTGGAGG | NM_002111.6 |
| 15 | IT15 (Htt) | AGACCGTGTGAATCATTGTCTGACAAT | NM_002111.6 |
| 16 | IT15 (Htt) | GGTTTTGTTAAAGGCCTTCATAGCGAA | NM_002111.6 |
| 17 | BACE1 | AAGGGTGTGTATGTGCCCTAC | NM_012104.3 |
| 18 | BACE1 | AATTGGCTTTGCTGTCAGCGC | NM_012104.3 |
| 19 | BACE1 | AAGACTGTGGCTACAACATTC | NM_012104.3 |
| 20 | BACE1 | AAGGCTGCCTGGAGAAAGGAT | NM_012104.3 |
| 21 | BACE1 | CACTGAATCGGACAAGTTCTT | NM_012104.3 |
| 22 | BACE1 | CATGATCATTGGTGGTATCGA | NM_012104.3 |
| 23 | BACE1 | CATCCTTCCTCAGCAATACCT | NM_012104.3 |
| 24 | BACE1 | CAGACGCTCAACATCCTGGTG | NM_012104.3 |
| 25 | α-synuclein | CTACGAACCTGAAGCCTAA | NM_000345.3 |
| 26 | α-synuclein | TCAAGACTACGAACCTGAA | NM_000345.3 |
| 27 | α-synuclein | CATTAGCCATGGATGTATT | NM_000345.3 |
| 28 | α-synuclein | ACGAACCTGAAGCCTAAGA | NM_000345.3 |
| 29 | α-synuclein | GTACAAGTGCTCAGTTCCA | NM_000345.3 |
| 30 | α-synuclein | GCTTCAATCTACGATGTTA | NM_000345.3 |
| 31 | α-synuclein | CTAAGTGACTACCACTTAT | NM_000345.3 |
| 32 | α-synuclein | GTTCAGAAGTTGTTAGTGA | NM_000345.3 |
| 33 | α-synuclein | AGTTGTTAGTGATTTGCTA | NM_000345.3 |
| 34 | α-synuclein | GACGTATTGTGAAATTTGT | NM_000345.3 |
| 35 | SOD1 | TCATCAATTTCGAGCAGAA | NM_000454.4 |

TABLE 3-continued

| SEQ ID NO: | Target Gene | Nucleotide Base Sequence | Target Gene Accession # |
|---|---|---|---|
| 36 | SOD1 | TGAGTTTGGAGATAATACA | NM_000454.4 |
| 37 | SOD1 | TGGCCGATGTGTCTATTGA | NM_000454.4 |
| 38 | SOD1 | CGATGTGTCTATTGAAGAT | NM_000454.4 |
| 39 | SOD1 | GCATTAAAGGACTGACTGA | NM_000454.4 |
| 40 | SOD1 | TCGTTTGGCTTGTGGTGTA | NM_000454.4 |
| 41 | SOD1 | AATTTCGAGCAGAAGGAAAGT | NM_000454.4 |
| 42 | SOD1 | AAGCATTAAAGGACTGACTGA | NM_000454.4 |
| 43 | SOD1 | AATGTGACTGCTGACAAAGAT | NM_000454.4 |
| 44 | SOD1 | AAGATTCTGTGATCTCACTCT | NM_000454.4 |
| 45 | TNF-a | CCAGGGACCTCTCTCTAAT | NM_000594.2 |
| 46 | TNF-a | AGGGACCTCTCTCTAATCA | NM_000594.2 |
| 47 | TNF-a | GCCTGTAGCCCATGTTGTA | NM_000594.2 |
| 48 | TNF-a | TGTAGCCCATGTTGTAGCA | NM_000594.2 |
| 49 | IL-1b | GTGAAATGATGGCTTATTA | NM_000576.2 |
| 50 | IL-1b | CGATGCACCTGTACGATCA | NM_000576.2 |
| 51 | IL-1b | TAACTGACTTCACCATGCA | NM_000576.2 |
| 52 | IL-1b | GAACCTATCTTCTTCGACA | NM_000576.2 |
| 53 | SCN9A | CAGAAGAACAGAAGAAATA | NM_002977.2 |
| 54 | SCN9A | TGAAGAAGCTAAACAGAAA | NM_002977.2 |
| 55 | SCN9A | GGTAAGAGCTACAAAGAAT | NM_002977.2 |
| 56 | SCN9A | AGGCAGAGGAAGAGATATA | NM_002977.2 |
| 57 | SCN9A | AGACAGAGATGATGATTTA | NM_002977.2 |
| 58 | SCN9A | GGGAAAGACAGCAAGGAAA | NM_002977.2 |
| 59 | SCN9A | GAACAAGACAGAACAGAAA | NM_002977.2 |
| 60 | SCN9A | GTGAAGAAGACTTTAGAAA | NM_002977.2 |
| 61 | SCN9A | CCAAAGATTTCCAGGGAGA | NM_002977.2 |
| 62 | SCN9A | TAACATAGAGTCAGGGAAA | NM_002977.2 |
| 63 | SCN9A | GAAAGAAGAAACAGAAGAA | NM_002977.2 |
| 64 | SCN9A | GGAGATAAGACAAGCAGAA | NM_002977.2 |
| 65 | SCN9A | CTGAATACTAAGAAGGAAA | NM_002977.2 |
| 66 | SCN9A | GAGAAGAAGCAGAGGCTGA | NM_002977.2 |
| 67 | SCN9A | GAAAGATGATGATGAAGAA | NM_002977.2 |
| 68 | SCN9A | TGGGAAACCTGAAGCATAA | NM_002977.2 |
| 69 | SCN9A | GAACACAGTTGGTTTGAAA | NM_002977.2 |
| 70 | SCN9A | TGACAGAAGAACAGAAGAA | NM_002977.2 |
| 71 | SCN9A | AAGAAGAAGCTGAGGCAAT | NM_002977.2 |
| 72 | SCN9A | TTTCAAAGGCAGAGGAAGA | NM_002977.2 |
| 73 | SCN9A | CTTGAAGAGTCCAGACAAA | NM_002977.2 |
| 74 | SCN9A | GCTAAAGAAAGAAGAAACA | NM_002977.2 |

TABLE 3-continued

| SEQ ID NO: | Target Gene | Nucleotide Base Sequence | Target Gene Accession # |
|---|---|---|---|
| 75 | SCN9A | AGAAGAAACAGAAGAAAGA | NM_002977.2 |
| 76 | SCN9A | GCTGAGAAATTGTCGAAAT | NM_002977.2 |
| 77 | SCN9A | GAGCAAGCATATTAACAAA | NM_002977.2 |
| 78 | SCN9A | CATAAAAGATGGAGACAGA | NM_002977.2 |
| 79 | SCN9A | TAACAAAGCCAGACAAAGA | NM_002977.2 |
| 80 | SCN9A | AAAGGAAGACAAAGGGAAA | NM_002977.2 |
| 81 | SCN9A | AAAGGGAGATGCTGAGAAA | NM_002977.2 |
| 82 | SCN9A | TAACAAACACTGTGGAAGA | NM_002977.2 |
| 83 | SCN9A | AGTATTGAACAAAGGGAAA | NM_002977.2 |
| 84 | SCN9A | AGGCGAAGCAGCAGAACAA | NM_002977.2 |
| 85 | SCN9A | TAGCAGATGTGGAAGGATT | NM_002977.2 |
| 86 | SCN9A | AAACAAACCTTACGTGAAT | NM_002977.2 |
| 87 | SCN9A | AAATATGAATGCTGAGGAA | NM_002977.2 |
| 88 | SCN9A | CCAAAGAAGAAAAGAAAGA | NM_002977.2 |
| 89 | SCN9A | CTGACAAACTGCATATTTA | NM_002977.2 |
| 90 | SCN9A | AGGGAGATGCTGAGAAATT | NM_002977.2 |
| 91 | SCN9A | CATTGAACATGCTGATTAA | NM_002977.2 |
| 92 | SCN9A | GCATGCAGCTCTTTGGTAA | NM_002977.2 |
| 93 | SCN9A | AGACAATCTTACAGCAATT | NM_002977.2 |
| 94 | SCN9A | AAGAAGACCCTGATGCAAA | NM_002977.2 |
| 95 | SCN9A | GGAAGACAGTGATGGTCAA | NM_002977.2 |
| 96 | SCN9A | CAGACAAGATCTTCACTTA | NM_002977.2 |
| 97 | SCN9A | AGCCAGACAAAGAGAAATA | NM_002977.2 |
| 98 | SCN9A | CTTCGAACTTTCAGAGTAT | NM_002977.2 |
| 99 | SCN9A | GAGTAGAGCAAGCATATTA | NM_002977.2 |
| 100 | SCN9A | TGTACTTGCTATAGGAAAT | NM_002977.2 |
| 101 | SCN9A | GGTCAAGCTATGTGCCTTA | NM_002977.2 |
| 102 | SCN9A | GAAACAAACCTTACGTGAA | NM_002977.2 |
| 103 | SCN9A | GATTATGGCTACACGAGCT | NM_002977.2 |
| 104 | SCN9A | GATGGATTCTCTTCGTTCA | NM_002977.2 |
| 105 | SCN9A | TGTTTCAGCTCTTCGAACT | NM_002977.2 |
| 106 | IKBKB | CCGACATTGTGGACTTACA | NM_001556.1 |
| 107 | IKBKB | GCTTAGATACCTTCATGAA | NM_001556.1 |
| 108 | IKBKB | GGGAACAAGACCAGAGTTT | NM_001556.1 |
| 109 | IKBKB | AGATTGACCTGGAGAAGTA | NM_001556.1 |
| 110 | IKBKB | CTGCTGGCCTGGAGGGAAA | NM_001556.1 |
| 111 | IKBKB | GCTTAATGAATGAGGATGA | NM_001556.1 |
| 112 | IKBKB | CAGCAGAAGTACACAGTGA | NM_001556.1 |
| 113 | IKBKB | GGACATTGTTGTTAGCGAA | NM_001556.1 |

TABLE 3-continued

| SEQ ID NO: | Target Gene | Nucleotide Base Sequence | Target Gene Accession # |
|---|---|---|---|
| 114 | IKBKB | ACTTAAAGCTGGTTCATAT | NM_001556.1 |
| 115 | IKBKB | TGACAGAGGATGAGAGTCT | NM_001556.1 |
| 116 | IKBKB | CTGCAGAGCTTGAAGGCCA | NM_001556.1 |
| 117 | IKBKB | GAGCTGTACAGGAGACTAA | NM_001556.1 |
| 118 | IKBKB | GAGAAGAAAGTGCGAGTGA | NM_001556.1 |
| 119 | IKBKB | GGAGAAGTACAGCGAGCAA | NM_001556.1 |
| 120 | IKBKB | AGAAAGTGCGAGTGATCTA | NM_001556.1 |
| 121 | IKBKB | GAAAGAGCGCCTTGGGACA | NM_001556.1 |
| 122 | IKBKB | GCTTCAAGGCCCTGGATGA | NM_001556.1 |
| 123 | IKBKB | GGTTACAGACGGAAGAAGA | NM_001556.1 |
| 124 | IKBKB | TGATGAATCTCCTCCGAAA | NM_001556.1 |
| 125 | IKBKB | AAGTGAAACTCCTGGTAGA | NM_001556.1 |
| 126 | IKBKB | GGAAACAGGTGAGCAGATT | NM_001556.1 |
| 127 | IKBKB | GCAAGTTAAATGAGGGCCA | NM_001556.1 |
| 128 | IKBKB | GAAGAAAGTGCGAGTGATC | NM_001556.1 |
| 129 | IKBKB | ATGAATGCCTCTCGACTTA | NM_001556.1 |
| 130 | IKBKB | GGGCCTGGGAAATGAAAGA | NM_001556.1 |
| 131 | IKBKB | GCGAAGACTTGAATGGAAC | NM_001556.1 |
| 132 | IKBKB | CCAATAATCTTAACAGTGT | NM_001556.1 |
| 133 | IKBKB | TTCAAGAGCCCAAGAGGAA | NM_001556.1 |
| 134 | IKBKB | GGGAAATGGAGCAGGCTGT | NM_001556.1 |
| 135 | IKBKB | AGACCGACATTGTGGACTT | NM_001556.1 |
| 136 | IKBKB | TACAGGAGACTAAGGGAAA | NM_001556.1 |
| 137 | IKBKB | GAAGAGGTGGTGAGCTTAA | NM_001556.1 |
| 138 | IKBKB | GGGAAATGAAAGAGCGCCT | NM_001556.1 |
| 139 | IKBKB | ACACAGTGACCGTCGACTA | NM_001556.1 |
| 140 | IKBKB | ATGAAGAATTCCATGGCTT | NM_001556.1 |
| 141 | IKBKB | GTTACAGACGGAAGAAGAA | NM_001556.1 |
| 142 | IKBKB | GGAAGTACCTGAACCAGTT | NM_001556.1 |
| 143 | IKBKB | TGGGATCACATCAGATAAA | NM_001556.1 |
| 144 | IKBKB | GAGCTTAATGAATGAGGAT | NM_001556.1 |
| 145 | IKBKB | CCAAGAAGAGTGAAGAACT | NM_001556.1 |
| 146 | IKBKB | TGACATTGCCTCTGCGCTT | NM_001556.1 |
| 147 | IKBKB | TGGCTGAGCGACTGGAGAA | NM_001556.1 |
| 148 | IKBKB | TTTCAGACGGCAAGTTAAA | NM_001556.1 |
| 149 | IKBKB | TGGACGACCTAGAGGAGCA | NM_001556.1 |
| 150 | IKBKB | TAATGAATGAGGATGAGAA | NM_001556.1 |
| 151 | IKBKB | AGCCAAGAAGAGTGAAGAA | NM_001556.1 |
| 152 | IKBKB | CAAGAAGAGTGAAGAACTG | NM_001556.1 |

TABLE 3-continued

| SEQ ID NO: | Target Gene | Nucleotide Base Sequence | Target Gene Accession # |
|---|---|---|---|
| 153 | IKBKB | AGAAGAGTGAGGTGGACAT | NM_001556.1 |
| 154 | IKBKB | AGCGAAGACTTGAATGAA | NM_001556.1 |
| 155 | IKBKB | AGGAAACAGGTGAGCAGAT | NM_001556.1 |
| 156 | IKBKB | CTTAGATACCTTCATGAAA | NM_001556.1 |
| 157 | RELA | GCATCCAGACCAACAACAA | NM_021975.3 |
| 158 | RELA | AGCGCATCCAGACCAACAA | NM_021975.3 |
| 159 | RELA | GTGACAAGGTGCAGAAAGA | NM_021975.3 |
| 160 | RELA | GGATTGAGGAGAAACGTAA | NM_021975.3 |
| 161 | RELA | CCCACGAGCTTGTAGGAAA | NM_021975.3 |
| 162 | RELA | GGAGAAACGTAAAAGGACA | NM_021975.3 |
| 163 | RELA | GGCGAGAGGAGCACAGATA | NM_021975.3 |
| 164 | RELA | CTACACAGGACCAGGGACA | NM_021975.3 |
| 165 | RELA | AAGAGGACATTGAGGTGTA | NM_021975.3 |
| 166 | RELA | GGAAAGGACTGCCGGGATG | NM_021975.3 |
| 167 | RELA | TCAAGAGCATCATGAAGAA | NM_021975.3 |
| 168 | RELA | TGGAGTACCCTGAGGCTAT | NM_021975.3 |
| 169 | RELA | GAATCCAGTGTGTGAAGAA | NM_021975.3 |
| 170 | RELA | TCAGTGAGCCCATGGAATT | NM_021975.3 |
| 171 | RELA | CGTAAAAGGACATATGAGA | NM_021975.3 |
| 172 | RELA | GGGAAGGAACGCTGTCAGA | NM_021975.3 |
| 173 | RELA | CCACGAGCTTGTAGGAAAG | NM_021975.3 |
| 174 | RELA | CTTCCAAGTTCCTATAGAA | NM_021975.3 |
| 175 | RELA | GCATCCAGACCAACAACAA | NM_021975.3 |
| 176 | RELA | CTCAAGATCTGCCGAGTGA | NM_021975.3 |
| 177 | RELA | CGGATTGAGGAGAAACGTA | NM_021975.3 |
| 178 | RELA | GATTGAGGAGAAACGTAAA | NM_021975.3 |
| 179 | RELA | GGACATATGAGACCTTCAA | NM_021975.3 |
| 180 | RELA | TCACCGGATTGAGGAGAAA | NM_021975.3 |
| 181 | RELA | CAACTGAGCCCATGCTGAT | NM_021975.3 |
| 182 | RELA | AGGAAAGGACTGCCGGGAT | NM_021975.3 |
| 183 | RELA | CCAACACTGCCGAGCTCAA | NM_021975.3 |
| 184 | RELA | GCTGCAGTTTGATGATGAA | NM_021975.3 |
| 185 | RELA | GACCAGGGACAGTGCGCAT | NM_021975.3 |
| 186 | RELA | GGGATGAGATCTTCCTACT | NM_021975.3 |
| 187 | RELA | AGGTGCAGAAAGAGGACAT | NM_021975.3 |
| 188 | RELA | AGGACATTGAGGTGTATTT | NM_021975.3 |
| 189 | RELA | GAGAAACGTAAAAGGACAT | NM_021975.3 |
| 190 | RELA | CATCAAGATCAATGGCTAC | NM_021975.3 |
| 191 | RELA | CCAAGTTCCTATAGAAGAG | NM_021975.3 |

TABLE 3-continued

| SEQ ID NO: | Target Gene | Nucleotide Base Sequence | Target Gene Accession # |
|---|---|---|---|
| 192 | RELA | AGATCTTCCTACTGTGTGA | NM_021975.3 |
| 193 | RELA | AGAAAGAGGACATTGAGGT | NM_021975.3 |
| 194 | RELA | GTCACCGGATTGAGGAGAA | NM_021975.3 |
| 195 | RELA | ACATATGAGACCTTCAAGA | NM_021975.3 |
| 196 | RELA | GCTATAACTCGCCTAGTGA | NM_021975.3 |
| 197 | RELA | TGCAGAAAGAGGACATTGA | NM_021975.3 |
| 198 | RELA | GAAAGAGGACATTGAGGTG | NM_021975.3 |
| 199 | RELA | AAGCTGATGTGCACCGACA | NM_021975.3 |
| 200 | RELA | GATCAATGGCTACACAGGA | NM_021975.3 |
| 201 | RELA | TGTGTGACAAGGTGCAGAA | NM_021975.3 |
| 202 | RELA | TTCCAGTACCTGCCAGATA | NM_021975.3 |
| 203 | RELA | GAGGAGAAACGTAAAAGGA | NM_021975.3 |
| 204 | RELA | TATGAGACCTTCAAGAGCA | NM_021975.3 |
| 205 | RELA | ATGAGACCTTCAAGAGCAT | NM_021975.3 |
| 206 | RELA | AAGAGCATCATGAAGAAGA | NM_021975.3 |
| 207 | RELA | TGGCAACAGCACAGACCCA | NM_021975.3 |
| 208 | RELA | CAAGATCAATGGCTACACA | NM_021975.3 |
| 209 | IKBKG | GGAAGAGCCAACTGTGTGA | NM_003639.3 |
| 210 | IKBKG | CCAAACAGGAGGTGATCGA | NM_003639.3 |
| 211 | IKBKG | GGACAAGGCCTCTGTGAAA | NM_003639.3 |
| 212 | IKBKG | GGAAACTGGTGGAGAGACT | NM_003639.3 |
| 213 | IKBKG | GGGAGAAGCTGGCCGAGAA | NM_003639.3 |
| 214 | IKBKG | GCGAGGAGCTTCTGCATTT | NM_003639.3 |
| 215 | IKBKG | GGATCGAGGACATGAGGAA | NM_003639.3 |
| 216 | IKBKG | CGGCCAGGATCGAGGACAT | NM_003639.3 |
| 217 | IKBKG | GAGGAATGCAGCTGGAAGA | NM_003639.3 |
| 218 | IKBKG | TCGATAAGCTGAAGGAGGA | NM_003639.3 |
| 219 | IKBKG | TGGAGAAGCTCGATCTGAA | NM_003639.3 |
| 220 | IKBKG | AAACAGGAGGTGATCGATA | NM_003639.3 |
| 221 | IKBKG | CCAAACAGGAGGTGATCGA | NM_003639.3 |
| 222 | IKBKG | AGCAGATGGCTGAGGACAA | NM_003639.3 |
| 223 | IKBKG | AGAAGCTGGCCGAGAAGAA | NM_003639.3 |
| 224 | IKBKG | GCTTGGAGGCTGCCACTAA | NM_003639.3 |
| 225 | IKBKG | TGGCCAAACAGGAGGTGAT | NM_003639.3 |
| 226 | IKBKG | GGAAGAGCCAACTGTGTGA | NM_003639.3 |
| 227 | IKBKG | AACAGGAGGTGATCGATAA | NM_003639.3 |
| 228 | IKBKG | GAATGCAGCTGGAAGATCT | NM_003639.3 |
| 229 | IKBKG | AGAGGGAGGAGAAGGAGTT | NM_003639.3 |
| 230 | IKBKG | AGGCGGACTTCCAGGCTGA | NM_003639.3 |

TABLE 3-continued

| SEQ ID NO: | Target Gene | Nucleotide Base Sequence | Target Gene Accession # |
|---|---|---|---|
| 231 | IKBKG | TGGAGCAGCTGCAGAGGGA | NM_003639.3 |
| 232 | IKBKG | GAGCAGCTGCAGAGGGAGT | NM_003639.3 |
| 233 | IKBKG | CGTACTGGGCGAAGAGTCT | NM_003639.3 |
| 234 | IKBKG | GGAGGAGAATCAAGAGCTC | NM_003639.3 |
| 235 | IKBKG | CCAGCCAGAGGGAGGAGAA | NM_003639.3 |
| 236 | IKBKG | GCCAGAGGGAGGAGAAGGA | NM_003639.3 |
| 237 | IKBKG | TGAAGAGGCAGAAGGAGCA | NM_003639.3 |
| 238 | IKBKG | TGGAAGATCTCAAACAGCA | NM_003639.3 |
| 239 | IKBKG | CTGAAGAGGCAGAAGGAGC | NM_003639.3 |
| 240 | IKBKG | AAGAATACGACAACCACAT | NM_003639.3 |
| 241 | IKBKG | GCAGAGGGAGTACAGCAAA | NM_003639.3 |
| 242 | IKBKG | CAGCAGATCAGGACGTACT | NM_003639.3 |
| 243 | IKBKG | AGTGAGCGGAAGCGAGGAA | NM_003639.3 |
| 244 | IKBKG | GAGCCAACTGTGTGAGATG | NM_003639.3 |
| 245 | IKBKG | CTGAAGGCCCAGGCGGATA | NM_003639.3 |
| 246 | IKBKG | CAGAGGGAGTACAGCAAAC | NM_003639.3 |
| 247 | IKBKG | CAGGAAACTGGTGGAGAGA | NM_003639.3 |
| 248 | IKBKG | TGAATAGGCACCTCTGGAA | NM_003639.3 |
| 249 | IKBKG | GAGGCTGCCACTAAGGAAT | NM_003639.3 |
| 250 | IKBKG | CCCAGTTGCAGGTGGCCTA | NM_003639.3 |
| 251 | IKBKG | GGGAGTACAGCAAACTGAA | NM_003639.3 |
| 252 | IKBKG | AGCGCTGCCTGGAGGAGAA | NM_003639.3 |
| 253 | IKBKG | AATCAAGAGCTCCGAGATG | NM_003639.3 |
| 254 | IKBKG | CGGCAGAGCAACCAGATTC | NM_003639.3 |
| 255 | IKBKG | AGAGATGCCAGCAGCAGAT | NM_003639.3 |
| 256 | IKBKG | AGGCCCAGGCGGATATCTA | NM_003639.3 |
| 257 | IKBKG | CTGCAGAGGGAGTACAGCA | NM_003639.3 |
| 258 | IKBKG | TGCAGAGGGAGTACAGCAA | NM_003639.3 |
| 259 | IKBKG | TGGACACCCTGCAGATACA | NM_003639.3 |
| 260 | IKBKG | GCACCTGCCTTCAGAACAG | NM_003639.3 |
| 261 | PLN | AAGTCCAATACCTCACTCGCT | NM_002667.3 |
| 262 | PLN | AAGCACGTCAAAAGCTACAGA | NM_002667.3 |
| 263 | PLN | AATTCTGTCTCATCTTAA | NM_002667.3 |
| 264 | PLN | GGTCTTCACCAAGTATCAA | NM_002667.3 |
| 265 | PLN | GGCCATACTCTTACATAAT | NM_002667.3 |
| 266 | PLN | GGCAAGGAAAATAAAAGAT | NM_002667.3 |
| 267 | PLN | GCACGTCAAAAGCTACAGA | NM_002667.3 |
| 268 | PLN | GGCACTGTAGTGAATTATC | NM_002667.3 |

TABLE 3-continued

| SEQ ID NO: | Target Gene | Nucleotide Base Sequence | Target Gene Accession # |
|---|---|---|---|
| 269 | PLN | GCTAGAGTTACCTAGCTTA | NM_002667.3 |
| 270 | PLN | AAGAAGAGCCTCAACCATT | NM_002667.3 |
| 271 | PLN | GTCAAAAGCTACAGAATCT | NM_002667.3 |
| 272 | PLN | CCTCACTCGCTCAGCTATA | NM_002667.3 |
| 273 | PLN | TCGCTCAGCTATAAGAAGA | NM_002667.3 |
| 274 | PLN | TGAAATGCCTCAACAAGCA | NM_002667.3 |
| 275 | PLN | AGCTATAAGAAGAGCCTCA | NM_002667.3 |
| 276 | PLN | TAATATGTCTCTTGCTGAT | NM_002667.3 |
| 277 | PLN | CCTCAACAAGCACGTCAAA | NM_002667.3 |
| 278 | PLN | GGAGAAAGTCCAATACCTC | NM_002667.3 |
| 279 | PLN | ACAAGCACGTCAAAGCTA | NM_002667.3 |
| 280 | PLN | CGTCAAAAGCTACAGAATC | NM_002667.3 |
| 281 | PLN | ACGTCAAAAGCTACAGAAT | NM_002667.3 |
| 282 | PLN | GCTACAGAATCTATTTATC | NM_002667.3 |
| 283 | PLN | GCTATAAGAAGAGCCTCAA | NM_002667.3 |
| 284 | PLN | ATAAGAAGAGCCTCAACCA | NM_002667.3 |
| 285 | PLN | TAAGAAGAGCCTCAACCAT | NM_002667.3 |
| 286 | PLN | GCCTCAACAAGCACGTCAA | NM_002667.3 |
| 287 | PLN | AGAAGAGCCTCAACCATTG | NM_002667.3 |
| 288 | PLN | CAATTTCTGTCTCATCTTA | NM_002667.3 |
| 289 | PLN | TCAACAAGCACGTCAAAAG | NM_002667.3 |
| 290 | PLN | TTAATATGTCTCTTGCTGA | NM_002667.3 |
| 291 | PLN | GTCTCTTGCTGATCTGTAT | NM_002667.3 |
| 292 | PLN | CTTAATATGTCTCTTGCTG | NM_002667.3 |
| 293 | PLN | TCAGCTATAAGAAGAGCCT | NM_002667.3 |
| 294 | PLN | CCAATACCTCACTCGCTCA | NM_002667.3 |
| 295 | PLN | CAAAAGCTACAGAATCTAT | NM_002667.3 |
| 296 | PLN | CATCTTAATATGTCTCTTG | NM_002667.3 |
| 297 | PLN | AGAAAGTCCAATACCTCAC | NM_002667.3 |
| 298 | PLN | CTATAAGAAGAGCCTCAAC | NM_002667.3 |
| 299 | PLN | ACTCGCTCAGCTATAAGAA | NM_002667.3 |
| 300 | PLN | TCAAAAGCTACAGAATCTA | NM_002667.3 |
| 301 | PLN | TATCAATTTCTGTCTCATC | NM_002667.3 |
| 302 | PLN | TGTCTCTTGCTGATCTGTA | NM_002667.3 |
| 303 | PLN | AAGCACGTCAAAAGCTACA | NM_002667.3 |
| 304 | PLN | GCACGTCAAAAGCTACAGA | NM_002667.3 |
| 305 | PLN | TCAATTTCTGTCTCATCTT | NM_002667.3 |
| 306 | PLN | TGCCTCAACAAGCACGTCA | NM_002667.3 |
| 307 | PLN | TCCAATACCTCACTCGCTC | NM_002667.3 |

TABLE 3-continued

| SEQ ID NO: | Target Gene | Nucleotide Base Sequence | Target Gene Accession # |
|---|---|---|---|
| 308 | PLN | CTCACTCGCTCAGCTATAA | NM_002667.3 |
| 309 | PLN | TACCTCACTCGCTCAGCTA | NM_002667.3 |
| 310 | PLN | CTGTCTCATCTTAATATGT | NM_002667.3 |
| 311 | PLN | CTCAACAAGCACGTCAAAA | NM_002667.3 |
| 312 | PLN | CAACAAGCACGTCAAAAGC | NM_002667.3 |
| 313 | PLN | TATAAGAAGAGCCTCAACC | NM_002667.3 |
| 314 | PLN | ATATGTCTCTTGCTGATCT | NM_002667.3 |
| 315 | PLN | CGCTCAGCTATAAGAAGAG | NM_002667.3 |
| 316 | PLN | ATCAATTTCTGTCTCATCT | NM_002667.3 |
| 317 | PLN | TGTCTCATCTTAATATGTC | NM_002667.3 |
| 318 | PLN | GTCTCATCTTAATATGTCT | NM_002667.3 |
| 319 | PLN | GTCCAATACCTCACTCGCT | NM_002667.3 |
| 320 | BIM | TGATGTAAGTTCTGAGTGT | NM_207002.2 |
| 321 | BIM | CCGAGAAGGTAGACAATTG | NM_207002.2 |
| 322 | BIM | TGACCGAGAAGGTAGACAA | NM_207002.2 |
| 323 | BIM | AAAGCAACCTTCTGATGTA | NM_207002.2 |
| 324 | BIM | ATGTAAGTTCTGAGTGTGA | NM_207002.2 |
| 325 | BIM | GTTCTGAGTGTGACCGAGA | NM_207002.2 |
| 326 | BIM | GACCGAGAAGGTAGACAAT | NM_207002.2 |
| 327 | BIM | GCACCCATGAGTTGTGACA | NM_207002.2 |
| 328 | BIM | CTACCTCCCTACAGACAGA | NM_207002.2 |
| 329 | BIM | CCCTACAGACAGAGCCACA | NM_207002.2 |
| 330 | BIM | GTGTGACCGAGAAGGTAGA | NM_207002.2 |
| 331 | BIM | AAGCAACCTTCTGATGTAA | NM_207002.2 |
| 332 | BIM | GAGTGTGACCGAGAAGGTA | NM_207002.2 |
| 333 | BIM | GCAACCTTCTGATGTAAGT | NM_207002.2 |
| 334 | BIM | TGACAAATCAACACAAACC | NM_207002.2 |
| 335 | BIM | GCAAAGCAACCTTCTGATG | NM_207002.2 |
| 336 | BIM | TGAGTGTGACCGAGAAGGT | NM_207002.2 |
| 337 | BIM | CAAAGCAACCTTCTGATGT | NM_207002.2 |
| 338 | BIM | GCCCAGCACCCATGAGTTG | NM_207002.2 |
| 339 | BIM | GTGACAAATCAACACAAAC | NM_207002.2 |
| 340 | BIM | CCTACAGACAGAGCCACAA | NM_207002.2 |
| 341 | BIM | AGTGTGACCGAGAAGGTAG | NM_207002.2 |
| 342 | BIM | GGCAAAGCAACCTTCTGAT | NM_207002.2 |
| 343 | BIM | CTCCCTACAGACAGAGCCA | NM_207002.2 |
| 344 | BIM | CTACAGACAGAGCCACAAG | NM_207002.2 |
| 345 | BIM | ACACAAACCCCAAGTCCTC | NM_207002.2 |
| 346 | BIM | GCCAGGCCTTCAACCACTA | NM_207002.2 |

TABLE 3-continued

| SEQ ID NO: | Target Gene | Nucleotide Base Sequence | Target Gene Accession # |
|---|---|---|---|
| 347 | BIM | GAGAAGGTAGACAATTGCA | NM_207002.2 |
| 348 | BIM | AAATCAACACAAACCCCAA | NM_207002.2 |
| 349 | BIM | GGTAGACAATTGCAGCCTG | NM_207002.2 |
| 350 | BIM | CCCTACCTCCCTACAGACA | NM_207002.2 |
| 351 | BIM | GAGCCCAGCACCCATGAGT | NM_207002.2 |
| 352 | BIM | CTTGCCAGGCCTTCAACCA | NM_207002.2 |
| 353 | BIM | AGAAGGTAGACAATTGCAG | NM_207002.2 |
| 354 | BIM | GAAGGTAGACAATTGCAGC | NM_207002.2 |
| 355 | BIM | TCTGAGTGTGACCGAGAAG | NM_207002.2 |
| 356 | BIM | GTGACCGAGAAGGTAGACA | NM_207002.2 |
| 357 | BIM | AAGTTCTGAGTGTGACCGA | NM_207002.2 |
| 358 | BIM | TGCCAGGCCTTCAACCACT | NM_207002.2 |
| 359 | BIM | CGAGAAGGTAGACAATTGC | NM_207002.2 |
| 360 | BIM | GTAAGTTCTGAGTGTGACC | NM_207002.2 |
| 361 | BIM | TCTGATGTAAGTTCTGAGT | NM_207002.2 |
| 362 | BIM | GCCCTACCTCCCTACAGA | NM_207002.2 |
| 363 | BIM | ACAGGAGCCCAGCACCCAT | NM_207002.2 |
| 364 | BIM | ACCGAGAAGGTAGACAATT | NM_207002.2 |
| 365 | BIM | AGCCCAGCACCCATGAGTT | NM_207002.2 |
| 366 | BIM | CAAATCAACACAAACCCCA | NM_207002.2 |
| 367 | BIM | CCTCCTTGCCAGGCCTTCA | NM_207002.2 |
| 368 | BIM | CTTCTGATGTAAGTTCTGA | NM_207002.2 |
| 369 | BIM | AGGTAGACAATTGCAGCCT | NM_207002.2 |

Further non-limiting examples of anti-htt siRNAs are provided in Table 4. It should be noted that in this table, the odd and even numbered siRNA strands are complementary to each other. It should be further noted that the siRNAs in table 4 are targeted to specific SNP variants of htt mRNA. The SNP nucleotide is shown in bold.

TABLE 4

| SEQ ID NO | SEQUENCE |
|---|---|
| 370 | 5'- aguggaugagggagcaggc -3' |
| 371 | 5'- gccugcucccucauccacu -3' |
| 372 | 5'- gcacacaguggaugaggga -3' |
| 373 | 5'- ucccucauccacugugugc -3' |
| 374 | 5'- ugaagugcacacaguggau -3' |
| 375 | 5'- auccacugugugcacuuca -3' |
| 376 | 5'- cacacaguggaugagggag -3' |
| 377 | 5'- cucccucauccacugugug -3' |
| 378 | 5'- gcacacaguagaugaggga -3' |
| 379 | 5'- ucccucaucuacugugugc -3' |
| 380 | 5'- ugaagugcacacaguagau -3' |
| 381 | 5'- aucuacugugugcacuuca -3' |
| 382 | 5'- aguagaugagggagcaggc -3' |
| 383 | 5'- gccugcucccucaucuacu -3' |
| 384 | 5'- cacacaguagaugagggag -3' |
| 385 | 5'- cucccucaucuacugugug -3' |
| 386 | 5'- ggcgcagacuuccaaaggc -3' |
| 387 | 5'- gccuuuggaagucugcgcc -3' |

TABLE 4-continued

| SEQ ID NO | SEQUENCE |
|---|---|
| 388 | 5'- cacaagggcgcagacuucc -3' |
| 389 | 5'- ggaagucugcgcccuugug -3' |
| 390 | 5'- gcagggcacaagggcgcag -3' |
| 391 | 5'- cugcgcccuugugcccugc -3' |
| 392 | 5'- acaagggcgcagacuucca -3' |
| 393 | 5'- uggaagucugcgcccuugu -3' |
| 394 | 5'- cacaagggcacagacuucc -3' |
| 395 | 5'- ggaagucugugcccuugug -3' |
| 396 | 5'- gcagggcacaagggcacag -3' |
| 397 | 5'- cugugcccuugugcccugc -3' |
| 398 | 5'- ggcacagacuuccaaaggc -3' |
| 399 | 5'- gccuuuggaagucugugcc -3' |
| 400 | 5'- acaagggcacagacuucca -3' |
| 401 | 5'- uggaagucugugcccuugu -3' |
| 402 | 5'- caaugguacagcucuuccu -3' |
| 403 | 5'- aggaagagcuguaccauug -3' |
| 404 | 5'- caucccaaugguacagcuc -3' |
| 405 | 5'- gagcuguaccauugggaug -3' |
| 406 | 5'- ccaucccaaugguacagcu -3' |
| 407 | 5'- agcuguaccauugggaugg -3' |
| 408 | 5'- uuguggccaucccaauggu -3' |
| 409 | 5'- accauugggauggccacaa -3' |
| 410 | 5'- caacgguacagcucuuccu -3' |
| 411 | 5'- aggaagagcuguaccguug -3' |
| 412 | 5'- caucccaacguacagcuc -3' |
| 413 | 5'- gagcuguaccguugggaug -3' |
| 414 | 5'- ccaucccaacguacagcu -3' |
| 415 | 5'- agcuguaccguugggaugg -3' |
| 416 | 5'- uuguggccaucccaacggu -3' |
| 417 | 5'- accguugggauggccacaa -3' |
| 418 | 5'- gucggcaagcagagcuccc -3' |
| 419 | 5'- gggagcucugcuugccgac -3' |
| 420 | 5'- agccagucggcaagcagag -3' |
| 421 | 5'- cucugcuugccgacuggcu -3' |
| 422 | 5'- cagccagucggcaagcagagc -3' |
| 423 | 5'- gcucugcuugccgacuggcug -3' |
| 424 | 5'- gucucacagccagucggca -3' |
| 425 | 5'- ugccgacuggcugugagac -3' |

| SEQ ID NO | SEQUENCE |
|---|---|
| 426 | 5'- gucagcaagcagagcuccc -3' |
| 427 | 5'- gggagcucugcuugcugac -3' |
| 428 | 5'- agccagucagcaagcagag -3' |
| 429 | 5'- cucugcuugcugacuggcu -3' |
| 430 | 5'- cagccagucagcaagcagagc -3' |
| 431 | 5'- gcucugcuugcugacuggcug -3' |
| 432 | 5'- gucucacagccagucagca -3' |
| 433 | 5'- ugcugacuggcugugagac -5' |
| 434 | 5'- cacauacauuagcucaaac -3' |
| 435 | 5'- guuugagcuaauguaugug -3' |
| 436 | 5'- cagcgucacauacauuagc -3' |
| 437 | 5'- gcuaauguaugugacgcug -3' |
| 438 | 5'- acauacauuagcucaaacu -3' |
| 439 | 5'- aguuugagcuaauguaugu -3' |
| 440 | 5'- cauuagcucaaacugguug -3' |
| 441 | 5'- caaccaguuugagcuaaug -3' |
| 442 | 5'- cacauacaucagcucaaac -3' |
| 443 | 5'- guuugagcugauguaugug -3' |
| 444 | 5'- cagcgucacauacaucagc -3' |
| 445 | 5'- gcugauguaugugacgcug -3' |
| 446 | 5'- acauacaucagcucaaacu -3' |
| 447 | 5'- aguuugagcugauguaugu -3' |
| 448 | 5'- caucagcucaaacugguug -3' |
| 449 | 5'- caaccaguuugagcugaug -3' |
| 450 | 5'- caacaucaaagcaucuuga -3' |
| 451 | 5'- ucaagaugcuuugauguug -3' |
| 452 | 5'- ccggccaacaucaaagcau -3' |
| 453 | 5'- augcuuugauguuggccgg -3' |
| 454 | 5'- uccggccaacaucaaagca -3' |
| 455 | 5'- ugcuuugauguuggccgga -3' |
| 456 | 5'- caaguuccggccaacauc -3' |
| 457 | 5'- gauguuggccggaaacuug -3' |
| 458 | 5'- caaaaucaaagcaucuuga -3' |
| 459 | 5'- ucaagaugcuuugauuuug -3' |
| 460 | 5'- ccggccaaaaucaaagcau -3' |
| 461 | 5'- augcuuugauuuggccgg -3' |
| 462 | 5'- uccggccaaaaucaaagca -3' |
| 463 | 5'- ugcuuugauuuuggccgga -3' |

TABLE 4-continued

| SEQ ID NO | SEQUENCE |
|---|---|
| 464 | 5'- caaguuuccggccaaaauc -3' |
| 465 | 5'- gauuuuggccggaaacuug -3' |
| 466 | 5'- gaauuacugucccaucuc -3' |
| 467 | 5'- gagauggggacaguaauuc -3' |
| 468 | 5'- gcguugaauuacugucccc -3' |
| 469 | 5'- ggggacaguaauucaacgc -3' |
| 470 | 5'- agcguugaauuacugucc -3' |
| 471 | 5'- gggacaguaauucaacgcu -3' |
| 472 | 5'- ucuucuagcguugaauuac -3' |
| 473 | 5'- guaauucaacgcuagaaga -3' |
| 474 | 5'- gaaguacugucccaucuc -3' |
| 475 | 5'- gagauggggacaguacuuc -3' |
| 476 | 5'- gcguugaaguacugucccc -3' |
| 477 | 5'- ggggacaguacuucaacgc -3' |
| 478 | 5'- agcguugaaguacugucc -3' |
| 479 | 5'- gggacaguacuucaacgcu -3' |
| 480 | 5'- ucuucuagcguugaaguac -3' |
| 481 | 5'- guacuucaacgcuagaaga -3' |
| 482 | 5'- uagcguugaauuacugucc -3' |
| 483 | 5'- ggacaguaauucaacgcua -3' |
| 484 | 5'- uagcguugacuuacugucc -3' |
| 485 | 5'- ggacaguaagucaacgcua -3' |
| 486 | 5'- uagcguugaaguacugucc -3' |
| 487 | 5'- ggacaguacuucaacgcua -3' |
| 488 | 5'- uagcguugauguacugucc -3' |
| 489 | 5'- ggacaguacaucaacgcua -3' |
| 490 | 5'- cacauacauuggcucaaac -3' |
| 491 | 5'- guuugagccaauguaugug -3' |
| 492 | 5'- cacauacaucggcucaaac -3' |
| 493 | 5'- guuugagccgauguaugug -3' |

The exemplary targets provided above are suitable for neurodegenerative diseases (e.g., anti-htt siRNAs, anti-RACE-1 siRNAs, etc), heart diseases (e.g., anti-phospholamban siRNAs), treatment of inflammation and diseases associated with inflammation, such as schiatica (e.g., anti-TNF, anti-IL-1b siRNAs, anti-IKBKG, Anti-relA siRNAs).

The indication for use of anti-BIM siRNA is for polycystic kidney disease. Anti-BIM siRNA (specifically shRNA) has been shown to prevent polycystic kidney disease in mice. Reference: Cell Death and Differentiation (2005) 12, 831-833. doi:10.1038/sj.cdd.4401603. The above reference also defines the siRNA complementary to target sequence: TGATGTAAGTTCTGAGTGTG (SEQ ID NO: 494) as being most efficacious.

Of course, other diseases may also be targeted. A person of ordinary skill in the art possesses sufficient knowledge to select the appropriate gene for the selected disease or a condition.

In some embodiments, and depending on the problem in front of the practitioner, other RNA interference agents may be used. These methods are particularly suitable for delivering RNA to cells which are concentrated in one location within a patient (e.g., a subthalamic nucleus or a tumor, including, without limitations, benign and malignant tumors). For example, these methods may be used to treat localized infections or inflammations, autoimmune diseases, certain viral diseases, particularly those where the pathogen resides in certain cell types (e.g., herpes zoster, where the virus resides in trigeminal nucleus).

The siRNA molecules targeted to desired sequences can be designed based on criteria well known in the art (e.g., Elbashir et al., *EMBO J.* 20:6877 (2001)). For example, the target segment of the target mRNA preferably should begin with AA (most preferred), TA, GA, or CA; the GC ratio of the siRNA molecule preferably should be 45-55%; the siRNA molecule preferably should not contain three of the same nucleotides in a row; the siRNA molecule preferably should not contain seven mixed G/Cs in a row; the siRNA molecule preferably should comprise two nucleotide overhangs (preferably TT) at each 3' terminus; the target segment preferably should be in the ORF region of the target mRNA and preferably should be at least 75 bp after the initiation ATG and at least 75 bp before the stop codon; and the target segment preferably should not contain more than 16-17 contiguous base pairs of homology to other coding sequences.

Based on some or all of these criteria, siRNA molecules targeted to desired sequences can be designed by one of skill in the art using the aforementioned criteria or other known criteria (e.g., Gilmore et al., *J. Drug Targeting* 12:315 (2004); Reynolds et al., *Nature Biotechnol.* 22:326 (2004); Ui-Tei et al., *Nucleic Acids Res.* 32:936 (2004)). Such criteria are available in various web-based program formats useful for designing and optimizing siRNA molecules (e.g., siDESIGN Center at Dharmacon; BLOCK-iT RNAi Designer at Invitrogen; siRNA Selector at Wistar Insitute; siRNA Selection Program at Whitehead Institute; siRNA Design at Integrated DNA Technologies; siRNA Target Finder at Ambion; and siRNA Target Finder at Genscript).

siRNA molecules targeted to desired sequences can be produced in vitro by annealing two complementary single-stranded RNA molecules together (one of which matches at least a portion of a desired nucleic acid sequence) (e.g., U.S. Pat. No. 6,506,559) or through the use of a short hairpin RNA (shRNA) molecule which folds back on itself to produce the requisite double-stranded portion (Yu et al., *Proc. Natl. Acad. Sci. USA* 99:6047 (2002)). Such single-stranded RNA molecules can be chemically synthesized (e.g., Elbashir et al., *Nature* 411:494 (2001)) or produced by in vitro transcription using DNA templates (e.g., Yu et al., *Proc. Natl. Acad. Sci. USA* 99:6047 (2002)). When chemically synthesized, chemical modifications can be introduced into the siRNA molecules to improve biological stability. Such modifications include phosphorothioate linkages, fluorine-derivatized nucleotides, deoxynucleotide overhangs, 2'-O-methylation, 2'-O-allylation, and locked nucleic acid (LNA) substitutions (Dorset and Tuschl, *Nat. Rev. Drug Discov.* 3:318 (2004); Gilmore et al., *J. Drug Targeting* 12:315 (2004)).

In other embodiments, the RNA of the instant invention is in a form of an aptamer, a spiegelmer, an antimir, or a combination thereof. Aptamers are nucleic acid structures which can bind to a target molecule in a way which is conceptually similar to antigen-antibody recognition. Aptamers may be selected by random library screening comprising, in different embodiments, more than $10^{15}$ different random sequences flanked by pre-determined sequences as to provide easily-identifiable PCR substrate.

Spiegelmers are subset of the aptamers which are created using L-nucleotides rather than naturally occurring D-nucleotides. Spiegelmers, therefore, are the mirror images of aptamers comprising D-nucleotides. The selection of spiegelmers is based on a simple logic: if an aptamer binds a mirror image of the target, then the mirror image of the aptamer (i.e., the spiegelmer) will bind the target itself. Thus, suitable spiegelmers may be selected by screening libraries of aptamers with mirror images of the targets.

Antimirs are short RNA molecules which bind to miRNAs naturally present in the cells. The methods of antimir selection are similar to those of siRNA selection, with the use of miRNA as a target.

In some embodiments, the RNA agents of the instant invention may be administered as vectorless RNA molecules.

In other embodiments, the dsRNA may be included within an RNA vector, which may be a single-stranded or a double-stranded RNA vector. The RNA strand (sense or antisense) which is to be incorporated into the vector, depends on whether the vector carries a positive or negative sense RNA. Suitable positive sense RNA vectors include, without limitations, Sindbis virus/replicons, Semliki Forest virus, Poliovirus, and Kunjin virus. Negative sense RNA viruses include, without limitations, Influenza virus, Rabies virus, Vesicular stomatitis virus, Respiratory syncytial virus, Sendai virus, SV5. The above represents a partial list of positive and negative sense RNA viruses, which have been genetically engineered to express foreign proteins. Some of the constructs give rise to infectious (attenuated) viruses, others form non-infectious replicons, which are restricted to replication (and expression of the foreign gene) in the transfected/infected cell. See, e.g, Palese, *Proc Natl Acad Sci* USA. 1998 Oct. 27; 95(22): 12750-12752. A person of ordinary skill in the art would appreciate that the vectors which do not result in the infection is generally preferred. See, e.g., Li et al., *J. of Virol.*, 2000, 74(14): 6564-6569.

The methods of preparing vectorless RNA, ssRNA viruses and dsRNA viruses are well-known in the art. For example, vectorless RNA agents may be produced by direct chemical synthesis. The RNA vectors may be produced according to the techniques described, for example, in U.S. Pat. Nos. 6,316,243, 6,544,785, 7,384,774, and 7,276,356.

The amount of the therapeutic of the present invention which will be effective in the treatment of a particular disorder or condition will depend on the nature of the disorder or condition, and can be determined by standard clinical techniques, well established in the administration of therapeutics. The precise dose to be employed in the formulation will also depend on the route of administration, and the seriousness of the disease or disorder, and should be decided according to the judgment of the practitioner and the patient's needs.

The concentration of the naked RNA may comprise, in different embodiments, up to 24 mg/ml, e.g., about 1 mg/ml, or about 2 mg/ml or about 3 mg/ml or about 4 mg/ml or about 5 mg/ml or about 6 mg/ml or about 7 mg/ml or about mg/ml or about 9 mg/ml or about 10 mg/ml or about 11 mg/ml or about 12 mg/ml or about 13 mg/ml or about 14 mg/ml or about 15 mg/ml or about 15 mg/ml or about 16 mg/ml or about 17 mg/ml or about 18 mg/ml or about 19 mg/ml or about 20 mg/ml or about 21 mg/ml or about 22 mg/ml or about 23 mg/ml.

If the RNA is administered within a virus, the dose of the virus may be between about $10^3$ to $10^{15}$ infectious units of viral vector per microliter delivered in 1 to 3000 microliters of single injection volume. In different embodiments, the additional amounts of infections units of vector per micro liter would generally contain about $10^4$, $10^5$, $10^6$, $10^7$, $10^8$, $10^9$, $10^{10}$, $10^{11}$, $10^{12}$, $10^{13}$, $10^{14}$ infectious units of viral vector delivered in about 10, 50, 100, 200, 500, 1000, or 2000 microliters.

In another embodiment, the RNA of the instant invention may be delivered systemically (in addition to, or instead of the local delivery). Thus, it would pass the electrostimulated area and be taken up by the cells in the target area. Various modes of systemic delivery are known in the art including without limitations, intravascular delivery (including both intravenous and intraarterial delivery), intrathecal delivery, intraventricular delivery, intramuscular delivery, ingestion, intranasal delivery, intraocular delivery, intrapulmonary delivery, etc.

Particularly advantageous in these embodiments would be a formulation which protects the RNA from endo- and exoribonucleases naturally present in the patient's body.

In these embodiments, the composition would be administered in a dose which does not result in a therapeutically effective intake of the RNA by the cell in the non-stimulated area. Preferably, the RNA is administered in sufficiently low dose to avoid or minimize potential side effects, including, without limitation, immune response. At the same time, the dose should be sufficient to provide high enough concentration of the RNA so that the intake of RNA by the cells which are electrically stimulated according to the methods of the instant invention, would result in a therapeutically effective change in the amount of the target mRNA or the target protein.

Also envisioned is an external system that would pass a patient's blood through an electrical stimulator, with the addition of siRNA, in order to treat a septic condition. In one embodiment, anti-BIM siRNA is used as an inhibitor of sepsis. See, e.g., Schwulst et al., *Shock.* 2008 30(2):127-34, which states that "Treatment with Bim siRNA in vivo has the potential to be an effective therapy in the treatment of sepsis."

Devices

In another broad aspect, the instant application provides devices suitable for the instant invention.

Generally, the devices of the instant invention comprise at least two electrodes and a catheter having an outlet opening for delivery of RNA. Generally, the outlet opening of the catheter is located between the electrodes. The catheter is fluidly connected to a reservoir comprising a composition comprising the RNA. Thus, for example, in one embodiment, the device comprises a plurality of electrodes; a catheter, comprising a wall and a cavity, wherein the members of said plurality of electrodes are disposed within or on the surface of said wall, a reservoir containing a composition comprising the nucleic acid sequence, said reservoir fluidly connected with said catheter, a pump operably connected to said reservoir, a processor operably connected to the members of said plurality of electrodes and adapted to receive electrical signals from said members and to deliver an electric field to said members. In one embodiment, the processor is adapted to actuate the pump after receiving a signal from the members of the plurality of electrodes. Further, considering that the strength of the electric field is the greatest on a straight line between the electrodes and predictably falls as the distance from that line increases, it is possible to provide a selected array of electrodes located as to provide the electric field of a pre-desired shape.

Other modifications of this basic device are possible. For example, the electrodes do not need to be integral with the catheter walls. Further, the electrodes may be configured in an external array which, in some embodiments would be placed onto the skin of the patient: e.g., an upper torso in the heart area, or a lower torso to provide a suitable electric field for the delivery of siRNA to kidneys, or the cranium for delivery of the RNA to the brain of the patient.

Considering that RNA is easily degradable, it may be advantageous in some embodiments to assure that the reservoir and the channels connecting the outlet opening and reservoir, and the composition are RNAse-free. This goal may be achieved, for example, by coating the surfaces with an RNAse inhibitor and/or by ultrafiltered water. See, e.g., Purad and Mabic, "RNase Undetectable In Water After Ultrafiltration" Biosci, Tech. 11: 26, 28 (2004). Another option of achieving the same result is preparing a DEPC-treated autoclaved water for the composition. During heat treatment, DEPC breaks down to ethanol and $CO_2$, and thus, the DEPC treated water is not toxic.

The devices may be further modified based on the organ which is to be treated (e.g., brain, heart, kidney, spinal cord). It should be further understood that if the use of the devices recited in the instant disclosure requires additional steps (e.g., the location of the predetermined area within a target organ), the methods of the instant invention may also entail optional additional steps, not necessarily limited to the structures of the devices recited in this application.

In one embodiment, the target area is within the central nervous system, e.g., the patient's brain. In this embodiment, the catheter may comprise an intracranial access catheter. The catheter will have a distal tip, which can be placed either in the parenchymal tissue of the brain or within a cerebral ventricle.

Generally, neurons affected with Huntington's disease reside in striatum, neurons affected with Alzheimer's disease reside in nucleus basalis of Meynart and the cerebral cortex, and neurons affected with Parkinson's disease reside in the substantia nigra. Thus, in different embodiments depending on the disease, the device delivers the therapies according to the methods of the instant invention to nucleus basalis of Meynart and the cerebral cortex, striatum, and/or the substantia nigra.

However, the methods of the instant invention are not limited to the target areas recited above. All substructures in central nervous system susceptible to DBS are also candidates for the treatment using the instant methods. For example, DBS targets subthalamic nucleus or globus pallidus in Parkinson's disease. There is a possibility of siRNA therapy in these regions too, e.g. to reduce neuron excitability (one of the mechanisms proposed by which DBS works) and enhance the effect of DBS.

Other applications of the instantly disclosed devices and methods to the treatment of nervous system include treatment of pain, sciatica, neuropathy, inflammation, etc. In these cases, the suitable targets may be inflammatory cytokines, NFκB, TNFα or voltage-gated sodium channels, SCN9A, and other compounds which are known to participate in generation, propagation, sustenance and/or amelioration of pain.

The target area may be located by many methods. For example, for some application, the targeted area may be located by stereotactical or gross anatomical atlases. In other embodiments, when the precise location of the targeted area is crucial, e.g., when the at least partially reversible gene therapy system is delivered into the brain of the patient, other mapping means may be used. Such mapping means include, without limitation, Positron Emission Tomography and Single Photon Emission Computed Tomography (PET and SPECT, respectively), pharmacological Magnetic Resonance Imaging (phMRI), functional MRI (fMRI), and contrast-enhanced computerized tomography (CT) scan.

In another embodiment, Computer-aided atlas-based functional neurosurgery methodology can be used to accurately and precisely inject the deoxyribonucleic acid of the present invention. Such methodologies permit three-dimensional display and real-time manipulation of cerebral structures. Neurosurgical planning with mutually preregistered multiple brain atlases in all three orthogonal orientations is therefore possible and permits increased accuracy of target definition for treatment injection or implantation, reduced time of the surgical procedure by decreasing the number of tracts, and facilitates planning of more sophisticated trajectories. See e.g. Nowinski W. L. et al., Computer-Aided Stereotactic Functional Neurosurgery Enhanced by the Use of the Multiple Brain Atlas Database, IEEE Trans Med Imaging 19(1); 62-69:2000.

Preferably, the pre-determined target area in the brain of the patient is determined on an individual basis, e.g., by real time image guidance, so that the neurosurgeon will see exactly where the catheter is being placed. Suitable systems exist for this particular embodiment, including, without limitation, STEALTH station developed by Surgical Navigation Technologies, a division of Medtronic. This tool incorporates preoperative images, including MRI, CT, and functional imaging studies into the computers in the operating room. A hand held probe linked to the computer can be used to point anywhere on the patients head or brain, with the corresponding area shown with great accuracy on a computer screen. Thus, there is no need to guess at the relationship between an area on or in the brain, inspected by sight and where that corresponds to the patient's preoperative images. Medtronic NT StealthStation® Treon™, further refines the computerized technologies of multi-dimensional imaging and navigation to enable neurosurgeons to precisely plan, re-plan, and visualize a procedure as it proceeds deep within the brain for treating neurological disorders in a living human patient.

As discussed above, the device may provide a plurality of electrodes positioned as to ensure the pre-determined shape of the electric field. In the embodiments where the brain is treated, the electrodes may be positioned as to achieve an electric field in the general shape of a pre-designed structure, e.g., in the shape of striatum, or caudate/putamen, thus further ensuring that the RNA of the instant invention is delivered to the desired brain structure. Similarly, if a ganglion (e.g., a dorsal root ganglion) is selected for the treatment, electrodes may be designed to ensure that the greatest electric field strength is within said ganglion.

In other embodiments, the location of the electrodes is verified after the insertion, e.g., through recording of the electric activity of the brain area surrounding the electrode. Optionally, the electrodes may be stimulated to invoke motor response from the patient to verify correct placement of catheter and then to apply the methods of the instant invention.

In other embodiments, e.g., where the heart is treated, the electrodes may also have the capability of sensing the pulses of naturally occurring electrical activity in the heart. The onset of such naturally occurring pulses would serve as a signal for delivering the coinciding bursts of the electrical activity according to the methods of the instant invention. Thus, in this embodiment, the electrodes would communicate the natural rhythms of the heart to the processor which, in turn, would initiate the delivery of the electrical field therapy to the heart.

In another aspect a kit is provided for practicing the methods according to any of the above-referenced embodiments.

Briefly, the kit comprises a plurality of electrodes, a composition comprising RNA, and a processor adapted to actuate an electric stimulation by the members of said plurality of electrodes, to receive a signal from the members of said plurality of electrodes and, to actuate release of at least a portion of said composition comprising RNA within a predetermined time period after receiving said signal from the members of said plurality of electrodes.

Thus, the processor receives the signal from the members of the plurality of electrodes at a predetermined time, preferably, upon the beginning of the stimulation or upon the end of the stimulation. After a pre-determined time period, the processor actuates the release of at least the portion of the composition comprising RNA. The pre-determined period of time may range from, e.g., immediately after the processor receives signal, and up to 24 hours later. Thus, in different embodiments, the RNA is delivered to the cells at least 1 minute, at least 5 minutes, at least 30 minutes, at least 45 minutes, at least hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or 24 hours after the processor receives the signal from electrodes.

In selected embodiments, the composition is provided within a reservoir which, preferably, can be connected, or is connected, to a pump, said pump adapted to receive the signal from the processor, thus actuating the release of at least the portion (preferably, having pre-determined volume) of the RNA composition into the patient.

Optionally, a catheter is also provided. The catheter should be connectable to the reservoir, so that the signal from the processor to the pump will result in release of at least the portion of the RNA composition through a distal opening of the catheter.

In certain embodiments, it may be beneficial to combine the members of the plurality of electrodes and the catheter. For example, the electrodes may be positioned within or on the surface of a wall, or walls, of the catheter. In these embodiments, advantageously, one needs to perform only one placement. However, this requirement is not crucial, and multiple placements (e.g., for each electrode and for the catheter) may be performed. Separate catheter and electrodes may also be used if the desired location is such that spatial consideration prevents positioning of the combined device.

Specific embodiments according to the methods of the present invention will now be described in the following examples. The examples are illustrative only, and are not intended to limit the remainder of the disclosure in any way.

EXAMPLES

Example 1

Electric Stimulation Leads to an Increased Uptake of RNA but not of DNA or Small Molecules HEK-293T cells were grown in Dulbecco's modified Eagle's medium (DMEM) supplemented with fetal bovine serum (10%), penicillin (100 IU/ml) and streptomycin (100 µg/ml) at 37° C. When the cells reached ≈70% confluency, they were electrically stimulated as follows:
DURATION 2 hours,
FREQUENCY 100 Hz,
FIELD STRENGTH 2 V/cm,
PULSE LENGTH 0.3 msec.
Immediately before stimulation, enhanced green fluorescent protein (GFP)-encoding supercoiled plasmid DNA (1 µg/ml) (pEGFP-C1, Clontech), rhodamine-conjugated 18-mer single stranded oligodeoxynucleotide (1 µg/ml) (Midland Certified Reagent Company), Alexa Fluor 660-conjugated short (530 base pairs) expression DNA cassettes (1 µg/ml), trypan blue dye (0.004%), or Alexa Fluor 555 hydrazide tris(triethylammonium salt) (1 µg/ml) (Invitrogen) were added to cells. Forty eight hours after stimulation, the cells were washed with sterile phosphate-buffered saline (pH 7.4) and nucleic acid uptake was estimated using fluorescence microscopy or dye uptake was estimated using bright-field microscopy.

Electrical stimulation did not increase the uptake of DNA or dye molecules in cells.

Example 2

Electrical Stimulation does not Affect Cell Viability

HEK-293 T cells were cultured as described in Example 1. Cells were treated with fluorophore-labeled RNA (siGLO Red, 1 µg/ml, Dharmacon). Electrical stimulation was performed as described in Example 1 with increasing electric field strength (0 V/cm; no stimulation group). Cell viability was accessed forty eight later using the MTT assay (performed per manufacturer's instructions; Trevigen Inc., Gaithersburg, Md.).

As shown in FIG. 1, stimulation with the electric fields of the chosen strength did not affect cell viability (FIG. 1).

Example 3

Uptake of RNA is Dependent on the Frequency of Electric Stimulation

HEK-293T cells were cultured as described in Example 1. Cells were treated with fluorophore-labeled RNA (siGLO Red, 1 µg/ml, Dharmacon). Electrical stimulation was performed as described in Example 1 with increasing frequencies (0 Hz; no stimulation group) as shown in Figure. After treatment, fluorophore uptake within cells was estimated using fluorescence microscopy.

This evidence suggests that even though low frequency stimulation (4 Hz) noticeably increased RNA uptake, stimulations with increased frequencies (60 Hz and 100 Hz) provide for a more efficient RNA uptake. These data also suggest that the electrical stimulation according to the methods of the instant invention does not disrupt membrane integrity of the stimulated cells.

Example 4

RNA Intake by Stimulated Cells is Due to a Cell-Based Process

HEK-293 cells were cultured as described above. Upon reaching ≈70% confluence, the cells were stimulated as described in Example 1 at 4° C. or 37° C. for 2 hours, followed by addition of 1 µg/ml of fluorophore-labeled RNA. It was found that the intake of RNA is temperature-dependent. Accordingly, it is likely that the electric stimulation triggered an active cell-based process for RNA intake.

Example 5

RNA Intake by Electrically Stimulated Cells is Attenuated by Inhibitors of Caveolae-Mediated Endocytosis To further elucidate the mechanism of RNA uptake caused by electrical stimulation, the cells were cultured as in Example 1 and pre-treated for 15 minutes prior to the electrical stimulation with PMA (100 nm), a known inhibitor of caveolae-mediated endocytosis, and sucrose (100 nM), a known inhibitor of clathrin-mediated endocytosis.

Figure 4:
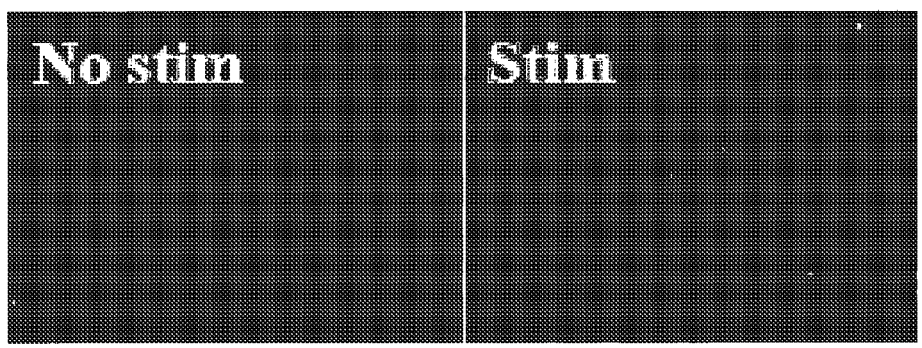
FIG. 4 demonstrates that the RNA uptake caused by electrical stimulation is at least partially due to a caveolae-mediated endocytotic pathway.
Figure 4:
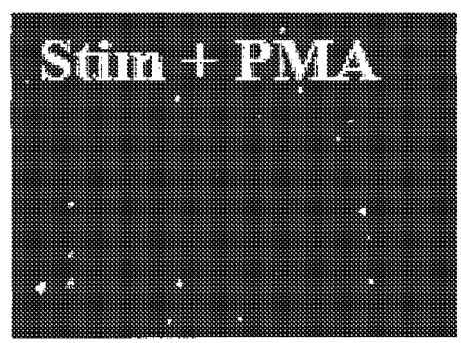
Figure 5A:
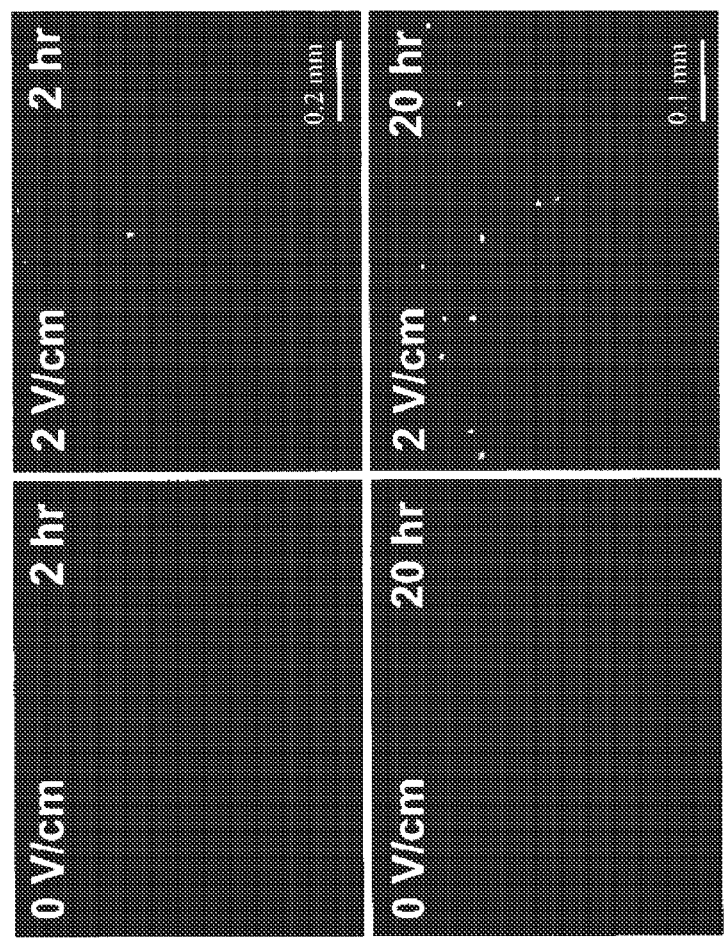
FIG. 5 demonstrates different embodiments of the instant methods and the results thereof in different cell types.
Figure 5B:
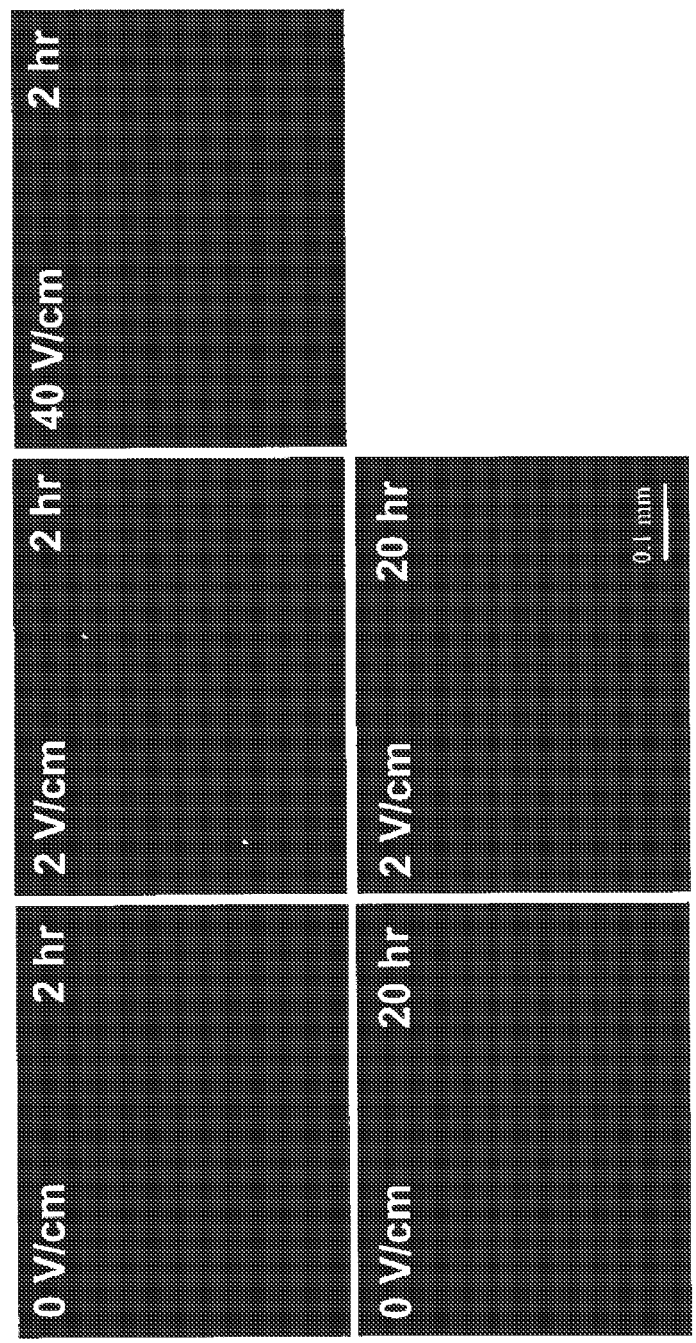
Figure 5C:
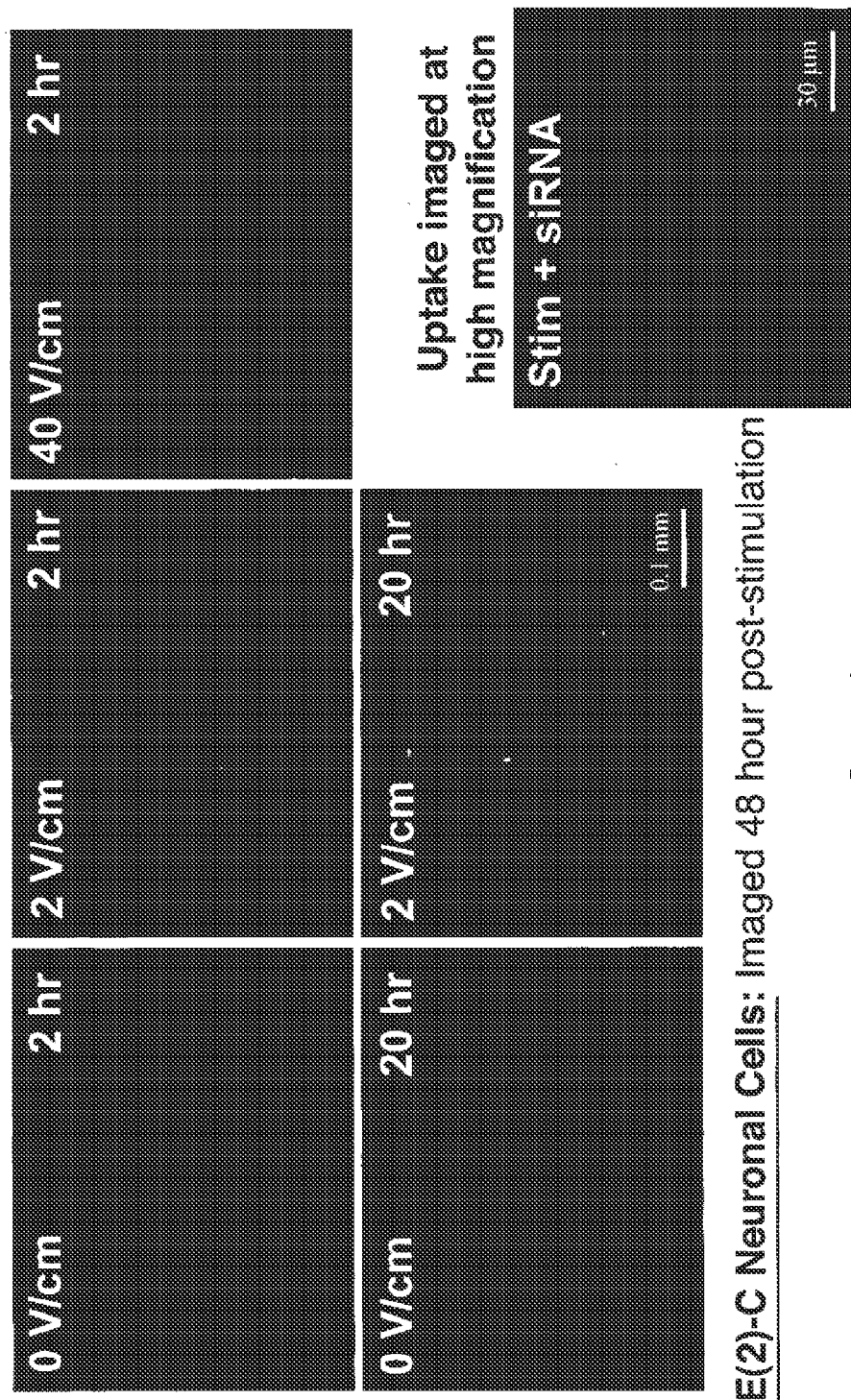
Figure 5D:
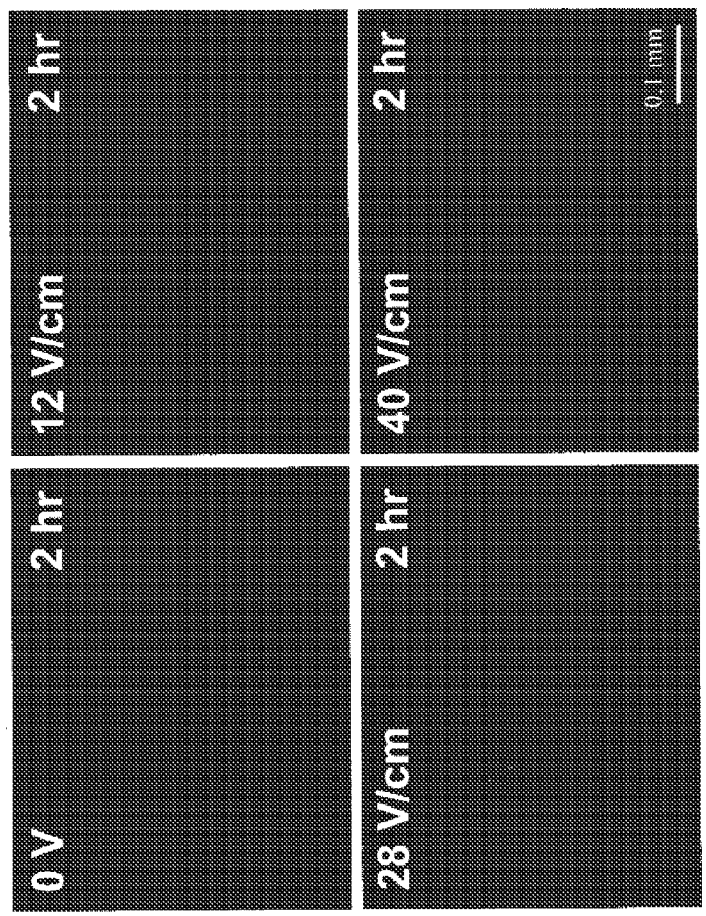

As was expected from the prior experiments, electrically stimulated cells ("Stim") demonstrated a marked increase in RNA uptake, compared to non-stimulated cells ("No stim"), as measured by fluorescence microscopy. See FIGS. 4.

Pre-treatment of PMA decreased the RNA intake (FIG. 4, "Stim + PMA"), suggesting the involvement of caveolae-mediated endocytosis in stimulation-enhanced uptake of RNA.

Pretreatment with sucrose also appeared to attenuate RNA intake, thus suggesting that clathrin mediated endocytosis is also involved in stimulation-enhanced uptake of RNA. However, due to cell loss in this group, it is impossible to draw any dispositive conclusions regarding the role of clathrin-mediated endocytosis.

Example 6

Electric Stimulation Improves Uptake of the RNA in Neuronal, Cardiac, and Kidney Cells in vitro To further elucidate the parameters of the electric stimulation on the selected cell types, the inventors conducted experiments in multiple cell types in addition to HEK-293T cells. Specifically, C2C12 myoblasts and neuronal Neuro2a and BE(2)-C cells were studied.

These cells were cultured similarly to HEK-293T cells (see Example 1), except that 1:1 ratio of DMEM and Earle's balanced salt solution were used instead of DMEM alone for Neuro2a cells. The results of RNA uptake, estimated by electron microscopy are shown in FIGS. 5A-5D, and are summarized in Table 5.

Electrical field strengths as low as 0.8 V/cm up to 12 V/cm applied for 2 hours at 100 Hz frequency and 0.3 msec pulse width enabled a substantial uptake of siRNA in the HEK-293T cells; the effect visibly reduced when the electrical field strength was reduced to 0.5 V/cm. In contrast, the same electrical parameters when applied for 20 hours were completely ineffective in delivering siRNA in these cells. Besides the duration of the applied electrical stimulation, siRNA uptake was also dependent on the frequency of electrical stimulation, such that frequencies <100 Hz (4 or 60 Hz) further reduced the degree of siRNA uptake in these cells.

The set of electrical parameters that enabled a robust uptake of siRNA in HEK-293T cells were distinct from the parameters required for achieving a similar outcome in C2C12 myoblasts. In the case of myoblasts, a burst-pulse protocol applied for longer duration (20 hours) of time was more effective in delivering siRNA, with 2 V/cm being the most effective and the effect slightly reducing with higher electrical field strengths (6 or 12 V/cm).

A longer duration of electrical stimulation was also more favorable for the delivery of siRNA in BE(2)-C human (predominantly dopaminergic) neuroblastoma cells. Testing the effects of electrical stimulation on siRNA uptake in yet another neuroblastoma cell-line, the mouse (predominantly cholinergic) Neuro2a cells, demonstrated a preference for a relatively higher electrical field strength (28 V/cm) applied for a relatively shorter duration of time (2 hours) to facilitate optimal siRNA uptake.

TABLE 5

Summary of RNA uptake efficiency caused by electric stimulations of different parameters.

| Cell type | siRNA uptake | Electrical field strength | Time of stimulation | Frequency | Pulse width |
|---|---|---|---|---|---|
| HEK-293T (kidney) | ++ | 0.5 V/cm | 2 hours | 100 Hz | 0.3 msec |
| | +++ | 0.8, 1, 2, 6 or 12 V/cm | 2 hours | 100 Hz | 0.3 msec |
| | − | 2, 6 or 12 V/cm | 20 hours | 100 Hz | 0.3 msec |
| | + | 2 V/cm | 2 hours | 4 Hz | 0.3 msec |
| | ++ | 2 V/cm | 2 hours | 60 Hz | 0.3 msec |
| | +++ | 2 V/cm | 2 hours | 100 Hz | 0.2 or 0.45 msec |
| C2C12 (cardiac) | + | 2, 6, or 12 V/cm | 2 hours, 20 hours | 100 Hz | 0.3 msec |
| | − | 2, 6 or 12 V/cm | 2 hours | 20 Hz (2 bursts of 10 pulses, separated by 500 msec) | 0.3 msec |
| | +++ | 2 V/cm | 20 hours | 20 Hz (2 bursts of 10 pulses, separated by 500 msec) | 0.3 msec |
| | ++ | 6 or 12 V/cm | 20 hours | 20 Hz (2 bursts of 10 pulses, separated by 500 msec) | 0.3 msec |
| BE(2)-C (neuronal, human) | + | 2, 6 or 12 V/cm | 2 hours | 100 Hz | 0.3 msec |
| | +++ | 2, 6 or 12 V/cm | 20 hours | 100 Hz | 0.3 msec |
| Neuro2a (neuronal, mouse) | − | 2, 6, 12 or 24 V/cm | 0.5, 1, 2 or 20 hours | 100 Hz | 0.3 msec |
| | +++ | 28 V/cm | 2 hours | 100 Hz | 0.3 msec |

Overall, these data demonstrate that the electric stimulation methods of the instant invention may be tailored to achieve optimal degree of siRNA uptake in specific cell types and at the same time the electric stimulation methods of the instant invention are sufficiently flexible to allow variability of different parameters without compromise in the effect of the RNA delivery. More importantly, the electrical stimulation parameters applied in this invention use much lower electrical field strengths (<40 V/cm) than used in electroporation (typically >200 V/cm) for delivering RNA in cells.

Example 7

The Increased Intake of RNA Persists for at Least 24 Hours After the Electrical Stimulation The temporal effect of the electrical stimulation on the intake of the RNA is discussed in this example 7.

Figure 6:
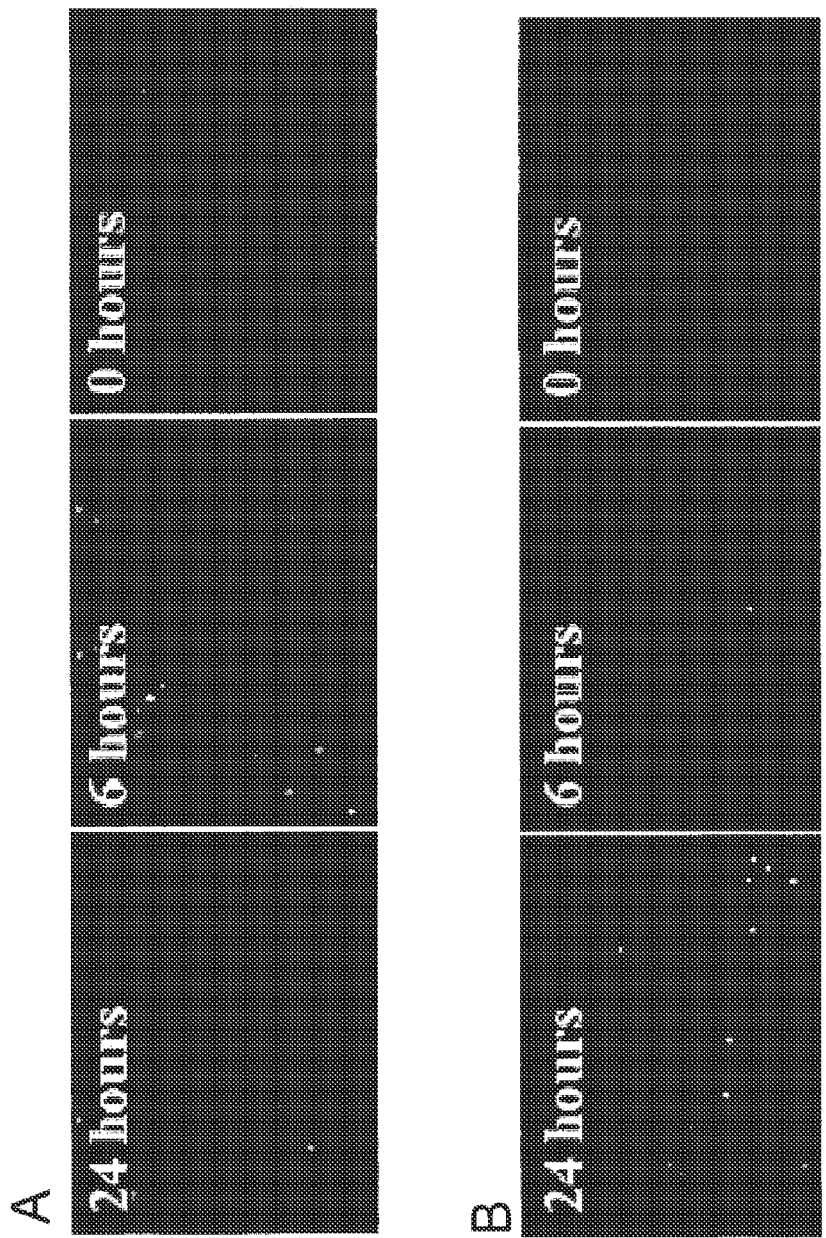
FIG. 6 demonstrates the long-term effect of electrical stimulation on the RNA intake.

The cells were cultured and electrically stimulated as described in Example 1. In one group, the RNA was added immediately after the stimulation, or six hours after the stimulation, or 24 hours after the stimulation. The cells were imaged for the uptake at 48 hours after the electrical stimulation. In this group, electrical stimulation increased the RNA intake in all three subsets of cells, as shown in FIG. 6A., indicating that the siRNA uptake in cells was possible even if the siRNA was added after a 24 hour "lag period" following application of electrical stimulation.

In another group, the RNA was added before performing the stimulation according to Example 1, and then removed 24 hours, or 6 hours or immediately after performing the stimulation. The cells were imaged for the uptake at 48 hours after the electrical stimulation. In this group, only the subset of cells where the RNA was removed 24 hours after the stimulation (but not 6 hours after the stimulation or immediately after the stimulation) demonstrated an increased intake of the RNA, as shown in FIG. 6B.

The presence of a "lag period" between the application of electrical stimulation and siRNA administration in this invention is unexpected when compared with the requirements of using electroporation for delivery of nucleic acids. As reviewed by Escoffre J M et al. 2009 (Escoffre J M, Portet T, Wasungu L, Teissie J, Rols M P, What is (still not) known of the mechanism by which electroporation mediates gene transfer and expression in cells and tissues, Molecular Biotechnology, 2009, 41: 286-295) and Prud'homme G J et al. 2006 (Prud'homme G J, Glinka Y, Khan A S, Draghia-Akli R, Electroporation-enhanced nonviral gene transfer for the prevention or treatment of immunological, endocrine and neoplastic diseases, Current Gene Therapy, 2006, 6:243-273), electroporation-mediated intracellular delivery of nucleic acids relies on the simultaneous presence of the nucleic acid during application of the electroporation parameters that transiently allow the permeation of nucleic acids across the target cell's membrane.

The data in this disclosure demonstrate that the electrical stimulation used herein ensue long-term rather than transient effects, necessary to enable intracellular uptake of RNA; the long-term cellular changes could possibly be the alteration of gene expression pattern in target cells.

Example 8

RNA Delivered After the Stimulation Retains its Biological Activity

Even though the electrical stimulation increases the intake of the RNA into the cells, the question remains whether this RNA is biologically active. This example proves that the uptaken RNA retains its biological activity.

HEK-293T cells were cultured in eight-well plates as in Example 1 and treated with 300 μsec impulses at 100 Hz and 2 V/cm for two hours. The anti-htt siRNA (GGAGTAT-TGTGGAACTTAT, SEQ ID NO: 5) at a concentration of 130 nM was added immediately before electrical stimulation.

In a control group the same siRNA at the same concentration was added to non-stimulated cells in a composition with TRANSIT-TKO® (Mirus Bio LLC, Madison, Wis.) according to manufacturer's instructions. Other control groups lacked one of the siRNA, TRANSIT-TKO® or the electric stimulation.

The cells were harvested 48 hours post-stimulation, and htt mRNA was quantified by qRT-PCR.

Figure 7:
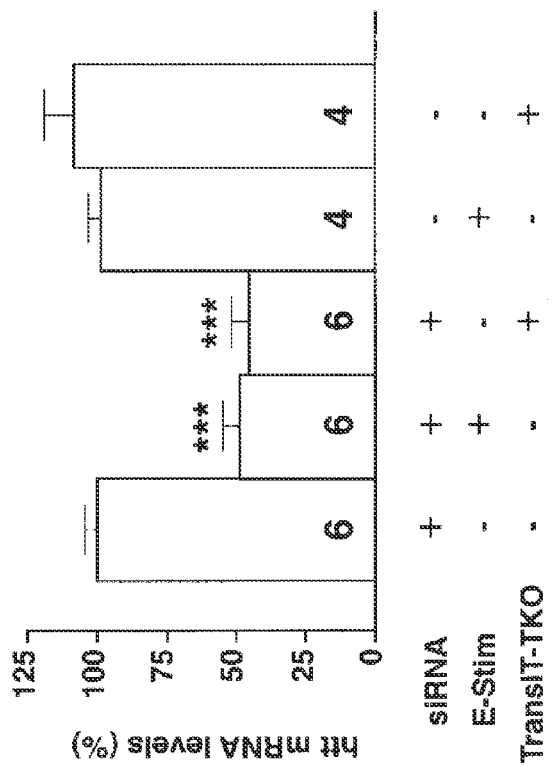
FIG. 7 demonstrates that RNA delivered according to the methods of the instant invention keeps its biologic function.

As shown in FIG. 7, the groups which received the siRNA in combination with TRANSIT-TKO® or with electrical stimulation exhibited significantly lower htt mRNA expression. In the group which received the siRNA in combination with the electrical stimulation, the htt mRNA level was about the same as in the group which received the siRNA in combination with TRANSIT-TKO®.

Accordingly, the siRNA delivered in conjunction with the electrical stimulation according to the instant invention retains its biological function.

Example 9

Electric Stimulation Improves Uptake of RNA in Neuronal Cells In Vivo

The next question which needed to be resolved was whether the results obtained in vitro reasonably correlate with the results obtainable in vivo. Thus, in the remaining examples, the in vivo data are discussed.

Figure 8:
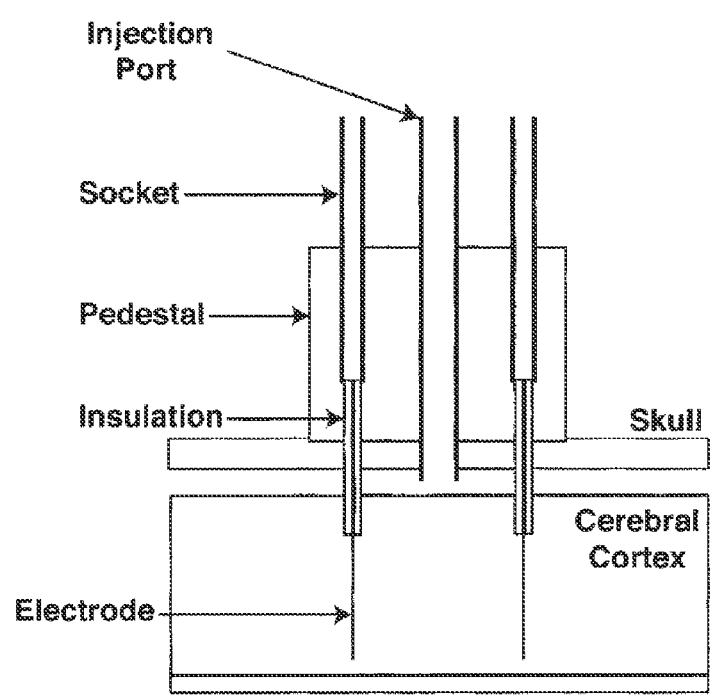
FIG. 8 is a schematic illustration of a device according to one embodiment of the instant invention.
Figure 9:
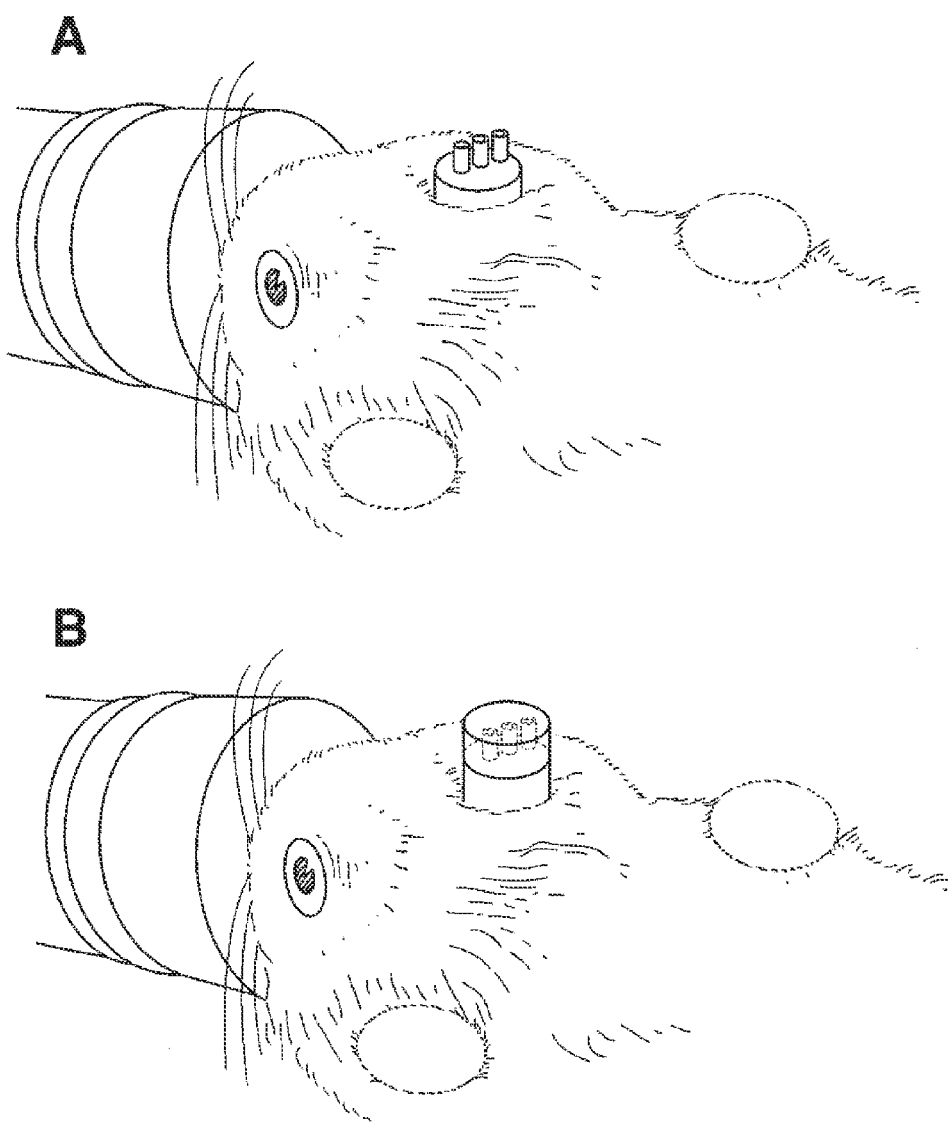
FIG. 9 is a photographic image of a rat with an implanted device without a cap (FIG. 9A) and with the cap (FIG. 9B).

The device illustrated in FIG. 8 has been prepared and implanted into a brain of Sprague-Dawley rats weighing over 250 gm and over 8 weeks old. FIG. 9A. After the implantation of the device, rats were kept in cages (one rat per cage, at light-dark cycle 12 hr:12 hr, switching at 6 AM and 6 PM having unlimited access to food and water. After the surgery, the rats were left to recover for at least 1 hour in a cage with its floor maintained at 37° C. After the recovery, the rats were in their respective home cages and the device of the instant invention was capped as shown in FIG. 9B.

At the time of the experiment, and 22 hours after electrical stimulation, 4 μl of a solution containing siRNA (siGLO Red, purchased from Dharmacon, Inc. (Lafayette, Colo.)), labeled with fluorophore DY-547 in sterile saline, pH=7.4 at a concentration, of 2.5 μg/μl, was injected using a stereotaxically guided syringe with a 33 gauge needle, at a rate of 0.25 μl/min.

Figure 10:
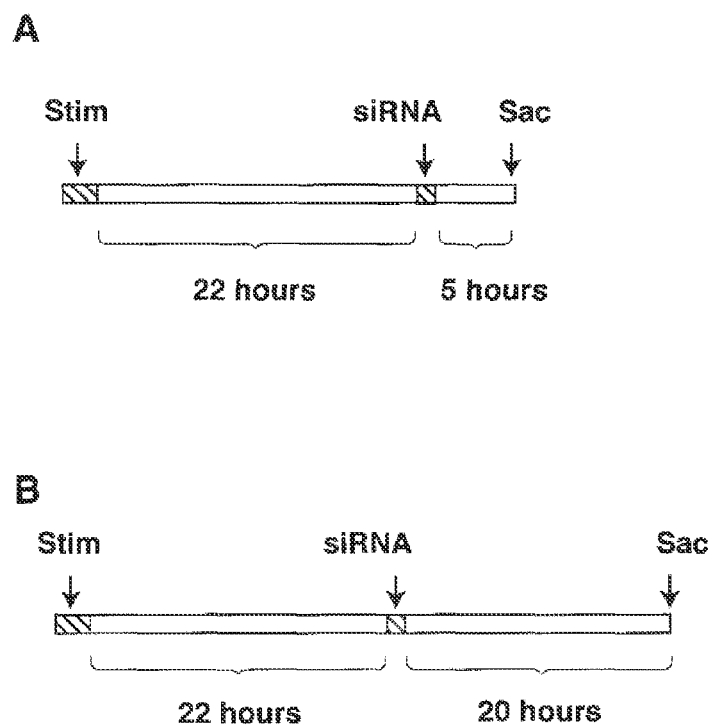
FIGS. 10A and 10B illustrate two protocols used for investigation of the RNA uptake in vivo.

The rats were randomly split into the following groups:
a) Voltage groups: 0, 2, 6, 10 V/cm (4 groups);
b) Within each of the four groups, further treatment according to each of the protocols illustrated in FIGS. 10A and 10B.

Electrical stimulation was conducted with the rats in a conscious state. No gross behavioral abnormalities indicating pain or discomfort were observed during the treatment except that the rats when stimulated in the later half of their light cycle (but not in the first half of their light cycle) at 10 V/cm exhibited a mild periodic movement of their contralateral forelimb.

Three rats per group were used. The parameters of the electrical stimulation (other than voltage) were as follows:

a) Frequency: 100 Hz for each group;
b) Duration of stimulation: 2 hours for each group;
c) Pulse width: 0.3 msec for each group;
d) 4 µl of a solution containing siRNA (siGLO Red, purchased from Dharmacon, Inc. (Lafayette, Colo.)), labeled with fluorophore DY-547 in sterile saline, pH=7.4 at a concentration of 2.5 µg/µl was stereotaxically injected. The site was determined as the mid-point of the area between the uninsulated electrodes, with the following coordinates relative to Bregma: anterior-posterior: ~0.7 mm; medial-lateral: ~3.2 mm; dorso-ventral: ~−2.0 mm.

Figure 11A:
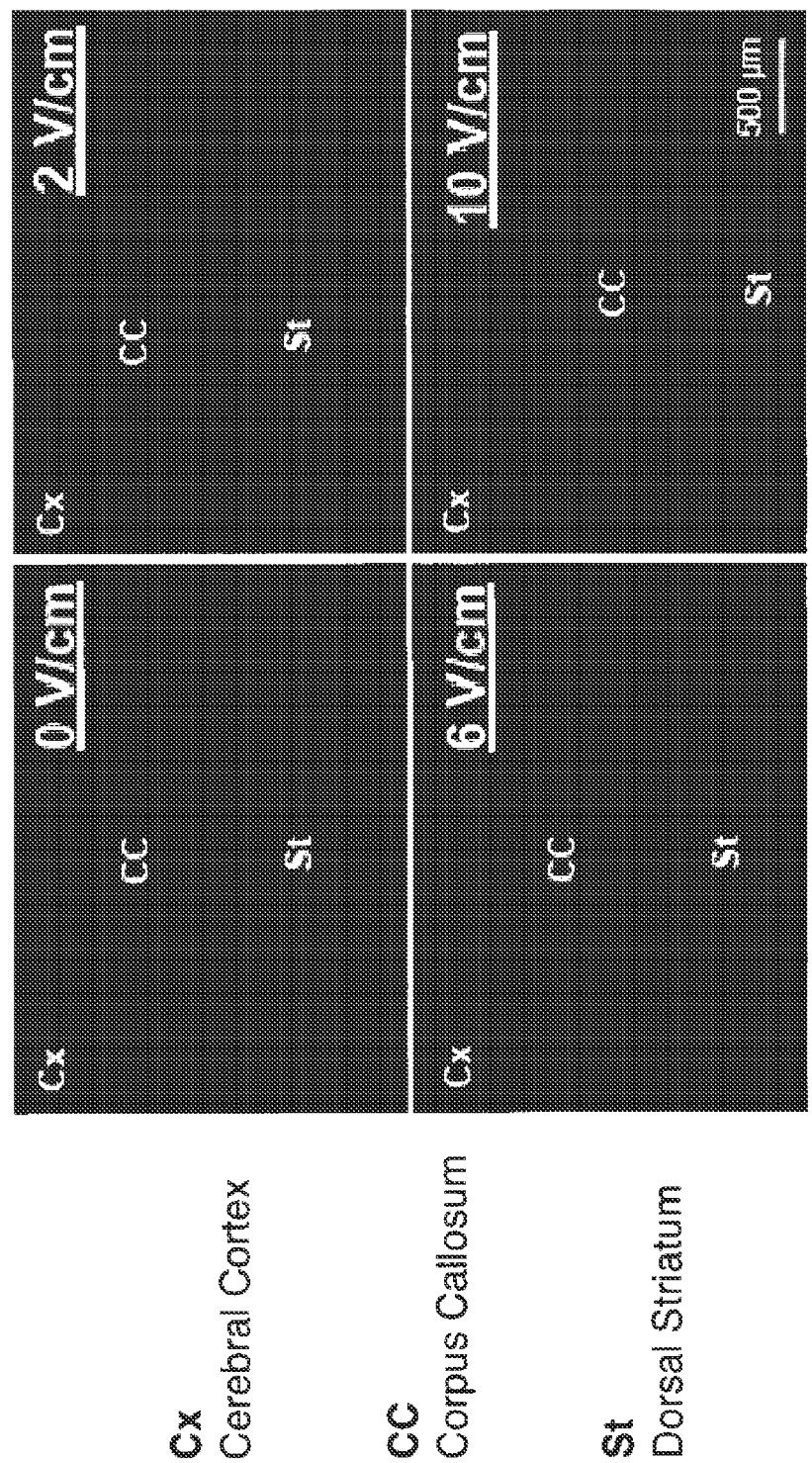
FIG. 11 demonstrates that electrical stimulation improves local uptake of dsRNA in neuronal cells in vivo.
Figure 11B:
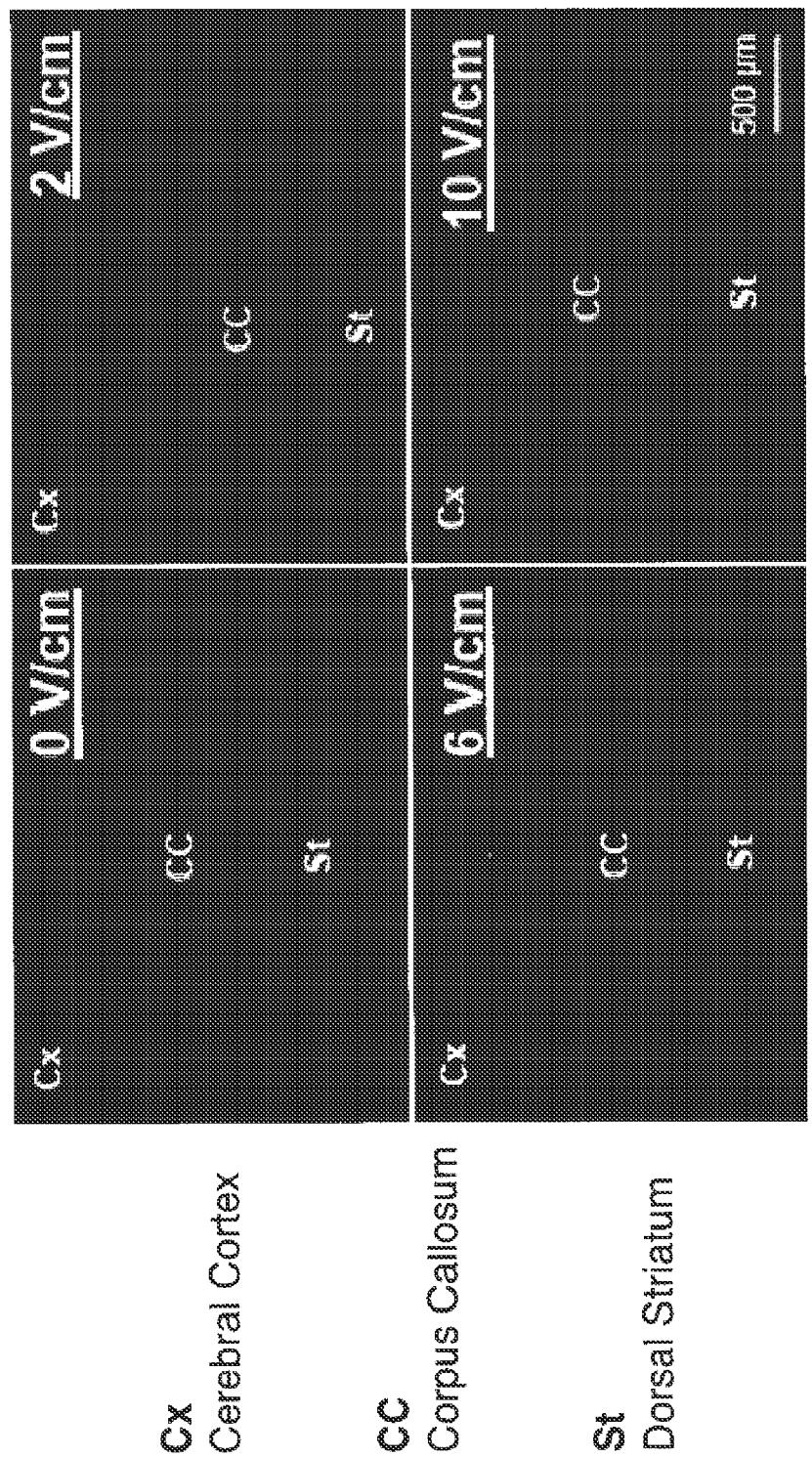

As shown in FIG. 11A, fluorescence imaging of brain sections revealed the intake of the RNA into the cells at five hours after the RNA injection at 2 V/cm, 6 V/cm, and, to a lesser extent, at 10 V/cm.

The intake of the RNA at 20 hours was not as well pronounced, but it was somewhat increased at 2 V/cm, 6 V/cm, and, to a lesser extent, 10 V/cm.

Figure 11C:
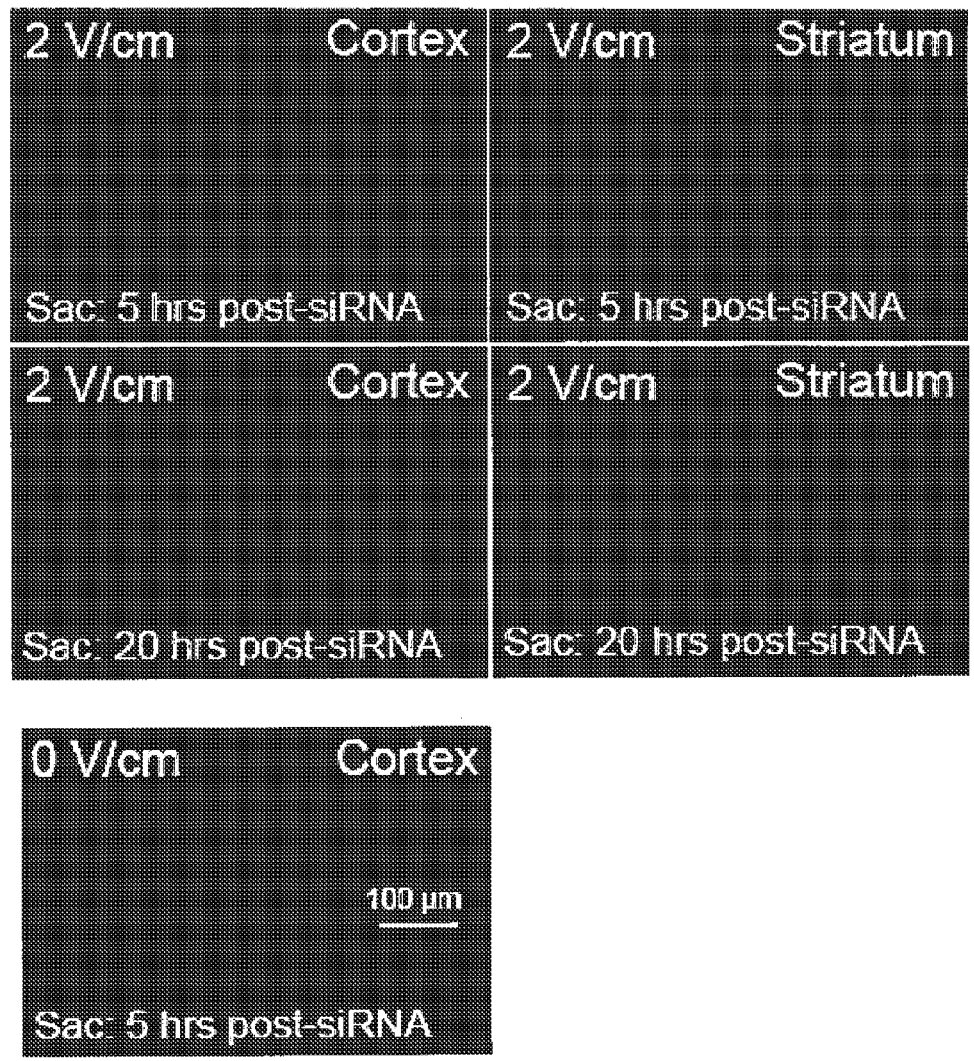

The greater magnification (20×), as shown in FIG. 11C revealed an intense fluorescence signal in both cortex and striatum at 5 hr post-siRNA group and 20 hr post siRNA groups who received electrical stimulation of 2 V/cm.

These data lead to several inferences. First, stimulation at 2-6 V/cm increases the uptake of siRNA that is injected for up to about 22 hours after electrical stimulation in the rat brain, and thus correlates with the results obtained in vitro. In other words, these in vivo results validate the in vitro findings by the inventors that application of low voltage and high frequency electrical stimulation facilitates the cellular uptake of siRNA that is administered after a "lag period" following stimulation.

Second, the facilitation of siRNA uptake was locally confined, dictated by the area of the electrical field. In the disclosed experiments, the local effects were as follows:
about 5 mm medio-laterally (inter-electrode distance was about 4.5 mm);
about 0.4 mm rostra-caudally (similar to the rostro-caudal distance between the electrodes); and
about 3 mm dorso-ventrally (electrode length was about 2 mm)

The electrical stimulation facilitated both the intracellular intake and extracellular distribution of the siRNA. The number of cells positive for the siRNA was increased at five hours post-siRNA injection, but only neuropil appeared positive at 20 hours post siRNA injection.

Example 10

Figure 12:
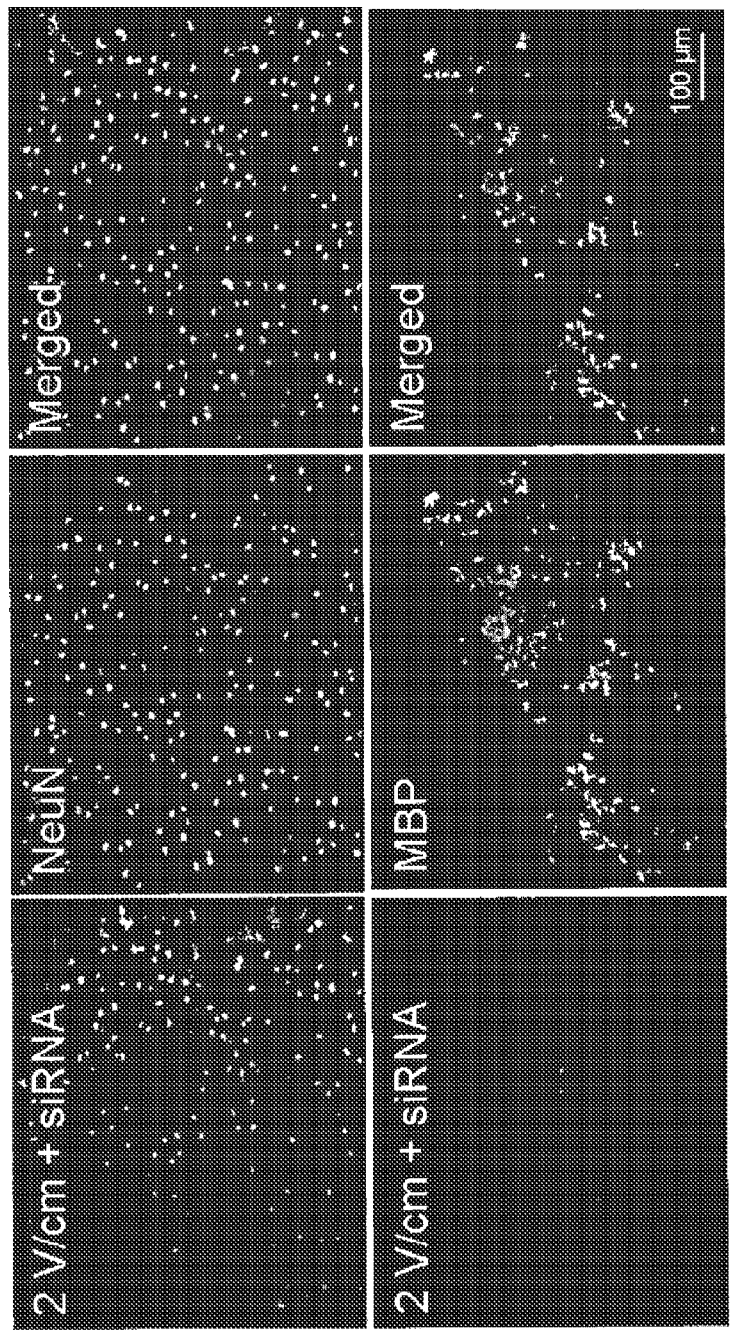
FIG. 12 demonstrates that neurons and glial cells are susceptible to pre-treatment with electric stimulation for enabling dsRNA uptake.

Neurons and Oligodendrocytes are Brain Cells Susceptible to Pre-Treatment with Electric Stimulation The inventors have further demonstrated that most of the cells visualized with the fluorophore were also visualized with NeuN and MBP (see FIG. 12), thus demonstrating that neurons and oligodendrocytes are the main cells types in the brain which are susceptible to electric stimulation treatment. Particularly, dopaminergic neurons (as determined by staining with DARPP32) also stained with fluorophore (data not shown).

Accordingly, neurons, particularly dopaminergic neurons, and oligodendrocytes are suitable targets for delivery of siRNA according to the instant methods.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Other suitable modifications and adaptations to the methods and applications described herein are suitable and may be made without departing from the scope-of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims.

The invention claimed is:

1. A method of increasing an uptake of a ribonucleic acid sequence by a cell, said cell being selected from the group consisting of neurons and glial cells, the method comprising:
   a) applying a plurality of pulses of an electric field to the cell for a time period between about two and about 24 hours;
   b) after the step a), administering the ribonucleic acid sequence to the cell;
   wherein:
      the electric field has strength of between about 0.5 V/cm and about 40 V/cm, calculated according to Formula I:

$$E = V/d$$

wherein in said formula E is the strength, V is Voltage and d is distance between electrodes.

2. The method of claim 1, wherein the frequency of said pulse is below 400 Hz.

3. The method of claim 1 or 2, wherein the duration of each member of the plurality of pulses is between about 100 μs and about 500 μs.

4. The method of claim 1 wherein the members of the plurality of pulses are uniform.

5. The method of claim 1 wherein the members of the plurality of pulses are not uniform.

6. The method of claim 1, wherein said ribonucleic acid sequence is a siRNA sequence, a shRNA sequence, an aptamer, a spiegelmer, an antimir, or a combination thereof.

7. The method of claim 6, wherein said ribonucleic acid sequence comprises at least one modified nucleotide.

8. The method of claim 6, wherein said ribonucleic acid sequence is a siRNA or a shRNA.

9. The method of claim 6, wherein said siRNA sequence or said shRNA sequence comprises a sense and an antisense strand, each having length between about 19 and about 30 nucleotides.

10. The method of claim 1 wherein
   a) the strength is between about 0.5 V/cm and about 10 V/cm, and
   b) the time period is between about 2 hours and about 22 hours.

11. The method of claim 10, wherein the strength is between about 1 V/cm and about 6 V/cm.

12. The method of claim 10 further comprising steps of
   locating a pre-determined area in a patient, said predetermined area being selected from a brain, a spinal cord, and a peripheral nerve of the patient; and
   placing a plurality of electrodes into said pre-determined area prior to applying the plurality of pulses.

13. The method of claim 12, wherein the placement of the electrodes results in a pre-determined shape of the electric field.

14. The method of claim 10, wherein the nucleic acid is administered to the pre-determined area through a catheter.

15. The method of claim 14, further comprising a step of verifying the placement of the catheter.

16. The method of claim 10, further comprising a step of verification of the placement of the electrodes.

17. The method of claim 1 wherein
   a) said cell is a neuron or a glial cell located within a nervous system of a patient,
   b) the patient is undergoing or is a suitable candidate for a deep brain stimulation or a spinal cord stimulation or a transcutaneous electric nerve stimulation, and
   c) the parameters of the electric stimulation are suitable for the deep brain stimulation, the spinal cord stimulation or the transcutaneous electric nerve stimulation.

18. The method of claim 1, wherein the ribonucleic acid sequence is administered in a composition comprising an imaging agent, the method further comprising: determining a distribution of the composition.

19. The method of claim 1, wherein step b) is conducted at least 1 minute, at least 5 minutes, at least 30 minutes, at least 45 minutes, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or 24 hours after step a) is conducted.

* * * * *

SEQUENCE LISTING

```
<160> NUMBER OF SEQ ID NOS: 507

<210> SEQ ID NO 1
<211> LENGTH: 38
<212> TYPE: DNA
<213> ORGANISM: Artificial Sequence
<220> FEATURE:
<223> OTHER INFORMATION: siRNA target

<400> SEQUENCE: 1
tgacagcagt gttgataaat gacagcagtg ttgataaa                        38

<210> SEQ ID NO 2
<211> LENGTH: 19
<212> TYPE: DNA
<213> ORGANISM: Artificial Sequence
<220> FEATURE:
<223> OTHER INFORMATION: siRNA target

<400> SEQUENCE: 2
tgacagcagt gttgataaa                                             19
```

```
<210> SEQ ID NO 3
<211> LENGTH: 19
<212> TYPE: DNA
<213> ORGANISM: Artificial Sequence
<220> FEATURE:
<223> OTHER INFORMATION: siRNA target

<400> SEQUENCE: 3
aagaacgagt gctcaataa                                                  19

<210> SEQ ID NO 4
<211> LENGTH: 19
<212> TYPE: DNA
<213> ORGANISM: Artificial Sequence
<220> FEATURE:
<223> OTHER INFORMATION: siRNA target

<400> SEQUENCE: 4
tttatgaact gacgttaca                                                  19

<210> SEQ ID NO 5
<211> LENGTH: 19
<212> TYPE: DNA
<213> ORGANISM: Artificial Sequence
<220> FEATURE:
<223> OTHER INFORMATION: siRNA target

<400> SEQUENCE: 5
ggagtattgt ggaacttat                                                  19

<210> SEQ ID NO 6
<211> LENGTH: 19
<212> TYPE: DNA
<213> ORGANISM: Artificial Sequence
<220> FEATURE:
<223> OTHER INFORMATION: siRNA target

<400> SEQUENCE: 6
gagtattgtg gaacttata                                                  19

<210> SEQ ID NO 7
<211> LENGTH: 19
<212> TYPE: DNA
<213> ORGANISM: Artificial Sequence
<220> FEATURE:
<223> OTHER INFORMATION: siRNA target

<400> SEQUENCE: 7
agaccgtgtg aatcattgt                                                  19

<210> SEQ ID NO 8
<211> LENGTH: 19
<212> TYPE: DNA
<213> ORGANISM: Artificial Sequence
<220> FEATURE:
<223> OTHER INFORMATION: siRNA target

<400> SEQUENCE: 8
ggttacagct cgagctcta                                                  19

<210> SEQ ID NO 9
<211> LENGTH: 19
<212> TYPE: DNA
<213> ORGANISM: Artificial Sequence
<220> FEATURE:
<223> OTHER INFORMATION: siRNA target
```

-continued

<400> SEQUENCE: 9
ggttttgtta aaggccttc                                                    19

<210> SEQ ID NO 10
<211> LENGTH: 27
<212> TYPE: DNA
<213> ORGANISM: Artificial Sequence
<220> FEATURE:
<223> OTHER INFORMATION: siRNA target

<400> SEQUENCE: 10
tgacagcagt gttgataaat ttgtgtt                                           27

<210> SEQ ID NO 11
<211> LENGTH: 27
<212> TYPE: DNA
<213> ORGANISM: Artificial Sequence
<220> FEATURE:
<223> OTHER INFORMATION: siRNA target

<400> SEQUENCE: 11
aagaacgagt gctcaataat gttgtca                                           27

<210> SEQ ID NO 12
<211> LENGTH: 27
<212> TYPE: DNA
<213> ORGANISM: Artificial Sequence
<220> FEATURE:
<223> OTHER INFORMATION: siRNA target

<400> SEQUENCE: 12
tttatgaact gacgttacat catacac                                           27

<210> SEQ ID NO 13
<211> LENGTH: 27
<212> TYPE: DNA
<213> ORGANISM: Artificial Sequence
<220> FEATURE:
<223> OTHER INFORMATION: siRNA target

<400> SEQUENCE: 13
ggagtattgt ggaacttata gctggag                                           27

<210> SEQ ID NO 14
<211> LENGTH: 27
<212> TYPE: DNA
<213> ORGANISM: Artificial Sequence
<220> FEATURE:
<223> OTHER INFORMATION: siRNA target

<400> SEQUENCE: 14
gagtattgtg gaacttatag ctggagg                                           27

<210> SEQ ID NO 15
<211> LENGTH: 27
<212> TYPE: DNA
<213> ORGANISM: Artificial Sequence
<220> FEATURE:
<223> OTHER INFORMATION: siRNA target

<400> SEQUENCE: 15
agaccgtgtg aatcattgtc tgacaat                                           27

<210> SEQ ID NO 16
<211> LENGTH: 27
<212> TYPE: DNA

```
<213> ORGANISM: Artificial Sequence
<220> FEATURE:
<223> OTHER INFORMATION: siRNA target

<400> SEQUENCE: 16
ggttttgtta aaggccttca tagcgaa                                          27

<210> SEQ ID NO 17
<211> LENGTH: 21
<212> TYPE: DNA
<213> ORGANISM: Artificial Sequence
<220> FEATURE:
<223> OTHER INFORMATION: siRNA target

<400> SEQUENCE: 17
aagggtgtgt atgtgcccta c                                                21

<210> SEQ ID NO 18
<211> LENGTH: 21
<212> TYPE: DNA
<213> ORGANISM: Artificial Sequence
<220> FEATURE:
<223> OTHER INFORMATION: siRNA target

<400> SEQUENCE: 18
aattggcttt gctgtcagcg c                                                21

<210> SEQ ID NO 19
<211> LENGTH: 21
<212> TYPE: DNA
<213> ORGANISM: Artificial Sequence
<220> FEATURE:
<223> OTHER INFORMATION: siRNA target

<400> SEQUENCE: 19
aagactgtgg ctacaacatt c                                                21

<210> SEQ ID NO 20
<211> LENGTH: 21
<212> TYPE: DNA
<213> ORGANISM: Artificial Sequence
<220> FEATURE:
<223> OTHER INFORMATION: siRNA target

<400> SEQUENCE: 20
aaggctgcct ggagaaagga t                                                21

<210> SEQ ID NO 21
<211> LENGTH: 21
<212> TYPE: DNA
<213> ORGANISM: Artificial Sequence
<220> FEATURE:
<223> OTHER INFORMATION: siRNA target

<400> SEQUENCE: 21
cactgaatcg gacaagttct t                                                21

<210> SEQ ID NO 22
<211> LENGTH: 21
<212> TYPE: DNA
<213> ORGANISM: Artificial Sequence
<220> FEATURE:
<223> OTHER INFORMATION: siRNA target

<400> SEQUENCE: 22
catgatcatt ggtggtatcg a                                                21
```

<210> SEQ ID NO 23
<211> LENGTH: 21
<212> TYPE: DNA
<213> ORGANISM: Artificial Sequence
<220> FEATURE:
<223> OTHER INFORMATION: siRNA target

<400> SEQUENCE: 23
catccttcct cagcaatacc t                                              21

<210> SEQ ID NO 24
<211> LENGTH: 21
<212> TYPE: DNA
<213> ORGANISM: Artificial Sequence
<220> FEATURE:
<223> OTHER INFORMATION: siRNA target

<400> SEQUENCE: 24
cagacgctca acatcctggt g                                              21

<210> SEQ ID NO 25
<211> LENGTH: 19
<212> TYPE: DNA
<213> ORGANISM: Artificial Sequence
<220> FEATURE:
<223> OTHER INFORMATION: siRNA target

<400> SEQUENCE: 25
ctacgaacct gaagcctaa                                                 19

<210> SEQ ID NO 26
<211> LENGTH: 19
<212> TYPE: DNA
<213> ORGANISM: Artificial Sequence
<220> FEATURE:
<223> OTHER INFORMATION: siRNA target

<400> SEQUENCE: 26
tcaagactac gaacctgaa                                                 19

<210> SEQ ID NO 27
<211> LENGTH: 19
<212> TYPE: DNA
<213> ORGANISM: Artificial Sequence
<220> FEATURE:
<223> OTHER INFORMATION: siRNA target

<400> SEQUENCE: 27
cattagccat ggatgtatt                                                 19

<210> SEQ ID NO 28
<211> LENGTH: 19
<212> TYPE: DNA
<213> ORGANISM: Artificial Sequence
<220> FEATURE:
<223> OTHER INFORMATION: siRNA target

<400> SEQUENCE: 28
acgaacctga agcctaaga                                                 19

<210> SEQ ID NO 29
<211> LENGTH: 19
<212> TYPE: DNA
<213> ORGANISM: Artificial Sequence
<220> FEATURE:
<223> OTHER INFORMATION: siRNA target

```
<400> SEQUENCE: 29
gtacaagtgc tcagttcca                                                      19

<210> SEQ ID NO 30
<211> LENGTH: 19
<212> TYPE: DNA
<213> ORGANISM: Artificial Sequence
<220> FEATURE:
<223> OTHER INFORMATION: siRNA target

<400> SEQUENCE: 30
gcttcaatct acgatgtta                                                      19

<210> SEQ ID NO 31
<211> LENGTH: 19
<212> TYPE: DNA
<213> ORGANISM: Artificial Sequence
<220> FEATURE:
<223> OTHER INFORMATION: siRNA target

<400> SEQUENCE: 31
ctaagtgact accacttat                                                      19

<210> SEQ ID NO 32
<211> LENGTH: 19
<212> TYPE: DNA
<213> ORGANISM: Artificial Sequence
<220> FEATURE:
<223> OTHER INFORMATION: siRNA target

<400> SEQUENCE: 32
gttcagaagt tgttagtga                                                      19

<210> SEQ ID NO 33
<211> LENGTH: 19
<212> TYPE: DNA
<213> ORGANISM: Artificial Sequence
<220> FEATURE:
<223> OTHER INFORMATION: siRNA target

<400> SEQUENCE: 33
agttgttagt gatttgcta                                                      19

<210> SEQ ID NO 34
<211> LENGTH: 19
<212> TYPE: DNA
<213> ORGANISM: Artificial Sequence
<220> FEATURE:
<223> OTHER INFORMATION: siRNA target

<400> SEQUENCE: 34
gacgtattgt gaaatttgt                                                      19

<210> SEQ ID NO 35
<211> LENGTH: 19
<212> TYPE: DNA
<213> ORGANISM: Artificial Sequence
<220> FEATURE:
<223> OTHER INFORMATION: siRNA target

<400> SEQUENCE: 35
tcatcaattt cgagcagaa                                                      19

<210> SEQ ID NO 36
<211> LENGTH: 19
<212> TYPE: DNA
```

```
<213> ORGANISM: Artificial Sequence
<220> FEATURE:
<223> OTHER INFORMATION: siRNA target

<400> SEQUENCE: 36
tgagtttgga gataataca                                                    19

<210> SEQ ID NO 37
<211> LENGTH: 19
<212> TYPE: DNA
<213> ORGANISM: Artificial Sequence
<220> FEATURE:
<223> OTHER INFORMATION: siRNA target

<400> SEQUENCE: 37
tggccgatgt gtctattga                                                    19

<210> SEQ ID NO 38
<211> LENGTH: 19
<212> TYPE: DNA
<213> ORGANISM: Artificial Sequence
<220> FEATURE:
<223> OTHER INFORMATION: siRNA target

<400> SEQUENCE: 38
cgatgtgtct attgaagat                                                    19

<210> SEQ ID NO 39
<211> LENGTH: 19
<212> TYPE: DNA
<213> ORGANISM: Artificial Sequence
<220> FEATURE:
<223> OTHER INFORMATION: siRNA target

<400> SEQUENCE: 39
gcattaaagg actgactga                                                    19

<210> SEQ ID NO 40
<211> LENGTH: 19
<212> TYPE: DNA
<213> ORGANISM: Artificial Sequence
<220> FEATURE:
<223> OTHER INFORMATION: siRNA target

<400> SEQUENCE: 40
tcgtttggct tgtggtgta                                                    19

<210> SEQ ID NO 41
<211> LENGTH: 21
<212> TYPE: DNA
<213> ORGANISM: Artificial Sequence
<220> FEATURE:
<223> OTHER INFORMATION: siRNA target

<400> SEQUENCE: 41
aatttcgagc agaaggaaag t                                                 21

<210> SEQ ID NO 42
<211> LENGTH: 21
<212> TYPE: DNA
<213> ORGANISM: Artificial Sequence
<220> FEATURE:
<223> OTHER INFORMATION: siRNA target

<400> SEQUENCE: 42
aagcattaaa ggactgactg a                                                 21
```

```
<210> SEQ ID NO 43
<211> LENGTH: 21
<212> TYPE: DNA
<213> ORGANISM: Artificial Sequence
<220> FEATURE:
<223> OTHER INFORMATION: siRNA target

<400> SEQUENCE: 43
aatgtgactg ctgacaaaga t                                              21

<210> SEQ ID NO 44
<211> LENGTH: 21
<212> TYPE: DNA
<213> ORGANISM: Artificial Sequence
<220> FEATURE:
<223> OTHER INFORMATION: siRNA target

<400> SEQUENCE: 44
aagattctgt gatctcactc t                                              21

<210> SEQ ID NO 45
<211> LENGTH: 19
<212> TYPE: DNA
<213> ORGANISM: Artificial Sequence
<220> FEATURE:
<223> OTHER INFORMATION: siRNA target

<400> SEQUENCE: 45
ccagggacct ctctctaat                                                 19

<210> SEQ ID NO 46
<211> LENGTH: 19
<212> TYPE: DNA
<213> ORGANISM: Artificial Sequence
<220> FEATURE:
<223> OTHER INFORMATION: siRNA target

<400> SEQUENCE: 46
agggacctct ctctaatca                                                 19

<210> SEQ ID NO 47
<211> LENGTH: 19
<212> TYPE: DNA
<213> ORGANISM: Artificial Sequence
<220> FEATURE:
<223> OTHER INFORMATION: siRNA target

<400> SEQUENCE: 47
gcctgtagcc catgttgta                                                 19

<210> SEQ ID NO 48
<211> LENGTH: 19
<212> TYPE: DNA
<213> ORGANISM: Artificial Sequence
<220> FEATURE:
<223> OTHER INFORMATION: siRNA target

<400> SEQUENCE: 48
tgtagcccat gttgtagca                                                 19

<210> SEQ ID NO 49
<211> LENGTH: 19
<212> TYPE: DNA
<213> ORGANISM: Artificial Sequence
<220> FEATURE:
<223> OTHER INFORMATION: siRNA target
```

-continued

<400> SEQUENCE: 49
gtgaaatgat ggcttatta                                                19

<210> SEQ ID NO 50
<211> LENGTH: 19
<212> TYPE: DNA
<213> ORGANISM: Artificial Sequence
<220> FEATURE:
<223> OTHER INFORMATION: siRNA target

<400> SEQUENCE: 50
cgatgcacct gtacgatca                                                19

<210> SEQ ID NO 51
<211> LENGTH: 19
<212> TYPE: DNA
<213> ORGANISM: Artificial Sequence
<220> FEATURE:
<223> OTHER INFORMATION: siRNA target

<400> SEQUENCE: 51
taactgactt caccatgca                                                19

<210> SEQ ID NO 52
<211> LENGTH: 19
<212> TYPE: DNA
<213> ORGANISM: Artificial Sequence
<220> FEATURE:
<223> OTHER INFORMATION: siRNA target

<400> SEQUENCE: 52
gaacctatct tcttcgaca                                                19

<210> SEQ ID NO 53
<211> LENGTH: 19
<212> TYPE: DNA
<213> ORGANISM: Artificial Sequence
<220> FEATURE:
<223> OTHER INFORMATION: siRNA target

<400> SEQUENCE: 53
cagaagaaca gaagaaata                                                19

<210> SEQ ID NO 54
<211> LENGTH: 19
<212> TYPE: DNA
<213> ORGANISM: Artificial Sequence
<220> FEATURE:
<223> OTHER INFORMATION: siRNA target

<400> SEQUENCE: 54
tgaagaagct aaacagaaa                                                19

<210> SEQ ID NO 55
<211> LENGTH: 19
<212> TYPE: DNA
<213> ORGANISM: Artificial Sequence
<220> FEATURE:
<223> OTHER INFORMATION: siRNA target

<400> SEQUENCE: 55
ggtaagagct acaaagaat                                                19

<210> SEQ ID NO 56
<211> LENGTH: 19
<212> TYPE: DNA

```
<213> ORGANISM: Artificial Sequence
<220> FEATURE:
<223> OTHER INFORMATION: siRNA target

<400> SEQUENCE: 56
aggcagagga agagatata                                              19

<210> SEQ ID NO 57
<211> LENGTH: 19
<212> TYPE: DNA
<213> ORGANISM: Artificial Sequence
<220> FEATURE:
<223> OTHER INFORMATION: siRNA target

<400> SEQUENCE: 57
agacagagat gatgattta                                              19

<210> SEQ ID NO 58
<211> LENGTH: 19
<212> TYPE: DNA
<213> ORGANISM: Artificial Sequence
<220> FEATURE:
<223> OTHER INFORMATION: siRNA target

<400> SEQUENCE: 58
gggaaagaca gcaaggaaa                                              19

<210> SEQ ID NO 59
<211> LENGTH: 19
<212> TYPE: DNA
<213> ORGANISM: Artificial Sequence
<220> FEATURE:
<223> OTHER INFORMATION: siRNA target

<400> SEQUENCE: 59
gaacaagaca gaacagaaa                                              19

<210> SEQ ID NO 60
<211> LENGTH: 19
<212> TYPE: DNA
<213> ORGANISM: Artificial Sequence
<220> FEATURE:
<223> OTHER INFORMATION: siRNA target

<400> SEQUENCE: 60
gtgaagaaga ctttagaaa                                              19

<210> SEQ ID NO 61
<211> LENGTH: 19
<212> TYPE: DNA
<213> ORGANISM: Artificial Sequence
<220> FEATURE:
<223> OTHER INFORMATION: siRNA target

<400> SEQUENCE: 61
ccaaagattt ccagggaga                                              19

<210> SEQ ID NO 62
<211> LENGTH: 19
<212> TYPE: DNA
<213> ORGANISM: Artificial Sequence
<220> FEATURE:
<223> OTHER INFORMATION: siRNA target

<400> SEQUENCE: 62
taacatagag tcagggaaa                                              19
```

```
<210> SEQ ID NO 63
<211> LENGTH: 19
<212> TYPE: DNA
<213> ORGANISM: Artificial Sequence
<220> FEATURE:
<223> OTHER INFORMATION: siRNA target

<400> SEQUENCE: 63
gaaagaagaa acagaagaa                                              19

<210> SEQ ID NO 64
<211> LENGTH: 19
<212> TYPE: DNA
<213> ORGANISM: Artificial Sequence
<220> FEATURE:
<223> OTHER INFORMATION: siRNA target

<400> SEQUENCE: 64
ggagataaga caagcagaa                                              19

<210> SEQ ID NO 65
<211> LENGTH: 19
<212> TYPE: DNA
<213> ORGANISM: Artificial Sequence
<220> FEATURE:
<223> OTHER INFORMATION: siRNA target

<400> SEQUENCE: 65
ctgaatacta agaaggaaa                                              19

<210> SEQ ID NO 66
<211> LENGTH: 19
<212> TYPE: DNA
<213> ORGANISM: Artificial Sequence
<220> FEATURE:
<223> OTHER INFORMATION: siRNA target

<400> SEQUENCE: 66
gagaagaagc agaggctga                                              19

<210> SEQ ID NO 67
<211> LENGTH: 19
<212> TYPE: DNA
<213> ORGANISM: Artificial Sequence
<220> FEATURE:
<223> OTHER INFORMATION: siRNA target

<400> SEQUENCE: 67
gaaagatgat gatgaagaa                                              19

<210> SEQ ID NO 68
<211> LENGTH: 19
<212> TYPE: DNA
<213> ORGANISM: Artificial Sequence
<220> FEATURE:
<223> OTHER INFORMATION: siRNA target

<400> SEQUENCE: 68
tgggaaacct gaagcataa                                              19

<210> SEQ ID NO 69
<211> LENGTH: 19
<212> TYPE: DNA
<213> ORGANISM: Artificial Sequence
<220> FEATURE:
<223> OTHER INFORMATION: siRNA target
```

```
<400> SEQUENCE: 69
gaacacagtt ggtttgaaa                                              19

<210> SEQ ID NO 70
<211> LENGTH: 19
<212> TYPE: DNA
<213> ORGANISM: Artificial Sequence
<220> FEATURE:
<223> OTHER INFORMATION: siRNA target

<400> SEQUENCE: 70
tgacagaaga acagaagaa                                              19

<210> SEQ ID NO 71
<211> LENGTH: 19
<212> TYPE: DNA
<213> ORGANISM: Artificial Sequence
<220> FEATURE:
<223> OTHER INFORMATION: siRNA target

<400> SEQUENCE: 71
aagaagaagc tgaggcaat                                              19

<210> SEQ ID NO 72
<211> LENGTH: 19
<212> TYPE: DNA
<213> ORGANISM: Artificial Sequence
<220> FEATURE:
<223> OTHER INFORMATION: siRNA target

<400> SEQUENCE: 72
tttcaaaggc agaggaaga                                              19

<210> SEQ ID NO 73
<211> LENGTH: 19
<212> TYPE: DNA
<213> ORGANISM: Artificial Sequence
<220> FEATURE:
<223> OTHER INFORMATION: siRNA target

<400> SEQUENCE: 73
cttgaagagt ccagacaaa                                              19

<210> SEQ ID NO 74
<211> LENGTH: 19
<212> TYPE: DNA
<213> ORGANISM: Artificial Sequence
<220> FEATURE:
<223> OTHER INFORMATION: siRNA target

<400> SEQUENCE: 74
gctaaagaaa gaagaaaca                                              19

<210> SEQ ID NO 75
<211> LENGTH: 19
<212> TYPE: DNA
<213> ORGANISM: Artificial Sequence
<220> FEATURE:
<223> OTHER INFORMATION: siRNA target

<400> SEQUENCE: 75
agaagaaaca gaagaaaga                                              19

<210> SEQ ID NO 76
<211> LENGTH: 19
<212> TYPE: DNA
```

```
<213> ORGANISM: Artificial Sequence
<220> FEATURE:
<223> OTHER INFORMATION: siRNA target

<400> SEQUENCE: 76
gctgagaaat tgtcgaaat                                                    19

<210> SEQ ID NO 77
<211> LENGTH: 19
<212> TYPE: DNA
<213> ORGANISM: Artificial Sequence
<220> FEATURE:
<223> OTHER INFORMATION: siRNA target

<400> SEQUENCE: 77
gagcaagcat attaacaaa                                                    19

<210> SEQ ID NO 78
<211> LENGTH: 19
<212> TYPE: DNA
<213> ORGANISM: Artificial Sequence
<220> FEATURE:
<223> OTHER INFORMATION: siRNA target

<400> SEQUENCE: 78
cataaaagat ggagacaga                                                    19

<210> SEQ ID NO 79
<211> LENGTH: 19
<212> TYPE: DNA
<213> ORGANISM: Artificial Sequence
<220> FEATURE:
<223> OTHER INFORMATION: siRNA target

<400> SEQUENCE: 79
taacaaagcc agacaaaga                                                    19

<210> SEQ ID NO 80
<211> LENGTH: 19
<212> TYPE: DNA
<213> ORGANISM: Artificial Sequence
<220> FEATURE:
<223> OTHER INFORMATION: siRNA target

<400> SEQUENCE: 80
aaaggaagac aaagggaaa                                                    19

<210> SEQ ID NO 81
<211> LENGTH: 19
<212> TYPE: DNA
<213> ORGANISM: Artificial Sequence
<220> FEATURE:
<223> OTHER INFORMATION: siRNA target

<400> SEQUENCE: 81
aaagggagat gctgagaaa                                                    19

<210> SEQ ID NO 82
<211> LENGTH: 19
<212> TYPE: DNA
<213> ORGANISM: Artificial Sequence
<220> FEATURE:
<223> OTHER INFORMATION: siRNA target

<400> SEQUENCE: 82
taacaaacac tgtggaaga                                                    19
```

```
<210> SEQ ID NO 83
<211> LENGTH: 19
<212> TYPE: DNA
<213> ORGANISM: Artificial Sequence
<220> FEATURE:
<223> OTHER INFORMATION: siRNA target

<400> SEQUENCE: 83
agtattgaac aaagggaaa                                              19

<210> SEQ ID NO 84
<211> LENGTH: 19
<212> TYPE: DNA
<213> ORGANISM: Artificial Sequence
<220> FEATURE:
<223> OTHER INFORMATION: siRNA target

<400> SEQUENCE: 84
aggcgaagca gcagaacaa                                              19

<210> SEQ ID NO 85
<211> LENGTH: 19
<212> TYPE: DNA
<213> ORGANISM: Artificial Sequence
<220> FEATURE:
<223> OTHER INFORMATION: siRNA target

<400> SEQUENCE: 85
tagcagatgt ggaaggatt                                              19

<210> SEQ ID NO 86
<211> LENGTH: 19
<212> TYPE: DNA
<213> ORGANISM: Artificial Sequence
<220> FEATURE:
<223> OTHER INFORMATION: siRNA target

<400> SEQUENCE: 86
aaacaaacct tacgtgaat                                              19

<210> SEQ ID NO 87
<211> LENGTH: 19
<212> TYPE: DNA
<213> ORGANISM: Artificial Sequence
<220> FEATURE:
<223> OTHER INFORMATION: siRNA target

<400> SEQUENCE: 87
aaatatgaat gctgaggaa                                              19

<210> SEQ ID NO 88
<211> LENGTH: 19
<212> TYPE: DNA
<213> ORGANISM: Artificial Sequence
<220> FEATURE:
<223> OTHER INFORMATION: siRNA target

<400> SEQUENCE: 88
ccaaagaaga aagaaaga                                               19

<210> SEQ ID NO 89
<211> LENGTH: 19
<212> TYPE: DNA
<213> ORGANISM: Artificial Sequence
<220> FEATURE:
<223> OTHER INFORMATION: siRNA target
```

```
<400> SEQUENCE: 89
ctgacaaact gcatattta                                               19

<210> SEQ ID NO 90
<211> LENGTH: 19
<212> TYPE: DNA
<213> ORGANISM: Artificial Sequence
<220> FEATURE:
<223> OTHER INFORMATION: siRNA target

<400> SEQUENCE: 90
agggagatgc tgagaaatt                                               19

<210> SEQ ID NO 91
<211> LENGTH: 19
<212> TYPE: DNA
<213> ORGANISM: Artificial Sequence
<220> FEATURE:
<223> OTHER INFORMATION: siRNA target

<400> SEQUENCE: 91
cattgaacat gctgattaa                                               19

<210> SEQ ID NO 92
<211> LENGTH: 19
<212> TYPE: DNA
<213> ORGANISM: Artificial Sequence
<220> FEATURE:
<223> OTHER INFORMATION: siRNA target

<400> SEQUENCE: 92
gcatgcagct ctttggtaa                                               19

<210> SEQ ID NO 93
<211> LENGTH: 19
<212> TYPE: DNA
<213> ORGANISM: Artificial Sequence
<220> FEATURE:
<223> OTHER INFORMATION: siRNA target

<400> SEQUENCE: 93
agacaatctt acagcaatt                                               19

<210> SEQ ID NO 94
<211> LENGTH: 19
<212> TYPE: DNA
<213> ORGANISM: Artificial Sequence
<220> FEATURE:
<223> OTHER INFORMATION: siRNA target

<400> SEQUENCE: 94
aagaagaccc tgatgcaaa                                               19

<210> SEQ ID NO 95
<211> LENGTH: 19
<212> TYPE: DNA
<213> ORGANISM: Artificial Sequence
<220> FEATURE:
<223> OTHER INFORMATION: siRNA target

<400> SEQUENCE: 95
ggaagacagt gatggtcaa                                               19

<210> SEQ ID NO 96
<211> LENGTH: 19
<212> TYPE: DNA
```

```
<213> ORGANISM: Artificial Sequence
<220> FEATURE:
<223> OTHER INFORMATION: siRNA target

<400> SEQUENCE: 96
cagacaagat cttcactta                                              19

<210> SEQ ID NO 97
<211> LENGTH: 19
<212> TYPE: DNA
<213> ORGANISM: Artificial Sequence
<220> FEATURE:
<223> OTHER INFORMATION: siRNA target

<400> SEQUENCE: 97
agccagacaa agagaaata                                              19

<210> SEQ ID NO 98
<211> LENGTH: 19
<212> TYPE: DNA
<213> ORGANISM: Artificial Sequence
<220> FEATURE:
<223> OTHER INFORMATION: siRNA target

<400> SEQUENCE: 98
cttcgaactt tcagagtat                                              19

<210> SEQ ID NO 99
<211> LENGTH: 19
<212> TYPE: DNA
<213> ORGANISM: Artificial Sequence
<220> FEATURE:
<223> OTHER INFORMATION: siRNA target

<400> SEQUENCE: 99
gagtagagca agcatatta                                              19

<210> SEQ ID NO 100
<211> LENGTH: 19
<212> TYPE: DNA
<213> ORGANISM: Artificial Sequence
<220> FEATURE:
<223> OTHER INFORMATION: siRNA target

<400> SEQUENCE: 100
tgtacttgct ataggaaat                                              19

<210> SEQ ID NO 101
<211> LENGTH: 19
<212> TYPE: DNA
<213> ORGANISM: Artificial Sequence
<220> FEATURE:
<223> OTHER INFORMATION: siRNA target

<400> SEQUENCE: 101
ggtcaagcta tgtgcctta                                              19

<210> SEQ ID NO 102
<211> LENGTH: 19
<212> TYPE: DNA
<213> ORGANISM: Artificial Sequence
<220> FEATURE:
<223> OTHER INFORMATION: siRNA target

<400> SEQUENCE: 102
gaaacaaacc ttacgtgaa                                              19
```

```
<210> SEQ ID NO 103
<211> LENGTH: 19
<212> TYPE: DNA
<213> ORGANISM: Artificial Sequence
<220> FEATURE:
<223> OTHER INFORMATION: siRNA target

<400> SEQUENCE: 103
gattatggct acacgagct                                               19

<210> SEQ ID NO 104
<211> LENGTH: 19
<212> TYPE: DNA
<213> ORGANISM: Artificial Sequence
<220> FEATURE:
<223> OTHER INFORMATION: siRNA target

<400> SEQUENCE: 104
gatggattct cttcgttca                                               19

<210> SEQ ID NO 105
<211> LENGTH: 19
<212> TYPE: DNA
<213> ORGANISM: Artificial Sequence
<220> FEATURE:
<223> OTHER INFORMATION: siRNA target

<400> SEQUENCE: 105
tgtttcagct cttcgaact                                               19

<210> SEQ ID NO 106
<211> LENGTH: 19
<212> TYPE: DNA
<213> ORGANISM: Artificial Sequence
<220> FEATURE:
<223> OTHER INFORMATION: siRNA target

<400> SEQUENCE: 106
ccgacattgt ggacttaca                                               19

<210> SEQ ID NO 107
<211> LENGTH: 19
<212> TYPE: DNA
<213> ORGANISM: Artificial Sequence
<220> FEATURE:
<223> OTHER INFORMATION: siRNA target

<400> SEQUENCE: 107
gcttagatac cttcatgaa                                               19

<210> SEQ ID NO 108
<211> LENGTH: 19
<212> TYPE: DNA
<213> ORGANISM: Artificial Sequence
<220> FEATURE:
<223> OTHER INFORMATION: siRNA target

<400> SEQUENCE: 108
gggaacaaga ccagagttt                                               19

<210> SEQ ID NO 109
<211> LENGTH: 19
<212> TYPE: DNA
<213> ORGANISM: Artificial Sequence
<220> FEATURE:
<223> OTHER INFORMATION: siRNA target
```

```
<400> SEQUENCE: 109
agattgacct ggagaagta                                               19

<210> SEQ ID NO 110
<211> LENGTH: 19
<212> TYPE: DNA
<213> ORGANISM: Artificial Sequence
<220> FEATURE:
<223> OTHER INFORMATION: siRNA target

<400> SEQUENCE: 110
ctgctggcct ggagggaaa                                               19

<210> SEQ ID NO 111
<211> LENGTH: 19
<212> TYPE: DNA
<213> ORGANISM: Artificial Sequence
<220> FEATURE:
<223> OTHER INFORMATION: siRNA target

<400> SEQUENCE: 111
gcttaatgaa tgaggatga                                               19

<210> SEQ ID NO 112
<211> LENGTH: 19
<212> TYPE: DNA
<213> ORGANISM: Artificial Sequence
<220> FEATURE:
<223> OTHER INFORMATION: siRNA target

<400> SEQUENCE: 112
cagcagaagt acacagtga                                               19

<210> SEQ ID NO 113
<211> LENGTH: 19
<212> TYPE: DNA
<213> ORGANISM: Artificial Sequence
<220> FEATURE:
<223> OTHER INFORMATION: siRNA target

<400> SEQUENCE: 113
ggacattgtt gttagcgaa                                               19

<210> SEQ ID NO 114
<211> LENGTH: 19
<212> TYPE: DNA
<213> ORGANISM: Artificial Sequence
<220> FEATURE:
<223> OTHER INFORMATION: siRNA target

<400> SEQUENCE: 114
acttaaagct ggttcatat                                               19

<210> SEQ ID NO 115
<211> LENGTH: 19
<212> TYPE: DNA
<213> ORGANISM: Artificial Sequence
<220> FEATURE:
<223> OTHER INFORMATION: siRNA target

<400> SEQUENCE: 115
tgacagagga tgagagtct                                               19

<210> SEQ ID NO 116
<211> LENGTH: 19
<212> TYPE: DNA
```

```
<213> ORGANISM: Artificial Sequence
<220> FEATURE:
<223> OTHER INFORMATION: siRNA target

<400> SEQUENCE: 116
ctgcagagct tgaaggcca                                              19

<210> SEQ ID NO 117
<211> LENGTH: 19
<212> TYPE: DNA
<213> ORGANISM: Artificial Sequence
<220> FEATURE:
<223> OTHER INFORMATION: siRNA target

<400> SEQUENCE: 117
gagctgtaca ggagactaa                                              19

<210> SEQ ID NO 118
<211> LENGTH: 19
<212> TYPE: DNA
<213> ORGANISM: Artificial Sequence
<220> FEATURE:
<223> OTHER INFORMATION: siRNA target

<400> SEQUENCE: 118
gagaagaaag tgcgagtga                                              19

<210> SEQ ID NO 119
<211> LENGTH: 19
<212> TYPE: DNA
<213> ORGANISM: Artificial Sequence
<220> FEATURE:
<223> OTHER INFORMATION: siRNA target

<400> SEQUENCE: 119
ggagaagtac agcgagcaa                                              19

<210> SEQ ID NO 120
<211> LENGTH: 19
<212> TYPE: DNA
<213> ORGANISM: Artificial Sequence
<220> FEATURE:
<223> OTHER INFORMATION: siRNA target

<400> SEQUENCE: 120
agaaagtgcg agtgatcta                                              19

<210> SEQ ID NO 121
<211> LENGTH: 19
<212> TYPE: DNA
<213> ORGANISM: Artificial Sequence
<220> FEATURE:
<223> OTHER INFORMATION: siRNA target

<400> SEQUENCE: 121
gaaagagcgc cttgggaca                                              19

<210> SEQ ID NO 122
<211> LENGTH: 19
<212> TYPE: DNA
<213> ORGANISM: Artificial Sequence
<220> FEATURE:
<223> OTHER INFORMATION: siRNA target

<400> SEQUENCE: 122
gcttcaaggc cctggatga                                              19
```

<210> SEQ ID NO 123
<211> LENGTH: 19
<212> TYPE: DNA
<213> ORGANISM: Artificial Sequence
<220> FEATURE:
<223> OTHER INFORMATION: siRNA target

<400> SEQUENCE: 123
ggttacagac ggaagaaga                                                    19

<210> SEQ ID NO 124
<211> LENGTH: 19
<212> TYPE: DNA
<213> ORGANISM: Artificial Sequence
<220> FEATURE:
<223> OTHER INFORMATION: siRNA target

<400> SEQUENCE: 124
tgatgaatct cctccgaaa                                                    19

<210> SEQ ID NO 125
<211> LENGTH: 19
<212> TYPE: DNA
<213> ORGANISM: Artificial Sequence
<220> FEATURE:
<223> OTHER INFORMATION: siRNA target

<400> SEQUENCE: 125
aagtgaaact cctggtaga                                                    19

<210> SEQ ID NO 126
<211> LENGTH: 19
<212> TYPE: DNA
<213> ORGANISM: Artificial Sequence
<220> FEATURE:
<223> OTHER INFORMATION: siRNA target

<400> SEQUENCE: 126
ggaaacaggt gagcagatt                                                    19

<210> SEQ ID NO 127
<211> LENGTH: 19
<212> TYPE: DNA
<213> ORGANISM: Artificial Sequence
<220> FEATURE:
<223> OTHER INFORMATION: siRNA target

<400> SEQUENCE: 127
gcaagttaaa tgagggcca                                                    19

<210> SEQ ID NO 128
<211> LENGTH: 19
<212> TYPE: DNA
<213> ORGANISM: Artificial Sequence
<220> FEATURE:
<223> OTHER INFORMATION: siRNA target

<400> SEQUENCE: 128
gaagaaagtg cgagtgatc                                                    19

<210> SEQ ID NO 129
<211> LENGTH: 19
<212> TYPE: DNA
<213> ORGANISM: Artificial Sequence
<220> FEATURE:
<223> OTHER INFORMATION: siRNA target

<400> SEQUENCE: 129
atgaatgcct ctcgactta                                                19

<210> SEQ ID NO 130
<211> LENGTH: 19
<212> TYPE: DNA
<213> ORGANISM: Artificial Sequence
<220> FEATURE:
<223> OTHER INFORMATION: siRNA target

<400> SEQUENCE: 130
gggcctggga aatgaaaga                                                19

<210> SEQ ID NO 131
<211> LENGTH: 19
<212> TYPE: DNA
<213> ORGANISM: Artificial Sequence
<220> FEATURE:
<223> OTHER INFORMATION: siRNA target

<400> SEQUENCE: 131
gcgaagactt gaatggaac                                                19

<210> SEQ ID NO 132
<211> LENGTH: 19
<212> TYPE: DNA
<213> ORGANISM: Artificial Sequence
<220> FEATURE:
<223> OTHER INFORMATION: siRNA target

<400> SEQUENCE: 132
ccaataatct taacagtgt                                                19

<210> SEQ ID NO 133
<211> LENGTH: 19
<212> TYPE: DNA
<213> ORGANISM: Artificial Sequence
<220> FEATURE:
<223> OTHER INFORMATION: siRNA target

<400> SEQUENCE: 133
ttcaagagcc caagaggaa                                                19

<210> SEQ ID NO 134
<211> LENGTH: 19
<212> TYPE: DNA
<213> ORGANISM: Artificial Sequence
<220> FEATURE:
<223> OTHER INFORMATION: siRNA target

<400> SEQUENCE: 134
gggaaatgga gcaggctgt                                                19

<210> SEQ ID NO 135
<211> LENGTH: 19
<212> TYPE: DNA
<213> ORGANISM: Artificial Sequence
<220> FEATURE:
<223> OTHER INFORMATION: siRNA target

<400> SEQUENCE: 135
agaccgacat tgtggactt                                                19

<210> SEQ ID NO 136
<211> LENGTH: 19
<212> TYPE: DNA

```
<213> ORGANISM: Artificial Sequence
<220> FEATURE:
<223> OTHER INFORMATION: siRNA target

<400> SEQUENCE: 136
tacaggagac taagggaaa                                                19

<210> SEQ ID NO 137
<211> LENGTH: 19
<212> TYPE: DNA
<213> ORGANISM: Artificial Sequence
<220> FEATURE:
<223> OTHER INFORMATION: siRNA target

<400> SEQUENCE: 137
gaagaggtgg tgagcttaa                                                19

<210> SEQ ID NO 138
<211> LENGTH: 19
<212> TYPE: DNA
<213> ORGANISM: Artificial Sequence
<220> FEATURE:
<223> OTHER INFORMATION: siRNA target

<400> SEQUENCE: 138
gggaaatgaa agagcgcct                                                19

<210> SEQ ID NO 139
<211> LENGTH: 19
<212> TYPE: DNA
<213> ORGANISM: Artificial Sequence
<220> FEATURE:
<223> OTHER INFORMATION: siRNA target

<400> SEQUENCE: 139
acacagtgac cgtcgacta                                                19

<210> SEQ ID NO 140
<211> LENGTH: 19
<212> TYPE: DNA
<213> ORGANISM: Artificial Sequence
<220> FEATURE:
<223> OTHER INFORMATION: siRNA target

<400> SEQUENCE: 140
atgaagaatt ccatggctt                                                19

<210> SEQ ID NO 141
<211> LENGTH: 19
<212> TYPE: DNA
<213> ORGANISM: Artificial Sequence
<220> FEATURE:
<223> OTHER INFORMATION: siRNA target

<400> SEQUENCE: 141
gttacagacg gaagaagaa                                                19

<210> SEQ ID NO 142
<211> LENGTH: 19
<212> TYPE: DNA
<213> ORGANISM: Artificial Sequence
<220> FEATURE:
<223> OTHER INFORMATION: siRNA target

<400> SEQUENCE: 142
ggaagtacct gaaccagtt                                                19
```

```
<210> SEQ ID NO 143
<211> LENGTH: 19
<212> TYPE: DNA
<213> ORGANISM: Artificial Sequence
<220> FEATURE:
<223> OTHER INFORMATION: siRNA target

<400> SEQUENCE: 143
tgggatcaca tcagataaa                                            19

<210> SEQ ID NO 144
<211> LENGTH: 19
<212> TYPE: DNA
<213> ORGANISM: Artificial Sequence
<220> FEATURE:
<223> OTHER INFORMATION: siRNA target

<400> SEQUENCE: 144
gagcttaatg aatgaggat                                            19

<210> SEQ ID NO 145
<211> LENGTH: 19
<212> TYPE: DNA
<213> ORGANISM: Artificial Sequence
<220> FEATURE:
<223> OTHER INFORMATION: siRNA target

<400> SEQUENCE: 145
ccaagaagag tgaagaact                                            19

<210> SEQ ID NO 146
<211> LENGTH: 19
<212> TYPE: DNA
<213> ORGANISM: Artificial Sequence
<220> FEATURE:
<223> OTHER INFORMATION: siRNA target

<400> SEQUENCE: 146
tgacattgcc tctgcgctt                                            19

<210> SEQ ID NO 147
<211> LENGTH: 19
<212> TYPE: DNA
<213> ORGANISM: Artificial Sequence
<220> FEATURE:
<223> OTHER INFORMATION: siRNA target

<400> SEQUENCE: 147
tggctgagcg actggagaa                                            19

<210> SEQ ID NO 148
<211> LENGTH: 19
<212> TYPE: DNA
<213> ORGANISM: Artificial Sequence
<220> FEATURE:
<223> OTHER INFORMATION: siRNA target

<400> SEQUENCE: 148
tttcagacgg caagttaaa                                            19

<210> SEQ ID NO 149
<211> LENGTH: 19
<212> TYPE: DNA
<213> ORGANISM: Artificial Sequence
<220> FEATURE:
<223> OTHER INFORMATION: siRNA target
```

```
<400> SEQUENCE: 149
tggacgacct agaggagca                                                    19

<210> SEQ ID NO 150
<211> LENGTH: 19
<212> TYPE: DNA
<213> ORGANISM: Artificial Sequence
<220> FEATURE:
<223> OTHER INFORMATION: siRNA target

<400> SEQUENCE: 150
taatgaatga ggatgagaa                                                    19

<210> SEQ ID NO 151
<211> LENGTH: 19
<212> TYPE: DNA
<213> ORGANISM: Artificial Sequence
<220> FEATURE:
<223> OTHER INFORMATION: siRNA target

<400> SEQUENCE: 151
agccaagaag agtgaagaa                                                    19

<210> SEQ ID NO 152
<211> LENGTH: 19
<212> TYPE: DNA
<213> ORGANISM: Artificial Sequence
<220> FEATURE:
<223> OTHER INFORMATION: siRNA target

<400> SEQUENCE: 152
caagaagagt gaagaactg                                                    19

<210> SEQ ID NO 153
<211> LENGTH: 19
<212> TYPE: DNA
<213> ORGANISM: Artificial Sequence
<220> FEATURE:
<223> OTHER INFORMATION: siRNA target

<400> SEQUENCE: 153
agaagagtga ggtggacat                                                    19

<210> SEQ ID NO 154
<211> LENGTH: 19
<212> TYPE: DNA
<213> ORGANISM: Artificial Sequence
<220> FEATURE:
<223> OTHER INFORMATION: siRNA target

<400> SEQUENCE: 154
agcgaagact tgaatggaa                                                    19

<210> SEQ ID NO 155
<211> LENGTH: 19
<212> TYPE: DNA
<213> ORGANISM: Artificial Sequence
<220> FEATURE:
<223> OTHER INFORMATION: siRNA target

<400> SEQUENCE: 155
aggaaacagg tgagcagat                                                    19

<210> SEQ ID NO 156
<211> LENGTH: 19
<212> TYPE: DNA
```

```
<213> ORGANISM: Artificial Sequence
<220> FEATURE:
<223> OTHER INFORMATION: siRNA target

<400> SEQUENCE: 156
cttagatacc ttcatgaaa                                                19

<210> SEQ ID NO 157
<211> LENGTH: 19
<212> TYPE: DNA
<213> ORGANISM: Artificial Sequence
<220> FEATURE:
<223> OTHER INFORMATION: siRNA target

<400> SEQUENCE: 157
gcatccagac caacaacaa                                                19

<210> SEQ ID NO 158
<211> LENGTH: 19
<212> TYPE: DNA
<213> ORGANISM: Artificial Sequence
<220> FEATURE:
<223> OTHER INFORMATION: siRNA target

<400> SEQUENCE: 158
agcgcatcca gaccaacaa                                                19

<210> SEQ ID NO 159
<211> LENGTH: 19
<212> TYPE: DNA
<213> ORGANISM: Artificial Sequence
<220> FEATURE:
<223> OTHER INFORMATION: siRNA target

<400> SEQUENCE: 159
gtgacaaggt gcagaaaga                                                19

<210> SEQ ID NO 160
<211> LENGTH: 19
<212> TYPE: DNA
<213> ORGANISM: Artificial Sequence
<220> FEATURE:
<223> OTHER INFORMATION: siRNA target

<400> SEQUENCE: 160
ggattgagga gaaacgtaa                                                19

<210> SEQ ID NO 161
<211> LENGTH: 19
<212> TYPE: DNA
<213> ORGANISM: Artificial Sequence
<220> FEATURE:
<223> OTHER INFORMATION: siRNA target

<400> SEQUENCE: 161
cccacgagct tgtaggaaa                                                19

<210> SEQ ID NO 162
<211> LENGTH: 19
<212> TYPE: DNA
<213> ORGANISM: Artificial Sequence
<220> FEATURE:
<223> OTHER INFORMATION: siRNA target

<400> SEQUENCE: 162
ggagaaacgt aaaaggaca                                                19
```

```
<210> SEQ ID NO 163
<211> LENGTH: 19
<212> TYPE: DNA
<213> ORGANISM: Artificial Sequence
<220> FEATURE:
<223> OTHER INFORMATION: siRNA target

<400> SEQUENCE: 163
ggcgagagga gcacagata                                                   19

<210> SEQ ID NO 164
<211> LENGTH: 19
<212> TYPE: DNA
<213> ORGANISM: Artificial Sequence
<220> FEATURE:
<223> OTHER INFORMATION: siRNA target

<400> SEQUENCE: 164
ctacacagga ccagggaca                                                   19

<210> SEQ ID NO 165
<211> LENGTH: 19
<212> TYPE: DNA
<213> ORGANISM: Artificial Sequence
<220> FEATURE:
<223> OTHER INFORMATION: siRNA target

<400> SEQUENCE: 165
aagaggacat tgaggtgta                                                   19

<210> SEQ ID NO 166
<211> LENGTH: 19
<212> TYPE: DNA
<213> ORGANISM: Artificial Sequence
<220> FEATURE:
<223> OTHER INFORMATION: siRNA target

<400> SEQUENCE: 166
ggaaaggact gccgggatg                                                   19

<210> SEQ ID NO 167
<211> LENGTH: 19
<212> TYPE: DNA
<213> ORGANISM: Artificial Sequence
<220> FEATURE:
<223> OTHER INFORMATION: siRNA target

<400> SEQUENCE: 167
tcaagagcat catgaagaa                                                   19

<210> SEQ ID NO 168
<211> LENGTH: 19
<212> TYPE: DNA
<213> ORGANISM: Artificial Sequence
<220> FEATURE:
<223> OTHER INFORMATION: siRNA target

<400> SEQUENCE: 168
tggagtaccc tgaggctat                                                   19

<210> SEQ ID NO 169
<211> LENGTH: 19
<212> TYPE: DNA
<213> ORGANISM: Artificial Sequence
<220> FEATURE:
<223> OTHER INFORMATION: siRNA target
```

```
<400> SEQUENCE: 169
gaatccagtg tgtgaagaa                                               19

<210> SEQ ID NO 170
<211> LENGTH: 19
<212> TYPE: DNA
<213> ORGANISM: Artificial Sequence
<220> FEATURE:
<223> OTHER INFORMATION: siRNA target

<400> SEQUENCE: 170
tcagtgagcc catggaatt                                               19

<210> SEQ ID NO 171
<211> LENGTH: 19
<212> TYPE: DNA
<213> ORGANISM: Artificial Sequence
<220> FEATURE:
<223> OTHER INFORMATION: siRNA target

<400> SEQUENCE: 171
cgtaaaagga catatgaga                                               19

<210> SEQ ID NO 172
<211> LENGTH: 19
<212> TYPE: DNA
<213> ORGANISM: Artificial Sequence
<220> FEATURE:
<223> OTHER INFORMATION: siRNA target

<400> SEQUENCE: 172
gggaaggaac gctgtcaga                                               19

<210> SEQ ID NO 173
<211> LENGTH: 19
<212> TYPE: DNA
<213> ORGANISM: Artificial Sequence
<220> FEATURE:
<223> OTHER INFORMATION: siRNA target

<400> SEQUENCE: 173
ccacgagctt gtaggaaag                                               19

<210> SEQ ID NO 174
<211> LENGTH: 19
<212> TYPE: DNA
<213> ORGANISM: Artificial Sequence
<220> FEATURE:
<223> OTHER INFORMATION: siRNA target

<400> SEQUENCE: 174
cttccaagtt cctatagaa                                               19

<210> SEQ ID NO 175
<211> LENGTH: 19
<212> TYPE: DNA
<213> ORGANISM: Artificial Sequence
<220> FEATURE:
<223> OTHER INFORMATION: siRNA target

<400> SEQUENCE: 175
gcatccagac caacaacaa                                               19

<210> SEQ ID NO 176
<211> LENGTH: 19
<212> TYPE: DNA
```

```
<213> ORGANISM: Artificial Sequence
<220> FEATURE:
<223> OTHER INFORMATION: siRNA target

<400> SEQUENCE: 176
ctcaagatct gccgagtga                                            19

<210> SEQ ID NO 177
<211> LENGTH: 19
<212> TYPE: DNA
<213> ORGANISM: Artificial Sequence
<220> FEATURE:
<223> OTHER INFORMATION: siRNA target

<400> SEQUENCE: 177
cggattgagg agaaacgta                                            19

<210> SEQ ID NO 178
<211> LENGTH: 19
<212> TYPE: DNA
<213> ORGANISM: Artificial Sequence
<220> FEATURE:
<223> OTHER INFORMATION: siRNA target

<400> SEQUENCE: 178
gattgaggag aaacgtaaa                                            19

<210> SEQ ID NO 179
<211> LENGTH: 19
<212> TYPE: DNA
<213> ORGANISM: Artificial Sequence
<220> FEATURE:
<223> OTHER INFORMATION: siRNA target

<400> SEQUENCE: 179
ggacatatga gaccttcaa                                            19

<210> SEQ ID NO 180
<211> LENGTH: 19
<212> TYPE: DNA
<213> ORGANISM: Artificial Sequence
<220> FEATURE:
<223> OTHER INFORMATION: siRNA target

<400> SEQUENCE: 180
tcaccggatt gaggagaaa                                            19

<210> SEQ ID NO 181
<211> LENGTH: 19
<212> TYPE: DNA
<213> ORGANISM: Artificial Sequence
<220> FEATURE:
<223> OTHER INFORMATION: siRNA target

<400> SEQUENCE: 181
caactgagcc catgctgat                                            19

<210> SEQ ID NO 182
<211> LENGTH: 19
<212> TYPE: DNA
<213> ORGANISM: Artificial Sequence
<220> FEATURE:
<223> OTHER INFORMATION: siRNA target

<400> SEQUENCE: 182
aggaaaggac tgccgggat                                            19
```

```
<210> SEQ ID NO 183
<211> LENGTH: 19
<212> TYPE: DNA
<213> ORGANISM: Artificial Sequence
<220> FEATURE:
<223> OTHER INFORMATION: siRNA target

<400> SEQUENCE: 183
ccaacactgc cgagctcaa                                               19

<210> SEQ ID NO 184
<211> LENGTH: 19
<212> TYPE: DNA
<213> ORGANISM: Artificial Sequence
<220> FEATURE:
<223> OTHER INFORMATION: siRNA target

<400> SEQUENCE: 184
gctgcagttt gatgatgaa                                               19

<210> SEQ ID NO 185
<211> LENGTH: 19
<212> TYPE: DNA
<213> ORGANISM: Artificial Sequence
<220> FEATURE:
<223> OTHER INFORMATION: siRNA target

<400> SEQUENCE: 185
gaccagggac agtgcgcat                                               19

<210> SEQ ID NO 186
<211> LENGTH: 19
<212> TYPE: DNA
<213> ORGANISM: Artificial Sequence
<220> FEATURE:
<223> OTHER INFORMATION: siRNA target

<400> SEQUENCE: 186
gggatgagat cttcctact                                               19

<210> SEQ ID NO 187
<211> LENGTH: 19
<212> TYPE: DNA
<213> ORGANISM: Artificial Sequence
<220> FEATURE:
<223> OTHER INFORMATION: siRNA target

<400> SEQUENCE: 187
aggtgcagaa agaggacat                                               19

<210> SEQ ID NO 188
<211> LENGTH: 19
<212> TYPE: DNA
<213> ORGANISM: Artificial Sequence
<220> FEATURE:
<223> OTHER INFORMATION: siRNA target

<400> SEQUENCE: 188
aggacattga ggtgtattt                                               19

<210> SEQ ID NO 189
<211> LENGTH: 19
<212> TYPE: DNA
<213> ORGANISM: Artificial Sequence
<220> FEATURE:
<223> OTHER INFORMATION: siRNA target
```

```
<400> SEQUENCE: 189
gagaaacgta aaggacat                                                   19

<210> SEQ ID NO 190
<211> LENGTH: 19
<212> TYPE: DNA
<213> ORGANISM: Artificial Sequence
<220> FEATURE:
<223> OTHER INFORMATION: siRNA target

<400> SEQUENCE: 190
catcaagatc aatggctac                                                  19

<210> SEQ ID NO 191
<211> LENGTH: 19
<212> TYPE: DNA
<213> ORGANISM: Artificial Sequence
<220> FEATURE:
<223> OTHER INFORMATION: siRNA target

<400> SEQUENCE: 191
ccaagttcct atagaagag                                                  19

<210> SEQ ID NO 192
<211> LENGTH: 19
<212> TYPE: DNA
<213> ORGANISM: Artificial Sequence
<220> FEATURE:
<223> OTHER INFORMATION: siRNA target

<400> SEQUENCE: 192
agatcttcct actgtgtga                                                  19

<210> SEQ ID NO 193
<211> LENGTH: 19
<212> TYPE: DNA
<213> ORGANISM: Artificial Sequence
<220> FEATURE:
<223> OTHER INFORMATION: siRNA target

<400> SEQUENCE: 193
agaaagagga cattgaggt                                                  19

<210> SEQ ID NO 194
<211> LENGTH: 19
<212> TYPE: DNA
<213> ORGANISM: Artificial Sequence
<220> FEATURE:
<223> OTHER INFORMATION: siRNA target

<400> SEQUENCE: 194
gtcaccggat tgaggagaa                                                  19

<210> SEQ ID NO 195
<211> LENGTH: 19
<212> TYPE: DNA
<213> ORGANISM: Artificial Sequence
<220> FEATURE:
<223> OTHER INFORMATION: siRNA target

<400> SEQUENCE: 195
acatatgaga ccttcaaga                                                  19

<210> SEQ ID NO 196
<211> LENGTH: 19
<212> TYPE: DNA
```

-continued

<213> ORGANISM: Artificial Sequence
<220> FEATURE:
<223> OTHER INFORMATION: siRNA target

<400> SEQUENCE: 196
gctataactc gcctagtga                                                19

<210> SEQ ID NO 197
<211> LENGTH: 19
<212> TYPE: DNA
<213> ORGANISM: Artificial Sequence
<220> FEATURE:
<223> OTHER INFORMATION: siRNA target

<400> SEQUENCE: 197
tgcagaaaga ggacattga                                                19

<210> SEQ ID NO 198
<211> LENGTH: 19
<212> TYPE: DNA
<213> ORGANISM: Artificial Sequence
<220> FEATURE:
<223> OTHER INFORMATION: siRNA target

<400> SEQUENCE: 198
gaaagaggac attgaggtg                                                19

<210> SEQ ID NO 199
<211> LENGTH: 19
<212> TYPE: DNA
<213> ORGANISM: Artificial Sequence
<220> FEATURE:
<223> OTHER INFORMATION: siRNA target

<400> SEQUENCE: 199
aagctgatgt gcaccgaca                                                19

<210> SEQ ID NO 200
<211> LENGTH: 19
<212> TYPE: DNA
<213> ORGANISM: Artificial Sequence
<220> FEATURE:
<223> OTHER INFORMATION: siRNA target

<400> SEQUENCE: 200
gatcaatggc tacacagga                                                19

<210> SEQ ID NO 201
<211> LENGTH: 19
<212> TYPE: DNA
<213> ORGANISM: Artificial Sequence
<220> FEATURE:
<223> OTHER INFORMATION: siRNA target

<400> SEQUENCE: 201
tgtgtgacaa ggtgcagaa                                                19

<210> SEQ ID NO 202
<211> LENGTH: 19
<212> TYPE: DNA
<213> ORGANISM: Artificial Sequence
<220> FEATURE:
<223> OTHER INFORMATION: siRNA target

<400> SEQUENCE: 202
ttccagtacc tgccagata                                                19

<210> SEQ ID NO 203
<211> LENGTH: 19
<212> TYPE: DNA
<213> ORGANISM: Artificial Sequence
<220> FEATURE:
<223> OTHER INFORMATION: siRNA target

<400> SEQUENCE: 203
gaggagaaac gtaaaagga                                          19

<210> SEQ ID NO 204
<211> LENGTH: 19
<212> TYPE: DNA
<213> ORGANISM: Artificial Sequence
<220> FEATURE:
<223> OTHER INFORMATION: siRNA target

<400> SEQUENCE: 204
tatgagacct tcaagagca                                          19

<210> SEQ ID NO 205
<211> LENGTH: 19
<212> TYPE: DNA
<213> ORGANISM: Artificial Sequence
<220> FEATURE:
<223> OTHER INFORMATION: siRNA target

<400> SEQUENCE: 205
atgagacctt caagagcat                                          19

<210> SEQ ID NO 206
<211> LENGTH: 19
<212> TYPE: DNA
<213> ORGANISM: Artificial Sequence
<220> FEATURE:
<223> OTHER INFORMATION: siRNA target

<400> SEQUENCE: 206
aagagcatca tgaagaaga                                          19

<210> SEQ ID NO 207
<211> LENGTH: 19
<212> TYPE: DNA
<213> ORGANISM: Artificial Sequence
<220> FEATURE:
<223> OTHER INFORMATION: siRNA target

<400> SEQUENCE: 207
tggcaacagc acagaccca                                          19

<210> SEQ ID NO 208
<211> LENGTH: 19
<212> TYPE: DNA
<213> ORGANISM: Artificial Sequence
<220> FEATURE:
<223> OTHER INFORMATION: siRNA target

<400> SEQUENCE: 208
caagatcaat ggctacaca                                          19

<210> SEQ ID NO 209
<211> LENGTH: 19
<212> TYPE: DNA
<213> ORGANISM: Artificial Sequence
<220> FEATURE:
<223> OTHER INFORMATION: siRNA target

```
<400> SEQUENCE: 209
ggaagagcca actgtgtga                                                19

<210> SEQ ID NO 210
<211> LENGTH: 19
<212> TYPE: DNA
<213> ORGANISM: Artificial Sequence
<220> FEATURE:
<223> OTHER INFORMATION: siRNA target

<400> SEQUENCE: 210
ccaaacagga ggtgatcga                                                19

<210> SEQ ID NO 211
<211> LENGTH: 19
<212> TYPE: DNA
<213> ORGANISM: Artificial Sequence
<220> FEATURE:
<223> OTHER INFORMATION: siRNA target

<400> SEQUENCE: 211
ggacaaggcc tctgtgaaa                                                19

<210> SEQ ID NO 212
<211> LENGTH: 19
<212> TYPE: DNA
<213> ORGANISM: Artificial Sequence
<220> FEATURE:
<223> OTHER INFORMATION: siRNA target

<400> SEQUENCE: 212
ggaaactggt ggagagact                                                19

<210> SEQ ID NO 213
<211> LENGTH: 19
<212> TYPE: DNA
<213> ORGANISM: Artificial Sequence
<220> FEATURE:
<223> OTHER INFORMATION: siRNA target

<400> SEQUENCE: 213
gggagaagct ggccgagaa                                                19

<210> SEQ ID NO 214
<211> LENGTH: 19
<212> TYPE: DNA
<213> ORGANISM: Artificial Sequence
<220> FEATURE:
<223> OTHER INFORMATION: siRNA target

<400> SEQUENCE: 214
gcgaggagct tctgcattt                                                19

<210> SEQ ID NO 215
<211> LENGTH: 19
<212> TYPE: DNA
<213> ORGANISM: Artificial Sequence
<220> FEATURE:
<223> OTHER INFORMATION: siRNA target

<400> SEQUENCE: 215
ggatcgagga catgaggaa                                                19

<210> SEQ ID NO 216
<211> LENGTH: 19
<212> TYPE: DNA
```

<213> ORGANISM: Artificial Sequence
<220> FEATURE:
<223> OTHER INFORMATION: siRNA target

<400> SEQUENCE: 216
cggccaggat cgaggacat                                              19

<210> SEQ ID NO 217
<211> LENGTH: 19
<212> TYPE: DNA
<213> ORGANISM: Artificial Sequence
<220> FEATURE:
<223> OTHER INFORMATION: siRNA target

<400> SEQUENCE: 217
gaggaatgca gctggaaga                                              19

<210> SEQ ID NO 218
<211> LENGTH: 19
<212> TYPE: DNA
<213> ORGANISM: Artificial Sequence
<220> FEATURE:
<223> OTHER INFORMATION: siRNA target

<400> SEQUENCE: 218
tcgataagct gaaggagga                                              19

<210> SEQ ID NO 219
<211> LENGTH: 19
<212> TYPE: DNA
<213> ORGANISM: Artificial Sequence
<220> FEATURE:
<223> OTHER INFORMATION: siRNA target

<400> SEQUENCE: 219
tggagaagct cgatctgaa                                              19

<210> SEQ ID NO 220
<211> LENGTH: 19
<212> TYPE: DNA
<213> ORGANISM: Artificial Sequence
<220> FEATURE:
<223> OTHER INFORMATION: siRNA target

<400> SEQUENCE: 220
aaacaggagg tgatcgata                                              19

<210> SEQ ID NO 221
<211> LENGTH: 19
<212> TYPE: DNA
<213> ORGANISM: Artificial Sequence
<220> FEATURE:
<223> OTHER INFORMATION: siRNA target

<400> SEQUENCE: 221
ccaaacagga ggtgatcga                                              19

<210> SEQ ID NO 222
<211> LENGTH: 19
<212> TYPE: DNA
<213> ORGANISM: Artificial Sequence
<220> FEATURE:
<223> OTHER INFORMATION: siRNA target

<400> SEQUENCE: 222
agcagatggc tgaggacaa                                              19

```
<210> SEQ ID NO 223
<211> LENGTH: 19
<212> TYPE: DNA
<213> ORGANISM: Artificial Sequence
<220> FEATURE:
<223> OTHER INFORMATION: siRNA target

<400> SEQUENCE: 223
agaagctggc cgagaagaa                                                  19

<210> SEQ ID NO 224
<211> LENGTH: 19
<212> TYPE: DNA
<213> ORGANISM: Artificial Sequence
<220> FEATURE:
<223> OTHER INFORMATION: siRNA target

<400> SEQUENCE: 224
gcttggaggc tgccactaa                                                  19

<210> SEQ ID NO 225
<211> LENGTH: 19
<212> TYPE: DNA
<213> ORGANISM: Artificial Sequence
<220> FEATURE:
<223> OTHER INFORMATION: siRNA target

<400> SEQUENCE: 225
tggccaaaca ggaggtgat                                                  19

<210> SEQ ID NO 226
<211> LENGTH: 19
<212> TYPE: DNA
<213> ORGANISM: Artificial Sequence
<220> FEATURE:
<223> OTHER INFORMATION: siRNA target

<400> SEQUENCE: 226
ggaagagcca actgtgtga                                                  19

<210> SEQ ID NO 227
<211> LENGTH: 19
<212> TYPE: DNA
<213> ORGANISM: Artificial Sequence
<220> FEATURE:
<223> OTHER INFORMATION: siRNA target

<400> SEQUENCE: 227
aacaggaggt gatcgataa                                                  19

<210> SEQ ID NO 228
<211> LENGTH: 19
<212> TYPE: DNA
<213> ORGANISM: Artificial Sequence
<220> FEATURE:
<223> OTHER INFORMATION: siRNA target

<400> SEQUENCE: 228
gaatgcagct ggaagatct                                                  19

<210> SEQ ID NO 229
<211> LENGTH: 19
<212> TYPE: DNA
<213> ORGANISM: Artificial Sequence
<220> FEATURE:
<223> OTHER INFORMATION: siRNA target
```

```
<400> SEQUENCE: 229
agagggagga gaaggagtt                                                  19

<210> SEQ ID NO 230
<211> LENGTH: 19
<212> TYPE: DNA
<213> ORGANISM: Artificial Sequence
<220> FEATURE:
<223> OTHER INFORMATION: siRNA target

<400> SEQUENCE: 230
aggcggactt ccaggctga                                                  19

<210> SEQ ID NO 231
<211> LENGTH: 19
<212> TYPE: DNA
<213> ORGANISM: Artificial Sequence
<220> FEATURE:
<223> OTHER INFORMATION: siRNA target

<400> SEQUENCE: 231
tggagcagct gcagaggga                                                  19

<210> SEQ ID NO 232
<211> LENGTH: 19
<212> TYPE: DNA
<213> ORGANISM: Artificial Sequence
<220> FEATURE:
<223> OTHER INFORMATION: siRNA target

<400> SEQUENCE: 232
gagcagctgc agagggagt                                                  19

<210> SEQ ID NO 233
<211> LENGTH: 19
<212> TYPE: DNA
<213> ORGANISM: Artificial Sequence
<220> FEATURE:
<223> OTHER INFORMATION: siRNA target

<400> SEQUENCE: 233
cgtactgggc gaagagtct                                                  19

<210> SEQ ID NO 234
<211> LENGTH: 19
<212> TYPE: DNA
<213> ORGANISM: Artificial Sequence
<220> FEATURE:
<223> OTHER INFORMATION: siRNA target

<400> SEQUENCE: 234
ggaggagaat caagagctc                                                  19

<210> SEQ ID NO 235
<211> LENGTH: 19
<212> TYPE: DNA
<213> ORGANISM: Artificial Sequence
<220> FEATURE:
<223> OTHER INFORMATION: siRNA target

<400> SEQUENCE: 235
ccagccagag ggaggagaa                                                  19

<210> SEQ ID NO 236
<211> LENGTH: 19
<212> TYPE: DNA
```

```
<213> ORGANISM: Artificial Sequence
<220> FEATURE:
<223> OTHER INFORMATION: siRNA target

<400> SEQUENCE: 236
gccagaggga ggagaagga                                                19

<210> SEQ ID NO 237
<211> LENGTH: 19
<212> TYPE: DNA
<213> ORGANISM: Artificial Sequence
<220> FEATURE:
<223> OTHER INFORMATION: siRNA target

<400> SEQUENCE: 237
tgaagaggca gaaggagca                                                19

<210> SEQ ID NO 238
<211> LENGTH: 19
<212> TYPE: DNA
<213> ORGANISM: Artificial Sequence
<220> FEATURE:
<223> OTHER INFORMATION: siRNA target

<400> SEQUENCE: 238
tggaagatct caaacagca                                                19

<210> SEQ ID NO 239
<211> LENGTH: 19
<212> TYPE: DNA
<213> ORGANISM: Artificial Sequence
<220> FEATURE:
<223> OTHER INFORMATION: siRNA target

<400> SEQUENCE: 239
ctgaagaggc agaaggagc                                                19

<210> SEQ ID NO 240
<211> LENGTH: 19
<212> TYPE: DNA
<213> ORGANISM: Artificial Sequence
<220> FEATURE:
<223> OTHER INFORMATION: siRNA target

<400> SEQUENCE: 240
aagaatacga caaccacat                                                19

<210> SEQ ID NO 241
<211> LENGTH: 19
<212> TYPE: DNA
<213> ORGANISM: Artificial Sequence
<220> FEATURE:
<223> OTHER INFORMATION: siRNA target

<400> SEQUENCE: 241
gcagagggag tacagcaaa                                                19

<210> SEQ ID NO 242
<211> LENGTH: 19
<212> TYPE: DNA
<213> ORGANISM: Artificial Sequence
<220> FEATURE:
<223> OTHER INFORMATION: siRNA target

<400> SEQUENCE: 242
cagcagatca ggacgtact                                                19
```

```
<210> SEQ ID NO 243
<211> LENGTH: 19
<212> TYPE: DNA
<213> ORGANISM: Artificial Sequence
<220> FEATURE:
<223> OTHER INFORMATION: siRNA target

<400> SEQUENCE: 243
agtgagcgga agcgaggaa                                                       19

<210> SEQ ID NO 244
<211> LENGTH: 19
<212> TYPE: DNA
<213> ORGANISM: Artificial Sequence
<220> FEATURE:
<223> OTHER INFORMATION: siRNA target

<400> SEQUENCE: 244
gagccaactg tgtgagatg                                                       19

<210> SEQ ID NO 245
<211> LENGTH: 19
<212> TYPE: DNA
<213> ORGANISM: Artificial Sequence
<220> FEATURE:
<223> OTHER INFORMATION: siRNA target

<400> SEQUENCE: 245
ctgaaggccc aggcggata                                                       19

<210> SEQ ID NO 246
<211> LENGTH: 19
<212> TYPE: DNA
<213> ORGANISM: Artificial Sequence
<220> FEATURE:
<223> OTHER INFORMATION: siRNA target

<400> SEQUENCE: 246
cagagggagt acagcaaac                                                       19

<210> SEQ ID NO 247
<211> LENGTH: 19
<212> TYPE: DNA
<213> ORGANISM: Artificial Sequence
<220> FEATURE:
<223> OTHER INFORMATION: siRNA target

<400> SEQUENCE: 247
caggaaactg gtggagaga                                                       19

<210> SEQ ID NO 248
<211> LENGTH: 19
<212> TYPE: DNA
<213> ORGANISM: Artificial Sequence
<220> FEATURE:
<223> OTHER INFORMATION: siRNA target

<400> SEQUENCE: 248
tgaataggca cctctggaa                                                       19

<210> SEQ ID NO 249
<211> LENGTH: 19
<212> TYPE: DNA
<213> ORGANISM: Artificial Sequence
<220> FEATURE:
<223> OTHER INFORMATION: siRNA target
```

<400> SEQUENCE: 249
gaggctgcca ctaaggaat						19

<210> SEQ ID NO 250
<211> LENGTH: 19
<212> TYPE: DNA
<213> ORGANISM: Artificial Sequence
<220> FEATURE:
<223> OTHER INFORMATION: siRNA target

<400> SEQUENCE: 250
cccagttgca ggtggccta						19

<210> SEQ ID NO 251
<211> LENGTH: 19
<212> TYPE: DNA
<213> ORGANISM: Artificial Sequence
<220> FEATURE:
<223> OTHER INFORMATION: siRNA target

<400> SEQUENCE: 251
gggagtacag caaactgaa						19

<210> SEQ ID NO 252
<211> LENGTH: 19
<212> TYPE: DNA
<213> ORGANISM: Artificial Sequence
<220> FEATURE:
<223> OTHER INFORMATION: siRNA target

<400> SEQUENCE: 252
agcgctgcct ggaggagaa						19

<210> SEQ ID NO 253
<211> LENGTH: 19
<212> TYPE: DNA
<213> ORGANISM: Artificial Sequence
<220> FEATURE:
<223> OTHER INFORMATION: siRNA target

<400> SEQUENCE: 253
aatcaagagc tccgagatg						19

<210> SEQ ID NO 254
<211> LENGTH: 19
<212> TYPE: DNA
<213> ORGANISM: Artificial Sequence
<220> FEATURE:
<223> OTHER INFORMATION: siRNA target

<400> SEQUENCE: 254
cggcagagca accagattc						19

<210> SEQ ID NO 255
<211> LENGTH: 19
<212> TYPE: DNA
<213> ORGANISM: Artificial Sequence
<220> FEATURE:
<223> OTHER INFORMATION: siRNA target

<400> SEQUENCE: 255
agagatgcca gcagcagat						19

<210> SEQ ID NO 256
<211> LENGTH: 19
<212> TYPE: DNA

```
<213> ORGANISM: Artificial Sequence
<220> FEATURE:
<223> OTHER INFORMATION: siRNA target

<400> SEQUENCE: 256
aggcccaggc ggatatcta                                                  19

<210> SEQ ID NO 257
<211> LENGTH: 19
<212> TYPE: DNA
<213> ORGANISM: Artificial Sequence
<220> FEATURE:
<223> OTHER INFORMATION: siRNA target

<400> SEQUENCE: 257
ctgcagaggg agtacagca                                                  19

<210> SEQ ID NO 258
<211> LENGTH: 19
<212> TYPE: DNA
<213> ORGANISM: Artificial Sequence
<220> FEATURE:
<223> OTHER INFORMATION: siRNA target

<400> SEQUENCE: 258
tgcagaggga gtacagcaa                                                  19

<210> SEQ ID NO 259
<211> LENGTH: 19
<212> TYPE: DNA
<213> ORGANISM: Artificial Sequence
<220> FEATURE:
<223> OTHER INFORMATION: siRNA target

<400> SEQUENCE: 259
tggacaccct gcagataca                                                  19

<210> SEQ ID NO 260
<211> LENGTH: 19
<212> TYPE: DNA
<213> ORGANISM: Artificial Sequence
<220> FEATURE:
<223> OTHER INFORMATION: siRNA target

<400> SEQUENCE: 260
gcacctgcct tcagaacag                                                  19

<210> SEQ ID NO 261
<211> LENGTH: 21
<212> TYPE: DNA
<213> ORGANISM: Artificial Sequence
<220> FEATURE:
<223> OTHER INFORMATION: siRNA target

<400> SEQUENCE: 261
aagtccaata cctcactcgc t                                               21

<210> SEQ ID NO 262
<211> LENGTH: 21
<212> TYPE: DNA
<213> ORGANISM: Artificial Sequence
<220> FEATURE:
<223> OTHER INFORMATION: siRNA target

<400> SEQUENCE: 262
aagcacgtca aaagctacag a                                               21
```

```
<210> SEQ ID NO 263
<211> LENGTH: 19
<212> TYPE: DNA
<213> ORGANISM: Artificial Sequence
<220> FEATURE:
<223> OTHER INFORMATION: siRNA target

<400> SEQUENCE: 263
aatttctgtc tcatcttaa                                                  19

<210> SEQ ID NO 264
<211> LENGTH: 19
<212> TYPE: DNA
<213> ORGANISM: Artificial Sequence
<220> FEATURE:
<223> OTHER INFORMATION: siRNA target

<400> SEQUENCE: 264
ggtcttcacc aagtatcaa                                                  19

<210> SEQ ID NO 265
<211> LENGTH: 19
<212> TYPE: DNA
<213> ORGANISM: Artificial Sequence
<220> FEATURE:
<223> OTHER INFORMATION: siRNA target

<400> SEQUENCE: 265
ggccatactc ttacataat                                                  19

<210> SEQ ID NO 266
<211> LENGTH: 19
<212> TYPE: DNA
<213> ORGANISM: Artificial Sequence
<220> FEATURE:
<223> OTHER INFORMATION: siRNA target

<400> SEQUENCE: 266
ggcaaggaaa ataaaagat                                                  19

<210> SEQ ID NO 267
<211> LENGTH: 19
<212> TYPE: DNA
<213> ORGANISM: Artificial Sequence
<220> FEATURE:
<223> OTHER INFORMATION: siRNA target

<400> SEQUENCE: 267
gcacgtcaaa agctacaga                                                  19

<210> SEQ ID NO 268
<211> LENGTH: 19
<212> TYPE: DNA
<213> ORGANISM: Artificial Sequence
<220> FEATURE:
<223> OTHER INFORMATION: siRNA target

<400> SEQUENCE: 268
ggcactgtag tgaattatc                                                  19

<210> SEQ ID NO 269
<211> LENGTH: 19
<212> TYPE: DNA
<213> ORGANISM: Artificial Sequence
<220> FEATURE:
<223> OTHER INFORMATION: siRNA target
```

```
<400> SEQUENCE: 269
gctagagtta cctagctta                                                  19

<210> SEQ ID NO 270
<211> LENGTH: 19
<212> TYPE: DNA
<213> ORGANISM: Artificial Sequence
<220> FEATURE:
<223> OTHER INFORMATION: siRNA target

<400> SEQUENCE: 270
aagaagagcc tcaaccatt                                                  19

<210> SEQ ID NO 271
<211> LENGTH: 19
<212> TYPE: DNA
<213> ORGANISM: Artificial Sequence
<220> FEATURE:
<223> OTHER INFORMATION: siRNA target

<400> SEQUENCE: 271
gtcaaaagct acagaatct                                                  19

<210> SEQ ID NO 272
<211> LENGTH: 19
<212> TYPE: DNA
<213> ORGANISM: Artificial Sequence
<220> FEATURE:
<223> OTHER INFORMATION: siRNA target

<400> SEQUENCE: 272
cctcactcgc tcagctata                                                  19

<210> SEQ ID NO 273
<211> LENGTH: 19
<212> TYPE: DNA
<213> ORGANISM: Artificial Sequence
<220> FEATURE:
<223> OTHER INFORMATION: siRNA target

<400> SEQUENCE: 273
tcgctcagct ataagaaga                                                  19

<210> SEQ ID NO 274
<211> LENGTH: 19
<212> TYPE: DNA
<213> ORGANISM: Artificial Sequence
<220> FEATURE:
<223> OTHER INFORMATION: siRNA target

<400> SEQUENCE: 274
tgaaatgcct caacaagca                                                  19

<210> SEQ ID NO 275
<211> LENGTH: 19
<212> TYPE: DNA
<213> ORGANISM: Artificial Sequence
<220> FEATURE:
<223> OTHER INFORMATION: siRNA target

<400> SEQUENCE: 275
agctataaga agagcctca                                                  19

<210> SEQ ID NO 276
<211> LENGTH: 19
<212> TYPE: DNA
```

```
<213> ORGANISM: Artificial Sequence
<220> FEATURE:
<223> OTHER INFORMATION: siRNA target

<400> SEQUENCE: 276
taatatgtct cttgctgat                                                19

<210> SEQ ID NO 277
<211> LENGTH: 19
<212> TYPE: DNA
<213> ORGANISM: Artificial Sequence
<220> FEATURE:
<223> OTHER INFORMATION: siRNA target

<400> SEQUENCE: 277
cctcaacaag cacgtcaaa                                                19

<210> SEQ ID NO 278
<211> LENGTH: 19
<212> TYPE: DNA
<213> ORGANISM: Artificial Sequence
<220> FEATURE:
<223> OTHER INFORMATION: siRNA target

<400> SEQUENCE: 278
ggagaaagtc caatacctc                                                19

<210> SEQ ID NO 279
<211> LENGTH: 19
<212> TYPE: DNA
<213> ORGANISM: Artificial Sequence
<220> FEATURE:
<223> OTHER INFORMATION: siRNA target

<400> SEQUENCE: 279
acaagcacgt caaaagcta                                                19

<210> SEQ ID NO 280
<211> LENGTH: 19
<212> TYPE: DNA
<213> ORGANISM: Artificial Sequence
<220> FEATURE:
<223> OTHER INFORMATION: siRNA target

<400> SEQUENCE: 280
cgtcaaaagc tacagaatc                                                19

<210> SEQ ID NO 281
<211> LENGTH: 19
<212> TYPE: DNA
<213> ORGANISM: Artificial Sequence
<220> FEATURE:
<223> OTHER INFORMATION: siRNA target

<400> SEQUENCE: 281
acgtcaaaag ctacagaat                                                19

<210> SEQ ID NO 282
<211> LENGTH: 19
<212> TYPE: DNA
<213> ORGANISM: Artificial Sequence
<220> FEATURE:
<223> OTHER INFORMATION: siRNA target

<400> SEQUENCE: 282
gctacagaat ctatttatc                                                19
```

```
<210> SEQ ID NO 283
<211> LENGTH: 19
<212> TYPE: DNA
<213> ORGANISM: Artificial Sequence
<220> FEATURE:
<223> OTHER INFORMATION: siRNA target

<400> SEQUENCE: 283
gctataagaa gagcctcaa                                                  19

<210> SEQ ID NO 284
<211> LENGTH: 19
<212> TYPE: DNA
<213> ORGANISM: Artificial Sequence
<220> FEATURE:
<223> OTHER INFORMATION: siRNA target

<400> SEQUENCE: 284
ataagaagag cctcaacca                                                  19

<210> SEQ ID NO 285
<211> LENGTH: 19
<212> TYPE: DNA
<213> ORGANISM: Artificial Sequence
<220> FEATURE:
<223> OTHER INFORMATION: siRNA target

<400> SEQUENCE: 285
taagaagagc ctcaaccat                                                  19

<210> SEQ ID NO 286
<211> LENGTH: 19
<212> TYPE: DNA
<213> ORGANISM: Artificial Sequence
<220> FEATURE:
<223> OTHER INFORMATION: siRNAt target

<400> SEQUENCE: 286
gcctcaacaa gcacgtcaa                                                  19

<210> SEQ ID NO 287
<211> LENGTH: 19
<212> TYPE: DNA
<213> ORGANISM: Artificial Sequence
<220> FEATURE:
<223> OTHER INFORMATION: siRNA target

<400> SEQUENCE: 287
agaagagcct caaccattg                                                  19

<210> SEQ ID NO 288
<211> LENGTH: 19
<212> TYPE: DNA
<213> ORGANISM: Artificial Sequence
<220> FEATURE:
<223> OTHER INFORMATION: siRNA target

<400> SEQUENCE: 288
caatttctgt ctcatctta                                                  19

<210> SEQ ID NO 289
<211> LENGTH: 19
<212> TYPE: DNA
<213> ORGANISM: Artificial Sequence
<220> FEATURE:
<223> OTHER INFORMATION: siRNA target
```

```
<400> SEQUENCE: 289
tcaacaagca cgtcaaaag                                          19

<210> SEQ ID NO 290
<211> LENGTH: 19
<212> TYPE: DNA
<213> ORGANISM: Artificial Sequence
<220> FEATURE:
<223> OTHER INFORMATION: siRNA target

<400> SEQUENCE: 290
ttaatatgtc tcttgctga                                          19

<210> SEQ ID NO 291
<211> LENGTH: 19
<212> TYPE: DNA
<213> ORGANISM: Artificial Sequence
<220> FEATURE:
<223> OTHER INFORMATION: siRNA target

<400> SEQUENCE: 291
gtctcttgct gatctgtat                                          19

<210> SEQ ID NO 292
<211> LENGTH: 19
<212> TYPE: DNA
<213> ORGANISM: Artificial Sequence
<220> FEATURE:
<223> OTHER INFORMATION: siRNA target

<400> SEQUENCE: 292
cttaatatgt ctcttgctg                                          19

<210> SEQ ID NO 293
<211> LENGTH: 19
<212> TYPE: DNA
<213> ORGANISM: Artificial Sequence
<220> FEATURE:
<223> OTHER INFORMATION: siRNA target

<400> SEQUENCE: 293
tcagctataa gaagagcct                                          19

<210> SEQ ID NO 294
<211> LENGTH: 19
<212> TYPE: DNA
<213> ORGANISM: Artificial Sequence
<220> FEATURE:
<223> OTHER INFORMATION: siRNA target

<400> SEQUENCE: 294 ccaataccte actcgctca                                          19

<210> SEQ ID NO 295
<211> LENGTH: 19
<212> TYPE: DNA
<213> ORGANISM: Artificial Sequence
<220> FEATURE:
<223> OTHER INFORMATION: siRNA target

<400> SEQUENCE: 295
caaaagctac agaatctat                                          19

<210> SEQ ID NO 296
<211> LENGTH: 19
<212> TYPE: DNA
```

```
<213> ORGANISM: Artificial Sequence
<220> FEATURE:
<223> OTHER INFORMATION: siRNA target

<400> SEQUENCE: 296
catcttaata tgtctcttg                                                   19

<210> SEQ ID NO 297
<211> LENGTH: 19
<212> TYPE: DNA
<213> ORGANISM: Artificial Sequence
<220> FEATURE:
<223> OTHER INFORMATION: siRNA target

<400> SEQUENCE: 297
agaaagtcca atacctcac                                                   19

<210> SEQ ID NO 298
<211> LENGTH: 19
<212> TYPE: DNA
<213> ORGANISM: Artificial Sequence
<220> FEATURE:
<223> OTHER INFORMATION: siRNA target

<400> SEQUENCE: 298
ctataagaag agcctcaac                                                   19

<210> SEQ ID NO 299
<211> LENGTH: 19
<212> TYPE: DNA
<213> ORGANISM: Artificial Sequence
<220> FEATURE:
<223> OTHER INFORMATION: siRNA target

<400> SEQUENCE: 299
actcgctcag ctataagaa                                                   19

<210> SEQ ID NO 300
<211> LENGTH: 19
<212> TYPE: DNA
<213> ORGANISM: Artificial Sequence
<220> FEATURE:
<223> OTHER INFORMATION: siRNA target

<400> SEQUENCE: 300
tcaaaagcta cagaatcta                                                   19

<210> SEQ ID NO 301
<211> LENGTH: 19
<212> TYPE: DNA
<213> ORGANISM: Artificial Sequence
<220> FEATURE:
<223> OTHER INFORMATION: siRNA target

<400> SEQUENCE: 301
tatcaatttc tgtctcatc                                                   19

<210> SEQ ID NO 302
<211> LENGTH: 19
<212> TYPE: DNA
<213> ORGANISM: Artificial Sequence
<220> FEATURE:
<223> OTHER INFORMATION: siRNA target

<400> SEQUENCE: 302
tgtctcttgc tgatctgta                                                   19
```

```
<210> SEQ ID NO 303
<211> LENGTH: 19
<212> TYPE: DNA
<213> ORGANISM: Artificial Sequence
<220> FEATURE:
<223> OTHER INFORMATION: siRNA target

<400> SEQUENCE: 303
aagcacgtca aaagctaca                                            19

<210> SEQ ID NO 304
<211> LENGTH: 19
<212> TYPE: DNA
<213> ORGANISM: Artificial Sequence
<220> FEATURE:
<223> OTHER INFORMATION: siRNA target

<400> SEQUENCE: 304
gcacgtcaaa agctacaga                                            19

<210> SEQ ID NO 305
<211> LENGTH: 19
<212> TYPE: DNA
<213> ORGANISM: Artificial Sequence
<220> FEATURE:
<223> OTHER INFORMATION: siRNA target

<400> SEQUENCE: 305
tcaatttctg tctcatctt                                            19

<210> SEQ ID NO 306
<211> LENGTH: 19
<212> TYPE: DNA
<213> ORGANISM: Artificial Sequence
<220> FEATURE:
<223> OTHER INFORMATION: siRNA target

<400> SEQUENCE: 306
tgcctcaaca agcacgtca                                            19

<210> SEQ ID NO 307
<211> LENGTH: 19
<212> TYPE: DNA
<213> ORGANISM: Artificial Sequence
<220> FEATURE:
<223> OTHER INFORMATION: siRNA target

<400> SEQUENCE: 307
tccaataccT cactcgctc                                            19

<210> SEQ ID NO 308
<211> LENGTH: 19
<212> TYPE: DNA
<213> ORGANISM: Artificial Sequence
<220> FEATURE:
<223> OTHER INFORMATION: siRNA target

<400> SEQUENCE: 308
ctcactcgct cagctataa                                            19

<210> SEQ ID NO 309
<211> LENGTH: 19
<212> TYPE: DNA
<213> ORGANISM: Artificial Sequence
<220> FEATURE:
<223> OTHER INFORMATION: siRNA target
```

```
<400> SEQUENCE: 309
tacctcactc gctcagcta                                                19

<210> SEQ ID NO 310
<211> LENGTH: 19
<212> TYPE: DNA
<213> ORGANISM: Artificial Sequence
<220> FEATURE:
<223> OTHER INFORMATION: siRNA target

<400> SEQUENCE: 310
ctgtctcatc ttaatatgt                                                19

<210> SEQ ID NO 311
<211> LENGTH: 19
<212> TYPE: DNA
<213> ORGANISM: Artificial Sequence
<220> FEATURE:
<223> OTHER INFORMATION: siRNA target

<400> SEQUENCE: 311
ctcaacaagc acgtcaaaa                                                19

<210> SEQ ID NO 312
<211> LENGTH: 19
<212> TYPE: DNA
<213> ORGANISM: Artificial Sequence
<220> FEATURE:
<223> OTHER INFORMATION: siRNA target

<400> SEQUENCE: 312
caacaagcac gtcaaaagc                                                19

<210> SEQ ID NO 313
<211> LENGTH: 19
<212> TYPE: DNA
<213> ORGANISM: Artificial Sequence
<220> FEATURE:
<223> OTHER INFORMATION: siRNA target

<400> SEQUENCE: 313
tataagaaga gcctcaacc                                                19

<210> SEQ ID NO 314
<211> LENGTH: 19
<212> TYPE: DNA
<213> ORGANISM: Artificial Sequence
<220> FEATURE:
<223> OTHER INFORMATION: siRNA target

<400> SEQUENCE: 314
atatgtctct tgctgatct                                                19

<210> SEQ ID NO 315
<211> LENGTH: 19
<212> TYPE: DNA
<213> ORGANISM: Artificial Sequence
<220> FEATURE:
<223> OTHER INFORMATION: siRNA target

<400> SEQUENCE: 315
cgctcagcta taagaagag                                                19

<210> SEQ ID NO 316
<211> LENGTH: 19
<212> TYPE: DNA
```

```
<213> ORGANISM: Artificial Sequence
<220> FEATURE:
<223> OTHER INFORMATION: siRNA target

<400> SEQUENCE: 316
atcaatttct gtctcatct                                                    19

<210> SEQ ID NO 317
<211> LENGTH: 19
<212> TYPE: DNA
<213> ORGANISM: Artificial Sequence
<220> FEATURE:
<223> OTHER INFORMATION: siRNA target

<400> SEQUENCE: 317
tgtctcatct taatatgtc                                                    19

<210> SEQ ID NO 318
<211> LENGTH: 19
<212> TYPE: DNA
<213> ORGANISM: Artificial Sequence
<220> FEATURE:
<223> OTHER INFORMATION: siRNA target

<400> SEQUENCE: 318
gtctcatctt aatatgtct                                                    19

<210> SEQ ID NO 319
<211> LENGTH: 19
<212> TYPE: DNA
<213> ORGANISM: Artificial Sequence
<220> FEATURE:
<223> OTHER INFORMATION: siRNA target

<400> SEQUENCE: 319
gtccaatacc tcactcgct                                                    19

<210> SEQ ID NO 320
<211> LENGTH: 19
<212> TYPE: DNA
<213> ORGANISM: Artificial Sequence
<220> FEATURE:
<223> OTHER INFORMATION: siRNA target

<400> SEQUENCE: 320
tgatgtaagt tctgagtgt                                                    19

<210> SEQ ID NO 321
<211> LENGTH: 19
<212> TYPE: DNA
<213> ORGANISM: Artificial Sequence
<220> FEATURE:
<223> OTHER INFORMATION: siRNA target

<400> SEQUENCE: 321
ccgagaaggt agacaattg                                                    19

<210> SEQ ID NO 322
<211> LENGTH: 19
<212> TYPE: DNA
<213> ORGANISM: Artificial Sequence
<220> FEATURE:
<223> OTHER INFORMATION: siRNA target

<400> SEQUENCE: 322
tgaccgagaa ggtagacaa                                                    19
```

```
<210> SEQ ID NO 323
<211> LENGTH: 19
<212> TYPE: DNA
<213> ORGANISM: Artificial Sequence
<220> FEATURE:
<223> OTHER INFORMATION: siRNA target

<400> SEQUENCE: 323
aaagcaacct tctgatgta                                              19

<210> SEQ ID NO 324
<211> LENGTH: 19
<212> TYPE: DNA
<213> ORGANISM: Artificial Sequence
<220> FEATURE:
<223> OTHER INFORMATION: siRNA target

<400> SEQUENCE: 324
atgtaagttc tgagtgtga                                              19

<210> SEQ ID NO 325
<211> LENGTH: 19
<212> TYPE: DNA
<213> ORGANISM: Artificial Sequence
<220> FEATURE:
<223> OTHER INFORMATION: siRNA target

<400> SEQUENCE: 325
gttctgagtg tgaccgaga                                              19

<210> SEQ ID NO 326
<211> LENGTH: 19
<212> TYPE: DNA
<213> ORGANISM: Artificial Sequence
<220> FEATURE:
<223> OTHER INFORMATION: siRNA target

<400> SEQUENCE: 326
gaccgagaag gtagacaat                                              19

<210> SEQ ID NO 327
<211> LENGTH: 19
<212> TYPE: DNA
<213> ORGANISM: Artificial Sequence
<220> FEATURE:
<223> OTHER INFORMATION: siRNA target

<400> SEQUENCE: 327
gcacccatga gttgtgaca                                              19

<210> SEQ ID NO 328
<211> LENGTH: 19
<212> TYPE: DNA
<213> ORGANISM: Artificial Sequence
<220> FEATURE:
<223> OTHER INFORMATION: siRNA target

<400> SEQUENCE: 328
ctacctccct acagacaga                                              19

<210> SEQ ID NO 329
<211> LENGTH: 19
<212> TYPE: DNA
<213> ORGANISM: Artificial Sequence
<220> FEATURE:
<223> OTHER INFORMATION: siRNA target
```

```
<400> SEQUENCE: 329
ccctacagac agagccaca                                               19

<210> SEQ ID NO 330
<211> LENGTH: 19
<212> TYPE: DNA
<213> ORGANISM: Artificial Sequence
<220> FEATURE:
<223> OTHER INFORMATION: siRNA target

<400> SEQUENCE: 330
gtgtgaccga aaggtaga                                                19

<210> SEQ ID NO 331
<211> LENGTH: 19
<212> TYPE: DNA
<213> ORGANISM: Artificial Sequence
<220> FEATURE:
<223> OTHER INFORMATION: siRNA target

<400> SEQUENCE: 331
aagcaacctt ctgatgtaa                                               19

<210> SEQ ID NO 332
<211> LENGTH: 19
<212> TYPE: DNA
<213> ORGANISM: Artificial Sequence
<220> FEATURE:
<223> OTHER INFORMATION: siRNA target

<400> SEQUENCE: 332
gagtgtgacc gagaaggta                                               19

<210> SEQ ID NO 333
<211> LENGTH: 19
<212> TYPE: DNA
<213> ORGANISM: Artificial Sequence
<220> FEATURE:
<223> OTHER INFORMATION: siRNA target

<400> SEQUENCE: 333
gcaaccttct gatgtaagt                                               19

<210> SEQ ID NO 334
<211> LENGTH: 19
<212> TYPE: DNA
<213> ORGANISM: Artificial Sequence
<220> FEATURE:
<223> OTHER INFORMATION: siRNA target

<400> SEQUENCE: 334
tgacaaatca acacaaacc                                               19

<210> SEQ ID NO 335
<211> LENGTH: 19
<212> TYPE: DNA
<213> ORGANISM: Artificial Sequence
<220> FEATURE:
<223> OTHER INFORMATION: siRNA target

<400> SEQUENCE: 335
gcaaagcaac cttctgatg                                               19

<210> SEQ ID NO 336
<211> LENGTH: 19
<212> TYPE: DNA
```

```
<213> ORGANISM: Artificial Sequence
<220> FEATURE:
<223> OTHER INFORMATION: siRNA target

<400> SEQUENCE: 336
tgagtgtgac cgagaaggt                                            19

<210> SEQ ID NO 337
<211> LENGTH: 19
<212> TYPE: DNA
<213> ORGANISM: Artificial Sequence
<220> FEATURE:
<223> OTHER INFORMATION: siRNA target

<400> SEQUENCE: 337
caaagcaacc ttctgatgt                                            19

<210> SEQ ID NO 338
<211> LENGTH: 19
<212> TYPE: DNA
<213> ORGANISM: Artificial Sequence
<220> FEATURE:
<223> OTHER INFORMATION: siRNA target

<400> SEQUENCE: 338
gcccagcacc catgagttg                                            19

<210> SEQ ID NO 339
<211> LENGTH: 19
<212> TYPE: DNA
<213> ORGANISM: Artificial Sequence
<220> FEATURE:
<223> OTHER INFORMATION: siRNA target

<400> SEQUENCE: 339
gtgacaaatc aacacaaac                                            19

<210> SEQ ID NO 340
<211> LENGTH: 19
<212> TYPE: DNA
<213> ORGANISM: Artificial Sequence
<220> FEATURE:
<223> OTHER INFORMATION: siRNA target

<400> SEQUENCE: 340
cctacagaca gagccacaa                                            19

<210> SEQ ID NO 341
<211> LENGTH: 19
<212> TYPE: DNA
<213> ORGANISM: Artificial Sequence
<220> FEATURE:
<223> OTHER INFORMATION: siRNA target

<400> SEQUENCE: 341
agtgtgaccg agaaggtag                                            19

<210> SEQ ID NO 342
<211> LENGTH: 19
<212> TYPE: DNA
<213> ORGANISM: Artificial Sequence
<220> FEATURE:
<223> OTHER INFORMATION: siRNA target

<400> SEQUENCE: 342
ggcaaagcaa ccttctgat                                            19
```

```
<210> SEQ ID NO 343
<211> LENGTH: 19
<212> TYPE: DNA
<213> ORGANISM: Artificial Sequence
<220> FEATURE:
<223> OTHER INFORMATION: siRNA target

<400> SEQUENCE: 343
ctccctacag acagagcca                                             19

<210> SEQ ID NO 344
<211> LENGTH: 19
<212> TYPE: DNA
<213> ORGANISM: Artificial Sequence
<220> FEATURE:
<223> OTHER INFORMATION: siRNA target

<400> SEQUENCE: 344
ctacagacag agccacaag                                             19

<210> SEQ ID NO 345
<211> LENGTH: 19
<212> TYPE: DNA
<213> ORGANISM: Artificial Sequence
<220> FEATURE:
<223> OTHER INFORMATION: siRNA target

<400> SEQUENCE: 345
acacaaaccc caagtcctc                                             19

<210> SEQ ID NO 346
<211> LENGTH: 19
<212> TYPE: DNA
<213> ORGANISM: Artificial Sequence
<220> FEATURE:
<223> OTHER INFORMATION: siRNA target

<400> SEQUENCE: 346
gccaggcctt caaccacta                                             19

<210> SEQ ID NO 347
<211> LENGTH: 19
<212> TYPE: DNA
<213> ORGANISM: Artificial Sequence
<220> FEATURE:
<223> OTHER INFORMATION: siRNA target

<400> SEQUENCE: 347
gagaaggtag acaattgca                                             19

<210> SEQ ID NO 348
<211> LENGTH: 19
<212> TYPE: DNA
<213> ORGANISM: Artificial Sequence
<220> FEATURE:
<223> OTHER INFORMATION: siRNA target

<400> SEQUENCE: 348
aaatcaacac aaaccccaa                                             19

<210> SEQ ID NO 349
<211> LENGTH: 19
<212> TYPE: DNA
<213> ORGANISM: Artificial Sequence
<220> FEATURE:
<223> OTHER INFORMATION: siRNA target
```

```
<400> SEQUENCE: 349
ggtagacaat tgcagcctg                                             19

<210> SEQ ID NO 350
<211> LENGTH: 19
<212> TYPE: DNA
<213> ORGANISM: Artificial Sequence
<220> FEATURE:
<223> OTHER INFORMATION: siRNA target

<400> SEQUENCE: 350
ccctacctcc ctacagaca                                             19

<210> SEQ ID NO 351
<211> LENGTH: 19
<212> TYPE: DNA
<213> ORGANISM: Artificial Sequence
<220> FEATURE:
<223> OTHER INFORMATION: siRNA target

<400> SEQUENCE: 351
gagcccagca cccatgagt                                             19

<210> SEQ ID NO 352
<211> LENGTH: 19
<212> TYPE: DNA
<213> ORGANISM: Artificial Sequence
<220> FEATURE:
<223> OTHER INFORMATION: siRNA target

<400> SEQUENCE: 352
cttgccaggc cttcaacca                                             19

<210> SEQ ID NO 353
<211> LENGTH: 19
<212> TYPE: DNA
<213> ORGANISM: Artificial Sequence
<220> FEATURE:
<223> OTHER INFORMATION: siRNA target

<400> SEQUENCE: 353
agaaggtaga caattgcag                                             19

<210> SEQ ID NO 354
<211> LENGTH: 19
<212> TYPE: DNA
<213> ORGANISM: Artificial Sequence
<220> FEATURE:
<223> OTHER INFORMATION: siRNA target

<400> SEQUENCE: 354
gaaggtagac aattgcagc                                             19

<210> SEQ ID NO 355
<211> LENGTH: 19
<212> TYPE: DNA
<213> ORGANISM: Artificial Sequence
<220> FEATURE:
<223> OTHER INFORMATION: siRNA target

<400> SEQUENCE: 355
tctgagtgtg accgagaag                                             19

<210> SEQ ID NO 356
<211> LENGTH: 19
<212> TYPE: DNA
```

```
<213> ORGANISM: Artificial Sequence
<220> FEATURE:
<223> OTHER INFORMATION: siRNA target

<400> SEQUENCE: 356
gtgaccgaga aggtagaca                                                    19

<210> SEQ ID NO 357
<211> LENGTH: 19
<212> TYPE: DNA
<213> ORGANISM: Artificial Sequence
<220> FEATURE:
<223> OTHER INFORMATION: siRNA target

<400> SEQUENCE: 357
aagttctgag tgtgaccga                                                    19

<210> SEQ ID NO 358
<211> LENGTH: 19
<212> TYPE: DNA
<213> ORGANISM: Artificial Sequence
<220> FEATURE:
<223> OTHER INFORMATION: siRNA target

<400> SEQUENCE: 358
tgccaggcct tcaaccact                                                    19

<210> SEQ ID NO 359
<211> LENGTH: 19
<212> TYPE: DNA
<213> ORGANISM: Artificial Sequence
<220> FEATURE:
<223> OTHER INFORMATION: siRNA target

<400> SEQUENCE: 359
cgagaaggta gacaattgc                                                    19

<210> SEQ ID NO 360
<211> LENGTH: 19
<212> TYPE: DNA
<213> ORGANISM: Artificial Sequence
<220> FEATURE:
<223> OTHER INFORMATION: siRNA target

<400> SEQUENCE: 360
gtaagttctg agtgtgacc                                                    19

<210> SEQ ID NO 361
<211> LENGTH: 19
<212> TYPE: DNA
<213> ORGANISM: Artificial Sequence
<220> FEATURE:
<223> OTHER INFORMATION: siRNA target

<400> SEQUENCE: 361
tctgatgtaa gttctgagt                                                    19

<210> SEQ ID NO 362
<211> LENGTH: 19
<212> TYPE: DNA
<213> ORGANISM: Artificial Sequence
<220> FEATURE:
<223> OTHER INFORMATION: siRNA target

<400> SEQUENCE: 362
gcccctacct ccctacaga                                                    19
```

```
<210> SEQ ID NO 363
<211> LENGTH: 19
<212> TYPE: DNA
<213> ORGANISM: Artificial Sequence
<220> FEATURE:
<223> OTHER INFORMATION: siRNA target

<400> SEQUENCE: 363
acaggagccc agcacccat                                                      19

<210> SEQ ID NO 364
<211> LENGTH: 19
<212> TYPE: DNA
<213> ORGANISM: Artificial Sequence
<220> FEATURE:
<223> OTHER INFORMATION: siRNA target

<400> SEQUENCE: 364
accgagaagg tagacaatt                                                      19

<210> SEQ ID NO 365
<211> LENGTH: 19
<212> TYPE: DNA
<213> ORGANISM: Artificial Sequence
<220> FEATURE:
<223> OTHER INFORMATION: siRNA target

<400> SEQUENCE: 365
agcccagcac ccatgagtt                                                      19

<210> SEQ ID NO 366
<211> LENGTH: 19
<212> TYPE: DNA
<213> ORGANISM: Artificial Sequence
<220> FEATURE:
<223> OTHER INFORMATION: siRNA target

<400> SEQUENCE: 366
caaatcaaca caaacccca                                                      19

<210> SEQ ID NO 367
<211> LENGTH: 19
<212> TYPE: DNA
<213> ORGANISM: Artificial Sequence
<220> FEATURE:
<223> OTHER INFORMATION: siRNA target

<400> SEQUENCE: 367
cctccttgcc aggccttca                                                      19

<210> SEQ ID NO 368
<211> LENGTH: 19
<212> TYPE: DNA
<213> ORGANISM: Artificial Sequence
<220> FEATURE:
<223> OTHER INFORMATION: siRNA target

<400> SEQUENCE: 368
cttctgatgt aagttctga                                                      19

<210> SEQ ID NO 369
<211> LENGTH: 19
<212> TYPE: DNA
<213> ORGANISM: Artificial Sequence
<220> FEATURE:
<223> OTHER INFORMATION: siRNA target
```

```
<400> SEQUENCE: 369
aggtagacaa ttgcagcct                                               19

<210> SEQ ID NO 370
<211> LENGTH: 19
<212> TYPE: RNA
<213> ORGANISM: Artificial Sequence
<220> FEATURE:
<223> OTHER INFORMATION: siRNA strand

<400> SEQUENCE: 370
aguggaugag ggagcaggc                                               19

<210> SEQ ID NO 371
<211> LENGTH: 19
<212> TYPE: RNA
<213> ORGANISM: Artificial Sequence
<220> FEATURE:
<223> OTHER INFORMATION: siRNA strand

<400> SEQUENCE: 371
gccugcuccc ucauccacu                                               19

<210> SEQ ID NO 372
<211> LENGTH: 19
<212> TYPE: RNA
<213> ORGANISM: Artificial Sequence
<220> FEATURE:
<223> OTHER INFORMATION: siRNA strand

<400> SEQUENCE: 372
gcacacagug gaugaggga                                               19

<210> SEQ ID NO 373
<211> LENGTH: 19
<212> TYPE: RNA
<213> ORGANISM: Artificial Sequence
<220> FEATURE:
<223> OTHER INFORMATION: siRNA strand

<400> SEQUENCE: 373
ucccucaucc acugugugc                                               19

<210> SEQ ID NO 374
<211> LENGTH: 19
<212> TYPE: RNA
<213> ORGANISM: Artificial Sequence
<220> FEATURE:
<223> OTHER INFORMATION: siRNA strand

<400> SEQUENCE: 374
ugaagugcac acaguggau                                               19

<210> SEQ ID NO 375
<211> LENGTH: 19
<212> TYPE: RNA
<213> ORGANISM: Artificial Sequence
<220> FEATURE:
<223> OTHER INFORMATION: siRNA strand

<400> SEQUENCE: 375
auccacugug ugcacuuca                                               19

<210> SEQ ID NO 376
<211> LENGTH: 19
<212> TYPE: RNA
```

```
<213> ORGANISM: Artificial Sequence
<220> FEATURE:
<223> OTHER INFORMATION: siRNA strand

<400> SEQUENCE: 376
cacacagugg augagggag                                                    19

<210> SEQ ID NO 377
<211> LENGTH: 19
<212> TYPE: RNA
<213> ORGANISM: Artificial Sequence
<220> FEATURE:
<223> OTHER INFORMATION: siRNA strand

<400> SEQUENCE: 377
cucccucauc cacugugug                                                    19

<210> SEQ ID NO 378
<211> LENGTH: 19
<212> TYPE: RNA
<213> ORGANISM: Artificial Sequence
<220> FEATURE:
<223> OTHER INFORMATION: siRNA strand

<400> SEQUENCE: 378
gcacacagua gaugaggga                                                    19

<210> SEQ ID NO 379
<211> LENGTH: 19
<212> TYPE: RNA
<213> ORGANISM: Artificial Sequence
<220> FEATURE:
<223> OTHER INFORMATION: siRNA strand

<400> SEQUENCE: 379
ucccucaucu acugugugc                                                    19

<210> SEQ ID NO 380
<211> LENGTH: 19
<212> TYPE: RNA
<213> ORGANISM: Artificial Sequence
<220> FEATURE:
<223> OTHER INFORMATION: siRNA strand

<400> SEQUENCE: 380
ugaagugcac acaguagau                                                    19

<210> SEQ ID NO 381
<211> LENGTH: 19
<212> TYPE: RNA
<213> ORGANISM: Artificial Sequence
<220> FEATURE:
<223> OTHER INFORMATION: siRNA strand

<400> SEQUENCE: 381
aucuacugug ugcacuuca                                                    19

<210> SEQ ID NO 382
<211> LENGTH: 19
<212> TYPE: RNA
<213> ORGANISM: Artificial Sequence
<220> FEATURE:
<223> OTHER INFORMATION: siRNA strand

<400> SEQUENCE: 382
aguagaugag ggagcaggc                                                    19
```

```
<210> SEQ ID NO 383
<211> LENGTH: 19
<212> TYPE: RNA
<213> ORGANISM: Artificial Sequence
<220> FEATURE:
<223> OTHER INFORMATION: siRNA strand

<400> SEQUENCE: 383
gccugcuccc ucaucuacu                                                 19

<210> SEQ ID NO 384
<211> LENGTH: 19
<212> TYPE: RNA
<213> ORGANISM: Artificial Sequence
<220> FEATURE:
<223> OTHER INFORMATION: siRNA strand

<400> SEQUENCE: 384
cacacaguag augagggag                                                 19

<210> SEQ ID NO 385
<211> LENGTH: 19
<212> TYPE: RNA
<213> ORGANISM: Artificial Sequence
<220> FEATURE:
<223> OTHER INFORMATION: siRNA strand

<400> SEQUENCE: 385
cucccucauc uacugugug                                                 19

<210> SEQ ID NO 386
<211> LENGTH: 19
<212> TYPE: RNA
<213> ORGANISM: Artificial Sequence
<220> FEATURE:
<223> OTHER INFORMATION: siRNA strand

<400> SEQUENCE: 386
ggcgcagacu uccaaaggc                                                 19

<210> SEQ ID NO 387
<211> LENGTH: 19
<212> TYPE: RNA
<213> ORGANISM: Artificial Sequence
<220> FEATURE:
<223> OTHER INFORMATION: siRNA strand

<400> SEQUENCE: 387
gccuuuggaa gucugcgcc                                                 19

<210> SEQ ID NO 388
<211> LENGTH: 19
<212> TYPE: RNA
<213> ORGANISM: Artificial Sequence
<220> FEATURE:
<223> OTHER INFORMATION: siRNA strand

<400> SEQUENCE: 388
cacaagggcg cagacuucc                                                 19

<210> SEQ ID NO 389
<211> LENGTH: 19
<212> TYPE: RNA
<213> ORGANISM: Artificial Sequence
<220> FEATURE:
<223> OTHER INFORMATION: siRNA strand
```

<400> SEQUENCE: 389
ggaagucugc gcccuugug            19

<210> SEQ ID NO 390
<211> LENGTH: 19
<212> TYPE: RNA
<213> ORGANISM: Artificial Sequence
<220> FEATURE:
<223> OTHER INFORMATION: siRNA strand

<400> SEQUENCE: 390
gcagggcaca agggcgcag            19

<210> SEQ ID NO 391
<211> LENGTH: 19
<212> TYPE: RNA
<213> ORGANISM: Artificial Sequence
<220> FEATURE:
<223> OTHER INFORMATION: siRNA strand

<400> SEQUENCE: 391
cugcgcccuu gugcccugc            19

<210> SEQ ID NO 392
<211> LENGTH: 19
<212> TYPE: RNA
<213> ORGANISM: Artificial Sequence
<220> FEATURE:
<223> OTHER INFORMATION: siRNA strand

<400> SEQUENCE: 392
acaagggcgc agacuucca            19

<210> SEQ ID NO 393
<211> LENGTH: 19
<212> TYPE: RNA
<213> ORGANISM: Artificial Sequence
<220> FEATURE:
<223> OTHER INFORMATION: siRNA strand

<400> SEQUENCE: 393
uggaagucug cgcccuugu            19

<210> SEQ ID NO 394
<211> LENGTH: 19
<212> TYPE: RNA
<213> ORGANISM: Artificial Sequence
<220> FEATURE:
<223> OTHER INFORMATION: siRNA strand

<400> SEQUENCE: 394
cacaagggca cagacuucc            19

<210> SEQ ID NO 395
<211> LENGTH: 19
<212> TYPE: RNA
<213> ORGANISM: Artificial Sequence
<220> FEATURE:
<223> OTHER INFORMATION: siRNA strand

<400> SEQUENCE: 395
ggaagucugu gcccuugug            19

<210> SEQ ID NO 396
<211> LENGTH: 19
<212> TYPE: RNA

```
<213> ORGANISM: Artificial Sequence
<220> FEATURE:
<223> OTHER INFORMATION: siRNA strand

<400> SEQUENCE: 396
gcagggcaca agggcacag                                                     19

<210> SEQ ID NO 397
<211> LENGTH: 19
<212> TYPE: RNA
<213> ORGANISM: Artificial Sequence
<220> FEATURE:
<223> OTHER INFORMATION: siRNA strand

<400> SEQUENCE: 397
cugugcccuu gugcccugc                                                     19

<210> SEQ ID NO 398
<211> LENGTH: 19
<212> TYPE: RNA
<213> ORGANISM: Artificial Sequence
<220> FEATURE:
<223> OTHER INFORMATION: siRNA strand

<400> SEQUENCE: 398
ggcacagacu uccaaaggc                                                     19

<210> SEQ ID NO 399
<211> LENGTH: 19
<212> TYPE: RNA
<213> ORGANISM: Artificial Sequence
<220> FEATURE:
<223> OTHER INFORMATION: siRNA strand

<400> SEQUENCE: 399
gccuuuggaa gucugugcc                                                     19

<210> SEQ ID NO 400
<211> LENGTH: 19
<212> TYPE: RNA
<213> ORGANISM: Artificial Sequence
<220> FEATURE:
<223> OTHER INFORMATION: siRNA strand

<400> SEQUENCE: 400
acaagggcac agacuucca                                                     19

<210> SEQ ID NO 401
<211> LENGTH: 19
<212> TYPE: RNA
<213> ORGANISM: Artificial Sequence
<220> FEATURE:
<223> OTHER INFORMATION: siRNA strand

<400> SEQUENCE: 401
uggaagucug ugcccuugu                                                     19

<210> SEQ ID NO 402
<211> LENGTH: 19
<212> TYPE: RNA
<213> ORGANISM: Artificial Sequence
<220> FEATURE:
<223> OTHER INFORMATION: siRNA strand

<400> SEQUENCE: 402
caaugguaca gcucuuccu                                                     19
```

```
<210> SEQ ID NO 403
<211> LENGTH: 19
<212> TYPE: RNA
<213> ORGANISM: Artificial Sequence
<220> FEATURE:
<223> OTHER INFORMATION: siRNA strand

<400> SEQUENCE: 403
aggaagagcu guaccauug                                                  19

<210> SEQ ID NO 404
<211> LENGTH: 19
<212> TYPE: RNA
<213> ORGANISM: Artificial Sequence
<220> FEATURE:
<223> OTHER INFORMATION: siRNA strand

<400> SEQUENCE: 404
caucccaaug guacagcuc                                                  19

<210> SEQ ID NO 405
<211> LENGTH: 19
<212> TYPE: RNA
<213> ORGANISM: Artificial Sequence
<220> FEATURE:
<223> OTHER INFORMATION: siRNA strand

<400> SEQUENCE: 405
gagcuguacc auugggaug                                                  19

<210> SEQ ID NO 406
<211> LENGTH: 19
<212> TYPE: RNA
<213> ORGANISM: Artificial Sequence
<220> FEATURE:
<223> OTHER INFORMATION: siRNA strand

<400> SEQUENCE: 406
ccaucccaau gguacagcu                                                  19

<210> SEQ ID NO 407
<211> LENGTH: 19
<212> TYPE: RNA
<213> ORGANISM: Artificial Sequence
<220> FEATURE:
<223> OTHER INFORMATION: siRNA strand

<400> SEQUENCE: 407
agcuguacca uugggaugg                                                  19

<210> SEQ ID NO 408
<211> LENGTH: 19
<212> TYPE: RNA
<213> ORGANISM: Artificial Sequence
<220> FEATURE:
<223> OTHER INFORMATION: siRNA strand

<400> SEQUENCE: 408
uuguggccau cccaauggu                                                  19

<210> SEQ ID NO 409
<211> LENGTH: 19
<212> TYPE: RNA
<213> ORGANISM: Artificial Sequence
<220> FEATURE:
<223> OTHER INFORMATION: siRNA strand
```

```
<400> SEQUENCE: 409
accauuggga uggccacaa                                                19

<210> SEQ ID NO 410
<211> LENGTH: 19
<212> TYPE: RNA
<213> ORGANISM: Artificial Sequence
<220> FEATURE:
<223> OTHER INFORMATION: siRNA strand

<400> SEQUENCE: 410
caacgguaca gcucuuccu                                                19

<210> SEQ ID NO 411
<211> LENGTH: 19
<212> TYPE: RNA
<213> ORGANISM: Artificial Sequence
<220> FEATURE:
<223> OTHER INFORMATION: siRNA strand

<400> SEQUENCE: 411
aggaagagcu guaccguug                                                19

<210> SEQ ID NO 412
<211> LENGTH: 19
<212> TYPE: RNA
<213> ORGANISM: Artificial Sequence
<220> FEATURE:
<223> OTHER INFORMATION: siRNA strand

<400> SEQUENCE: 412
caucccaacg guacagcuc                                                19

<210> SEQ ID NO 413
<211> LENGTH: 19
<212> TYPE: RNA
<213> ORGANISM: Artificial Sequence
<220> FEATURE:
<223> OTHER INFORMATION: siRNA strand

<400> SEQUENCE: 413
gagcuguacc guugggaug                                                19

<210> SEQ ID NO 414
<211> LENGTH: 19
<212> TYPE: RNA
<213> ORGANISM: Artificial Sequence
<220> FEATURE:
<223> OTHER INFORMATION: siRNA strand

<400> SEQUENCE: 414
ccaucccaac gguacagcu                                                19

<210> SEQ ID NO 415
<211> LENGTH: 19
<212> TYPE: RNA
<213> ORGANISM: Artificial Sequence
<220> FEATURE:
<223> OTHER INFORMATION: siRNA strand

<400> SEQUENCE: 415
agcuguaccg uugggaugg                                                19

<210> SEQ ID NO 416
<211> LENGTH: 19
<212> TYPE: RNA
```

```
<213> ORGANISM: Artificial Sequence
<220> FEATURE:
<223> OTHER INFORMATION: siRNA strand

<400> SEQUENCE: 416
uuguggccau cccaacggu                                          19

<210> SEQ ID NO 417
<211> LENGTH: 19
<212> TYPE: RNA
<213> ORGANISM: Artificial Sequence
<220> FEATURE:
<223> OTHER INFORMATION: siRNA stand

<400> SEQUENCE: 417
accguuggga uggccacaa                                          19

<210> SEQ ID NO 418
<211> LENGTH: 19
<212> TYPE: RNA
<213> ORGANISM: Artificial Sequence
<220> FEATURE:
<223> OTHER INFORMATION: siRNA strand

<400> SEQUENCE: 418
gucggcaagc agagcuccc                                          19

<210> SEQ ID NO 419
<211> LENGTH: 19
<212> TYPE: RNA
<213> ORGANISM: Artificial Sequence
<220> FEATURE:
<223> OTHER INFORMATION: siRNA strand

<400> SEQUENCE: 419
gggagcucug cuugccgac                                          19

<210> SEQ ID NO 420
<211> LENGTH: 19
<212> TYPE: RNA
<213> ORGANISM: Artificial Sequence
<220> FEATURE:
<223> OTHER INFORMATION: siRNA strand

<400> SEQUENCE: 420
agccagucgg caagcagag                                          19

<210> SEQ ID NO 421
<211> LENGTH: 19
<212> TYPE: RNA
<213> ORGANISM: Artificial Sequence
<220> FEATURE:
<223> OTHER INFORMATION: siRNA strand

<400> SEQUENCE: 421
cucugcuugc cgacuggcu                                          19

<210> SEQ ID NO 422
<211> LENGTH: 21
<212> TYPE: RNA
<213> ORGANISM: Artificial Sequence
<220> FEATURE:
<223> OTHER INFORMATION: siRNA strand

<400> SEQUENCE: 422
cagccagucg gcaagcagag c                                       21
```

```
<210> SEQ ID NO 423
<211> LENGTH: 21
<212> TYPE: RNA
<213> ORGANISM: Artificial Sequence
<220> FEATURE:
<223> OTHER INFORMATION: siRNA strand

<400> SEQUENCE: 423
gcucugcuug ccgacuggcu g                                              21

<210> SEQ ID NO 424
<211> LENGTH: 19
<212> TYPE: RNA
<213> ORGANISM: Artificial Sequence
<220> FEATURE:
<223> OTHER INFORMATION: siRNA strand

<400> SEQUENCE: 424
gucucacagc cagucggca                                                 19

<210> SEQ ID NO 425
<211> LENGTH: 19
<212> TYPE: RNA
<213> ORGANISM: Artificial Sequence
<220> FEATURE:
<223> OTHER INFORMATION: siRNA strand

<400> SEQUENCE: 425
ugccgacugg cugugagac                                                 19

<210> SEQ ID NO 426
<211> LENGTH: 19
<212> TYPE: RNA
<213> ORGANISM: Artificial Sequence
<220> FEATURE:
<223> OTHER INFORMATION: siRNA strand

<400> SEQUENCE: 426
gucagcaagc agagcuccc                                                 19

<210> SEQ ID NO 427
<211> LENGTH: 19
<212> TYPE: RNA
<213> ORGANISM: Artificial Sequence
<220> FEATURE:
<223> OTHER INFORMATION: siRNA strand

<400> SEQUENCE: 427
gggagcucug cuugcugac                                                 19

<210> SEQ ID NO 428
<211> LENGTH: 19
<212> TYPE: RNA
<213> ORGANISM: Artificial Sequence
<220> FEATURE:
<223> OTHER INFORMATION: siRNA strand

<400> SEQUENCE: 428
agccagucag caagcagag                                                 19

<210> SEQ ID NO 429
<211> LENGTH: 19
<212> TYPE: RNA
<213> ORGANISM: Artificial Sequence
<220> FEATURE:
<223> OTHER INFORMATION: siRNA strand
```

```
<400> SEQUENCE: 429
cucugcuugc ugacuggcu                                                  19

<210> SEQ ID NO 430
<211> LENGTH: 21
<212> TYPE: RNA
<213> ORGANISM: Artificial Sequence
<220> FEATURE:
<223> OTHER INFORMATION: siRNA strand

<400> SEQUENCE: 430
cagccaguca gcaagcagag c                                               21

<210> SEQ ID NO 431
<211> LENGTH: 21
<212> TYPE: RNA
<213> ORGANISM: Artificial Sequence
<220> FEATURE:
<223> OTHER INFORMATION: siRNA strand

<400> SEQUENCE: 431
gcucugcuug cugacuggcu g                                               21

<210> SEQ ID NO 432
<211> LENGTH: 19
<212> TYPE: RNA
<213> ORGANISM: Artificial Sequence
<220> FEATURE:
<223> OTHER INFORMATION: siRNA strand

<400> SEQUENCE: 432
gucucacagc cagucagca                                                  19

<210> SEQ ID NO 433
<211> LENGTH: 19
<212> TYPE: RNA
<213> ORGANISM: Artificial Sequence
<220> FEATURE:
<223> OTHER INFORMATION: siRNA strand

<400> SEQUENCE: 433
ugcugacugg cugugagac                                                  19

<210> SEQ ID NO 434
<211> LENGTH: 19
<212> TYPE: RNA
<213> ORGANISM: Artificial Sequence
<220> FEATURE:
<223> OTHER INFORMATION: siRNA strand

<400> SEQUENCE: 434
cacauacauu agcucaaac                                                  19

<210> SEQ ID NO 435
<211> LENGTH: 19
<212> TYPE: RNA
<213> ORGANISM: Artificial Sequence
<220> FEATURE:
<223> OTHER INFORMATION: siRNA strand

<400> SEQUENCE: 435
guuugagcua auguaugug                                                  19

<210> SEQ ID NO 436
<211> LENGTH: 19
<212> TYPE: RNA
```

```
<213> ORGANISM: Artificial Sequence
<220> FEATURE:
<223> OTHER INFORMATION: siRNA strand

<400> SEQUENCE: 436
cagcgucaca uacauuagc                                            19

<210> SEQ ID NO 437
<211> LENGTH: 19
<212> TYPE: RNA
<213> ORGANISM: Artificial Sequence
<220> FEATURE:
<223> OTHER INFORMATION: siRNA strand

<400> SEQUENCE: 437
gcuaauguau gugacgcug                                            19

<210> SEQ ID NO 438
<211> LENGTH: 19
<212> TYPE: RNA
<213> ORGANISM: Artificial Sequence
<220> FEATURE:
<223> OTHER INFORMATION: siRNA strand

<400> SEQUENCE: 438
acauacauua gcucaaacu                                            19

<210> SEQ ID NO 439
<211> LENGTH: 19
<212> TYPE: RNA
<213> ORGANISM: Artificial Sequence
<220> FEATURE:
<223> OTHER INFORMATION: siRNA strand

<400> SEQUENCE: 439
aguuugagcu aauguaugu                                            19

<210> SEQ ID NO 440
<211> LENGTH: 19
<212> TYPE: RNA
<213> ORGANISM: Artificial Sequence
<220> FEATURE:
<223> OTHER INFORMATION: siRNA strand

<400> SEQUENCE: 440
cauuagcuca aacugguug                                            19

<210> SEQ ID NO 441
<211> LENGTH: 19
<212> TYPE: RNA
<213> ORGANISM: Artificial Sequence
<220> FEATURE:
<223> OTHER INFORMATION: siRNA strand

<400> SEQUENCE: 441
caaccaguuu gagcuaaug                                            19

<210> SEQ ID NO 442
<211> LENGTH: 19
<212> TYPE: RNA
<213> ORGANISM: Artificial Sequence
<220> FEATURE:
<223> OTHER INFORMATION: siRNA strand

<400> SEQUENCE: 442
cacauacauc agcucaaac                                            19
```

```
<210> SEQ ID NO 443
<211> LENGTH: 19
<212> TYPE: RNA
<213> ORGANISM: Artificial Sequence
<220> FEATURE:
<223> OTHER INFORMATION: siRNA strand

<400> SEQUENCE: 443
guuugagcug auguaugug                                              19

<210> SEQ ID NO 444
<211> LENGTH: 19
<212> TYPE: RNA
<213> ORGANISM: Artificial Sequence
<220> FEATURE:
<223> OTHER INFORMATION: siRNA strand

<400> SEQUENCE: 444
cagcgucaca uacaucagc                                              19

<210> SEQ ID NO 445
<211> LENGTH: 19
<212> TYPE: RNA
<213> ORGANISM: Artificial Sequence
<220> FEATURE:
<223> OTHER INFORMATION: siRNA strand

<400> SEQUENCE: 445
gcugauguau gugacgcug                                              19

<210> SEQ ID NO 446
<211> LENGTH: 19
<212> TYPE: RNA
<213> ORGANISM: Artificial Sequence
<220> FEATURE:
<223> OTHER INFORMATION: siRNA strand

<400> SEQUENCE: 446
acauacauca gcucaaacu                                              19

<210> SEQ ID NO 447
<211> LENGTH: 19
<212> TYPE: RNA
<213> ORGANISM: Artificial Sequence
<220> FEATURE:
<223> OTHER INFORMATION: siRNA strand

<400> SEQUENCE: 447
aguuugagcu gauguaugu                                              19

<210> SEQ ID NO 448
<211> LENGTH: 19
<212> TYPE: RNA
<213> ORGANISM: Artificial Sequence
<220> FEATURE:
<223> OTHER INFORMATION: siRNA strand

<400> SEQUENCE: 448
caucagcuca aacugguug                                              19

<210> SEQ ID NO 449
<211> LENGTH: 19
<212> TYPE: RNA
<213> ORGANISM: Artificial Sequence
<220> FEATURE:
<223> OTHER INFORMATION: siRNA strand
```

```
<400> SEQUENCE: 449
caaccaguuu gagcugaug                                              19

<210> SEQ ID NO 450
<211> LENGTH: 19
<212> TYPE: RNA
<213> ORGANISM: Artificial Sequence
<220> FEATURE:
<223> OTHER INFORMATION: siRNA strand

<400> SEQUENCE: 450
caacaucaaa gcaucuuga                                              19

<210> SEQ ID NO 451
<211> LENGTH: 19
<212> TYPE: RNA
<213> ORGANISM: Artificial Sequence
<220> FEATURE:
<223> OTHER INFORMATION: siRNA strand

<400> SEQUENCE: 451
ucaagaugcu uugauguug                                              19

<210> SEQ ID NO 452
<211> LENGTH: 19
<212> TYPE: RNA
<213> ORGANISM: Artificial Sequence
<220> FEATURE:
<223> OTHER INFORMATION: siRNA strand

<400> SEQUENCE: 452
ccggccaaca ucaaagcau                                              19

<210> SEQ ID NO 453
<211> LENGTH: 19
<212> TYPE: RNA
<213> ORGANISM: Artificial Sequence
<220> FEATURE:
<223> OTHER INFORMATION: siRNA strand

<400> SEQUENCE: 453
augcuuugau guuggccgg                                              19

<210> SEQ ID NO 454
<211> LENGTH: 19
<212> TYPE: RNA
<213> ORGANISM: Artificial Sequence
<220> FEATURE:
<223> OTHER INFORMATION: siRNA strand

<400> SEQUENCE: 454
uccggccaac aucaaagca                                              19

<210> SEQ ID NO 455
<211> LENGTH: 19
<212> TYPE: RNA
<213> ORGANISM: Artificial Sequence
<220> FEATURE:
<223> OTHER INFORMATION: siRNA strand

<400> SEQUENCE: 455
ugcuuugaug uuggccgga                                              19

<210> SEQ ID NO 456
<211> LENGTH: 19
<212> TYPE: RNA
```

```
<213> ORGANISM: Artificial Sequence
<220> FEATURE:
<223> OTHER INFORMATION: siRNA strand

<400> SEQUENCE: 456 caaguuccg gccaacauc                                                    19

<210> SEQ ID NO 457
<211> LENGTH: 19
<212> TYPE: RNA
<213> ORGANISM: Artificial Sequence
<220> FEATURE:
<223> OTHER INFORMATION: siRNA strand

<400> SEQUENCE: 457
gauguuggcc ggaaacuug                                                   19

<210> SEQ ID NO 458
<211> LENGTH: 19
<212> TYPE: RNA
<213> ORGANISM: Artificial Sequence
<220> FEATURE:
<223> OTHER INFORMATION: siRNA strand

<400> SEQUENCE: 458
caaaaucaaa gcaucuuga                                                   19

<210> SEQ ID NO 459
<211> LENGTH: 19
<212> TYPE: RNA
<213> ORGANISM: Artificial Sequence
<220> FEATURE:
<223> OTHER INFORMATION: siRNA strand

<400> SEQUENCE: 459
ucaagaugcu uugauuuug                                                   19

<210> SEQ ID NO 460
<211> LENGTH: 19
<212> TYPE: RNA
<213> ORGANISM: Artificial Sequence
<220> FEATURE:
<223> OTHER INFORMATION: siRNA strand

<400> SEQUENCE: 460
ccggccaaaa ucaaagcau                                                   19

<210> SEQ ID NO 461
<211> LENGTH: 19
<212> TYPE: RNA
<213> ORGANISM: Artificial Sequence
<220> FEATURE:
<223> OTHER INFORMATION: siRNA strand

<400> SEQUENCE: 461
augcuuugau uuuggccgg                                                   19

<210> SEQ ID NO 462
<211> LENGTH: 19
<212> TYPE: RNA
<213> ORGANISM: Artificial Sequence
<220> FEATURE:
<223> OTHER INFORMATION: siRNA strand

<400> SEQUENCE: 462
uccggccaaa aucaaagca                                                   19
```

<210> SEQ ID NO 463
<211> LENGTH: 19
<212> TYPE: RNA
<213> ORGANISM: Artificial Sequence
<220> FEATURE:
<223> OTHER INFORMATION: siRNA strand

<400> SEQUENCE: 463
ugcuuugauu uuggccgga                                              19

<210> SEQ ID NO 464
<211> LENGTH: 19
<212> TYPE: RNA
<213> ORGANISM: Artificial Sequence
<220> FEATURE:
<223> OTHER INFORMATION: siRNA strand

<400> SEQUENCE: 464 caaguuccg gccaaaauc                                               19

<210> SEQ ID NO 465
<211> LENGTH: 19
<212> TYPE: RNA
<213> ORGANISM: Artificial Sequence
<220> FEATURE:
<223> OTHER INFORMATION: siRNA strand

<400> SEQUENCE: 465 gauuuggcc ggaaacuug                                               19

<210> SEQ ID NO 466
<211> LENGTH: 19
<212> TYPE: RNA
<213> ORGANISM: Artificial Sequence
<220> FEATURE:
<223> OTHER INFORMATION: siRNA strand

<400> SEQUENCE: 466
gaauuacugu ccccaucuc                                              19

<210> SEQ ID NO 467
<211> LENGTH: 19
<212> TYPE: RNA
<213> ORGANISM: Artificial Sequence
<220> FEATURE:
<223> OTHER INFORMATION: siRNA strand

<400> SEQUENCE: 467 gagauggga caguaauuc                                               19

<210> SEQ ID NO 468
<211> LENGTH: 19
<212> TYPE: RNA
<213> ORGANISM: Artificial Sequence
<220> FEATURE:
<223> OTHER INFORMATION: siRNA strand

<400> SEQUENCE: 468
gcguugaauu acugucccc                                              19

<210> SEQ ID NO 469
<211> LENGTH: 19
<212> TYPE: RNA
<213> ORGANISM: Artificial Sequence
<220> FEATURE:
<223> OTHER INFORMATION: siRNA strand

```
<400> SEQUENCE: 469
ggggacagua auucaacgc                                                    19

<210> SEQ ID NO 470
<211> LENGTH: 19
<212> TYPE: RNA
<213> ORGANISM: Artificial Sequence
<220> FEATURE:
<223> OTHER INFORMATION: siRNA strand

<400> SEQUENCE: 470
agcguugaau uacugucccc                                                   19

<210> SEQ ID NO 471
<211> LENGTH: 19
<212> TYPE: RNA
<213> ORGANISM: Artificial Sequence
<220> FEATURE:
<223> OTHER INFORMATION: siRNA strand

<400> SEQUENCE: 471
gggacaguaa uucaacgcu                                                    19

<210> SEQ ID NO 472
<211> LENGTH: 19
<212> TYPE: RNA
<213> ORGANISM: Artificial Sequence
<220> FEATURE:
<223> OTHER INFORMATION: siRNA strand

<400> SEQUENCE: 472
ucuucuagcg uugaauuac                                                    19

<210> SEQ ID NO 473
<211> LENGTH: 19
<212> TYPE: RNA
<213> ORGANISM: Artificial Sequence
<220> FEATURE:
<223> OTHER INFORMATION: siRNA strand

<400> SEQUENCE: 473
guaauucaac gcuagaaga                                                    19

<210> SEQ ID NO 474
<211> LENGTH: 19
<212> TYPE: RNA
<213> ORGANISM: Artificial Sequence
<220> FEATURE:
<223> OTHER INFORMATION: siRNA strand

<400> SEQUENCE: 474
gaaguacugu ccccaucuc                                                    19

<210> SEQ ID NO 475
<211> LENGTH: 19
<212> TYPE: RNA
<213> ORGANISM: Artificial Sequence
<220> FEATURE:
<223> OTHER INFORMATION: siRNA strand

<400> SEQUENCE: 475
gagaugggga caguacuuc                                                    19

<210> SEQ ID NO 476
<211> LENGTH: 19
<212> TYPE: RNA
```

```
<213> ORGANISM: Artificial Sequence
<220> FEATURE:
<223> OTHER INFORMATION: siRNA strand

<400> SEQUENCE: 476
gcguugaagu acugcccc                                                 19

<210> SEQ ID NO 477
<211> LENGTH: 19
<212> TYPE: RNA
<213> ORGANISM: Artificial Sequence
<220> FEATURE:
<223> OTHER INFORMATION: siRNA strand

<400> SEQUENCE: 477
ggggacagua cuucaacgc                                                19

<210> SEQ ID NO 478
<211> LENGTH: 19
<212> TYPE: RNA
<213> ORGANISM: Artificial Sequence
<220> FEATURE:
<223> OTHER INFORMATION: siRNA strand

<400> SEQUENCE: 478
agcguugaag uacuguccc                                                19

<210> SEQ ID NO 479
<211> LENGTH: 19
<212> TYPE: RNA
<213> ORGANISM: Artificial Sequence
<220> FEATURE:
<223> OTHER INFORMATION: siRNA strand

<400> SEQUENCE: 479
gggacaguac uucaacgcu                                                19

<210> SEQ ID NO 480
<211> LENGTH: 19
<212> TYPE: RNA
<213> ORGANISM: Artificial Sequence
<220> FEATURE:
<223> OTHER INFORMATION: siRNA strand

<400> SEQUENCE: 480
ucuucuagcg uugaaguac                                                19

<210> SEQ ID NO 481
<211> LENGTH: 19
<212> TYPE: RNA
<213> ORGANISM: Artificial Sequence
<220> FEATURE:
<223> OTHER INFORMATION: siRNA strand

<400> SEQUENCE: 481
guacuucaac gcuagaaga                                                19

<210> SEQ ID NO 482
<211> LENGTH: 19
<212> TYPE: RNA
<213> ORGANISM: Artificial Sequence
<220> FEATURE:
<223> OTHER INFORMATION: siRNA stand

<400> SEQUENCE: 482
uagcguugaa uuacugucc                                                19
```

<210> SEQ ID NO 483
<211> LENGTH: 19
<212> TYPE: RNA
<213> ORGANISM: Artificial Sequence
<220> FEATURE:
<223> OTHER INFORMATION: siRNA strand

<400> SEQUENCE: 483
ggacaguaau ucaacgcua                                              19

<210> SEQ ID NO 484
<211> LENGTH: 19
<212> TYPE: RNA
<213> ORGANISM: Artificial Sequence
<220> FEATURE:
<223> OTHER INFORMATION: siRNA strand

<400> SEQUENCE: 484
uagcguugac uuacugucc                                              19

<210> SEQ ID NO 485
<211> LENGTH: 19
<212> TYPE: RNA
<213> ORGANISM: Artificial Sequence
<220> FEATURE:
<223> OTHER INFORMATION: siRNA strand

<400> SEQUENCE: 485
ggacaguaag ucaacgcua                                              19

<210> SEQ ID NO 486
<211> LENGTH: 19
<212> TYPE: RNA
<213> ORGANISM: Artificial Sequence
<220> FEATURE:
<223> OTHER INFORMATION: siRNA strand

<400> SEQUENCE: 486
uagcguugaa guacugucc                                              19

<210> SEQ ID NO 487
<211> LENGTH: 19
<212> TYPE: RNA
<213> ORGANISM: Artificial Sequence
<220> FEATURE:
<223> OTHER INFORMATION: siRNA strand

<400> SEQUENCE: 487
ggacaguacu ucaacgcua                                              19

<210> SEQ ID NO 488
<211> LENGTH: 19
<212> TYPE: RNA
<213> ORGANISM: Artificial Sequence
<220> FEATURE:
<223> OTHER INFORMATION: siRNA strand

<400> SEQUENCE: 488
uagcguugau guacugucc                                              19

<210> SEQ ID NO 489
<211> LENGTH: 19
<212> TYPE: RNA
<213> ORGANISM: Artificial Sequence
<220> FEATURE:
<223> OTHER INFORMATION: siRNA strand -continued

```
<400> SEQUENCE: 489
ggacaguaca ucaacgcua                                                    19

<210> SEQ ID NO 490
<211> LENGTH: 19
<212> TYPE: RNA
<213> ORGANISM: Artificial Sequence
<220> FEATURE:
<223> OTHER INFORMATION: siRNA strand

<400> SEQUENCE: 490
cacauacauu ggcucaaac                                                    19

<210> SEQ ID NO 491
<211> LENGTH: 19
<212> TYPE: RNA
<213> ORGANISM: Artificial Sequence
<220> FEATURE:
<223> OTHER INFORMATION: siRNA strand

<400> SEQUENCE: 491
guuugagcca auguaugug                                                    19

<210> SEQ ID NO 492
<211> LENGTH: 19
<212> TYPE: RNA
<213> ORGANISM: Artificial Sequence
<220> FEATURE:
<223> OTHER INFORMATION: siRNA strand

<400> SEQUENCE: 492
cacauacauc ggcucaaac                                                    19

<210> SEQ ID NO 493
<211> LENGTH: 19
<212> TYPE: RNA
<213> ORGANISM: Artificial Sequence
<220> FEATURE:
<223> OTHER INFORMATION: siRNA strand

<400> SEQUENCE: 493
guuugagccg auguaugug                                                    19

<210> SEQ ID NO 494
<211> LENGTH: 20
<212> TYPE: DNA
<213> ORGANISM: Artificial Sequence
<220> FEATURE:
<223> OTHER INFORMATION: siRNA target

<400> SEQUENCE: 494
tgatgtaagt tctgagtgtg                                                   20

<210> SEQ ID NO 495
<211> LENGTH: 10636
<212> TYPE: DNA
<213> ORGANISM: Homo sapiens

<400> SEQUENCE: 495
gaggagagag cagagtatac cgcagacatc atttctacta cagtggcgga gccgtacagg       60
acctgtttca ctgcaggggg atccaaaaca agccccgtgg agcagcagcc agagcaacag      120
cagccgcaag acattgtttc tctccctctg cccccccttc cccacgcaac cccagatcca      180
tttacacttt acagttttac ctcacaaaaa ctactacaag caccaagctc cctgatggaa      240
```

```
aggagcatcg tgcatcaagt caccagggtg gtccattcaa gctgcagatt tgtttgtcat    300
ccttgtacag caatctcctc ctccactgcc actacaggga agtgcatcac atgtcagcat    360
actggagcat agtgaaagag tctattttga agcttcaaac ttagtgctgc tgcagaccag    420
gaacaagaga gaaagagtgg atttcagcct gcacggatgg tcttgaaaca caaatggttt    480
ttggtctagg cgttttacac tgagattctc cactgccacc ctttctactc aagcaaaatc    540
ttcgtgaaaa gatctgctgc aaggaactga tagcttatgg ttctccattg tgatgaaagc    600
acatggtaca gttttccaaa gaaattagac cattttcttc gtgagaaaga aatcgacgtg    660
ctgttttcat agggtatttc tcacttctct gtgaaaggaa gaaagaacac gcctgagccc    720
aagagccctc aggagccctc cagagcctgt gggaagtctc catggtgaag tataggctga    780
ggctacctgt gaacagtacg cagtgaatgt tcatccagag ctgctgttgg cggattgtac    840
ccacggggag atgattcctc atgaagagcc tggatcccct acagaaatca aatgtgactt    900
tccgtttatc agactaaaat cagagccatc cagacagtga aacagtcacc gtggagggg    960
gacggcgaaa aatgaaatcc aaccaagagc ggagcaacga atgcctgcct cccaagaagc   1020
gcgagatccc cgccaccagc cggtcctccg aggagaaggc ccctaccctg cccagcgaca   1080
accaccgggt ggagggcaca gcatggctcc cgggcaaccc tggtggccgg ggccacgggg   1140
gcgggaggca tgggccggca gggacctcgg tggagcttgg tttacaacag gaataggtt   1200
tacacaaagc attgtccaca gggctggact actccccgcc cagcgctccc aggtctgtcc   1260
ccgtggccac cacgctgcct gccgcgtacg ccaccccgca gccagggacc ccggtgtccc   1320
ccgtgcagta cgctcacctg ccgcacacct tccagttcat tgggtcctcc caatacagtg   1380
gaacctatgc cagcttcatc ccatcacagc tgatccccc aaccgccaac cccgtcacca   1440
gtgcagtggc ctcggccgca ggggccacca ctccatccca gcgctcccag ctggaggcct   1500
attccactct gctggccaac atgggcagtc tgagccagac gccggacac aaggctgagc   1560
agcagcagca gcagcagcag cagcagcagc agcagcatca gcatcagcag cagcagcagc   1620
agcagcagca gcagcagcag cagcagcacc tcagcagggc tccggggctc atcaccccgg   1680
ggtcccccc accagcccag cagaaccagt acgtccacat ttccagttct ccgcagaaca   1740
ccggccgcac cgcctctcct ccggccatcc ccgtccacct ccaccccac cagacgatga   1800
tcccacacac gctcaccctg ggccccccct cccaggtcgt catgcaatac gccgactccg   1860
gcagccactt tgtccctcgg gaggccacca gaaagctga gagcagccgg ctgcagcagg   1920
ccatccaggc caaggaggtc ctgaacgtg agatggagaa gagccggcgg tacgggccc   1980
cgtcctcagc cgacctgggc ctgggcaagg caggcggcaa gtcggttcct cacccgtacg   2040
agtccaggca cgtggtggtc cacccgagcc cctcagacta cagcagtcgt gatccttcgg   2100
gggtccgggc ctctgtgatg gtcctgccca acagcaacac gcccgcagct gacctggagg   2160
tgcaacaggc cactcatcgt gaagcctccc cttctaccct caacgacaaa agtgcctgc   2220
atttagggaa gcctggccac cggtcctacg cgctctcacc ccacacggtc attcagacca   2280
cacacagtgc ttcagagcca ctcccggtgg gactgccagc cacggccttc tacgcaggga   2340
ctcaacccc tgtcatcggc tacctgagcg gccagcagca agcaatcacc tacgccggca   2400
gcctgccccca gcacctggtg atccccggca cacagccct gctcatcccg gtcggcagca   2460
ctgacatgga agcgtcgggg gcagccccgg ccatagtcac gtcatccccc cagtttgctg   2520
cagtgcctca cacgttcgtc accaccgccc ttcccaagag cgagaacttc aaccctgagg   2580
ccctggtcac ccaggccgcc tacccagcca tggtgcaggc ccagatccac ctgcctgtgg   2640
```

```
tgcagtccgt ggcctcccg gcggcggctc ccctacgct gcctcctac ttcatgaaag    2700
gctccatcat ccagttggcc aacgggagc taaagaaggt ggaagactta aaacagaag     2760
atttcatcca gagtgcagag ataagcaacg acctgaagat cgactccagc accgtagaga   2820
ggattgaaga cagccatagc ccgggcgtgg ccgtgataca gttcgccgtc ggggagcacc   2880
gagcccaggt cagcgttgaa gttttggtag agtatccttt ttttgtgttt ggacagggct   2940
ggtcatcctg ctgtccggag agaaccagcc agctctttga tttgccgtgt tccaaactct   3000
cagttgggga tgtctgcatc tcgcttaccc tcaagaacct gaagaacggc tctgttaaaa   3060
agggccagcc cgtggatccc gccagcgtcc tgctgaagca ctcaaaggcc gacggcctgg   3120
cgggcagcag acacaggtat gccgagcagg aaaacggaat caaccagggg agtgcccaga   3180
tgctctctga aatggcgaa ctgaagtttc cagagaaaat gggattgcct gcagcgccct    3240
tcctcaccaa aatagaaccc agcaagcccg cggcaacgag aagaggagg tggtcggcgc    3300
cagagagccg caaactggag aagtcagaag acgaaccacc tttgactctt cctaagcctt   3360
ctctaattcc tcaggaggtt aagatttgca ttgaaggccg gtctaatgta ggcaagtaga   3420
ggcagcgtgg gggaaggaa acgtggctct cccttatcat ttgtatccag attactgtac    3480
tgtaggctaa aataacacag tatttacatg ttatcttctt aattttaggt ttctgttcta   3540
accttgtcat tagagttaca gcaggtgtgt cgcaggagac tggtgcatat gctttttcca   3600
cgagtgtctg tcagtgagcg ggcgggagga agggcacagc aggagcggtc agggctccag   3660
gcatccccgg ggaagaaagg aacgggcctt cacagtgcct gccttctcta gcggcacaga   3720
agcagccggg ggcgctgact cccgctagtg tcaggagaaa agtcccgtgg aagggtcct    3780
gcaggggtgc agggttgcac gcatgtgggg gtgcacaggc gctgtggcgg cgagtgaggg   3840
tctctttttc tctgcctccc tctgcctcac tctcttgcta tcggcatggg ccgggggggt   3900
tcagagcagt gtcctcctgg ggttcccacg tgcaaaatca acatcaggaa cccagcttca   3960
gggcatcgcg gagacgcgtc agatggcaga tttggaaagt taaccattta aaagaacatt   4020
tttctctcca acatatttta caataaaagc aacttttaat tgtatagata tatatttccc   4080
cctatggggc ctgactgcac tgatatatat tttttttaaa gagcaactgc cacatgcggg   4140
atttcatttc tgcttttttac tagtgcagcg atgtcaccag ggtgttgtgg tggacaggga   4200
agcccctgct gtcatggccc cacatgggt aaggggggtt ggggtgggg gagagggaga    4260
gagcgaacac ccacgctggt ttctgtgcag tgttaggaaa accaatcagg ttattgcatt   4320
gacttcactc ccaagaggta gatgcaaact gcccttcagt gagagcaaca gaagctcttc   4380
acgttgagtt tgcgaaatct ttttgtcttt gaactctagt actgtttata gttcatgact   4440
atggacaact cgggtgccac ttttttttttt tttcagattc cagtgtgaca tgaggaatta   4500
gattttgaag atgagcatat attactatct ttaagcattt aaaaatactg ttcacacttt   4560
attaccaagc atcttggtct ctcattcaac aagtactgta tctcacttta aactctttgg   4620
ggaaaaaaca aaacaaaaa aaactaagtt gctttcttt tttcaacact gtaactacat     4680
ttcagctctg cagaattgct gaagagcaag atattgaaag tttcaatgtg gtttaaaggg   4740
atgaatgtga attatgaact agtatgtgac aataaatgac caccaagtac tacctgacgg   4800
gaggcacttt tcactttgat gtctgagaat cagttcaagg catatgcaga gttggcagag   4860
aaactgagag aaaagggatg gagaagagaa tactcatttt tgtccagtgt ttttctttt    4920
aagatgaact tttaaagaac cttgcgattt gcacatattg agtttataac ttgtgtgata   4980
ttcctgcagt ttttatccaa taacattgtg ggaaaggttt gggggactga acgagcataa   5040
```

```
ataaatgtag caaaatttct ttctaacctg cctaaactct aggccatttt ataaggttat    5100
gttcctttga aaattcattt tggtcttttt accacatctg tcacaaaaag ccaggtctta    5160
gcgggctctt agaaactctg agaattttct tcagattcat tgagagagtt ttccataaag    5220
acatttatat atgtgagcaa gattttttttt aaacaattac tttattattg ttgttattaa    5280
tgttattttc agaatggctt ttttttttct attcaaaatc aaatcgagat ttaatgtttg    5340
gtacaaaccc agaaagggta tttcatagtt tttaaacctt tcattcccag agatccgaaa    5400
tatcatttgt gggttttgaa tgcatcttta aagtgcttta aaaaaaagtt ttataagtag    5460
ggagaaattt ttaaatattc ttacttggat ggctgcaact aaactgaaca aatacctgac    5520
ttttctttta ccccattgaa aatagtactt tcttcgtttc acaaattaaa aaaaaaatct    5580
ggtatcaacc cacattttgg ctgtctagta ttcatttaca tttagggttc accaggacta    5640 atgatttta taaaccgttt tctggggtgt accaaaaaca tttgaatagg tttagaatag    5700
ctagaatagt tccttgactt tcctcgaatt tcattaccct ctcagcatgc ttgcagagag    5760
ctgggtgggc tcattcttgc agtcatactg cttatttagt gctgtatttt ttaaacgttt    5820
ctgttcagag aacttgctta atcttccata tattctgctc agggcacttg caattattag    5880
gttttgtttt tcttttttgtt ttttagcctt tgatggtaag aggaatacgg gctgccacat    5940
agactttgtt ctcattaata tcactattta caactcatgt ggactcagaa aaacacacac    6000 cacctttttgg cttacttcga gtattgaatt gactggatcc actaaaccaa cactaagatg    6060
ggaaaacaca catggtttgg agcaatagga acatcatcat aattttttgtg gttctatttc    6120 aggtatagga attataaaat aattggttct ttctaaacac ttgtcccatt tcattctctt    6180
gcttttttag catgtgcaat actttctgtg ccaatagagt ctgaccagtg tgctatatag    6240
ttaaagctca ttcccttttg ctttttcct tgtttggttg atcttcccca ttctggccag    6300
agcagggctg gagggaagga gccaggaggg agagagcctc ccacctttcc cctgctgcgg    6360
atgctgagtg ctgggcggg gagccttcag gagccccgtg cgtctgccgc cacgttgcag    6420
aaagagccag ccaaggagac ccggggggagg aaccgcagtg tcccctgtca ccacacggaa    6480
tagtgaatgt ggagtgtgga gaggaaggag gcagattcat ttctaagacg cactctggag    6540
ccatgtagcc tggagtcaac ccattttcca cggtcttttc tgcaagtggg caggcccctc    6600 ctcgggtct gtgtccttga gacttggagc cctgcctctg agcctggacg ggaagtgtgg    6660
cctgttgtgt gtgtgcgttc tgagcgtgtt ggccagtggc tgtggagggg accacctgcc    6720
acccacggtc accactccct tgtggcagct ttctcttcaa ataggaagaa cgcacagagg    6780
gcaggagcct cctgtttgca gacgttggcg ggccccgagg ctcccagagc agcctctgtc    6840
accgcttctg tgtagcaaac attaacgatg acagggtag aaattcttcg gtgccgttca    6900
gcttacaagg atcagccatg tgcctctgta ctatgtccac tttgcaatat ttaccgacag    6960
ccgtcttttg ttctttcttt cctgtttcc atttttaaac tagtaacagc aggccttttg    7020
cgtttacaat ggaacacaat caccaagaaa ttagtcaggg cgaaagaaa aaaataatac    7080 tattaataag aaaccaacaa acaagaacct ctctttctag ggatttctaa atatataaaa    7140
tgactgttcc ttagaatgtt taacttaaga attatttcag tttgtctggg ccacactggg    7200
gcagaggggg gagggaggga tacagagatg gatgccactt acctcagatc tttttaaagtg    7260 gaaatccaaa ttgaattttc atttggactt tcaggataat tttctatgtt ggtcaacttt    7320
tcgttttccc taactcaccc agtttagttt gggatgattt gatttctgtt gttgttgatc    7380
ccatttctaa cttggaattg tgagcctcta tgttttctgt taggtgagtg tgttgggttt    7440
```

```
tttcccccca ccaggaagtg gcagcatccc tccttctccc ctaaagggac tctgcggaac   7500
ctttcacacc tctttctcag ggacggggca ggtgtgtgtg tggtacactg acgtgtccag   7560
aagcagcact ttgactgctc tggagtaggg ttgtacaatt tcaaggaatg tttggatttc   7620
ctgcatcttg tggattactc cttagatacc gcatagattg caatataatg ctgcatgttc   7680
aagatgaaca gtagctccta gtaatcataa aatccactct ttgcacagtt tgatctttac   7740
tgaaatatgt tgccaaaatt tattttttgtt gttgtagctc tggattttgt tttgttttgt   7800
tttttaagga aacgattgac aatacccttt aacatctgtg actactaagg aaacctattt   7860
ctttcataga gagaaaaatc tccaatgctt ttgaagacac taataccgtg ctatttcaga   7920
tatgggtgag gaagcagagc tctcggtacc gaaggccggg cttcttgagc tgtgttggtt   7980
gtcatggcta ctgtttcatg aaccacaagc agctcaacag actggtctgt tgccttctga   8040 aacccttgc acttcaattt gcaccaggtg aaaacagggc cagcagactc catggcccaa    8100 ttcggttct tcggtggtga tgtgaaagga gagaattaca cttttttttt ttttaagtgg     8160
cgtggaggcc tttgcttcca catttgtttt taacccagaa tttctgaaat agagaattta   8220
agaacacatc aagtaataaa tatacagaga atatactttt ttataaagca catgcatctg   8280
ctattgtgtt gggttggttt cctctctttt ccacggacag tgttgtgttt ctggcatagg   8340
gaaactccaa acaacttgca cacctctact ccggagctga gatttctttt acatagatga   8400
cctcgcttca aatacgttac cttactgatg ataggatctt tcttgtagc actataccctt   8460 gtgggaattt tttttaaat gtacacctga tttgagaagc tgaagaaaac aaaatttga      8520 agcactcact ttgaggagta caggtaatgt tttaaaaaat tgcacaaaag aaaaatgaat   8580
gtcgaaatga ttcattcagt gtttgaaaga tatggctctg ttgaaacaat gagtttcata   8640
ctttgtttgt aaaaaaaaaa aagcagagaa gggttgaaag ttacatgttt ttttgtatat   8700
agaaatttgt catgtctaaa tgatcagatt tgtatggtta tggcctggaa gaattactac   8760
gtaaaaggct cttaaactat acctatgctt attgttattt ttgttacata tagccctcgt   8820
ctgggggagg ggaactcggt attctgcgat ttgagaatac tgttcattcc tatgctgaaa   8880
gtacttctct gagctccctt cttagtctaa actcttaagc cattgcaact tctttttctt   8940
cagagatgat gtttgacatt ttcagcactt cctgttccta taaacccaaa gaatataatc   9000
ttgaacacga agtgtttgta acaagggatc caggctacca atcaaacagg actcattatg   9060
gggacaaaaa aaaaaattat ttcaccttct ttcccccac acctcattta aatgggggga     9120
gtaaaaacat gatttcaatg taaatgcctc attttatttt agtttatttt tgattttat     9180 ttaatataaa gaggccagaa taaatacgga gcatcttctc agaatagtat tcctgtccaa   9240
aaatcaagcc ggacagtgga aactggacag ctgtggggat attaagcacc cccacttaca   9300
attcttaaat tcagaatctc gtccctccc ttctcgttga aggcaactgt tctggtagct    9360
aactttctcc tgtgtaatgg cgggagggaa caccggcttc agttttcat gtccccatga    9420 cttgcataca aatggttcaa ctgtattaaa attaagtgca tttggccaat aggtagtatc   9480
tatacaataa caacaatctc taagaatttc cataactttt cttatctgaa aggactcaag   9540
tcttccactg cagatacatt ggaggcttca cccacgtttt ctttcccttt agtttgtttg   9600
ctgtctggat ggccaatgag cctgtctcct tttctgtggc caatctgaag gcttcgttg    9660 gaagtgttgt ttacagtaat ccttaccaag ataacatact gtcctccaga ataccaagta   9720
ttaggtgaca ctagctcaag ctgttgtctt cagagcagtt accaagaagc tcggtgcaca   9780
ggttttctct ggttcttaca ggaaccacct actctttcag ttttctggcc caggagtggg   9840
```

```
gtaaatcctt tagttagtgc atttgaactt gatacctgtg cattcagttc tgtgaatact      9900
gccctttttg gcggggtttc ctcatctccc cagcctgaac tgctcaactc taaacccaaa      9960
ttagtgtcag ccgaaaggag gtttcaagat agtcctgtca gtatttgtgg tgaccttcag     10020
attagacagt cttcatttcc agccagtgga gtcctggctc cagagccatc tctgagactc     10080
gtactactgg atgttttaat atcagatcat tacccaccat atgcctccca caggccaagg     10140
gaaaacagac accagaactt gggttgaggg cactaccaga ctgacatggc cagtacagag     10200
gagaactagg gaaggaatga tgttttgcac cttattgaaa agaaaatttt aagtgcatac     10260
ataatagtta agagctttta ttgtgacagg agaactttt tccatatgcg tgcatactct      10320
ctgtaattcc agtgtaaaat attgtacttg cactagcttt tttaaacaaa tattaaaaaa     10380
tggaagaatt catattctat tttctaatcg tggtgtgtct atttgtagga tacactcgag     10440
tctgtttatt gaattttatg gtccctttct ttgatggtgc ttgcaggttt tctaggtaga     10500
aattatttca ttattataat aaaacaatgt ttgattcaaa atttgaacaa aattgtttta     10560
aataaattgt ctgtatacca gtacaagttt attgtttcag tatactcgta ctaataaaat     10620
aacagtgcca attgca                                                     10636

<210> SEQ ID NO 496
<211> LENGTH: 13481
<212> TYPE: DNA
<213> ORGANISM: Homo sapiens

<400> SEQUENCE: 496
gctgccggga cgggtccaag atggacggcc gctcaggttc tgcttttacc tgcggcccag        60
agccccattc attgccccgg tgctgagcgg cgccgcgagt cggcccgagg cctccgggga       120
ctgccgtgcc gggcgggaga ccgccatggc gaccctggaa aagctgatga aggccttcga       180
gtccctcaag tccttccagc agcagcagca gcagcagcag cagcagcagc agcagcagca       240
gcagcagcag cagcagcagc aacagccgcc accgccgccg ccgccgccgc cgcctcctca       300
gcttcctcag ccgccgccgc aggcacagcc gctgctgcct cagccgcagc cgccccgcc       360 gccgccccg ccgccaccg gcccggctgt ggctgaggag ccgctgcacc gaccaaagaa      420
agaactttca gctaccaaga aagaccgtgt gaatcattgt ctgacaatat gtgaaaacat       480
agtggcacag tctgtcagaa attctccaga atttcagaaa cttctgggca tcgctatgga       540 acttttctg ctgtgcagtg atgacgcaga gtcagatgtc aggatggtgg ctgacgaatg       600
cctcaacaaa gttatcaaag ctttgatgga ttctaatctt ccaaggttac agctcgagct       660
ctataaggaa attaaaaaga atggtgcccc tcggagtttg cgtgctgccc tgtggaggtt       720
tgctgagctg ctcaccgtgg tcggcctca gaaatgcagg ccttacctgg tgaaccttct       780
gccgtgcctg actcgaacaa gcaagagacc cgaagaatca gtccaggaga ccttggctgc       840
agctgttccc aaaattatgg cttcttttgg caatttgca aatgacaatg aaattaaggt       900
tttgttaaag gccttcatag cgaacctgaa gtcaagctcc cccaccattc ggcggacagc       960
ggctggatca gcagtgagca tctgccagca ctcaagaagg acacaatatt tctatagttg      1020
gctactaaat gtgctcttag gcttactcgt tcctgtcgag gatgaacact ccactctgct      1080
gattcttggc gtgctgctca ccctgaggta tttggtgccc ttgctgcagc agcaggtcaa      1140
ggacacaagc ctgaaaggca gcttcggagt gacaaggaaa gaaatggaag tctctccttc      1200
tgcagagcag cttgtccagg tttatgaact gacgttacat catacacagc accaagacca      1260
caatgttgtg accggagccc tggagctgtt gcagcagctc ttcagaacgc ctccacccga      1320
```

```
gcttctgcaa accctgaccg cagtcggggg cattgggcag ctcaccgctg ctaaggagga    1380
gtctggtggc cgaagccgta gtgggagtat tgtggaactt atagctggag ggggttcctc    1440
atgcagccct gtccttcaa gaaaacaaaa aggcaaagtg ctcttaggag aagaagaagc     1500
cttggaggat gactctgaat cgagatcgga tgtcagcagc tctgccttaa cagcctcagt    1560
gaaggatgag atcagtggag agctggctgc ttcttcaggg gtttccactc cagggtcagc    1620
aggtcatgac atcatcacag aacagccacg gtcacagcac acactgcagg cggactcagt    1680
ggatctggcc agctgtgact tgacaagctc tgccactgat ggggatgagg aggatatctt    1740
gagccacagc tccagccagg tcagcgccgt cccatctgac cctgccatgg acctgaatga    1800
tgggacccag gcctcgtcgc ccatcagcga cagctcccag accaccaccg aagggcctga    1860
ttcagctgtt accccttcag acagttctga aattgtgtta gacggtaccg acaaccagta    1920
tttgggcctg cagattggac agccccagga tgaagatgag aagccacag gtattcttcc     1980
tgatgaagcc tcggaggcct tcaggaactc ttccatggcc cttcaacagg cacatttatt    2040
gaaaaacatg agtcactgca ggcagccttc tgacagcagt gttgataaat tgtgttgag    2100
agatgaagct actgaaccgg gtgatcaaga aacaagcct tgccgcatca aggtgacat     2160
tggacagtcc actgatgatg actctgcacc tcttgtccat tgtgtccgcc ttttatctgc    2220
ttcgttttg ctaacagggg gaaaaaatgt gctggttccg acagggatg tgagggtcag     2280
cgtgaaggcc ctggccctca gctgtgtggg agcagctgtg gccctccacc cggaatcttt    2340
cttcagcaaa ctctataaag ttcctcttga caccacggaa tacctgagg aacagtatgt     2400
ctcagacatc ttgaactaca tcgatcatgg agacccacag gttcgaggag ccactgccat    2460
tctctgtggg accctcatct gctccatcct cagcaggtcc cgcttccacg tgggagattg    2520
gatgggcacc attagaaccc tcacaggaaa tacatttct ttggcggatt gcattcttt     2580
gctgcggaaa acactgaagg atgagtcttc tgttacttgc aagttagctt gtacagctgt    2640
gaggaactgt gtcatgagtc tctgcagcag cagctacagt gagttaggac tgcagctgat    2700
catcgatgtg ctgactctga ggaacagttc ctattggctg gtgaggacag agcttctgga    2760
aacccttgca gagattgact tcaggctggt gagcttttg gaggcaaaag cagaaaactt     2820
acacagaggg gctcatcatt atacagggct tttaaaactg caagaacgag tgctcaataa    2880
tgttgtcatc catttgcttg gagatgaaga ccccagggtg cgacatgttg ccgcagcatc    2940
actaattagg cttgtcccaa agctgttta taaatgtgac caaggacaag ctgatccagt     3000
agtggccgtg gcaagagatc aaagcagtgt ttacctgaaa cttctcatgc atgagacgca    3060
gcctccatct catttctccg tcagcacaat aaccagaata tatagaggct ataacctact    3120
accaagcata acagacgtca ctatggaaaa taaccttca agagttattg cagcagttc      3180
tcatgaacta atcacatcaa ccaccagagc actcacattt ggatgctgtg aagctttgtg    3240
tcttcttcc actgccttcc cagttttgcat ttggagttta ggttggcact gtggagtgcc    3300
tccactgagt gcctcagatg agtctaggaa gagctgtacc gttgggatgg ccacaatgat    3360
tctgaccctg ctctcgtcag cttggttccc attggatctc tcagcccatc aagatgcttt    3420
gattttggcc ggaaacttgc ttgcagccag tgctcccaaa tctctgagaa gttcatgggc    3480
ctctgaagaa gaagccaacc cagcagccac caagcaagag gaggtctggc cagccctggg    3540
ggaccgggcc ctggtgccca tgtggagca gctcttctct cacctgctga aggtgattaa     3600
catttgtgcc cacgtcctgg atgacgtggc tcctggaccc gcaataaagg cagccttgcc    3660
ttctctaaca aacccccctt ctctaagtcc catccgacga aaggggaagg agaaagaacc    3720
```

```
aggagaacaa gcatctgtac cgttgagtcc caagaaaggc agtgaggcca gtgcagcttc    3780
tagacaatct gataccctcag gtcctgttac aacaagtaaa tcctcatcac tggggagttt    3840
ctatcatctt ccttcatacc tcaaactgca tgatgtcctg aaagctacac acgctaacta    3900
caaggtcacg ctggatcttc agaacagcac ggaaaagttt ggagggtttc tccgctcagc    3960
cttggatgtt cttctctcaga tactagagct ggccacactg caggacattg gaagtgtgt    4020 tgaagagatc ctaggatacc tgaaatcctg ctttagtcga gaaccaatga tggcaactgt    4080
ttgtgttcaa caattgttga agactctctt tggcacaaac ttggcctccc agtttgatgg    4140
cttatcttcc aaccccagca agtcacaagg ccgagcacag cgccttggct cctccagtgt    4200
gaggccaggc ttgtaccact actgcttcat ggccccgtac acccacttca cccaggccct    4260
cgctgacgcc agcctgagga acatggtgca ggcggagcag gagaacgaca cctcgggatg    4320
gtttgatgtc ctccagaaag tgtctaccca gttgaagaca aacctcacga gtgtcacaaa    4380
gaaccgtgca gataagaatg ctattcataa tcacattcgt ttgtttgaac tcttgttat    4440 aaaagcttta aaacagtaca cgactacaac atgtgtgcag ttacagaagc aggttttaga    4500
tttgctggcg cagctggttc agttacgggt taattactgt cttctggatt cagatcaggt    4560
gtttattggc tttgtattga aacagtttga atacattgaa gtgggccagt tcagggaatc    4620
agaggcaatc attccaaaca tcttttttctt cttggtatta ctatcttatg aacgctatca    4680
ttcaaaacag atcattggaa ttcctaaaat cattcagctc tgtgatggca tcatggccag    4740
tggaaggaag gctgtgacac atgccatacc ggctctgcag cccatagtcc acgacctctt    4800
tgtattaaga ggaacaaata aagctgatgc aggaaaagag cttgaaaccc aaaaagaggt    4860
ggtggtgtca atgttactga gactcatcca gtaccatcag gtgttggaga tgttcattct    4920
tgtcctgcag cagtgccaca aggagaatga agacaagtgg aagcgactgt ctcgacagat    4980
agctgacatc atcctcccaa tgttagccaa acagcagatg cacattgact ctcatgaagc    5040
ccttggagtg ttaaatacat tatttgagat tttggccccct tcctccctcc gtccggtaga    5100 catgcttttta cggagtatgt tcgtcactcc aaacacaatg gcgtccgtga gcactgttca    5160 actgtgata tcgggaattc tggccatttt gagggttctg atttccccagt caactgaaga    5220 tattgttctt tctcgtattc aggagctctc cttctctccg tatttaatct cctgtacagt    5280
aattaatagg ttaagagatg gggacagtac ttcaacgcta aagaacaca gtgaagggaa    5340 acaaataaag aatttgccag aagaaacatt ttcaaggttt ctattacaac tggttggtat    5400
tcttttagaa gacattgtta caaaacagct gaaggtggaa atgagtgagc agcaacatac    5460
tttctattgc caggaactag gcacactgct aatgtgtctg atccacatct tcaagtctgg    5520
aatgttccgg agaatcacag cagctgccac taggctgttc cgcagtgatg gctgtggcgg    5580
cagtttctac accctggaca gcttgaactt gcgggctcgt tccatgatca ccacccaccc    5640
ggccctggtg ctgctctggt gtcagatact gctgcttgtc aaccacaccg actaccgctg    5700
gtgggcagaa gtgcagcaga ccccgaaaag acacagtctg tccagcacaa agttacttag    5760
tccccagatg tctggagaag aggaggattc tgacttggca gccaaacttg gaatgtgcaa    5820
tagagaaata gtacgaagag gggctctcat tctcttctgt gattatgtct gtcagaacct    5880
ccatgactcc gagcacttaa cgtggctcat tgtaaatcac attcaagatc tgatcagcct    5940
ttcccacgag cctccagtac aggacttcat cagtgccgtt catcggaact ctgctgccag    6000
cggcctgttc atccaggcaa ttcagtctcg ttgtgaaaac cttcaactc caaccatgct    6060 gaagaaaact cttcagtgct tggaggggat ccatctcagc cagtcgggag ctgtgctcac    6120
```

```
gctgtatgtg gacaggcttc tgtgcacccc tttccgtgtg ctggctcgca tggtcgacat    6180
ccttgcttgt cgccgggtag aaatgcttct ggctgcaaat ttacagagca gcatggccca    6240
gttgccaatg gaagaactca acagaatcca ggaataccct cagagcagcg ggctcgctca    6300
gagacaccaa aggctctatt ccctgctgga caggtttcgt ctctccacca tgcaagactc    6360
acttagtccc tctcctccag tctcttccca cccgctggac ggggatgggc acgtgtcact    6420
ggaaacagtg agtccggaca aagactggta cgttcatctt gtcaaatccc agtgttggac    6480
caggtcagat tctgcactgc tggaaggtgc agagctggtg aatcggattc ctgctgaaga    6540
tatgaatgcc ttcatgatga actcggagtt caacctaagc ctgctagctc catgcttaag    6600
cctagggatg agtgaaattt ctggtggcca aagagtgcc cttttgaag cagcccgtga    6660 ggtgactctg gcccgtgtga gcggcaccgt gcagcagctc cctgctgtcc atcatgtctt    6720
ccagcccgag ctgcctgcag agccggcggc ctactggagc aagttgaatg atctgtttgg    6780
ggatgctgca ctgtatcagt ccctgcccac tctggcccgg ccctggcac agtacctggt    6840 ggtggtctcc aaactgccca gtcatttgca ccttcctcct gagaaagaga aggacattgt    6900
gaaattcgtg gtggcaaccc ttgaggccct gtcctggcat ttgatccatg agcagatccc    6960
gctgagtctg gatctccagg cagggctgga ctgctgctgc ctggccctgc agctgcctgg    7020
cctctggagc gtggtctcct ccacagagtt tgtgacccac gcctgctccc tcatctactg    7080
tgtgcacttc atcctggagg ccgttgcagt gcagcctgga gagcagcttc ttagtccaga    7140
aagaaggaca aataccccaa aagccatcag cgaggaggag gaggaagtag atccaaacac    7200
acagaatcct aagtatatca ctgcagcctg tgagatggtg gcagaaatgg tggagtctct    7260
gcagtcggtg ttggccttgg gtcataaaag gaatagcggc gtgccggcgt ttctcacgcc    7320
attgctaagg aacatcatca tcagcctggc ccgcctgccc cttgtcaaca gctacacacg    7380 tgtgcccca ctggtgtgga agcttggatg gtcaccaaa ccgggagggg attttggcac    7440
agcattccct gagatccccg tggagttcct ccaggaaaag gaagtcttta aggagttcat    7500
ctaccgcatc aacacactag gctggaccag tcgtactcag tttgaagaaa cttgggccac    7560
cctccttggt gtcctggtga cgcagcccct cgtgatggag caggaggaga gcccaccaga    7620
agaagacaca gagaggaccc agatcaacgt cctggccgtg caggccatca cctcactggt    7680
gctcagtgca atgactgtgc ctgtggccgg caacccagct gtaagctgct ggagcagca    7740 gccccggaac aagcctctga agctctcga caccaggttt gggaggaagc tgagcattat    7800
cagagggatt gtggagcaag agattcaagc aatggtttca aagagagaga atattgccac    7860
ccatcattta tatcaggcat gggatcctgt cccttctctg tctccggcta ctacaggtgc    7920
cctcatcagc cacgagaagc tgctgctaca gatcaacccc gagcgggagc tggggagcat    7980
gagctacaaa ctcggccagg tgtccataca ctccgtgtgg ctggggaaca gcatcacacc    8040
cctgagggag gaggaatggg acgaggaaga ggaggaggag gccgacgccc ctgcaccttc    8100
gtcaccaccc acgtctccag tcaactccag gaaacaccgg gctggagttg acatccactc    8160
ctgttcgcag ttttttgcttg agttgtacag ccgctggatc ctgccgtcca gctcagccag    8220 gaggacccg gccatcctga tcagtgaggt ggtcagatcc cttctagtgg tctcagactt    8280
gttcaccgag cgcaaccagt ttgagctgat gtatgtgacg ctgacagaac tgcgaagggt    8340
gcacccttca gaagacgaga tcctcgctca gtacctggtg cctgccacct gcaaggcagc    8400
tgccgtcctt gggatggaca aggccgtggc ggagcctgtc agccgcctgc tggagagcac    8460
gctcaggagc agccacctgc ccagcagggt tggagccctg cacggcgtcc tctatgtgct    8520
```

-continued

```
ggagtgcgac ctgctggacg acactgccaa gcagctcatc ccggtcatca gcgactatct    8580
cctctccaac ctgaaaggga tcgcccactg cgtgaacatt cacagccagc agcacgtact    8640
ggtcatgtgt gccactgcgt tttacctcat tgagaactat cctctggacg tagggccgga    8700
attttcagca tcaataatac agatgtgtgg ggtgatgctg tctggaagtg aggagtccac    8760
cccctccatc atttaccact gtgccctcag aggcctggag cgcctcctgc tctctgagca    8820
gctctcccgc ctggatgcag aatcgctggt caagctgagt gtggacagag tgaacgtgca    8880
cagcccgcac cgggccatgg cggctctggg cctgatgctc acctgcatgt acacaggaaa    8940
ggagaaagtc agtccgggta gaacttcaga ccctaatcct gcagccccg acagcgagtc     9000 agtgattgtt gctatggagc gggtatctgt tcttttttgat aggatcagga aaggcttttcc  9060 ttgtgaagcc agagtggtgg ccaggatcct gccccagttt ctagacgact tcttcccacc    9120
ccaggacatc atgaacaaag tcatcggaga gtttctgtcc aaccagcagc cataccccca    9180
gttcatggcc accgtggtgt ataaggtgtt tcagactctg cacagcaccg gcagtcgtc    9240 catggtccgg gactgggtca tgctgtccct ctccaacttc acgcagaggg ccccggtcgc    9300
catggccacg tggagcctct cctgcttctt tgtcagcgcg tccaccagcc cgtgggtcgc    9360
ggcgatcctc ccacatgtca tcagcaggat gggcaagctg gagcaggtgg acgtgaacct    9420
tttctgcctg gtcgccacag acttctacag acaccagata gaggaggagc tcgaccgcag    9480
ggccttccag tctgtgcttg aggtggttgc agccccagga agcccatatc accggctgct    9540
gacttgttta cgaaatgtcc acaaggtcac cacctgctga gcgccatggt gggagagact    9600
gtgaggcggc agctggggcc ggagcctttg gaagtctgcg cccttgtgcc ctgcctccac    9660
cgagccagct tggtccctat ggcttccgc acatgccgcg ggcggccagg caacgtgcgt     9720
gtctctgcca tgtggcagaa gtgctctttg tggcagtggc caggcaggga gtgtctgcag    9780
tcctggtggg gctgagcctg aggccttcca gaaagcagga gcagctgtgc tgcaccccat    9840
gtgggtgacc aggtcctttc tcctgatagt cacctgctgg ttgttgccag gttgcagctg    9900
ctcttgcatc tgggccagaa gtcctccctc ctgcaggctg gctgttggcc cctctgctgt    9960
cctgcagtag aaggtgccgt gagcaggctt tgggaacact ggcctgggtc tccctggtgg    10020
ggtgtgcatg ccacgccccg tgtctggatg cacagatgcc atggcctgtg ctgggccagt    10080
ggctgggggt gctagacacc cggcaccatt ctcccttctc tcttttcttc tcaggattta    10140
aaatttaatt atatcagtaa agagattaat tttaacgtaa ctctttctat gcccgtgtaa    10200
agtatgtgaa tcgcaaggcc tgtgctgcat gcgacagcgt ccggggtggt ggacagggcc    10260
cccggccacg ctccctctcc tgtagccact ggcatagccc tcctgagcac ccgctgacat    10320
ttccgttgta catgttcctg tttatgcatt cacaaggtga ctgggatgta gagaggcgtt    10380
agtgggcagg tggccacagc aggactgagg acaggccccc attatcctag gggtgcgctc    10440
acctgcagcc cctcctcctc gggcacagac gactgtcgtt ctccacccac cagtcaggga    10500
cagcagcctc cctgtcactc agctgagaag gccagccctc cctggctgtg agcagcctcc    10560
actgtgtcca gagacatggg cctcccactc ctgttccttg ctagccctgg ggtgcgtct     10620 gcctaggagc tggctggcag gtgttgggac ctgctgctcc atggatgcat gccctaagag    10680
tgtcactgag ctgtgttttg tctgagcctc tctcggtcaa cagcaaagct tggtgtcttg    10740
gcactgttag tgacagagcc cagcatccct tctgcccccg ttccagctga catcttgcac    10800
ggtgacccct tttagtcagg agagtgcaga tctgtgctca tcggagactg ccccacggcc    10860
ctgtcagagc cgccactcct atccccaggc caggtccctg gaccagcctc ctgtttgcag    10920
```

```
gcccagagga gccaagtcat taaaatggaa gtggattctg gatggccggg ctgctgctga    10980
tgtaggagct ggatttggga gctctgcttg ccgactggct gtgagacgag gcagggctc     11040
tgcttcctca gccctagagg cgagccaggc aaggttggcg actgtcatgt ggcttggttt    11100
ggtcatgccc gtcgatgttt tgggtattga atgtggtaag tggaggaaat gttggaactc    11160
tgtgcaggtg ctgccttgag accccccaagc ttccacctgt ccctctccta tgtggcagct   11220
ggggagcagc tgagatgtgg acttgtatgc tgcccacata cgtgagggggg agctgaaagg   11280
gagcccctcc tctgagcagc ctctgccagg cctgtatgag gcttttccca ccagctccca    11340
acagaggcct cccccagcca ggaccacctc gtcctcgtgg cggggcagca ggagcggtag    11400
aaaggggtcc gatgtttgag gaggcccttta agggaagcta ctgaattata acacgtaaga   11460
aaatcaccat tccgtattgg ttgggggctc ctgtttctca tcctagcttt ttcctggaaa    11520
gcccgctaga aggtttggga acgaggggaa agttctcaga actgttggct gctccccacc    11580
cgcctcccgc ctcccccgca ggttatgtca gcagctctga gacagcagta tcacaggcca    11640
gatgttgttc ctggctagat gtttacatttt gtaagaaata acactgtgaa tgtaaaacag    11700
agccattccc ttggaatgca tatcgctggg ctcaacatag agtttgtctt cctcttgttt    11760
acgacgtgat ctaaaccagt ccttagcaag gggctcagaa caccccgctc tggcagtagg    11820
tgtcccccac ccccaaagac ctgcctgtgt gctccggaga tgaatatgag ctcattagta    11880
aaaatgactt cacccacgca tatacataaa gtatccatgc atgtgcatat agacacatct    11940
ataattttac acacacacct ctcaagacgg agatgcatgg cctctaagag tgcccgtgtc    12000
ggttcttcct ggaagttgac tttccttaga cccgccaggt caagttagcc gcgtgacgga    12060
catccaggcg tgggacgtgg tcagggcagg gctcattcat tgcccactag gatcccactg    12120
gcgaagatgg tctccatatc agctctctgc agaagggagg aagactttat catgttccta    12180
aaaatctgtg gcaagcaccc atcgtattat ccaaatttttg ttgcaaatgt gattaatttg    12240
gttgtcaagt tttgggggtg ggctgtgggg agattgcttt tgttttcctg ctggtaatat    12300
cgggaaagat tttaatgaaa ccagggtaga attgtttggc aatgcactga agcgtgtttc    12360
tttcccaaaa tgtgcctccc ttccgctgcg ggcccagctg agtctatgta ggtgatgttt    12420
ccagctgcca agtgctcttt gttactgtcc accctcattt ctgccagcgc atgtgtcctt    12480
tcaaggggaa aatgtgaagc tgaaccccct ccagacaccc agaatgtagc atctgagaag    12540
gccctgtgcc ctaaaggaca cccctcgccc ccatcttcat ggaggggtc atttcagagc     12600
cctcggagcc aatgaacagc tcctcctctt ggagctgaga tgagcccac gtggagctcg     12660
ggacggatag tagacagcaa taactcggtg tgtggccgcc tggcaggtgg aacttcctcc    12720
cgttgcgggg tggagtgagg ttagttctgt gtgtctggtg ggtggagtca ggcttctctt    12780
gctacctgtg agcatccttc ccagcagaca tcctcatcgg gctttgtccc tcccccgctt    12840
cctccctctg cggggaggac ccgggaccac agctgctggc cagggtagac ttggagctgt    12900
cctccagagg ggtcacgtgt aggagtgaga agaaggaaga tcttgagagc tgctgaggga   12960
ccttggagag ctcaggatgg ctcagacgag gacactcgct tgccgggcct gggcctcctg    13020
ggaaggaggg agctgctcag aatgccgcat gacaactgaa ggcaacctgg aaggttcagg    13080
ggccgctctt cccccatgtg cctgtcacgc tctggtgcag tcaaggaac gccttcccct     13140
cagttgtttc taagagcaga gtctcccgct gcaatctggg tggtaactgc cagccttgga    13200
ggatcgtggc caacgtggac ctgcctacga agggtgggct ctgacccaag tggggcctcc    13260
ttgtccaggt ctcactgctt tgcaccgtgg tcagagggac tgtcagctga gcttgagctc    13320
```

| | | | | | |
|---|---|---|---|---|---|
| ccctggagcc | agcagggctg | tgatgggcga | gtcccggagc | cccacccaga | cctgaatgct | 13380 |
| tctgagagca | aagggaagga | ctgacgagag | atgtatattt | aattttttaa | ctgctgcaaa | 13440 |
| cattgtacat | ccaaattaaa | ggaaaaaaat | ggaaaccatc | a | | 13481 |

<210> SEQ ID NO 497
<211> LENGTH: 5850
<212> TYPE: DNA
<213> ORGANISM: Homo sapiens

<400> SEQUENCE: 497

| | | | | | |
|---|---|---|---|---|---|
| acaagtctttt | ccgcctcccc | agcccgcccg | ggagctgcga | gccgcgagct | ggattatggt | 60 |
| ggcctgagca | gccaacgcag | ccgcaggagc | ccggagccct | tgcccctgcc | cgcgccgccg | 120 |
| cccgccgggg | ggaccaggga | agccgccacc | ggcccgccat | gcccgcccct | ccagccccg | 180 |
| ccgggagccc | gcgcccgctg | cccaggctgg | ccgccgccgt | gccgatgtag | cgggctccgg | 240 |
| atcccagcct | ctccctgct | cccgtgctct | gcggatctcc | cctgaccgct | ctccacagcc | 300 |
| cggacccggg | ggctggccca | gggccctgca | ggccctggcg | tcctgatgcc | cccaagctcc | 360 |
| ctctcctgag | aagccaccag | caccacccag | acttggggc | aggcgccagg | gacggacgtg | 420 |
| ggccagtgcg | agcccagagg | gcccgaaggc | cggggcccac | catggcccaa | gccctgccct | 480 |
| ggctcctgct | gtggatgggc | gcgggagtgc | tgcctgccca | cggcacccag | cacggcatcc | 540 |
| ggctgcccct | gcgcagcggc | ctgggggcg | cccccctggg | gctgcggctg | ccccgggaga | 600 |
| ccgacgaaga | gcccgaggag | cccggccgga | ggggcagctt | tgtggagatg | gtggacaacc | 660 |
| tgagggggcaa | gtcggggcag | ggctactacg | tggagatgac | cgtgggcagc | cccccgcaga | 720 |
| cgctcaacat | cctggtggat | acaggcagca | gtaactttgc | agtgggtgct | gccccccacc | 780 |
| ccttcctgca | tcgctactac | cagaggcagc | tgtccagcac | ataccgggac | ctccggaagg | 840 |
| gtgtgtatgt | gcctacacc | cagggcaagt | gggaagggga | gctgggcacc | gacctggtaa | 900 |
| gcatccccca | tggccccaac | gtcactgtgc | gtgccaacat | tgctgccatc | actgaatcag | 960 |
| acaagttctt | catcaacggc | tccaactggg | aaggcatcct | ggggctggcc | tatgctgaga | 1020 |
| ttgccaggcc | tgacgactcc | ctggagcctt | tctttgactc | tctggtaaag | cagacccacg | 1080 |
| ttcccaacct | cttctccctg | cagctttgtg | gtgctggctt | cccctcaac | cagtctgaag | 1140 |
| tgctggcctc | tgtcggaggg | agcatgatca | ttggaggtat | cgaccactcg | ctgtacacag | 1200 |
| gcagtctctg | gtatacaccc | atccggcggg | agtggtatta | tgaggtgatc | attgtgcggg | 1260 |
| tggagatcaa | tggacaggat | ctgaaaatgg | actgcaagga | gtacaactat | gacaagagca | 1320 |
| ttgtggacag | tggcaccacc | aaccttcgtt | tgcccaagaa | agtgtttgaa | gctgcagtca | 1380 |
| aatccatcaa | ggcagcctcc | tccacggaga | agttccctga | tggtttctgg | ctaggagagc | 1440 |
| agctggtgtg | ctggcaagca | ggcaccaccc | cttggaacat | tttcccagtc | atctcactct | 1500 |
| acctaatggg | tgaggttacc | aaccagtcct | tccgcatcac | catccttccg | cagcaatacc | 1560 |
| tgcggccagt | ggaagatgtg | gccacgtccc | aagacgactg | ttacaagttt | gccatctcac | 1620 |
| agtcatccac | gggcactgtt | atgggagctg | ttatcatgga | gggcttctac | gttgtctttg | 1680 |
| atcgggcccg | aaaacgaatt | ggctttgctg | tcagcgcttg | ccatgtgcac | gatgagttca | 1740 |
| ggacggcagc | ggtggaaggc | cttttttgtca | ccttggacat | ggaagactgt | ggctacaaca | 1800 |
| ttccacagac | agatgagtca | accctcatga | ccatagccta | tgtcatggct | gccatctgcg | 1860 |
| ccctcttcat | gctgccactc | tgcctcatgg | tgtgtcagtg | gcgctgcctc | cgctgcctgc | 1920 |
| gccagcagca | tgatgacttt | gctgatgaca | tctccctgct | gaagtgagga | ggcccatggg | 1980 |

```
cagaagatag agattccect ggaccacacc tccgtggttc actttggtca caagtaggag    2040
acacagatgg cacctgtggc cagagcacct caggaccctc cccacccacc aaatgcctct    2100
gccttgatgg agaaggaaaa ggctggcaag gtgggttcca gggactgtac ctgtaggaaa    2160
cagaaaagag aagaaagaag cactctgctg gcgggaatac tcttggtcac ctcaaattta    2220
agtcgggaaa ttctgctgct tgaaacttca gccctgaacc tttgtccacc attcctttaa    2280
attctccaac ccaaagtatt cttcttttct tagtttcaga agtactggca tcacacgcag    2340
gttaccttgg cgtgtgtccc tgtggtaccc tggcagagaa gagaccaagc ttgtttccct    2400
gctggccaaa gtcagtagga gaggatgcac agtttgctat ttgctttaga gacagggact    2460
gtataaacaa gcctaacatt ggtgcaaaga ttgcctcttg aattaaaaaa aaaaactaga    2520
ttgactattt atacaaatgg gggcggctgg aaagaggaga aggagaggga gtacaaagac    2580
agggaatagt gggatcaaag ctaggaaagg cagaaacaca accactcacc agtcctagtt    2640
ttagacctca tctccaagat agcatcccat ctcagaagat gggtgttgtt ttcaatgttt    2700
tcttttctgt ggttgcagcc tgaccaaaag tgagatggga agggcttatc tagccaaaga    2760 gctcttttt  agctctctta aatgaagtgc ccactaagaa gttccactta acacatgaat    2820
ttctgccata ttaatttcat tgtctctatc tgaaccaccc tttattctac atatgatagg    2880
cagcactgaa atatcctaac cccctaagct ccaggtgccc tgtgggagag caactggact    2940
atagcagggc tgggctctgt cttcctggtc ataggctcac tctttccccc aaatcttcct    3000
ctggagcttt gcagccaagg tgctaaaagg aataggtagg agacctcttc tatctaatcc    3060
ttaaaagcat aatgttgaac attcattcaa cagctgatgc cctataaccc ctgcctggat    3120
ttcttcctat taggctataa gaagtagcaa gatctttaca taattcagag tggtttcatt    3180
gccttcctac cctctctaat ggcccctcca tttatttgac taaagcatca cacagtggca    3240
ctagcattat accaagagta tgagaaatac agtgctttat ggctctaaca ttactgcctt    3300
cagtatcaag gctgcctgga gaaaggatgg cagcctcagg gcttccttat gtcctccacc    3360
acaagagctc cttgatgaag gtcatctttt tcccctatcc tgttcttccc ctccccgctc    3420
ctaatggtac gtgggtaccc aggctggttc ttgggctagg tagtggggac caagttcatt    3480
acctccctat cagttctagc atagtaaact acggtaccag tgttagtggg aagagctggg    3540
ttttcctagt atcccactg  catcctactc ctacctggtc aacccgctgc ttccaggtat    3600
gggacctgct aagtgtggaa ttacctgata agggagaggg aaatacaagg agggcctctg    3660
gtgttcctgg cctcagccag ctgcccacaa gccataaacc aataaaacaa gaatactgag    3720
tcagtttttt atctgggttc tcttcattcc cactgcactt ggtgctgctt tggctgactg    3780
ggaacacccc ataactacag agtctgacag gaagactgga gactgtccac ttctagctcg    3840
gaacttactg tgtaaataaa ctttcagaac tgctaccatg aagtgaaaat gccacatttt    3900
gctttataat ttctacccat gttgggaaaa actggctttt tcccagccct ttccagggca    3960
taaaactcaa cccttcgat  agcaagtccc atcagcctat tatttttta  aagaaaactt    4020 gcacttgttt ttctttttac agttacttcc ttcctgcccc aaaattataa actctaagtg    4080
taaaaaaaag tcttaacaac agcttcttgc ttgtaaaaat atgtattata catctgtatt    4140
tttaaattct gctcctgaaa aatgactgtc ccattctcca ctcactgcat ttggggcctt    4200
tcccattggt ctgcatgtct tttatcattg caggccagtg gacagaggga gaagggagaa    4260 cagggggtcgc caaacttgt  gttgctttct gactgatcct gaacaagaaa gagtaacact    4320
gaggcgctcg ctcccatgca caactctcca aaacactat  cctcctgcaa gagtgggctt    4380
```

```
tccagggtct ttactgggaa gcagttaagc cccctcctca cccccttcctt ttttctttct    4440 ttactcctttt ggcttcaaag gattttggaa aagaaacaat atgctttaca ctcattttca    4500
atttctaaat ttgcagggga tactgaaaaa tacggcaggt ggcctaaggc tgctgtaaag    4560
ttgaggggag aggaaatctt aagattacaa gataaaaaac gaatcccta aacaaaaga     4620 acaatagaac tggtcttcca ttttgccacc tttcctgttc atgacagcta ctaacctgga    4680
gacagtaaca tttcattaac caaagaaagt gggtcacctg acctctgaag agctgagtac    4740
tcaggccact ccaatcaccc tacaagatgc caaggaggtc ccaggaagtc cagctcctta    4800
aactgacgct agtcaataaa cctgggcaag tgaggcaaga gaaatgagga agaatccatc    4860
tgtgaggtga caggcaagga tgaaagacaa agaaggaaaa gagtatcaaa ggcagaaagg    4920
agatcattta gttgggtctg aaaggaaaag tctttgctat ccgacatgta ctgctagtac    4980
ctgtaagcat tttaggtccc agaatggaaa aaaaaatcag ctattggtaa tataataatg    5040
tcctttccct ggagtcagtt tttttaaaaa gttaactctt agttttttact tgtttaattc    5100 taaaagagaa gggagctgag gccattccct gtaggagtaa agataaaagg ataggaaaag    5160
attcaaagct ctaatagagt cacagctttc ccaggtataa aacctaaaat taagaagtac    5220
aataagcaga ggtggaaaat gatctagttc ctgatagcta cccacagagc aagtgattta    5280
taaatttgaa atccaaacta ctttcttaat atcactttgg tctccatttt tcccaggaca    5340
ggaaatatgt ccccccctaa ctttcttgct tcaaaatta aaatccagca tcccaagatc      5400
attctacaag taattttgca cagacatctc ctcaccccag tgcctgtctg gagctcaccc    5460
aaggtcacca acaacttgg ttgtgaacca actgccttaa ccttctgggg gaggggatt      5520 agctagacta ggagaccaga agtgaatggg aaagggtgag gacttcacaa tgttggcctg    5580
tcagagcttg attagaagcc aagacagtgg cagcaaagga agacttggcc caggaaaaac    5640
ctgtgggttg tgctaatttc tgtccagaaa ataggggtgga cagaagcttg tggggtacat    5700
ggaggaattg ggacctggtt atgttgttat tctcggactg tgaattttgg tgatgtaaaa    5760
cagaatattc tgtaaaccta atgtctgtat aaataatgag cgttaacaca gtaaaatatt    5820
caataagaag tcaaaaaaaa aaaaaaaaaa                                     5850
```

<210> SEQ ID NO 498
<211> LENGTH: 3215
<212> TYPE: DNA
<213> ORGANISM: Homo sapiens

<400> SEQUENCE: 498

```
aggagaagga gaaggaggag gactaggagg aggaggacgg cgacgaccag aagggggccca    60 agagaggggg cgagcgaccg agcgccgcga cgcggaagtg aggtgcgtgc gggctgcagc    120
gcagaccccg gcccggcccc tccgagagcg tcctgggcgc tccctcacgc cttgccttca    180
agccttctgc ctttccaccc tcgtgagcgg agaactggga gtggccattc gacgacagtg    240
tggtgtaaag gaattcatta gccatggatg tattcatgaa aggactttca aaggccaagg    300
agggagttgt ggctgctgct gagaaaacca acagggtgt ggcagaagca gcaggaaaga     360
caaaagaggg tgttctctat gtaggctcca aaaccaagga gggagtggtg catggtgtgg    420
caacagtggc tgagaagacc aaagagcaag tgacaaatgt tggaggagca gtggtgacgg    480
gtgtgacagc agtagcccag aagacagtgg agggagcagg gagcattgca gcagccactg    540
gctttgtcaa aaaggaccag ttgggcaaga atgaagaagg agcccacag gaaggaattc      600 tggaagatat gcctgtggat cctgacaatg aggcttatga aatgccttct gaggaagggt    660
```

```
atcaagacta cgaacctgaa gcctaagaaa tatctttgct cccagtttct tgagatctgc    720
tgacagatgt tccatcctgt acaagtgctc agttccaatg tgcccagtca tgacatttct    780
caaagttttt acagtgtatc tcgaagtctt ccatcagcag tgattgaagt atctgtacct    840
gcccccactc agcatttcgg tgcttccctt tcactgaagt gaatacatgg tagcagggtc    900
tttgtgtgct gtggattttg tggcttcaat ctacgatgtt aaaacaaatt aaaaacacct    960
aagtgactac cacttatttc taaatcctca ctattttttt gttgctgttg ttcagaagtt   1020
gttagtgatt tgctatcata tattataaga ttttttaggtg tcttttaatg atactgtcta   1080
agaataatga cgtattgtga aatttgttaa tatatataat acttaaaaat atgtgagcat   1140
gaaactatgc acctataaat actaaatatg aaattttacc attttgcgat gtgttttatt   1200
cacttgtgtt tgtatataaa tggtgagaat taaaataaaa cgttatctca ttgcaaaaat   1260
attttatttt tatcccatct cactttaata ataaaaatca tgcttataag caacatgaat   1320
taagaactga cacaaaggac aaaaatataa agttattaat agccatttga agaaggagga   1380
attttagaag aggtagagaa aatggaacat taaccctaca ctcggaattc cctgaagcaa   1440
cactgccaga agtgtgtttt ggtatgcact ggttccttaa gtggctgtga ttaattattg   1500
aaagtggggt gttgaagacc ccaactacta ttgtagagtg gtctatttct cccttcaatc   1560
ctgtcaatgt ttgctttacg tattttgggg aactgttgtt tgatgtgtat gtgtttataa   1620
ttgttataca tttttaattg agcctttttat taacatatat tgttattttt gtctcgaaat   1680 aatttttttag ttaaaatcta ttttgtctga tattggtgtg aatgctgtac ctttctgaca   1740
ataaataata ttcgaccatg aataaaaaaa aaaaaaaagt gggttcccgg gaactaagca   1800
gtgtagaaga tgattttgac tacaccctcc ttagagagcc ataagacaca ttagcacata   1860
ttagcacatt caaggctctg agagaatgtg gttaactttg tttaactcag cattcctcac   1920
tttttttttt taatcatcag aaattctctc tctctctctc tcttttttctc tcgctctctt   1980 tttttttttt tttttacagg aaatgccttt aaacatcgtt ggaactacca gagtcacctt   2040
aaaggagatc aattctctag actgataaaa atttcatggc ctcctttaaa tgttgccaaa   2100
tatatgaatt ctaggatttt tccttaggaa aggttttttct ctttcaggga agatctatta   2160
actccccatg ggtgctgaaa ataaacttga tggtgaaaaa ctctgtataa attaatttaa   2220
aaattatttg gtttctcttt ttaattattc tggggcatag tcatttctaa aagtcactag   2280
tagaaagtat aatttcaaga cagaatattc tagacatgct agcagtttat atgtattcat   2340
gagtaatgtg atatatattg ggcgctggtg aggaaggaag gaggaatgag tgactataag   2400
gatggttacc atagaaactt cctttttttac ctaattgaag agagactact acagagtgct   2460
aagctgcatg tgtcatctta cactagagag aaatggtaag tttcttgttt tatttaagtt   2520
atgtttaagc aaggaaagga tttgttattg aacagtatat ttcaggaagg ttagaaagtg   2580
gcggttagga tatattttaa atctacctaa agcagcatat tttaaaaatt taaaagtatt   2640
ggtattaaat taagaaatag aggacagaac tagactgata gcagtgacct agaacaattt   2700
gagattagga aagttgtgac catgaattta aggatttatg tggatacaaa ttctcccttta   2760 aagtgtttct tcccttaata tttatctgac ggtaattttt gagcagtgaa ttactttata   2820
tatcttaata gttatttttgg gaccaaacac ttaaacaaaa agttcttttaa gtcatataag   2880 cctttttcagg aagcttgtct catattcact cccgagacat tcacctgcca agtggcctga   2940
ggatcaatcc agtcctaggt ttattttgca gacttacatt ctcccaagtt attcagcctc   3000
atatgactcc acggtcggct ttaccaaaac agttcagagt gcactttggc acacaattgg   3060
```

| | |
|---|---|
| gaacagaaca atctaatgtg tggtttggta ttccaagtgg ggtctttttc agaatctctg | 3120 |
| cactagtgtg agatgcaaac atgtttcctc atctttctgg cttatccagt atgtagctat | 3180 |
| ttgtgacata ataaatatat acatatatga aaata | 3215 |

<210> SEQ ID NO 499
<211> LENGTH: 981
<212> TYPE: DNA
<213> ORGANISM: Homo sapiens

<400> SEQUENCE: 499

| | |
|---|---|
| gtttggggcc agagtgggcg aggcgcggag gtctggccta taaagtagtc gcggagacgg | 60 |
| ggtgctggtt tgcgtcgtag tctcctgcag cgtctggggt ttccgttgca gtcctcggaa | 120 |
| ccaggacctc ggcgtggcct agcgagttat ggcgacgaag gccgtgtgcg tgctgaaggg | 180 |
| cgacggccca gtgcagggca tcatcaattt cgagcagaag gaaagtaatg gaccagtgaa | 240 |
| ggtgtgggga agcattaaag gactgactga aggcctgcat ggattccatg ttcatgagtt | 300 |
| tggagataat acagcaggct gtaccagtgc aggtcctcac tttaatcctc tatccagaaa | 360 |
| acacggtggg ccaaaggatg aagagaggca tgttggagac ttgggcaatg tgactgctga | 420 |
| caaagatggt gtggccgatg tgtctattga agattctgtg atctcactct caggagacca | 480 |
| ttgcatcatt ggccgcacac tggtggtcca tgaaaaagca gatgacttgg gcaaggtgg | 540 |
| aaatgaagaa agtacaaaga caggaaacgc tggaagtcgt ttggcttgtg gtgtaattgg | 600 |
| gatcgcccaa taaacattcc cttggatgta gtctgaggcc ccttaactca tctgttatcc | 660 |
| tgctagctgt agaaatgtat cctgataaac attaaacact gtaatcttaa aagtgtaatt | 720 |
| gtgtgacttt ttcagagttg ctttaaagta cctgtagtga gaaactgatt tatgatcact | 780 |
| tggaagattt gtatagtttt ataaaactca gttaaaatgt ctgtttcaat gacctgtatt | 840 |
| ttgccagact taaatcacag atgggtatta aacttgtcag aatttctttg tcattcaagc | 900 |
| ctgtgaataa aaaccctgta tggcacttat tatgaggcta ttaaaagaat ccaaattcaa | 960 |
| actaaaaaaa aaaaaaaaa a | 981 |

<210> SEQ ID NO 500
<211> LENGTH: 1669
<212> TYPE: DNA
<213> ORGANISM: Homo sapiens

<400> SEQUENCE: 500

| | |
|---|---|
| ctccctcagc aaggacagca gaggaccagc taagagggag agaagcaact acagaccccc | 60 |
| cctgaaaaca accctcagac gccacatccc ctgacaagct gccaggcagg ttctcttcct | 120 |
| ctcacatact gacccacggc tccaccctct ctcccctgga aaggcacacca tgagcactga | 180 |
| aagcatgatc cgggacgtgg agctggccga ggaggcgctc cccaagaaga caggggggcc | 240 |
| ccagggctcc aggcggtgct tgttcctcag cctcttctcc ttcctgatcg tggcaggcgc | 300 |
| caccacgctc ttctgcctgc tgcactttgg agtgatcggc ccccagaggg aagagttccc | 360 |
| cagggacctc tctctaatca gccctctggc ccaggcagtc agatcatctt ctcgaacccc | 420 |
| gagtgacaag cctgtagccc atgttgtagc aaaccctcaa gctgaggggc agctccagtg | 480 |
| gctgaaccgc cgggccaatg ccctcctggc caatggcgtg gagctgagag ataaccagct | 540 |
| ggtggtgcca tcagagggcc tgtacctcat ctactcccag gtcctcttca agggccaagg | 600 |
| ctgcccctcc acccatgtgc tcctcaccca caccatcagc cgcatcgccg tctcctacca | 660 |
| gaccaaggtc aacctcctct ctgccatcaa gagcccctgc cagagggaga ccccagaggg | 720 |

-continued

```
ggctgaggcc aagccctggt atgagcccat ctatctggga ggggtcttcc agctggagaa    780
gggtgaccga ctcagcgctg agatcaatcg gcccgactat ctcgactttg ccgagtctgg    840
gcaggtctac tttgggatca ttgccctgtg aggaggacga acatccaacc ttcccaaacg    900
cctcccctgc cccaatccct ttattacccc ctccttcaga caccctcaac ctcttctggc    960
tcaaaaagag aattgggggc ttagggtcgg aacccaagct tagaaacttta agcaacaaga   1020
ccaccacttc gaaacctggg attcaggaat gtgtggcctg cacagtgaag tgctggcaac   1080
cactaagaat tcaaactggg gcctccagaa ctcactgggg cctacagctt tgatccctga   1140
catctggaat ctggagacca gggagccttt ggttctggcc agaatgctgc aggacttgag   1200
aagacctcac ctagaaattg acacaagtgg accttaggcc ttcctctctc cagatgtttc   1260
cagacttcct tgagacacgg agcccagccc tccccatgga gccagctccc tctatttatg   1320
tttgcacttg tgattattta ttatttattt attatttatt tatttacaga tgaatgtatt   1380
tatttgggag accggggtat cctgggggac ccaatgtagg agctgccttg gctcagacat   1440
gttttccgtg aaaacggagc tgaacaatag gctgttccca tgtagccccc tggcctctgt   1500
gccttctttt gattatgttt tttaaaatat ttatctgatt aagttgtcta acaatgctg    1560
atttggtgac caactgtcac tcattgctga gcctctgctc cccaggggag ttgtgtctgt   1620
aatcgcccta ctattcagtg gcgagaaata agtttgcttt agaaaagaa                1669
```

<210> SEQ ID NO 501
<211> LENGTH: 1498
<212> TYPE: DNA
<213> ORGANISM: Homo sapiens

<400> SEQUENCE: 501

```
accaaacctc ttcgaggcac aaggcacaac aggctgctct gggattctct tcagccaatc     60
ttcattgctc aagtgtctga agcagccatg gcagaaagtac ctgagctcgc cagtgaaatg    120
atggcttatt acagtggcaa tgaggatgac ttgttctttg aagctgatgg ccctaaacag    180
atgaagtgct ccttccagga cctggacctc tgccctctgg atggcggcat ccagctacga    240
atctccgacc accactacag caagggcttc aggcaggccg cgtcagttgt tgtggccatg    300
gacaagctga ggaagatgct ggttccctgc ccacagacct tccaggagaa tgacctgagc    360
accttctttc ccttcatctt tgaagaagaa cctatcttct tcgacacatg ggataacgag    420
gcttatgtgc acgatgcacc tgtacgatca ctgaactgca cgctccggga ctcacagcaa    480
aaaagcttgt tgatgtctgg tccatatgaa ctgaaagctc tccacctcca gggacaggat    540
atggagcaac aagtggtgtt ctccatgtcc tttgtacaag agaagaaag taatgacaaa    600
atacctgtgg ccttgggcct caaggaaaag aatctgtacc tgtcctgcgt gttgaaagat    660
gataagccca ctctacagct ggagagtgta gatcccaaaa attacccaaa gaagaagatg    720
gaaaagcgat ttgtcttcaa caagatagaa atcaataaca gctgaaatt tgagtctgcc    780
cagttcccca actggtacat cagcacctct caagcagaaa acatgcccgt cttcctggga    840
gggaccaaag gcggcagga tataactgac ttcaccatgc aatttgtgtc ttcctaaaga    900
gagctgtacc cagagagtcc tgtgctgaat gtggactcaa tccctagggc tggcagaaag    960
ggaacagaaa ggttttttgag tacggctata gcctggactt tcctgttgtc tacaccaatg   1020
cccaactgcc tgccttaggg tagtgctaag aggatctcct gtccatcagc caggacagtc   1080
agctctctcc tttcagggcc aatcccagc ccttttgttg agccaggcct ctctcacctc    1140
tcctactcac ttaaagcccg cctgacagaa accacggcca catttggttc taagaaaccc   1200
```

| | |
|---|---|
| tctgtcattc gctcccacat tctgatgagc aaccgcttcc ctatttattt atttatttgt | 1260 |
| ttgtttgttt tattcattgg tctaatttat tcaaaggggg caagaagtag cagtgtctgt | 1320 |
| aaaagagcct agttttaat agctatggaa tcaattcaat ttggactggt gtgctctctt | 1380 |
| taaatcaagt cctttaatta agactgaaaa tatataagct cagattattt aaatgggaat | 1440 |
| atttataaat gagcaaatat catactgttc aatggttctg aaataaactt cactgaag | 1498 |

<210> SEQ ID NO 502
<211> LENGTH: 9469
<212> TYPE: DNA
<213> ORGANISM: Homo sapiens

<400> SEQUENCE: 502

| | |
|---|---|
| ctcttatgtg aggagctgaa gaggaattaa aatatacagg atgaaaagat ggcaatgttg | 60 |
| cctcccccag gacctcagag ctttgtccat ttcacaaaac agtctcttgc cctcattgaa | 120 |
| caacgcattg ctgaaagaaa atcaaaggaa cccaaagaag aaaagaaaga tgatgatgaa | 180 |
| gaagccccaa agccaagcag tgacttggaa gctggcaaac agctgcccttt catctatggg | 240 |
| gacattcctc ccggcatggt gtcagagccc tggaggact tggaccccta ctatgcagac | 300 |
| aaaaagactt tcatagtatt gaacaaaggg aaaacaatct tccgtttcaa tgccacacct | 360 |
| gctttatata tgctttctcc tttcagtcct ctaagaagaa tatctattaa gattttagta | 420 |
| cactccttat tcagcatgct catcatgtgc actattctga caaactgcat atttatgacc | 480 |
| atgaataacc caccggactg gaccaaaaat gtcgagtaca cttttactgg aatatatact | 540 |
| tttgaatcac ttgtaaaaat ccttgcaaga ggcttctgtg taggagaatt cactttctctt | 600 |
| cgtgacccgt ggaactggct ggattttgtc gtcattgttt ttgcgtattt aacagaattt | 660 |
| gtaaacctag gcaatgtttc agctcttcga actttcagag tattgagagc tttgaaaact | 720 |
| atttctgtaa tcccaggcct gaagacaatt gtagggggctt tgatccagtc agtgaagaag | 780 |
| cttttctgatg tcatgatcct gactgtgttc tgtctgagtg tgtttgcact aattggacta | 840 |
| cagctgttca tgggaaacct gaagcataaa tgttttcgaa attcacttga aaataatgaa | 900 |
| acattagaaa gcataatgaa taccctagag agtgaagaag actttagaaa atattttat | 960 |
| tacttggaag gatccaaaga tgctctcctt tgtggtttca gcacagattc aggtcagtgt | 1020 |
| ccagaggggt acacctgtgt gaaaattggc agaaacctg attatggcta cacgagcttt | 1080 |
| gacactttca gctgggcctt cttagccttg tttaggctaa tgacccaaga ttactgggaa | 1140 |
| aacctttacc aacagacgct gcgtgctgct ggcaaaacct acatgatctt ctttgtcgta | 1200 |
| gtgatttttcc tgggctcctt ttatctaata aacttgatcc tggctgtggt tgccatggca | 1260 |
| tatgaagaac agaaccaggc aaacattgaa gaagctaaac agaagaatt agaatttcaa | 1320 |
| cagatgttag accgtcttaa aaaagagcaa gaagaagctg aggcaattgc agcggcagcg | 1380 |
| gctgaatata caagtattag gagaagcaga attatgggcc tctcagagag ttcttctgaa | 1440 |
| acatccaaac tgagctctaa aagtgctaaa gaaagaagaa acagaagaaa gaaaaagaat | 1500 |
| caaaagaagc tctccagtgg agaggaaaag ggagatgctg agaaattgtc gaaatcagaa | 1560 |
| tcagaggaca gcatcagaag aaaaagtttc caccttggtg tcgaagggca taggcgagca | 1620 |
| catgaaaaga ggttgtctac ccccaatcag tcaccactca gcattcgtgg ctccttgttt | 1680 |
| tctgcaaggc gaagcagcag aacaagtctt tttagtttca aggcagagg aagagatata | 1740 |
| ggatctgaga ctgaatttgc cgatgatgag cacagcattt ttggagacaa tgagagcaga | 1800 |
| aggggctcac tgtttgtgcc ccacagaccc caggagcgac gcagcagtaa catcagccaa | 1860 |

```
gccagtaggt ccccaccaat gctgccggtg aacgggaaaa tgcacagtgc tgtggactgc    1920
aacggtgtgg tctccctggt tgatggacgc tcagccctca tgctccccaa tggacagctt    1980
ctgccagagg gcacgaccaa tcaaatacac aagaaaaggc gttgtagttc ctatctcctt    2040
tcagaggata tgctgaatga tcccaacctc agacagagag caatgagtag agcaagcata    2100
ttaacaaaca ctgtggaaga acttgaagag tccagacaaa aatgtccacc ttggtggtac    2160
agatttgcac acaaattctt gatctggaat tgctctccat attggataaa attcaaaaag    2220
tgtatctatt ttattgtaat ggatcctttt gtagatcttg caattaccat ttgcatagtt    2280
ttaaacacat tatttatggc tatggaacac cacccaatga ctgaggaatt caaaaatgta    2340
cttgctatag gaaatttggt ctttactgga atctttgcag ctgaaatggt attaaaactg    2400
attgccatgg atccatatga gtatttccaa gtaggctgga atattttga cagccttatt    2460 gtgactttaa gtttagtgga gctctttcta gcagatgtgg aaggattgtc agttctgcga    2520
tcattcagac tgctccgagt cttcaagttg gcaaaatcct ggccaacatt gaacatgctg    2580
attaagatca ttggtaactc agtaggggct ctaggtaacc tcaccttagt gttggccatc    2640
atcgtcttca ttttttgctgt ggtcggcatg cagctctttg gtaagagcta caaagaatgt    2700
gtctgcaaga tcaatgatga ctgtacgctc ccacggtggc acatgaacga cttcttccac    2760
tccttcctga ttgtgttccg cgtgctgtgt ggagagtgga tagagaccat gtgggactgt    2820
atggaggtcg ctggtcaagc tatgtgcctt attgtttaca tgatggtcat ggtcattgga    2880
aacctggtgg tcctaaacct atttctggcc ttattattga gctcatttag ttcagacaat    2940
cttacagcaa ttgaagaaga ccctgatgca aacaacctcc agattgcagt gactagaatt    3000
aaaaagggaa taaattatgt gaaacaaacc ttacgtgaat ttattctaaa agcattttcc    3060
aaaaagccaa agatttccag ggagataaga caagcagaag atctgaatac taagaaggaa    3120
aactatattt ctaaccatac acttgctgaa atgagcaaag gtcacaattt cctcaaggaa    3180
aaagataaaa tcagtggttt tggaagcagc gtggacaaac acttgatgga agacagtgat    3240
ggtcaatcat ttattcacaa tcccagcctc acagtgacag tgccaattgc acctggggaa    3300
tccgatttgg aaaatatgaa tgctgaggaa cttagcagtg attcggatag tgaatacagc    3360
aaagtgagat taaaccggtc aagctcctca gagtgcagca cagttgataa ccctttgcct    3420
ggagaaggag aagaagcaga ggctgaacct atgaattccg atgagccaga ggcctgtttc    3480
acagatggtt gtgtacggag gttctcatgc tgccaagtta acatagagtc agggaaagga    3540
aaaatctggt ggaacatcag gaaaacctgc tacaagattg ttgaacacag ttggtttgaa    3600
agcttcattg tcctcatgat cctgctcagc agtggtgccc tggcttttga agatatttat    3660
attgaaagga aaaagaccat taagattatc ctggagtatg cagacaagat cttcacttac    3720
atcttcattc tggaaatgct tctaaaatgg ataagcatatg gttataaaac atatttcacc    3780
aatgcctggt gttggctgga tttcctaatt gttgatgttt ctttggttac tttagtggca    3840
aacactcttg gctactcaga tcttggcccc attaaatccc ttcggacact gagagcttta    3900
agacctctaa gagcccttatc tagatttgaa ggaatgaggg tcgttgtgaa tgcactcata    3960
ggagcaattc cttccatcat gaatgtgcta cttgtgtgtc ttatattctg gctgatattc    4020
agcatcatgg gagtaaattt gtttgctggc aagttctatg agtgtattaa caccacagat    4080
gggtcacggt ttcctgcaag tcaagttcca atcgttccg aatgttttgc ccttatgaat    4140
gttagtcaaa atgtgcgatg gaaaaacctg aaagtgaact ttgataatgt cggacttggt    4200
tacctatctc tgcttcaagt tgcaactttt aagggatgga cgattattat gtatgcagca    4260
```

```
gtggattctg ttaatgtaga caagcagccc aaatatgaat atagcctcta catgtatatt    4320 tatttttgtcg tctttatcat ctttgggtca ttcttcactt tgaacttgtt cattggtgtc    4380
atcatagata atttcaacca acagaaaaag aagcttggag gtcaagacat ctttatgaca    4440
gaagaacaga agaaatacta taatgcaatg aaaaagctgg ggtccaagaa gccacaaaag    4500
ccaattcctc gaccagggaa caaaatccaa ggatgtatat ttgacctagt gacaaatcaa    4560
gcctttgata ttagtatcat ggttcttatc tgtctcaaca tggtaaccat gatggtagaa    4620
aaggagggtc aaagtcaaca tatgactgaa gttttatatt ggataaatgt ggtttttata    4680 atcctttca ctggagaatg tgtgctaaaa ctgatctccc tcagacacta ctacttcact    4740
gtaggatgga atattttga ttttgtggtt gtgattatct ccattgtagg tatgttttcta    4800 gctgatttga ttgaaacgta ttttgtgtcc cctaccctgt tccgagtgat ccgtcttgcc    4860
aggattggcc gaatcctacg tctagtcaaa ggagcaaagg ggatccgcac gctgctcttt    4920
gctttgatga tgtcccttcc tgcgttgttt aacatcggcc tcctgctctt cctggtcatg    4980
ttcatctacg ccatctttgg aatgtccaac tttgcctatg ttaaaaagga agatggaatt    5040
aatgacatgt tcaattttga gacctttggc aacagtatga tttgcctgtt ccaaattaca    5100
acctctgctg gctgggatgg attgctagca cctattctta acagtaagcc acccgactgt    5160
gacccaaaaa aagttcatcc tggaagttca gttgaaggag actgtggtaa cccatctgtt    5220
ggaatattct actttgttag ttatatcatc atatccttcc tggttgtggt gaacatgtac    5280
attgcagtca tactgagaa ttttagtgtt gccactgaag aaagtactga acctctgagt    5340
gaggatgact ttgagatgtt ctatgaggtt tgggagaagt ttgatcccga tgcgacccag    5400
tttatagagt tctctaaact ctctgatttt gcagctgccc tggatcctcc tcttctcata    5460
gcaaaaccca acaaagtcca gctcattgcc atggatctgc ccatggttag tggtgaccgg    5520
atccattgtc ttgacatctt atttgctttt acaaagcgtg ttttgggtga gagtggggag    5580
atggattctc ttcgttcaca gatggaagaa aggttcatgt ctgcaaatcc ttccaaagtg    5640
tcctatgaac ccatcacaac cacactaaaa cggaaacaag aggatgtgtc tgctactgtc    5700
attcagcgtg cttatagacg ttaccgctta aggcaaaatg tcaaaaatat atcaagtata    5760
tacataaaag atggagacag agatgatgat ttactcaata aaaaagatat ggcttttgat    5820
aatgttaatg agaactcaag tccagaaaaa acagatgcca cttcatccac cacctctcca    5880
ccttcatatg atagtgtaac aaagccagac aaagagaaat atgaacaaga cagaacagaa    5940
aaggaagaca aagggaaaga cagcaaggaa agcaaaaaat agagcttcat ttttgatata    6000
ttgtttacag cctgtgaaag tgatttattt gtgttaataa aactcttttg aggaagtcta    6060
tgccaaaatc cttttatca aaatattctc gaaggcagtg cagtcactaa ctctgatttc    6120
ctaagaaagg tgggcagcat tagcagatgg ttattttgc actgatgatt ctttaagaat    6180
cgtaagagaa ctctgtagga attattgatt atagcataca aaagtgattc agttttttgg    6240
tttttaataa atcagaagac catgtagaaa acttttacat ctgccttgtc atcttttcac    6300
aggattgtaa ttagtcttgt ttcccatgta aataaacaac acacgcatac agaaaaatct    6360
attatttatc tattatttgg aaatcaacaa aagtatttgc cttggctttg caatgaaatg    6420
cttgatagaa gtaatggaca ttagttatga atgtttagtt aaaatgcatt attagggagc    6480 ttgactttt atcaatgtac agaggttatt ctatattttg aggtgcttaa atttattcta    6540
cattgcatca gaaccaattt atatgtgcct ataaaatgcc atgggattaa aaatatatgt    6600
aggctattca tttctacaaa tgttttttcat tcatcttgac tcacatgcca acaaggataa    6660
```

```
gacttacctt tagagtattg tgtttcatag cctttcttct ttcatatccc tttttgttca    6720
tagaataacc acagaacttg aaaaattatt ctaagtacat attacactcc tcaaaaaaaa    6780
caaagataac tgagaaaaaa gttattgaca gaagttctat ttgctattat ttacatagcc    6840
taacatttga ctgtgctgcc caaaatactg ataatagtct cttaaactct tttgtcaaat    6900
tttcctgctt tcttatgcag tattgtttag tcatcctttc gctgtaagca aagttgatga    6960
aatccttcct gatatgcagt tagttgtttg accacggtac atacttgagc agataataac    7020
ttgggcacag tatttattgc atcacttgta tacaatcccg tgtttggcaa gctttcaaat    7080
catgtaatat gacagacttt acacagatat gtgtttagta tgaataaaaa agcattgaaa    7140
tagggattct tgccaacttg ctctcttgcc accaacttac tttcctaaat tatggaagta    7200 atctttttg gatatacttc aatgtataca atgaggaaga tgtcaccttc tccttaaaat     7260
tctatgatgt gaaatatatt ttgcctcaat caacacagta ccatgggctt ctaatttatc    7320
aagcacatat tcattttgca ttagctgtag acatctagtt ttttgaaaac acctattaat    7380
agtaatttga aaagaaataa ccataatgct ttttttcgtg agtttatttc aggaatatga    7440
gatctttctt ctataaagtt attcatgcac aggcaaaaat tgagctacac aggtagaatg    7500
tagttttact tagaagatt ttgtgggagg ttttgaagca aatatataaa acaactttca     7560
ctaatttgct ttccatattt aaaaaataat aaattacatt tatataataa atgtttaaag    7620
cacatatttt ttgttgttct ggcaatttaa aaagaaagag gatttaaacg tacctataga    7680
aacaaagatt tatggttaaa gaatgagatc agaagtctag aatgttttta aattgtgata    7740
tattttacaa catccgttat tactttgaga catttgtcct aatctacgta taaaactcaa    7800
tctagggcta aagattcttt ataccatctt aggttcattc atcttaggct atttgaacca    7860 cttttaatt taatatgaaa gacaccatgc agtgttttcc gagactacat agatcattt     7920 atcacatacc taccaagcct gttggaaata ggttttgata atttaagtag ggacctatac    7980
aaaatatatt acatttatca gatttttaaa tacattcaat taagaattta acatcacctt    8040
aaatttgaat tcaatctacc gttatttcaa actcacaaat ataactgcat tatgaatact    8100
tacataatgt agtaagacaa gatgtttgac aggttcgtgt gtaattttct attaatgttt    8160
ttacattgcc ttgttttat gtaaaataaa aaatatgggc aactggtttg ttaacaacac      8220
aatttcttct tagcatttca aaaatatata taaagttgtt cttttteccta tttcatgaac    8280 tatgttttt tttaaaataa catggttaag ttttatatat atttacgttt gtttcaggaa     8340
tgtctacttg tgactttta tcaattaaaa ataatatttg gaagaaagag cttattaagt     8400
ataagcttga agtaaaatta gacctctctt tccatgtaga ttactgtttg tactgatggt    8460
ttcacccttc agaaggcact gtcatattaa tatttaaatt ttataatcgc tgaacttatt    8520
acacccaaca atacagaaag gcagttacac tgaagaactt aacttagaat aaaatggaag    8580
caaacaggtt ttctaaaaac ttttttaagt gaccaggtct cgctctgtca cccaggctag    8640
agtgcaatgg catgatcata gctctctgca gcctcaactc tgggctcaag caaccctcct    8700
gcctcagcct cccaagtagc taagactaca ggtacatgcc accatgcctg gctaatattt    8760 aaattttgt agataagggg tcttgctatg ttgcccaggc tagtctcaaa ctcctggctt     8820
caagtgttcc tactgtcatg acctgccaac atgctgggt tacaggcatg agccaccatg      8880
ccccaaacag gtttgaacac aaatctttcg gatgaaaatt agagaaccta attttagctt    8940
tttgatagtt acctagtttg caaaagattt gggtgacttg tgagctgttt ttaaatgctg    9000
attgttgaac atcacaaccc aaaatactta gcatgatttt atagagtttt gatagcttta    9060
```

| | |
|---|---|
| ttaaaaagag tgaaaataaa atgcatatgt aaataaagca gttctaaata gctatttcag | 9120 |
| agaaatgtta atagaagtgc tgaaagaagg gccaactaaa ttaggatggc cagggaattg | 9180 |
| gcctgggttt aggacctatg tatgaaggcc accaattttt taaaaatatc tgtggtttat | 9240 |
| tatgttatta tcttcttgag gaaaacaatc aagaattgct tcatgaaaat aaataaatag | 9300 |
| ccatgaatat cataaagctg tttacatagg attctttaca aatttcatag atctatgaat | 9360 |
| gctcaaaatg tttgagtttg ccataaaatta tattgtagtt atattgtagt tatacttgag | 9420 |
| actgacacat tgtaatataa tctaagaata aaagttatac aaaataaaa | 9469 |

<210> SEQ ID NO 503
<211> LENGTH: 3916
<212> TYPE: DNA
<213> ORGANISM: Homo sapiens

<400> SEQUENCE: 503

| | |
|---|---|
| gagcaggaag tgtttgagga agtcgcgccg cgctgcccgc gttaagattc ccgcattta | 60 |
| atgttttcag gggggtgtca tagccccggg tttggccgcc ccagcccgc cttcccgcc | 120 |
| ccggggagcc cgcccctgc cccgcgtccc tgccgacaga gttagcacga catcagtatg | 180 |
| agctggtcac cttccctgac aacgcagaca tgtggggcct gggaaatgaa agagcgcctt | 240 |
| gggacagggg gatttggaaa tgtcatccga tggcacaatc aggaaacagg tgagcagatt | 300 |
| gccatcaagc agtgccggca ggagctcagc ccccggaacc gagagcggtg gtgcctggag | 360 |
| atccagatca tgagaaggct gacccacccc aatgtggtgg ctgcccgaga tgtccctgag | 420 |
| gggatgcaga acttggcgcc caatgacctg cccctgctgg ccatggagta ctgccaagga | 480 |
| ggagatctcc ggaagtacct gaaccagttt gagaactgct gtggtctgcg ggaaggtgcc | 540 |
| atcctcacct tgctgagtga cattgcctct gcgcttagat accttcatga aaacagaatc | 600 |
| atccatcggg atctaaagcc agaaaacatc gtcctgcagc aaggagaaca gaggttaata | 660 |
| cacaaaatta ttgacctagg atatgccaag gagctggatc agggcagtct ttgcacatca | 720 |
| ttcgtgggga ccctgcagta cctgccccca gagctactgg agcagcagaa gtacacagtg | 780 |
| accgtcgact actggagctt cggcaccctg gcctttgagt gcatcacggg cttccggccc | 840 |
| ttcctcccca ctggcagcc cgtgcagtgg cattcaaaag tgcggcagaa gagtgaggtg | 900 |
| gacattgttg ttagcgaaga cttgaatgga acggtgaagt tttcaagctc tttaccctac | 960 |
| cccaataatc ttaacagtgt cctggctgag cgactggaga agtggctgca actgatgctg | 1020 |
| atgtggcacc cccgacagag gggcacggat cccacgtatg ggcccaatgg ctgcttcaag | 1080 |
| gccctggatg acatcttaaa cttaaagctg gttcatatct tgaacatggt cacgggcacc | 1140 |
| atccacacct accctgtgac agaggatgag agtctgcaga gcttgaaggc cagaatccaa | 1200 |
| caggacacgg gcatcccaga ggaggaccag gagctgctgc aggaagcggg cctggcgttg | 1260 |
| atccccgata agcctgccac tcagtgtatt tcagacggca agttaaatga gggccacaca | 1320 |
| ttggacatgg atcttgtttt tctctttgac aacagtaaaa tcacctatga gactcagatc | 1380 |
| tccccacggc cccaacctga aagtgtcagc tgtatccttc aagagcccaa gaggaatctc | 1440 |
| gccttcttcc agctgaggaa ggtgtgggc caggtctggc acagcatcca gaccctgaag | 1500 |
| gaagattgca accggctgca gcagggacag cgagccgcca tgatgaatct cctccgaaac | 1560 |
| aacagctgcc tctccaaaat gaagaattcc atggcttcca tgtctcagca gctcaaggcc | 1620 |
| aagttggatt tcttcaaaac cagcatccag attgacctgg agaagtacag cgagcaaacc | 1680 |
| gagtttggga tcacatcaga taaactgctg ctggcctgga gggaaatgga gcaggctgtg | 1740 |

```
gagctctgtg ggcgggagaa cgaagtgaaa ctcctggtag aacggatgat ggctctgcag   1800
accgacattg tggacttaca gaggagcccc atgggccgga agcaggggg aacgctggac    1860 gacctagagg agcaagcaag ggagctgtac aggagactaa gggaaaaacc tcgagaccag    1920
cgaactgagg gtgacagtca ggaaatggta cggctgctgc ttcaggcaat tcagagcttc    1980
gagaagaaag tgcgagtgat ctatacgcag ctcagtaaaa ctgtggtttg caagcagaag    2040
gcgctggaac tgttgcccaa ggtggaagag gtggtgagct taatgaatga ggatgagaag    2100
actgttgtcc ggctgcagga aagcggcag aaggagctct ggaatctcct gaagattgct    2160
tgtagcaagg tccgtggtcc tgtcagtgga agcccggata gcatgaatgc ctctcgactt    2220
agccagcctg ggcagctgat gtctcagccc tccacggcct ccaacagctt acctgagcca    2280
gccaagaaga gtgaagaact ggtggctgaa gcacataacc tctgcaccct gctagaaaat    2340
gccatacagg acactgtgag ggaacaagac cagagtttca cggccctaga ctggagctgg    2400
ttacagacgg aagaagaaga gcacagctgc ctggagcagg cctcatgatg tgggggggact    2460 cgacccccctg acatggggca gcccatagca ggccttgtgc agtgggggga ctcgaccccc    2520
tgacatgggg ctgcctggag caggccgcgt gacgtgggc tgcctggccg cggctctcac    2580
atggtggttc ctgctgcact gatggcccag gggtctctgg tatccagatg gagctctcgc    2640
ttcctcagca gctgtgactt tcacccagga cccaggacgc agccctccgt gggcactgcc    2700
ggcgccttgt ctgcacactg gaggtcctcc attacagagg cccagcgcac atcgctggcc    2760
ccacaaacgt tcaggggtac agccatggca gctccttcct ctgccgtgag aaaagtgctt    2820
ggagtacggt ttgccacaca cgtgactgga cagtgtccaa ttcaaatctt tcagggcaga    2880
gtccgagcag cgcttggtga cagcctgtcc tctcctgctc tccaaaggcc ctgctccctg    2940
tcctctctca ctttacagct tgtgtttctt ctggattcag cttctcctaa acagacagtt    3000
taattatagt tgcggcctgg ccccatcctc acttcctctt tttatttcac tgctgctaaa    3060
attgtgtttt tacctactac tttggtggtt gtcctcttt cggcaaagtt ggagcgagtg    3120
ccaagctctc catctgtggt cctttctgcc aagagcgact catagtaacc aggatgggag    3180
agcagctgcc ttattctgaa tcccaaaaat tacttggggg tgattgtcac agaggaggga    3240
cagaaagggt atctgctgac caccagcctg cctacccatg cccatgtctc cattcctgct    3300
caagcgtgtg tgctgggccg gggagtccct gtctctcaca gcatctagca gtattattaa    3360
atggattcat tttaaaaata gctcctatat tttgtaacat gtctcaaaca ctcatactgg    3420
gttccacaat ccactgttag aatacctatg gttagggctt ctgaactaaa ataatggaaa    3480 atttttaacaa tttgtatagt gcctggatca ttactagtgc cataaccctg cttcttcaac    3540
atttcacaga acttctcttt tatataaagg caagagcaca aaatgagttc agatgatcac    3600
aaacaggtga gttttgttgg agaagaaagt tggagtagga gactttcaca agtggtttcc    3660
atggagatag aatgaagcat tctgtggtca agtaagttta gggagctatt catgtttcac    3720
ttgctttgtg gagattcaca ctatgcactg ggaaagtatc tgaaaagtct tataataaag    3780
aaacaggctt aactttgtgt aagaacactg tttatcaatg tcatttggct atagaaacat    3840
tttctcctgc tgattgtgtg tgtgaaacat gtattaacat tccaatgaac tagcatttaa    3900
taaagcacaa ttttgg                                                    3916
```

<210> SEQ ID NO 504
<211> LENGTH: 2595
<212> TYPE: DNA
<213> ORGANISM: Homo sapiens

<400> SEQUENCE: 504

```
agcgcgcagg cgcggccgga ttccgggcag tgacgcgacg gcgggccgcg cggcgcattt      60
ccgcctctgg cgaatggctc gtctgtagtg cacgccgcgg gcccagctgc gaccccggcc     120
ccgcccccgg gaccccggcc atggacgaac tgttcccccct catcttcccg gcagagccag    180
cccaggcctc tggcccctat gtggagatca ttgagcagcc caagcagcgg ggcatgcgct     240
tccgctacaa gtgcgagggg cgctccgcgg gcagcatccc aggcgagagg agcacagata     300
ccaccaagac ccacccccacc atcaagatca atggctacac aggaccaggg acagtgcgca    360
tctcccctggt caccaaggac cctcctcacc ggcctcaccc ccacgagctt gtaggaaagg    420
actgccggga tggcttctat gaggctgagc tctgcccgga ccgctgcatc cacagtttcc     480
agaacctggg aatccagtgt gtgaagaagc gggacctgga gcaggctatc agtcagcgca     540
tccagaccaa caacaacccc ttccaagttc ctatagaaga gcagcgtggg gactacgacc     600
tgaatgctgt gcggctctgc ttccaggtga cagtgcggga cccatcaggc aggcccctcc     660
gcctgccgcc tgtcctttct catcccatct ttgacaatcg tgcccccaac actgccgagc     720
tcaagatctg ccgagtgaac cgaaactctg cagctgcct cggtggggat gagatcttcc      780
tactgtgtga aaggtgcag aaagaggaca ttgaggtgta tttcacggga ccaggctggg      840
aggcccgagg ctccttttcg caagctgatg tgcaccgaca agtggccatt gtgttccgga     900
cccctcccta cgcagacccc agcctgcagg ctcctgtgcg tgtctccatg cagctgcggc     960
ggccttccga ccgggagctc agtgagccca tggaattcca gtacctgcca gatacagacg    1020
atcgtcaccg gattgaggag aaacgtaaaa ggacatatga gaccttcaag agcatcatga    1080
agaagagtcc tttcagcgga cccaccgacc cccggcctcc acctcgacgc attgctgtgc    1140
cttcccgcag ctcagcttct gtcccaagc cagcaccccca gccctatccc tttacgtcat    1200
ccctgagcac catcaactat gatgagtttc ccaccatggt gtttccttct gggcagatca    1260
gccaggcctc ggccttggcc ccggcccctc cccaagtcct gccccaggct ccagcccctg    1320
cccctgctcc agccatggta tcagctctgg ccaggcccc agcccctgtc ccagtcctag     1380
ccccaggccc tcctcaggct gtggccccac ctgccccaa gcccccacag cctggggaag     1440
gaacgctgtc agaggccctg ctgcagctgc agtttgatga tgaagacctg ggggccttgc    1500
ttggcaacag cacagaccca gctgtgttca cagacctggc atccgtcgac aactccgagt    1560
ttcagcagct gctgaaccag ggcatacctg tggccccccca cacaactgag cccatgctga    1620
tggagtaccc tgaggctata actgccctag tgacaggggc ccagaggccc cccgaccccag   1680
ctcctgctcc actgggggcc ccggggctcc ccaatggcct cctttcagga gatgaagact    1740
tctcctccat tgcggacatg gacttctcag ccctgctgag tcagatcagc tcctaaggggg   1800
gtgacgcctg ccctccccag agcactgggt tgcagggggat tgaagccctc caaaagcact    1860
tacggattct ggtggggtgt gttccaactg ccccccaactt tgtggatgtc ttccttggag    1920
ggggggagcca tatttttattc ttttattgtc agtatctgta tctctctctc tttttggagg    1980
tgcttaagca gaagcattaa cttctctgga aaggggggag ctgggggaaac tcaaactttt    2040
cccctgtcct gatggtcagc tcccttctct gtagggaact ctgggggtccc ccatccccat    2100
cctccagctt ctggtactct cctagagaca gaagcaggct ggaggtaagg cctttgagcc    2160
cacaaagcct tatcaagtgt cttccatcat ggattcatta cagcttaatc aaaataacgc    2220
cccagatacc agccctgta tggcactggc attgtccctg tgcctaacac cagcgtttga     2280
ggggctggcc ttcctgccct acagaggtct ctgccggctc tttccttgct caaccatggc    2340
```

```
tgaaggaaac cagtgcaaca gcactggctc tctccaggat ccagaagggg tttggtctgg    2400
gacttccttg ctctccctct tctcaagtgc cttaatagta gggtaagttg ttaagagtgg    2460
gggagagcag gctggcagct ctccagtcag gaggcatagt ttttactgaa caatcaaagc    2520
acttggactc ttgctctttc tactctgaac taataaatct gttgccaagc tggctagaaa    2580
aaaaaaaaaa aaaaa                                                     2595

<210> SEQ ID NO 505
<211> LENGTH: 2120
<212> TYPE: DNA
<213> ORGANISM: Homo sapiens

<400> SEQUENCE: 505
agcccgttcc tgctccgcgc ttctggagca ctggccaagg cgggccgatt caggacccag      60
gttacttggg cggcgagctg gactgttttct actcctccct cctcctccac tgcggggtct    120
gaccctactc cttgtgtgag gactcctcta gttcagagac atattctgtt caccaaaactt    180 gactgcgctc tatcgaggtc gttaaattct tcggaaatgc ctcacatata gtttggcagc     240
tagcccttgc cctgttggat gaataggcac ctctggaaga gccaactgtg tgagatggtg     300
cagcccagtg gtggcccggc agcagatcag gacgtactgg gcgaagagtc tcctctgggg     360
aagccagcca tgctgcacct gccttcagaa cagggcgctc ctgagaccct ccagcgctgc     420
ctggaggaga atcaagagct ccgagatgcc atccggcaga gcaaccagat tctgcgggag     480
cgctgcgagg agcttctgca tttccaagcc agccagaggg aggagaagga gttcctcatg     540
tgcaagttcc aggaggccag gaaactggtg gagagactcg gcctggagaa gctcgatctg     600
aagaggcaga aggagcaggc tctgcgggag gtggagcacc tgaagagatg ccagcagcag     660
atggctgagg acaaggcctc tgtgaaagcc aggtgacgt ccttgctcgg ggagctgcag      720
gagagccaga gtcgcttgga ggctgccact aaggaatgcc aggctctgga gggtcgggcc     780
cgggcggcca gcgagcaggc gcggcagctg gagagtgagc gcgaggcgct gcagcagcag     840
cacagcgtgc aggtggacca gctgcgcatg cagggccaga gcgtggaggc cgcgctccgc     900
atggagcgcc aggccgcctc ggaggagaag aggaagctgg cccagttgca ggtggcctat     960
caccagctct ccaagaata cgacaaccac atcaagagca gcgtggtggg cagtgagcgg    1020
aagcgaggaa tgcagctgga agatctcaaa cagcagctcc agcaggccga ggaggccctg    1080
gtggccaaac aggaggtgat cgataagctg aaggaggagg ccgagcagca caagattgtg    1140
atggagaccg ttccggtgct gaaggcccag gcggatatct acaaggcgga cttccaggct    1200
gagaggcagg cccgggagaa gctggccgag aagaaggagc tcctgcagga gcagctggag    1260
cagctgcaga gggagtacag caaactgaag gccagctgtc aggagtcggc caggatcgag    1320
gacatgagga agcggcatgt cgaggtctcc caggccccct gccccccgc ccctgcctac     1380 ctctcctctc ccctgccct gcccagccag aggaggagcc cccccgagga gccacctgac    1440
ttctgctgtc ccaagtgcca gtatcaggcc cctgatatgg acaccctgca gatacatgtc    1500
atggagtgca ttgagtaggg ccggccagtg caaggccact gcctgccgag gacgtgcccg    1560
ggaccgtgca gtctgcgctt tcctctcccg cctgcctagc ccaggatgaa gggctgggtg    1620
gccacaactg ggatgccacc tggagcccca cccaggagct ggccgcggca ccttacgctt    1680
cagctgttga tccgctggtc ccctcttttg gggtagatgc ggccccgatc aggcctgact    1740
cgctgctctt tttgttccct tctgtctgct cgaaccactt gcctcgggct aatccctccc    1800
tcttcctcca cccggcactg gggaagtcaa gaatggggcc tggggctctc agggagaact    1860
```

-continued

| | |
|---|---|
| gcttccctg gcagagctgg gtggcagctc ttcctcccac cggacaccga cccgcccgct | 1920 |
| gctgtgccct gggagtgctg ccctcttacc atgcacacgg gtgctctcct tttgggctgc | 1980 |
| atgctattcc attttgcagc cagaccgatg tgtatttaac cagtcactat tgatggacat | 2040 |
| ttgggttgtt tcccatcttt ttgttaccat aaataatggc atagtaaaaa tccttgtgca | 2100 |
| ttaaaaaaaa aaaaaaaaa | 2120 |

<210> SEQ ID NO 506
<211> LENGTH: 1669
<212> TYPE: DNA
<213> ORGANISM: Homo sapiens

<400> SEQUENCE: 506

| | |
|---|---|
| ctccctcagc aaggacagca gaggaccagc taagagggag agaagcaact acagaccccc | 60 |
| cctgaaaaca accctcagac gccacatccc ctgacaagct gccaggcagg ttctcttcct | 120 |
| ctcacatact gacccacggc tccaccctct ctccctgga aaggacacca tgagcactga | 180 |
| aagcatgatc cgggacgtgg agctggccga ggaggcgctc cccaagaaga caggggggcc | 240 |
| ccagggctcc aggcggtgct tgttcctcag cctcttctcc ttcctgatcg tggcaggcgc | 300 |
| caccacgctc ttctgcctgc tgcactttgg agtgatcggc cccagagggg aagagttccc | 360 |
| cagggacctc tctctaatca gccctctggc ccaggcagtc agatcatctt ctcgaacccc | 420 |
| gagtgacaag cctgtagccc atgttgtagc aaaccctcaa gctgaggggc agctccagtg | 480 |
| gctgaaccgc cgggccaatg ccctcctggc caatggcgtg gagctgagag ataaccagct | 540 |
| ggtggtgcca tcagagggcc tgtacctcat ctactcccag gtcctcttca agggccaagg | 600 |
| ctgcccctcc acccatgtgc tcctcaccca caccatcagc cgcatcgccg tctcctacca | 660 |
| gaccaaggtc aacctcctct ctgccatcaa gagcccctgc cagagggaga ccccagaggg | 720 |
| ggctgaggcc aagccctggt atgagcccat ctatctggga ggggtcttcc agctggagaa | 780 |
| gggtgaccga ctcagcgctg agatcaatcg gcccgactat ctcgactttg ccgagtctgg | 840 |
| gcaggtctac tttgggatca ttgccctgtg aggaggacga acatccaacc ttcccaaacg | 900 |
| cctcccctgc cccaatccct ttattacccc ctccttcaga caccctcaac ctcttctggc | 960 |
| tcaaaaagag aattggggc ttagggtcgg aacccaagct tagaacttta agcaacaaga | 1020 |
| ccaccacttc gaaacctggg attcaggaat gtgtggcctg cacagtgaag tgctggcaac | 1080 |
| cactaagaat tcaaactggg gcctccagaa ctcactgggg cctacagctt tgatccctga | 1140 |
| catctggaat ctggagacca gggagccttt ggttctggcc agaatgctgc aggacttgag | 1200 |
| aagacctcac ctagaaattg acacaagtgg accttaggcc ttcctctctc cagatgtttc | 1260 |
| cagacttcct tgagacacgg agcccagccc tccccatgga gccagctccc tctatttatg | 1320 |
| tttgcacttg tgattatta ttatttattt attatttatt tatttacaga tgaatgtatt | 1380 |
| tatttgggag accgggggtat cctgggggac ccaatgtagg agctgccttg gctcagacat | 1440 |
| gttttccgtg aaaacggagc tgaacaatag gctgttccca tgtagccccc tggcctctgt | 1500 |
| gccttctttt gattatgttt tttaaaatat ttatctgatt aagttgtcta acaatgctg | 1560 |
| atttggtgac caactgtcac tcattgctga gcctctgctc cccaggggag ttgtgtctgt | 1620 |
| aatcgcccta ctattcagtg gcgagaaata aagtttgctt agaaaagaa | 1669 |

<210> SEQ ID NO 507
<211> LENGTH: 722
<212> TYPE: DNA
<213> ORGANISM: Homo sapiens -continued

```
<400> SEQUENCE: 507
acttcgctcc gcgcagccgc ctggtctgca gtttgttgga gctctgcgtc cagcgccgct      60
gccgctgccg ccgccgccgc cgccgccgcc gccgccgccg ccgccgccac taccaccact     120
tgattcttgc agccaccctg cgaaccctgc cacactgcga tcgcatcatc gcggtattcg     180
gttcgctgcg ttcccgccgc caccgcctcg gcgcccttc ttggcccttg ttcccccaaa     240
tgtctgactc tgactctcgg actgagaaac gcaagaaaaa aagaccaaat ggcaaagcaa     300
ccttctgatg taagttctga gtgtgaccga gaaggtagac aattgcagcc tgcggagagg     360
cctccccagc tcagacctgg ggcccctacc tccctacaga cagagccaca agacaggagc     420
ccagcaccca tgagttgtga caaatcaaca caaacccaa gtcctccttg ccaggccttc      480
aaccactatc tcagtgcaat ggtagtcatc ctagaggata taggtgatct ttcactgtgc     540
tttggattta tatttactgg cttagatttg tatggccacc accatagtca agatacagaa     600
caactcaacc acaaggattt ctcatgatac cttttatag ccacagccac ctctctccct     660
cttccttgag cattttgtca tatggtcatt ggtgattaaa taaaatgtat tttaatattg     720
ac                                                                     722
```